United States Patent
Ng et al.

(10) Patent No.: US 9,556,201 B2
(45) Date of Patent: Jan. 31, 2017

(54) BICYCLIC PYRIDINES AND ANALOGS AS SIRTUIN MODULATORS

(75) Inventors: Pui Yee Ng, Boston, MA (US); Charles Blum, Westbrook, CT (US); Lauren McPherson, Somerville, MA (US); Robert B. Perni, Marlborough, MA (US); Chi B. Vu, Arlington, MA (US); Mohammed Mahmood Ahmed, The Helios (SG); Jeremy S. Disch, Natick, MA (US)

(73) Assignee: GLAXOSMITHKLINE LLC, Wilmington, DE (US)

( * ) Notice: Subject to any disclaimer, the term of this patent is extended or adjusted under 35 U.S.C. 154(b) by 573 days.

(21) Appl. No.: 13/504,134

(22) PCT Filed: Oct. 29, 2010

(86) PCT No.: PCT/US2010/054880
§ 371 (c)(1),
(2), (4) Date: Jun. 15, 2012

(87) PCT Pub. No.: WO2011/059839
PCT Pub. Date: May 19, 2011

(65) Prior Publication Data
US 2012/0252780 A1 Oct. 4, 2012

Related U.S. Application Data

(60) Provisional application No. 61/256,269, filed on Oct. 29, 2009.

(51) Int. Cl.
| | |
|---|---|
| A61K 31/55 | (2006.01) |
| A61K 31/551 | (2006.01) |
| A61K 31/553 | (2006.01) |
| A61K 31/4375 | (2006.01) |
| A61K 31/437 | (2006.01) |
| A61K 31/5365 | (2006.01) |
| A61K 31/4985 | (2006.01) |
| C07D 471/04 | (2006.01) |
| C07D 487/04 | (2006.01) |
| C07D 519/00 | (2006.01) |
| C07D 498/04 | (2006.01) |

(52) U.S. Cl.
CPC .......... *C07D 498/04* (2013.01); *C07D 471/04* (2013.01)

(58) Field of Classification Search
CPC .... A61K 31/55; A61K 31/551; A61K 31/553; A61K 31/4375; A61K 31/437; A61K 31/5365; A61K 31/4985; C07D 471/04; C07D 487/04; C07D 519/00
USPC .................. 514/249; 544/257, 258, 259, 350
See application file for complete search history.

(56) References Cited

U.S. PATENT DOCUMENTS

| | | | | |
|---|---|---|---|---|
| 7,345,178 | B2 | 3/2008 | Nunes et al. | 548/154 |
| 7,829,556 | B2 | 11/2010 | Bemis et al. | 514/233.2 |
| 7,855,289 | B2 | 12/2010 | Nunes et al. | 544/235 |
| 7,893,086 | B2 | 2/2011 | Bemis et al. | 514/301 |
| 8,088,928 | B2 | 1/2012 | Nunes et al. | 548/218 |
| 8,093,401 | B2 | 1/2012 | Nunes et al. | 548/309.7 |
| 8,343,997 | B2 | 1/2013 | Oalmann et al. | 514/301 |
| 8,846,664 | B2 * | 9/2014 | Huang | A61K 9/0019 514/221 |
| 2011/0046110 | A1 | 2/2011 | Vu et al. | 544/106 |
| 2011/0077248 | A1 | 3/2011 | Vu et al. | 544/106 |
| 2011/0124637 | A1 | 5/2011 | Vu et al. | 544/106 |
| 2011/0257174 | A1 | 10/2011 | Oalmann et al. | 544/106 |
| 2011/0263564 | A1 | 10/2011 | Narayan et al. | 514/252.1 |
| 2011/0306612 | A1 | 12/2011 | Vu et al. | 544/106 |
| 2011/0319411 | A1 | 12/2011 | Vu et al. | 544/106 |
| 2012/0108585 | A1 | 5/2012 | Vu et al. | 544/106 |

FOREIGN PATENT DOCUMENTS

| | | |
|---|---|---|
| DE | 1 108 698 | 6/1961 |
| EP | 2 476 682 A1 | 7/2012 |
| WO | WO 2006/094210 A2 | 9/2006 |
| WO | WO 2006/094233 A1 | 9/2006 |
| WO | WO 2006/094235 A1 | 9/2006 |
| WO | WO 2006/094236 A1 | 9/2006 |
| WO | WO 2006/094237 A2 | 9/2006 |
| WO | WO 2006/094239 A2 | 9/2006 |
| WO | WO 2006/094246 A2 | 9/2006 |

(Continued)

OTHER PUBLICATIONS

Milne, J. C. & Denu, J. M. The Sirtuin family: therapeutic targets to treat diseases of aging, *Current Opinion in Chemical Biology*, 12:11-17 (2008).
Porcu et al., "The emerging therapeutic potential of sirtuin-interacting drugs: from cell death to lifespan extension," *Trends in Pharmacological Sciences*, 26(2):94-103 (2005).
Baur, et al. *Nature Reviews Drug Discovery*, 11: 443-461 (2012).
Beher, et al. *Chem. Biol. Drug Des.*, 74: 619-624 (2009).
Bemis, et al. *Bioorg. & Med. Chem. Letters*, 19: 2350-2353 (2009).
Blander, et al. *J. Biol. Chem.*, 280(11): 9780-9785 (2005).
Blum, et al. *J. Med. Chem.*, 54: 417-432 (2011).

(Continued)

*Primary Examiner* — Brenda Coleman
(74) *Attorney, Agent, or Firm* — Grace C. Hsu; Kathryn A. Lutomski; Edward R. Gimmi

(57) ABSTRACT

Provided herein are novel sirtuin-modulating compounds and methods of use thereof. The sirtuin-modulating compounds may be used for increasing the lifespan of a cell, and treating and/or preventing a wide variety of diseases and disorders including, for example, diseases or disorders related to aging or stress, diabetes, obesity, neurodegenerative diseases, cardiovascular disease, blood clotting disorders, inflammation, cancer, and/or flushing as well as diseases or disorders that would benefit from increased mitochondrial activity. Also provided are compositions comprising a sirtuin-modulating compound in combination with another therapeutic agent.

18 Claims, No Drawings

(56) References Cited

FOREIGN PATENT DOCUMENTS

| WO | WO 2006/094248 A1 | 9/2006 |
|---|---|---|
| WO | WO 2006/105403 A2 | 10/2006 |
| WO | WO 2006/105440 A2 | 10/2006 |
| WO | WO 2006/127987 A2 | 11/2006 |
| WO | WO 2007/008548 A2 | 1/2007 |
| WO | WO 2007/019344 A1 | 2/2007 |
| WO | WO 2007/019345 A1 | 2/2007 |
| WO | WO 2007/019416 A1 | 2/2007 |
| WO | WO 2007/019417 A1 | 2/2007 |
| WO | WO 2007/064902 A2 | 6/2007 |
| WO | WO 2007/102861 A2 | 9/2007 |
| WO | WO 2008/027379 A2 | 3/2008 |
| WO | WO 2008/060400 A2 | 5/2008 |
| WO | WO 2008/073451 A2 | 6/2008 |
| WO | WO 2008/100376 A2 | 8/2008 |
| WO | WO 2008/100423 A1 | 8/2008 |
| WO | WO 2008/115518 A2 | 9/2008 |
| WO | WO2008/156866 A1 | 12/2008 |
| WO | WO 2008/156869 A2 | 12/2008 |
| WO | WO 2009/058348 A1 | 5/2009 |
| WO | WO 2009/061453 A1 | 5/2009 |
| WO | WO 2009/085226 A2 | 7/2009 |
| WO | WO 2009/089011 A2 | 7/2009 |
| WO | WO2009/134973 | 11/2009 |
| WO | WO 2009/140562 A1 | 11/2009 |
| WO | WO2009/146358 | 12/2009 |
| WO | WO2010/003048 | 1/2010 |
| WO | WO2010/019606 | 2/2010 |
| WO | WO 2010/027002 A1 | 3/2010 |
| WO | WO2010/037127 | 4/2010 |
| WO | WO2010/037129 | 4/2010 |
| WO | WO 2010/056311 A1 | 5/2010 |
| WO | WO2010/056549 | 5/2010 |
| WO | WO2010/071853 | 6/2010 |
| WO | WO2010/077686 | 7/2010 |
| WO | WO2010/077947 | 7/2010 |
| WO | WO2010/088574 | 8/2010 |
| WO | WO2010/101949 | 9/2010 |
| WO | WO2011/116176 | 9/2011 |

OTHER PUBLICATIONS

Borra, et al. J. Biol. Chem., 280(17): 17187-17195 (2005).
Buchen, et al. Nature (2010). http://www.nature.com/news/2010/100119/full/news.2010.18.html.
Buck, et al. J. Leukocyte Biol., 75: 939-950 (2004).
Bundgaard. Design and application of prodrugs, Textbook of Drug Design and Development, pp. 113-191 (1991).
Burnett, et al. Nature, 477: 482-486 (2011).
Canto, et al. Nature, 477: 411 (2011).
ClinicalTrials.gov—Search of SRT2104—List results. http://clinicaltrials.gov/ct2/results?term=SRT2104 (retrieved on May 24, 2012).
ClinicalTrials.gov—Search of SRT2379—List results. http://clinicaltrials.gov/ct2/results?term=SRT2379 (retrieved on May 27, 2012).
ClinicalTrials.gov—Search of SRT3025—List results. http://clinicaltrials.gov/ct2/results?term=SRT3025 (retrieved on May 27, 2012).
Couzin-Frankel. Science, 334: 1194-1198 (2011).
Csiszar, et al. Am. J. Physiol. Heart Circ. Physiol., 294: H2721-H2735 (2008).
Dai, et al. J. Biol. Chem., 285(43): 32695-32703 (2010).
Dittenhafer-Reed, et al. ChemBioChem., 12: 281-289 (2011).
Feige, et al. Cell Metab., 8: 347-358(2008).
European Supplemental Search Report dated Mar. 28, 2013, 6 pages.
Hoffman, et al, "Pharmacokinetics and Tolerability of SRT2104, a First-In-Class Small Molecule Activator of SIRT1, after Single and Repeated Oral Administraion in Man, " Br J Clin Pharmacol, Electronic publication ahead of print, May 23, 2012, http://www.ncbi.nlm.nih.gov/pubmed/22616762.
Howitz, et al. Nature, 425: 191-196 (2003).
Huber, et al. Future Med. Chem., 2(12): 1751-1759 (2010).
Kaeberlein, et al. J. Biol. Chem., 280(17): 17038-17045 (2005).
Kaeberlein, et al. Aging Cell, 6: 415-416 (2007).
Keystone Symposia on Molecular and Cellular Biology "Sirtuins in Metabolism, Aging and Disease", Feb. 12-16, 2012.
Kubinyi. "3D QSAR in Drug Design Ligand-Protein Internations and Molecular Similarity", Springer, 800 pages, vol. 2-3: 243-244 provided (1998).
Ledford. Nature, 464: 480-481 (2010).
Lombard, et al. Nature, 477: 410 (2011).
Milne, et al. Nature, 450: 712-716 (2007).
Minor, et al. Scientific Reports, 1-48 (2011).
Pacholec, et al. J. Biol. Chem., 285(11): 8340-8351, Mar. 12, 2010.
Pacholec, et al. JBC Papers in Press, Manuscript M1 09.088682, Jan. 8, 2010.
Pacholec, et al. FASEB Summer Research Conferences; NAD Metabolism and Signaling, Jun. 21-26, 2009.
Papers of the Week. "A Resveratrol Reversal", DO110.1074/jbc.P109.088682. Mar. 10, 2010 (Abst).
Park, et al. Cell, 148: 421-433 (2012).
Park, et al. Toxicology Letters, 120: 281-291 (2011).
Pfister, et al. PLOS One, 3(12): 1-8 (2008).
Silverman. "The Organic Chemistry of Drug Design and Drug Action," Elsevier, 29-32 (2004).
Stünkel, et al., J. of Biomolecular Screening, 16(10): 1153-1169 (2011).
Terfloth, et al. "Electronic Screening: Lead Finding From Database Mining," Wermuth, The Practice of Med. Chem., 2nd Ed. Chapters 9-10, pp. 131-157 (2003).
Timmers, et al. Cell Metabolism, 14: 612-622 (2011).
Viswanathan & Guarente. Nature, 477: E1-E2 (2011).
Venkatasubramanian, et al., "Cardiovascular Effects of a Novel SIRT 1 Activator, SRT2104, in Otherwise Healthy Cigarette Smokers", Abstract for AHA 2012 Meeting.
Yamazaki, et al. Am. J. Physiol. Endocrinol. Metab., 297: E1179-E1186 (2009).
Written Opinion of the International Searching Authority dated Jan. 18, 2011, 7 pages.
Yamori, et al. Drug Delivery System, 18(4): 385-393 (2003). Abstract only.
Yoshizaki, et al. Am. J. Physiol. Endocrinol. Metab., 298: E419-E428 (2010).
Yoshizaki, et al. Molecular and Cellular Biology, 29(5): 1363-1374 (2009).
Zarse, et al. Ilform. Metab. Res., 42(12): 837-839 (2010).

* cited by examiner

```
                           SEQUENCE LISTING

<160> NUMBER OF SEQ ID NOS: 2

<210> SEQ ID NO 1
<211> LENGTH: 20
<212> TYPE: PRT
<213> ORGANISM: Artificial Sequence
<220> FEATURE:
<223> OTHER INFORMATION: Synthetic peptide
<220> FEATURE:
<223> OTHER INFORMATION: N-term acetylated
<220> FEATURE:
<221> NAME/KEY: MOD_RES
<222> LOCATION: (3)...(3)
<223> OTHER INFORMATION: Lys (biotin)
<220> FEATURE:
<221> NAME/KEY: MOD_RES
<222> LOCATION: (12)...(12)
<223> OTHER INFORMATION: Lys (Ac)
<220> FEATURE:
<221> NAME/KEY: MOD_RES
<222> LOCATION: (13)...(13)
<223> OTHER INFORMATION: Norleucine
<220> FEATURE:
<221> NAME/KEY: MOD_RES
<222> LOCATION: (18)...(18)
<223> OTHER INFORMATION: Lys (5TMR)
<220> FEATURE:
<223> OTHER INFORMATION: C-term amidated

<400> SEQUENCE: 1

Glu Glu Lys Gly Gln Ser Thr Ser Ser His Ser Lys Leu Ser Thr Glu
 1               5                  10                  15

Gly Lys Glu Glu
            20

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide

<400> SEQUENCE: 2

Arg His Lys Lys
 1
```

BICYCLIC PYRIDINES AND ANALOGS AS SIRTUIN MODULATORS

This application is a §371 of International Application No. PCT/US2010/054880, filed 29 Oct. 2010, which claims the benefit of U.S. Provisional Application No. 61/256,269, filed 29 Oct. 2009, which are incorporated herein in their entireties.

REFERENCE TO RELATED APPLICATION

This application claims the benefit of U.S. Provisional Application No. 61/256,269, filed Oct. 29, 2009, the disclosure of which is incorporated herein by reference thereto.

BACKGROUND

The Silent Information Regulator (SIR) family of genes represents a highly conserved group of genes present in the genomes of organisms ranging from archaebacteria to eukaryotes. The encoded SIR proteins are involved in diverse processes from regulation of gene silencing to DNA repair. The proteins encoded by members of the SIR gene family show high sequence conservation in a 250 amino acid core domain. A well-characterized gene in this family is *S. cerevisiae* SIR2, which is involved in silencing HM loci that contain information specifying yeast mating type, telomere position effects and cell aging. The yeast Sir2 protein belongs to a family of histone deacetylases. The Sir2 homolog, CobB, in *Salmonella typhimurium*, functions as an NAD (nicotinamide adenine dinucleotide)-dependent ADP-ribosyl transferase.

The Sir2 protein is a class III deacetylase which uses NAD as a cosubstrate. Unlike other deacetylases, many of which are involved in gene silencing, Sir2 is insensitive to class I and II histone deacetylase inhibitors like trichostatin A (TSA).

Deacetylation of acetyl-lysine by Sir2 is tightly coupled to NAD hydrolysis, producing nicotinamide and a novel acetyl-ADP ribose compound. The NAD-dependent deacetylase activity of Sir2 is essential for its functions which can connect its biological role with cellular metabolism in yeast. Mammalian Sir2 homologs have NAD-dependent histone deacetylase activity.

Biochemical studies have shown that Sir2 can readily deacetylate the amino-terminal tails of histones H3 and H4, resulting in the formation of 1-O-acetyl-ADP-ribose and nicotinamide. Strains with additional copies of SIR2 display increased rDNA silencing and a 30% longer life span. It has recently been shown that additional copies of the *C. elegans* SIR2 homolog, sir-2.1, and the *D. melanogaster* dSir2 gene greatly extend life span in those organisms. This implies that the SIR2-dependent regulatory pathway for aging arose early in evolution and has been well conserved. Today, Sir2 genes are believed to have evolved to enhance an organism's health and stress resistance to increase its chance of surviving adversity.

In humans, there are seven Sir2-like genes (SIRT1-SIRT7) that share the conserved catalytic domain of Sir2. SIRT1 is a nuclear protein with the highest degree of sequence similarity to Sir2. SIRT1 regulates multiple cellular targets by deacetylation including the tumor suppressor p53, the cellular signaling factor NF-κB, and the FOXO transcription factor.

SIRT3 is a homolog of SIRT1 that is conserved in prokaryotes and eukaryotes. The SIRT3 protein is targeted to the mitochondrial cristae by a unique domain located at the N-terminus. SIRT3 has NAD+-dependent protein deacetylase activity and is ubiquitously expressed, particularly in metabolically active tissues. Upon transfer to the mitochondria, SIRT3 is believed to be cleaved into a smaller, active form by a mitochondrial matrix processing peptidase (MPP).

Caloric restriction has been known for over 70 years to improve the health and extend the lifespan of mammals. Yeast life span, like that of metazoans, is also extended by interventions that resemble caloric restriction, such as low glucose. The discovery that both yeast and flies lacking the SIR2 gene do not live longer when calorically restricted provides evidence that SIR2 genes mediate the beneficial health effects of a restricted calorie diet. Moreover, mutations that reduce the activity of the yeast glucose-responsive cAMP (adenosine 3',5'-monophosphate)-dependent (PKA) pathway extend life span in wild type cells but not in mutant sir2 strains, demonstrating that SIR2 is likely to be a key downstream component of the caloric restriction pathway.

SUMMARY

Provided herein are novel sirtuin-modulating compounds and methods of use thereof.

In one aspect, the invention provides sirtuin-modulating compounds of Structural Formulas (I) to (VI) as are described in detail below.

In another aspect, the invention provides methods for using sirtuin-modulating compounds, or compositions comprising sirtuin-modulating compounds. In certain embodiments, sirtuin-modulating compounds that increase the level and/or activity of a sirtuin protein may be used for a variety of therapeutic applications including, for example, increasing the lifespan of a cell, and treating and/or preventing a wide variety of diseases and disorders including, for example, diseases or disorders related to aging or stress, diabetes, obesity, neurodegenerative diseases, chemotherapeutic induced neuropathy, neuropathy associated with an ischemic event, ocular diseases and/or disorders, cardiovascular disease, blood clotting disorders, inflammation, and/or flushing, etc. Sirtuin-modulating compounds that increase the level and/or activity of a sirtuin protein may also be used for treating a disease or disorder in a subject that would benefit from increased mitochondrial activity, for enhancing muscle performance, for increasing muscle ATP levels, or for treating or preventing muscle tissue damage associated with hypoxia or ischemia. In other embodiments, sirtuin-modulating compounds that decrease the level and/or activity of a sirtuin protein may be used for a variety of therapeutic applications including, for example, increasing cellular sensitivity to stress, increasing apoptosis, treatment of cancer, stimulation of appetite, and/or stimulation of weight gain, etc. As described further below, the methods comprise administering to a subject in need thereof a pharmaceutically effective amount of a sirtuin-modulating compound.

In certain aspects, the sirtuin-modulating compounds may be administered alone or in combination with other compounds, including other sirtuin-modulating compounds, or other therapeutic agents.

DETAILED DESCRIPTION

1. Definitions

As used herein, the following terms and phrases shall have the meanings set forth below. Unless defined otherwise, all technical and scientific terms used herein have the same meaning as commonly understood to one of ordinary skill in the art.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues. The activity of such agents may render it suitable as a "therapeutic agent" which is a biologically, physiologically, or pharmacologically active substance (or substances) that acts locally or systemically in a subject.

The term "bioavailable" when referring to a compound is art-recognized and refers to a form of a compound that allows for it, or a portion of the amount of compound administered, to be absorbed by, incorporated into, or otherwise physiologically available to a subject or patient to whom it is administered.

"Biologically active portion of a sirtuin" refers to a portion of a sirtuin protein having a biological activity, such as the ability to deacetylate. Biologically active portions of a sirtuin may comprise the core domain of sirtuins. Biologically active portions of SIRT1 having GenBank Accession No. NP_036370 that encompass the NAD+ binding domain and the substrate binding domain, for example, may include without limitation, amino acids 62-293 of GenBank Accession No. NP_036370, which are encoded by nucleotides 237 to 932 of GenBank Accession No. NM_012238. Therefore, this region is sometimes referred to as the core domain. Other biologically active portions of SIRT1, also sometimes referred to as core domains, include about amino acids 261 to 447 of GenBank Accession No. NP_036370, which are encoded by nucleotides 834 to 1394 of GenBank Accession No. NM_012238; about amino acids 242 to 493 of GenBank Accession No. NP_036370, which are encoded by nucleotides 777 to 1532 of GenBank Accession No. NM_012238; or about amino acids 254 to 495 of GenBank Accession No. NP_036370, which are encoded by nucleotides 813 to 1538 of GenBank Accession No. NM_012238.

The term "companion animals" refers to cats and dogs. As used herein, the term "dog(s)" denotes any member of the species *Canis familiaris*, of which there are a large number of different breeds. The term "cat(s)" refers to a feline animal including domestic cats and other members of the family Felidae, genus *Felis*.

"Diabetes" refers to high blood sugar or ketoacidosis, as well as chronic, general metabolic abnormalities arising from a prolonged high blood sugar status or a decrease in glucose tolerance. "Diabetes" encompasses both the type I and type II (Non Insulin Dependent Diabetes Mellitus or NIDDM) forms of the disease. The risk factors for diabetes include the following factors: waistline of more than 40 inches for men or 35 inches for women, blood pressure of 130/85 mmHg or higher, triglycerides above 150 mg/dl, fasting blood glucose greater than 100 mg/dl or high-density lipoprotein of less than 40 mg/dl in men or 50 mg/dl in women.

The term "$ED_{50}$" refers to the art-recognized measure of effective dose. In certain embodiments, $ED_{50}$ means the dose of a drug which produces 50% of its maximum response or effect, or alternatively, the dose which produces a predetermined response in 50% of test subjects or preparations. The term "$LD_{50}$" refers to the art-recognized measure of lethal dose. In certain embodiments, $LD_{50}$ means the dose of a drug which is lethal in 50% of test subjects.

The term "therapeutic index" is an art-recognized term which refers to the therapeutic index of a drug, defined as $LD_{50}/ED_{50}$.

The term "hyperinsulinemia" refers to a state in an individual in which the level of insulin in the blood is higher than normal.

The term "insulin resistance" refers to a state in which a normal amount of insulin produces a subnormal biologic response relative to the biological response in a subject that does not have insulin resistance.

An "insulin resistance disorder," as discussed herein, refers to any disease or condition that is caused by or contributed to by insulin resistance. Examples include: diabetes, obesity, metabolic syndrome, insulin-resistance syndromes, syndrome X, insulin resistance, high blood pressure, hypertension, high blood cholesterol, dyslipidemia, hyperlipidemia, atherosclerotic disease including stroke, coronary artery disease or myocardial infarction, hyperglycemia, hyperinsulinemia and/or hyperproinsulinemia, impaired glucose tolerance, delayed insulin release, diabetic complications, including coronary heart disease, angina pectoris, congestive heart failure, stroke, cognitive functions in dementia, retinopathy, peripheral neuropathy, nephropathy, glomerulonephritis, glomerulosclerosis, nephrotic syndrome, hypertensive nephrosclerosis, some types of cancer (such as endometrial, breast, prostate, and colon), complications of pregnancy, poor female reproductive health (such as menstrual irregularities, infertility, irregular ovulation, polycystic ovarian syndrome (PCOS)), lipodystrophy, cholesterol related disorders, such as gallstones, cholecystitis and cholelithiasis, gout, obstructive sleep apnea and respiratory problems, osteoarthritis, and bone loss, e.g. osteoporosis in particular.

The term "livestock animals" refers to domesticated quadrupeds, which includes those being raised for meat and various byproducts, e.g., a bovine animal including cattle and other members of the genus *Bos*, a porcine animal including domestic swine and other members of the genus *Sus*, an ovine animal including sheep and other members of the genus *Ovis*, domestic goats and other members of the genus *Capra*; domesticated quadrupeds being raised for specialized tasks such as use as a beast of burden, e.g., an equine animal including domestic horses and other members of the family Equidae, genus *Equus*.

The term "mammal" is known in the art, and exemplary mammals include humans, primates, livestock animals (including bovines, porcines, etc.), companion animals (e.g., canines, felines, etc.) and rodents (e.g., mice and rats).

"Obese" individuals or individuals suffering from obesity are generally individuals having a body mass index (BMI) of at least 25 or greater. Obesity may or may not be associated with insulin resistance.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, and intrasternal injection and infusion.

A "patient", "subject", "individual" or "host" refers to either a human or a non-human animal.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prophylactic" or "therapeutic" treatment is art-recognized and refers to administration of a drug to a host. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "pyrogen-free", with reference to a composition, refers to a composition that does not contain a pyrogen in an amount that would lead to an adverse effect (e.g., irritation, fever, inflammation, diarrhea, respiratory distress, endotoxic shock, etc.) in a subject to which the composition has been administered. For example, the term is meant to encompass compositions that are free of, or substantially free of, an endotoxin such as, for example, a lipopolysaccharide (LPS).

"Replicative lifespan" of a cell refers to the number of daughter cells produced by an individual "mother cell." "Chronological aging" or "chronological lifespan," on the other hand, refers to the length of time a population of non-dividing cells remains viable when deprived of nutrients. "Increasing the lifespan of a cell" or "extending the lifespan of a cell," as applied to cells or organisms, refers to increasing the number of daughter cells produced by one cell; increasing the ability of cells or organisms to cope with stresses and combat damage, e.g., to DNA, proteins; and/or increasing the ability of cells or organisms to survive and exist in a living state for longer under a particular condition, e.g., stress (for example, heatshock, osmotic stress, high energy radiation, chemically-induced stress, DNA damage, inadequate salt level, inadequate nitrogen level, or inadequate nutrient level). Lifespan can be increased by at least about 10%, 20%, 30%, 40%, 50%, 60% or between 20% and 70%, 30% and 60%, 40% and 60% or more using methods described herein.

"Sirtuin-activating compound" refers to a compound that increases the level of a sirtuin protein and/or increases at least one activity of a sirtuin protein. In an exemplary embodiment, a sirtuin-activating compound may increase at least one biological activity of a sirtuin protein by at least about 10%, 25%, 50%, 75%, 100%, or more. Exemplary biological activities of sirtuin proteins include deacetylation, e.g., of histones and p53; extending lifespan; increasing genomic stability; silencing transcription; and controlling the segregation of oxidized proteins between mother and daughter cells.

"Sirtuin protein" refers to a member of the sirtuin deacetylase protein family, or preferably to the sir2 family, which include yeast Sir2 (GenBank Accession No. P53685), *C. elegans* Sir-2.1 (GenBank Accession No. NP_501912), and human SIRT1 (GenBank Accession No. NM_012238 and NP_036370 (or AF083106)) and SIRT2 (GenBank Accession No. NM_012237, NM_030593, NP_036369, NP_085096, and AF083107) proteins. Other family members include the four additional yeast Sir2-like genes termed "HST genes" (homologues of Sir two) HST1, HST2, HST3 and HST4, and the five other human homologues hSIRT3, hSIRT4, hSIRT5, hSIRT6 and hSIRT7 (Brachmann et al. (1995) Genes Dev. 9:2888 and Frye et al. (1999) BBRC 260:273). Preferred sirtuins are those that share more similarities with SIRT1, i.e., hSIRT1, and/or Sir2 than with SIRT2, such as those members having at least part of the N-terminal sequence present in SIRT1 and absent in SIRT2 such as SIRT3 has.

"SIRT1 protein" refers to a member of the sir2 family of sirtuin deacetylases. In one embodiment, a SIRT1 protein includes yeast Sir2 (GenBank Accession No. P53685), *C. elegans* Sir-2.1 (GenBank Accession No. NP_501912), human SIRT1 (GenBank Accession No. NM_012238 or NP_036370 (or AF083106)), and equivalents and fragments thereof. In another embodiment, a SIRT1 protein includes a polypeptide comprising a sequence consisting of, or consisting essentially of, the amino acid sequence set forth in GenBank Accession Nos. NP_036370, NP 501912, NP_085096, NP_036369, or P53685. SIRT1 proteins include polypeptides comprising all or a portion of the amino acid sequence set forth in GenBank Accession Nos. NP_036370, NP_501912, NP_085096, NP_036369, or P53685; the amino acid sequence set forth in GenBank Accession Nos. NP_036370, NP_501912, NP_085096, NP_036369, or P53685 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to GenBank Accession Nos. NP_036370, NP_501912, NP_085096, NP_036369, or P53685, and functional fragments thereof. Polypeptides of the invention also include homologs (e.g., orthologs and paralogs), variants, or fragments, of GenBank Accession Nos. NP_036370, NP_501912, NP_085096, NP_036369, or P53685.

As used herein "SIRT2 protein", "SIRT3 protein", "SIRT4 protein", SIRT5 protein", "SIRT6 protein", and "SIRT7 protein" refer to other mammalian, e.g. human, sirtuin deacetylase proteins that are homologous to SIRT1 protein, particularly in the approximately 275 amino acid conserved catalytic domain. For example, "SIRT3 protein" refers to a member of the sirtuin deacetylase protein family that is homologous to SIRT1 protein. In one embodiment, a SIRT3 protein includes human SIRT3 (GenBank Accession No. AAH01042, NP_036371, or NP_001017524) and mouse SIRT3 (GenBank Accession No. NP_071878) proteins, and equivalents and fragments thereof. In another embodiment, a SIRT3 protein includes a polypeptide comprising a sequence consisting of, or consisting essentially of, the amino acid sequence set forth in GenBank Accession Nos. AAH01042, NP_036371, NP_001017524, or NP_071878. SIRT3 proteins include polypeptides comprising all or a portion of the amino acid sequence set forth in GenBank Accession AAH01042, NP_036371, NP_001017524, or NP_071878; the amino acid sequence set forth in GenBank Accession Nos. AAH01042, NP_036371, NP_001017524, or NP_071878 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to GenBank Accession Nos. AAH01042, NP_036371, NP_001017524, or NP_071878, and functional fragments thereof. Polypeptides of the invention also include homologs (e.g., orthologs and paralogs), variants, or fragments, of GenBank Accession Nos. AAH01042, NP_036371, NP_001017524, or NP_071878. In one embodiment, a SIRT3 protein includes a fragment of SIRT3 protein that is produced by cleavage with a mitochondrial matrix processing peptidase (MPP) and/or a mitochondrial intermediate peptidase (MIP).

The terms "systemic administration," "administered systemically," "peripheral administration" and "administered peripherally" are art-recognized and refer to the administration of a subject composition, therapeutic or other material other than directly into the central nervous system, such that it enters the patient's system and, thus, is subject to metabolism and other like processes.

The term "tautomer" as used herein is art-regcognized and refers to the formal migration of a hydrogen atom, i.e., proton, accompanied by a switch of a single bond and adjacent double bond. When used herein to describe a compound or genus of compounds, tautomer includes any portion of a compound or the entire compound such as a single substituent of a compound, multiple substitutents of a compound or, for example, the entire compound. For example, the tautomer of a compound that includes a hydroxyl-substituted pyridine ring (A) is the keto-enol substituted ring (B):

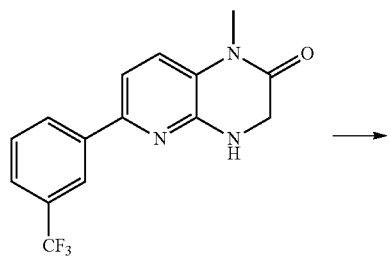

101

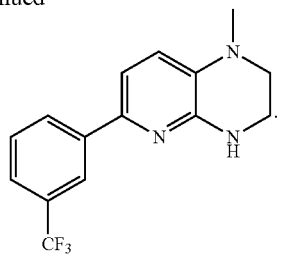

102

The term "therapeutic agent" is art-recognized and refers to any chemical moiety that is a biologically, physiologically, or pharmacologically active substance that acts locally or systemically in a subject. The term also means any substance intended for use in the diagnosis, cure, mitigation, treatment or prevention of disease or in the enhancement of desirable physical or mental development and/or conditions in an animal or human.

The term "therapeutic effect" is art-recognized and refers to a local or systemic effect in animals, particularly mammals, and more particularly humans caused by a pharmacologically active substance. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions described herein may be administered in a sufficient amount to produce a desired effect at a reasonable benefit/risk ratio applicable to such treatment.

"Treating" a condition or disease refers to curing as well as ameliorating at least one symptom of the condition or disease.

The term "vision impairment" refers to diminished vision, which is often only partially reversible or irreversible upon treatment (e.g., surgery). Particularly severe vision impairment is termed "blindness" or "vision loss", which refers to a complete loss of vision, vision worse than 20/200 that cannot be improved with corrective lenses, or a visual field of less than 20 degrees diameter (10 degrees radius).

2. Sirtuin Modulators

In one aspect, the invention provides novel sirtuin-modulating compounds for treating and/or preventing a wide variety of diseases and disorders including, for example, diseases or disorders related to aging or stress, diabetes, obesity, neurodegenerative diseases, ocular diseases and disorders, cardiovascular disease, blood clotting disorders, inflammation, cancer, and/or flushing, etc. Sirtuin-modulating compounds that increase the level and/or activity of a sirtuin protein may also be used for treating a disease or disorder in a subject that would benefit from increased mitochondrial activity, for enhancing muscle performance, for increasing muscle ATP levels, or for treating or preventing muscle tissue damage associated with hypoxia or ischemia. Other compounds disclosed herein may be suitable for use in a pharmaceutical composition and/or one or more methods disclosed herein.

In one embodiment, the invention provides a compound of Structural Formula (I):

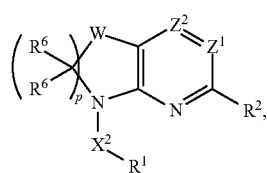

a tautomer, or a salt thereof, wherein:
each of $Z^1$ and $Z^2$ is independently selected from N and CR, wherein:
at least one of $Z^1$ and $Z^2$ is CR; and
each R is independently selected from hydrogen, halo, —OH, —C≡N, fluoro-substituted $C_1$-$C_2$ alkyl, —O—($C_1$-$C_2$) fluoro-substituted alkyl, —S—($C_1$-$C_2$) fluoro-substituted alkyl, $C_1$-$C_4$ alkyl, —O—($C_1$-$C_4$) alkyl, —S—($C_1$-$C_4$) alkyl; $C_3$-$C_7$ cycloalkyl, —($C_1$-$C_2$) alkyl-N($R^3$)($R^3$), —O—CH$_2$CH(OH)CH$_2$OH, —O—($C_1$-$C_3$) alkyl-N($R^3$)($R^3$), and —N($R^3$)($R^3$);
W is selected from —O—, —NH—, —N($C_1$-$C_4$ alkyl)-, —S—, —S(O)—, —S(O)$_2$— and —C($R^6$)($R^6$)—,
each $R^6$ is independently selected from hydrogen, $C_1$-$C_4$ alkyl and fluoro-substituted $C_1$-$C_4$ alkyl, or two $R^6$ bound to the same carbon atom are taken together to form =O,
$R^1$ is selected from a carbocycle and a heterocycle, wherein $R^1$ is optionally substituted with one or more substituents independently selected from halo, —C≡N, $C_1$-$C_4$ alkyl, =O, $C_3$-$C_7$ cycloalkyl, fluoro-substituted $C_1$-$C_2$ alkyl, —O—$R^3$, —S—$R^3$, —($C_1$-$C_4$ alkyl)-N($R^3$)($R^3$), —N($R^3$)($R^3$), —O—($C_1$-$C_4$ alkyl)-N($R^3$)($R^3$), —($C_1$-$C_4$ alkyl)-O—($C_1$-$C_4$ alkyl)-N($R^3$)($R^3$), —C(O)—N($R^3$)($R^3$), and —($C_1$-$C_4$ alkyl)-C(O)—N($R^3$)($R^3$), and when $R^1$ is phenyl, $R^1$ is also optionally substituted with —O-(saturated heterocycle), —O-(fluoro-substituted saturated heterocycle), $C_1$-$C_4$ alkyl-substituted saturated heterocycle, 3,4-methylenedioxy, fluoro-substituted 3,4-methylenedioxy, 3,4-ethylenedioxy, or fluoro-substituted 3,4-ethylenedioxy,
$R^2$ is selected from a carbocycle and a heterocycle, wherein $R^2$ is optionally substituted with one or more substituents independently selected from halo, —C≡N, $C_1$-$C_4$ alkyl, $C_3$-$C_7$ cycloalkyl, $C_1$-$C_2$ fluoro-substituted alkyl, —O—$R^3$, —S—$R^3$, —SO$_2$—$R^3$, =O, —($C_1$-$C_4$ alkyl)-N($R^3$)($R^3$), —N($R^3$)($R^3$), —O—($C_1$-$C_4$ alkyl)-N($R^3$)($R^3$), —($C_1$-$C_4$ alkyl)-O—($C_1$-$C_4$ alkyl)-N($R^3$)($R^3$), —C(O)—N($R^3$)($R^3$), —($C_1$-$C_4$ alkyl)-C(O)—N($R^3$)($R^3$), —O-phenyl, phenyl, and a second heterocycle, and when $R^2$ is phenyl, $R^2$ is also optionally substituted with —O-(saturated heterocycle), 3,4-methylenedioxy, fluoro-substituted 3,4-methylenedioxy, 3,4-ethylenedioxy, or fluoro-substituted 3,4-ethylenedioxy, wherein any phenyl, saturated heterocycle, or second heterocycle substituent of $R^2$ is optionally substituted with halo, —C≡N, $C_1$-$C_4$ alkyl, fluoro-substituted $C_1$-$C_2$ alkyl, —O—($C_1$-$C_2$) fluoro-substituted alkyl, —O—($C_1$-$C_4$) alkyl, —S—($C_1$-$C_4$) alkyl, —S—($C_1$-$C_2$) fluoro-substituted alkyl, —NH—($C_1$-$C_4$) alkyl, and —N—($C_1$-$C_4$)$_2$ alkyl;
each $R^3$ is independently selected from hydrogen and —$C_1$-$C_4$ alkyl; or
two $R^3$ are taken together with the nitrogen atom to which they are bound to form a 4- to 8-membered saturated heterocycle optionally comprising one additional heteroatom selected from N, S, S(=O), S(=O)$_2$, and O, wherein:

when $R^3$ is alkyl, the alkyl is optionally substituted with one or more substituents selected from —OH, fluoro, —NH$_2$, —NH($C_1$-$C_4$ alkyl), —N($C_1$-$C_4$ alkyl)$_2$, —NH(CH$_2$CH$_2$OCH$_3$), or —N(CH$_2$CH$_2$OCH$_3$)$_2$ and when two $R^3$ are taken together with the nitrogen atom to which they are bound to form a 4- to 8-membered saturated heterocycle, the saturated heterocycle is optionally substituted at any carbon atom with —OH, —$C_1$-$C_4$ alkyl, fluoro, —NH$_2$, —NH($C_1$-$C_4$ alkyl), —N($C_1$-$C_4$ alkyl)$_2$, —NH(CH$_2$CH$_2$OCH$_3$), or —N(CH$_2$CH$_2$OCH$_3$)$_2$; and optionally substituted at any substitutable nitrogen atom with hydrogen, —$C_1$-$C_4$ alkyl, fluoro-substituted $C_1$-$C_4$ alkyl, or —(CH$_2$)$_z$—O—CH$_3$;

p is 1, 2 or 3;

$X^2$ is selected from —C(=O)-†, —C(=O)—O†, —C(=O)—C$R^4R^5$-†, —S(=O)-†, —S(=O)$_2$-†, —S(=O)—C$R^4R^5$-†, —S(=O)$_2$—C$R^4R^5$-†, —C(=S)-†, —C(=S)—C$R^4R^5$-†, —C(=O)—NH-†, —C(=S) —NH-†, —S(=O)—NH-†, —S(=O)$_2$—NH-†, —C$R^4R^5$—NH-†, —C(=N$R^4$)—NH-†, —C(=O)—NH—C$R^4R^5$-†, —C$R^4R^5$—NH—C(O)-†, —C$R^4R^5$—C(=S)—NH-†, —C$R^4R^5$—S(O)—NH-†, —C$R^4R^5$—S(O)$_2$—NH-†, —C$R^4R^5$—O—C(=O)—NH-†, and —C$R^4R^5$—NH—C(=O)—O-†;

† represents where $X^2$ is bound to $R^1$; and each $R^4$ and $R^5$ is independently selected from hydrogen, $C_1$-$C_4$ alkyl, —CF$_3$ and ($C_1$-$C_3$ alkyl)-CF$_3$.

The compound of structural formula (I) may be represented by structural formula (II):

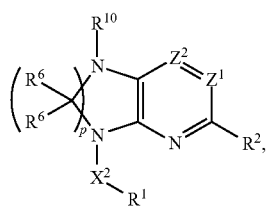

wherein $R^{10}$ is $C_1$-$C_4$ alkyl.

The compound of structural formula (I) may also be represented by structural formula (III):

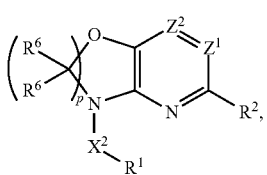

wherein $R^1$ is selected from a heterocycle and an aliphatic carbocycle.

In one embodiment, the invention provides a compound represented by structural formula (IV):

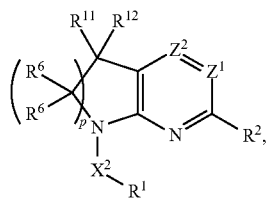

(IV)

a tautomer, or a salt thereof, wherein:
each of $Z^1$ and $Z^2$ is independently selected from N and CR, wherein:
at least one of $Z^1$ and $Z^2$ is CR; and
each R is independently selected from hydrogen, halo, —OH, —C≡N, fluoro-substituted $C_1$-$C_2$ alkyl, —O—($C_1$-$C_2$) fluoro-substituted alkyl, —S—($C_1$-$C_2$) fluoro-substituted alkyl, $C_1$-$C_4$ alkyl, —O—($C_1$-$C_4$) alkyl, —S—($C_1$-$C_4$) alkyl; $C_3$-$C_7$ cycloalkyl, —($C_1$-$C_2$) alkyl-N($R^3$)($R^3$), —O—$CH_2$CH(OH)$CH_2$OH, —O—($C_1$-$C_3$) alkyl-N($R^3$)($R^3$), and —N($R^3$)($R^3$);
$R^{11}$ is selected from halogen and $R^{12}$ is selected from hydrogen, halogen, $C_1$-$C_4$ alkyl and fluoro-substituted $C_1$-$C_4$ alkyl,
each $R^6$ is independently selected from hydrogen, $C_1$-$C_4$ alkyl and fluoro-substituted $C_1$-$C_4$ alkyl, or two $R^6$ bound to the same carbon atom are taken together to form =O,
$R^1$ is selected from a carbocycle and a heterocycle, wherein $R^1$ is optionally substituted with one or more substituents independently selected from halo, —C≡N, $C_1$-$C_4$ alkyl, =O, $C_3$-$C_7$ cycloalkyl, fluoro-substituted $C_1$-$C_2$ alkyl, —O—$R^3$, —S—$R^3$, —($C_1$-$C_4$ alkyl)-N($R^3$)($R^3$), —N($R^3$)($R^3$), —O—($C_1$-$C_4$ alkyl)-N($R^3$)($R^3$), —($C_1$-$C_4$ alkyl)-O—($C_1$-$C_4$ alkyl)-N($R^3$)($R^3$), —C(O)—N($R^3$)($R^3$), and —($C_1$-$C_4$ alkyl)-C(O)—N($R^3$)($R^3$), and when $R^1$ is phenyl, $R^1$ is also optionally substituted with —O-(saturated heterocycle), —O-(fluoro-substituted saturated heterocycle), $C_1$-$C_4$ alkyl-substituted saturated heterocycle, 3,4-methylenedioxy, fluoro-substituted 3,4-methylenedioxy, 3,4-ethylenedioxy, or fluoro-substituted 3,4-ethylenedioxy;
$R^2$ is selected from a carbocycle and a heterocycle, wherein $R^2$ is optionally substituted with one or more substituents independently selected from halo, —C≡N, $C_1$-$C_4$ alkyl, $C_3$-$C_7$ cycloalkyl, $C_1$-$C_2$ fluoro-substituted alkyl, —O—$R^3$, —S—$R^3$, —$SO_2$—$R^3$, =O, —($C_1$-$C_4$ alkyl)-N($R^3$)($R^3$), —N($R^3$)($R^3$), —O—($C_1$-$C_4$ alkyl)-N($R^3$)($R^3$), —($C_1$-$C_4$ alkyl)-O—($C_1$-$C_4$ alkyl)-N($R^3$)($R^3$), —C(O)—N($R^3$)($R^3$), —($C_1$-$C_4$ alkyl)-C(O)—N($R^3$)($R^3$), —O-phenyl, phenyl, and a second heterocycle, and when $R^2$ is phenyl, $R^2$ is also optionally substituted with —O-(saturated heterocycle), 3,4-methylenedioxy, fluoro-substituted 3,4-methylenedioxy, 3,4-ethylenedioxy, or fluoro-substituted 3,4-ethylenedioxy, wherein any phenyl, saturated heterocycle, or second heterocycle substituent of $R^2$ is optionally substituted with halo, —C≡N, $C_1$-$C_4$ alkyl, fluoro-substituted $C_1$-$C_2$ alkyl, —O—($C_1$-$C_2$) fluoro-substituted alkyl, —O—($C_1$-$C_4$) alkyl, —S—($C_1$-$C_4$) alkyl, —S—($C_1$-$C_2$) fluoro-substituted alkyl, —NH—($C_1$-$C_4$) alkyl, and —N—($C_1$-$C_4$)$_2$ alkyl;
each $R^3$ is independently selected from hydrogen and —$C_1$-$C_4$ alkyl; or
two $R^3$ are taken together with the nitrogen atom to which they are bound to form a 4- to 8-membered saturated heterocycle optionally comprising one additional heteroatom selected from N, S, S(=O), S(=O)$_2$, and O, wherein:
when $R^3$ is alkyl, the alkyl is optionally substituted with one or more substituents selected from —OH, fluoro, —$NH_2$, —NH($C_1$-$C_4$ alkyl), —N($C_1$-$C_4$ alkyl)$_2$, —NH($CH_2CH_2OCH_3$), and —N($CH_2CH_2OCH_3$)$_2$, and
when two $R^3$ are taken together with the nitrogen atom to which they are bound to form a 4- to 8-membered saturated heterocycle, the saturated heterocycle is optionally substituted at any carbon atom with —OH, —$C_1$-$C_4$ alkyl, fluoro, —$NH_2$, —NH($C_1$-$C_4$ alkyl), —N($C_1$-$C_4$ alkyl)$_2$, —NH($CH_2CH_2OCH_3$), or —N($CH_2CH_2OCH_3$)$_2$; and optionally substituted at any substitutable nitrogen atom with hydrogen, —$C_1$-$C_4$ alkyl, fluoro-substituted $C_1$-$C_4$ alkyl, or —($CH_2$)$_2$—O—$CH_3$;
p is 1, 2 or 3; and
$X^2$ is selected from —C(=O)-†, —C(=O)—O†, —C(=O)—$CR^4R^5$—R—, —S(=O)-†, —S(=O)$_2$-†, —S(=O)—$CR^4R^5$-†, —S(=O)$_2$—$CR^4R^5$-†, —C(=S)-†, —C(=S)—$CR^4R^5$-†, —C(=O)—NH-†, —C(=S)—NH-†, —S(=O)—NH-†, —S(=O)$_2$—NH-†, —$CR^4R^5$—NH-†, —C(=$NR^4$)—NH-†, —C(=O)—NH—$CR^4R^5$-†, —$CR^4$R—NH—C(O)-†, —$CR^4R^5$—C(=S)—NH-†, —$CR^4R^5$—S(O)—NH-†, —$CR^4R^5$—S(O)$_2$—NH-†, —$CR^4R^5$—O—C(=O)—NH-†, and —$CR^4R^5$—NH—C(=O)—O-†, wherein:
† represents where $X^2$ is bound to $R^1$; and
each $R^4$ and $R^5$ is independently selected from hydrogen, $C_1$-$C_4$ alkyl, —$CF_3$ and ($C_1$-$C_3$ alkyl)-$CF_3$.

A compound represented by structural formula (IV) may have $R^{11}$ and $R^{12}$ each selected from halogen. For example, each of $R^{11}$ and $R^{12}$ may be fluorine.

In another embodiment, the invention provides a compound represented by structural formula (V):

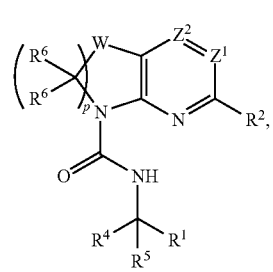

(V)

a tautomer, or a salt thereof, wherein:
each of $Z^1$ and $Z^2$ is independently selected from N and CR, wherein:
at least one of $Z^1$ and $Z^2$ is CR; and
each R is independently selected from hydrogen, halo, —OH, —C≡N, fluoro-substituted $C_1$-$C_2$ alkyl, —O—($C_1$-$C_2$) fluoro-substituted alkyl, —S—($C_1$-$C_2$) fluoro-substituted alkyl, $C_1$-$C_4$ alkyl, —O—($C_1$-$C_4$) alkyl, —S—($C_1$-$C_4$) alkyl; $C_3$-$C_7$ cycloalkyl, —($C_1$-$C_2$) alkyl-N($R^3$)($R^3$), —O—$CH_2$CH(OH)$CH_2$OH, —O—($C_1$-$C_3$) alkyl-N($R^3$)($R^3$), and —N($R^3$)($R^3$);
W is selected from —O—, —NH—, —N($C_1$-$C_4$ alkyl)-, —S—, —S(O)—, —S(O)$_2$— and —C($R^6$)($R^6$)—, and
each $R^6$ is independently selected from hydrogen, halogen, $C_1$-$C_4$ alkyl and fluoro-substituted $C_1$-$C_4$ alkyl, or two $R^6$ bound to the same carbon atom are taken together to form =O, $R^1$ is selected from a carbocycle and a heterocycle, wherein $R^1$ is optionally substituted with one or more substituents independently selected from halo, —C≡N, $C_1$-$C_4$ alkyl, =O, $C_3$-$C_7$ cycloalkyl, fluoro-substituted $C_1$-$C_2$ alkyl, —O—$R^3$, —S—$R^3$, —($C_1$-$C_4$ alkyl)-N($R^3$)($R^3$), —N($R^3$)($R^3$), —O—($C_1$-$C_4$ alkyl)-N($R^3$)($R^3$), —($C_1$-$C_4$ alkyl)-O—($C_1$-$C_4$ alkyl)-N($R^3$)($R^3$), —C(O)—N($R^3$)($R^3$), and —($C_1$-$C_4$ alkyl)-C(O)—N($R^3$)($R^3$), and when $R^1$ is phenyl, $R^1$ is also optionally substituted with —O-(saturated heterocycle), —O-(fluoro-substituted saturated heterocycle), $C_1$-$C_4$ alkyl-substituted saturated heterocycle, 3,4-methylenedioxy, fluoro-substituted 3,4-methylenedioxy, 3,4-ethylenedioxy, or fluoro-substituted 3,4-ethylenedioxy;

$R^2$ is selected from a carbocycle and a heterocycle, wherein $R^2$ is optionally substituted with one or more substituents independently selected from halo, —C≡N, $C_1$-$C_4$ alkyl, $C_3$-$C_7$ cycloalkyl, $C_1$-$C_2$ fluoro-substituted alkyl, —O—$R^3$, —S—$R^3$, —$SO_2$—$R^3$, =O, —($C_1$-$C_4$ alkyl)-N($R^3$)($R^3$), —N($R^3$)($R^3$), —O—($C_1$-$C_4$ alkyl)-N($R^3$)($R^3$), —($C_1$-$C_4$ alkyl)-O—($C_1$-$C_4$ alkyl)-N($R^3$)($R^3$), —C(O)—N($R^3$)($R^3$), —($C_1$-$C_4$ alkyl)-C(O)—N($R^3$)($R^3$), —O-phenyl, phenyl, and a second heterocycle, and when $R^2$ is phenyl, $R^2$ is also optionally substituted with —O-(saturated heterocycle), 3,4-methylenedioxy, fluoro-substituted 3,4-methylenedioxy, 3,4-ethylenedioxy, or fluoro-substituted 3,4-ethylenedioxy, wherein any phenyl, saturated heterocycle, or second heterocycle substituent of $R^2$ is optionally substituted with halo, —C≡N, $C_1$-$C_4$ alkyl, fluoro-substituted $C_1$-$C_2$ alkyl, —O—($C_1$-$C_2$) fluoro-substituted alkyl, —O—($C_1$-$C_4$) alkyl, —S—($C_1$-$C_4$) alkyl, —S—($C_1$-$C_2$) fluoro-substituted alkyl, —NH—($C_1$-$C_4$) alkyl, and —N—($C_1$-$C_4$)$_2$ alkyl;

each $R^3$ is independently selected from hydrogen and —$C_1$-$C_4$ alkyl; or two $R^3$ are taken together with the nitrogen atom to which they are bound to form a 4- to 8-membered saturated heterocycle optionally comprising one additional heteroatom selected from N, S, S(=O), S(=O)$_2$, and O, wherein:

when $R^3$ is alkyl, the alkyl is optionally substituted with one or more substituents selected from —OH, fluoro, —$NH_2$, —NH($C_1$-$C_4$ alkyl), —N($C_1$-$C_4$ alkyl)$_2$, —NH($CH_2CH_2OCH_3$), and —N($CH_2CH_2OCH_3$)$_2$, and when two $R^3$ are taken together with the nitrogen atom to which they are bound to form a 4- to 8-membered saturated heterocycle, the saturated heterocycle is optionally substituted at any carbon atom with —OH, —$C_1$-$C_4$ alkyl, fluoro, —$NH_2$, —NH($C_1$-$C_4$ alkyl), —N($C_1$-$C_4$ alkyl)$_2$, —NH($CH_2CH_2OCH_3$), or —N($CH_2CH_2OCH_3$)$_2$; and optionally substituted at any substitutable nitrogen atom with hydrogen, —$C_1$-$C_4$ alkyl, fluoro-substituted $C_1$-$C_4$ alkyl, or —($CH_2$)$_2$—O—$CH_3$;

p is 1, 2 or 3; and $R^4$ and $R^5$ taken together form a 3- to 6-membered saturated carbocycle or heterocycle.

For a compound represented by structural formula (V), $R^4$ and $R^5$ may be taken together may form a carbocycle. For example, $R^4$ and $R^5$ taken together may form a cyclopropyl ring.

In yet another embodiment, the invention provides a compound represented by structural formula (VI):

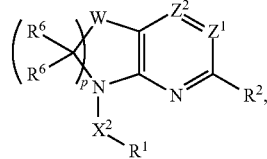

(VI)

a tautomer, or a salt thereof, wherein:

each of $Z^1$ and $Z^2$ is independently selected from N and CR, wherein:
  at least one of $Z^1$ and $Z^2$ is CR; and
  each R is independently selected from hydrogen, halo, —OH, —C≡N, fluoro-substituted $C_1$-$C_2$ alkyl, —O—($C_1$-$C_2$) fluoro-substituted alkyl, —S—($C_1$-$C_2$) fluoro-substituted alkyl, $C_1$-$C_4$ alkyl, —O—($C_1$-$C_4$) alkyl, —S—($C_1$-$C_4$) alkyl; $C_3$-$C_7$ cycloalkyl, —($C_1$-$C_2$) alkyl-N($R^3$)($R^3$), —O—$CH_2CH(OH)CH_2OH$, —O—($C_1$-$C_3$) alkyl-N($R^3$)($R^3$), and —N($R^3$)($R^3$);

W is selected from —O—, —NH—, —N($C_1$-$C_4$ alkyl)-, —S—, —S(O)—, —S(O)$_2$— and —C($R^6$)($R^6$)—, and each $R^6$ is independently selected from hydrogen, halogen, $C_1$-$C_4$ alkyl and fluoro-substituted $C_1$-$C_4$ alkyl, or two $R^6$ bound to the same carbon atom are taken together to form =O, $R^1$ is selected from a carbocycle and a heterocycle, wherein $R^1$ is substituted with a spiro bicycle and $R^1$ is optionally further substituted with one or more substituents independently selected from halo, —C≡N, $C_1$-$C_4$ alkyl, =O, $C_3$-$C_7$ cycloalkyl, fluoro-substituted $C_1$-$C_2$ alkyl, —O—$R^3$, —S—$R^3$, —($C_1$-$C_4$ alkyl)-N($R^3$)($R^3$), —N($R^3$)($R^3$), —O—($C_1$-$C_4$ alkyl)-N($R^3$)($R^3$), —($C_1$-$C_4$ alkyl)-O—($C_1$-$C_4$ alkyl)-N($R^3$)($R^3$), —C(O)—N($R^3$)($R^3$), and —($C_1$-$C_4$ alkyl)-C(O)—N($R^3$)($R^3$), and when $R^1$ is phenyl, $R^1$ is also optionally further substituted with —O-(saturated heterocycle), —O-(fluoro-substituted saturated heterocycle), $C_1$-$C_4$ alkyl-substituted saturated heterocycle, 3,4-methylenedioxy, fluoro-substituted 3,4-methylenedioxy, 3,4-ethylenedioxy, or fluoro-substituted 3,4-ethylenedioxy;

$R^2$ is selected from a carbocycle and a heterocycle, wherein $R^2$ is optionally substituted with one or more substituents independently selected from halo, —C≡N, $C_1$-$C_4$ alkyl, $C_3$-$C_7$ cycloalkyl, $C_1$-$C_2$ fluoro-substituted alkyl, —O—$R^3$, —S—$R^3$, —$SO_2$—$R^3$, =O, —($C_1$-$C_4$ alkyl)-N($R^3$)($R^3$), —N($R^3$)($R^3$), —O—($C_1$-$C_4$ alkyl)-N($R^3$)($R^3$), —($C_1$-$C_4$ alkyl)-O—($C_1$-$C_4$ alkyl)-N($R^3$)($R^3$), —C(O)—N($R^3$)($R^3$), —($C_1$-$C_4$ alkyl)-C(O)—N($R^3$)($R^3$), —O-phenyl, phenyl, and a second heterocycle, and when $R^2$ is phenyl, $R^2$ is also optionally substituted with —O-(saturated heterocycle), 3,4-methylenedioxy, fluoro-substituted 3,4-methylenedioxy, 3,4-ethylenedioxy, or fluoro-substituted 3,4-ethylenedioxy, wherein any phenyl, saturated heterocycle, or second heterocycle substituent of $R^2$ is optionally substituted with halo, —C≡N, $C_1$-$C_4$ alkyl, fluoro-substituted $C_1$-$C_2$ alkyl, —O—($C_1$-$C_2$) fluoro-substituted alkyl, —O—($C_1$-$C_4$) alkyl, —S—($C_1$-$C_4$) alkyl, —S—($C_1$-$C_2$) fluoro-substituted alkyl, —NH—($C_1$-$C_4$) alkyl, and —N—($C_1$-$C_4$)$_2$ alkyl;

each $R^3$ is independently selected from hydrogen and —$C_1$-$C_4$ alkyl; or two $R^3$ are taken together with the nitrogen atom to which they are bound to form a 4- to 8-membered saturated heterocycle optionally comprising one additional heteroatom selected from N, S, S(=O), S(=O)$_2$, and O, wherein:

when R³ is alkyl, the alkyl is optionally substituted with one or more substituents selected from —OH, fluoro, —NH₂, —NH(C₁-C₄ alkyl), —N(C₁-C₄ alkyl)₂, —NH(CH₂CH₂OCH₃), and —N(CH₂CH₂OCH₃)₂, and when two R³ are taken together with the nitrogen atom to which they are bound to form a 4- to 8-membered saturated heterocycle, the saturated heterocycle is optionally substituted at any carbon atom with —OH, —C₁-C₄ alkyl, fluoro, —NH₂, —NH(C₁-C₄ alkyl), —N(C₁-C₄ alkyl)₂, —NH(CH₂CH₂OCH₃), or —N(CH₂CH₂OCH₃)₂; and optionally substituted at any substitutable nitrogen atom with hydrogen, —C₁-C₄ alkyl, fluoro-substituted C₁-C₄ alkyl, or —(CH₂)₂—O—CH₃;

p is 1, 2 or 3; and

X² is selected from —C(=O)-†, —C(=O)—O†, —C(=O)—CR⁴R⁵-†, —S(=O)-†, —S(=O)₂-†, —S(=O)—CR⁴R⁵-†, —S(=O)₂—CR⁴R⁵—, —C(=S)-†, —C(=S)—CR⁴R⁵-†, —C(=O)—NH-†, —C(=S)—NH-†, —S(=O)—NH-†, —S(=O)₂—NH-†, —CR⁴R⁵—NH-†, —C(=NR⁴)—NH-†, —C(=O)—NH—CR⁴R⁵-†, —CR⁴R⁵—NH—C(O)-†, —CR⁴R⁵—C(=S)—NH-†, —CR⁴R⁵—S(O)—NH-†, —CR⁴R⁵—S(O)₂—NH-†, —CR⁴R⁵—O—C(=O)—NH-†, and —CR⁴R⁵—NH—C(=O)—O-†, wherein:

† represents where X² is bound to R¹; and each R⁴ and R⁵ is independently selected from hydrogen, C₁-C₄ alkyl, —CF₃ and (C₁-C₃ alkyl)-CF₃ and when X² is —C(=O)—NH—CR⁴R⁵-†, R⁴ and R⁵ may also be taken together to form a 3- to 6-membered saturated carbocycle or heterocycle.

In certain embodiments, for a compound represented by structural formula (VI), when X² is —C(=O)—NH—CR⁴R⁵-†, R⁴ and R⁵ may be taken together to form a carbocycle. For example, R⁴ and R⁵ taken together may form a cyclopropyl ring.

For a compound represented by structural formula (VI), the spiro bicycle may be a 4-4 heterobicycle. In certain embodiments, the 4-4 heterobicycle is represented by the structure:

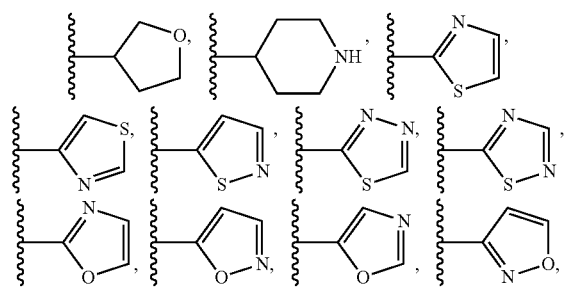

In certain embodiments, wherein R¹ is substituted with a spiro bicycle, R¹ is selected from

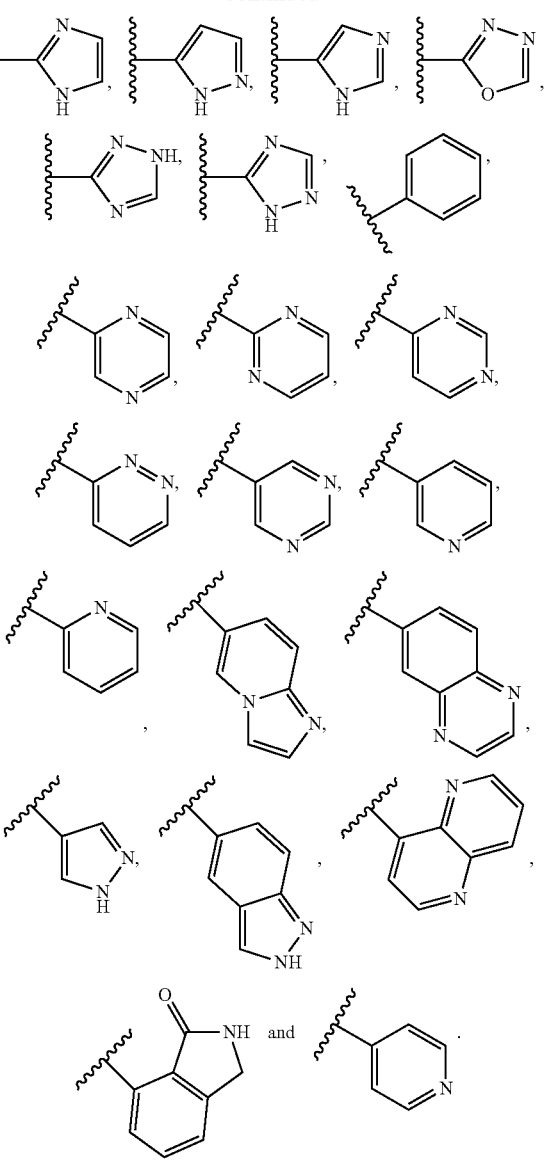

R¹ of a compound represented by structural formula (VI) may be a pyridyl. In certain embodiments, R¹ is

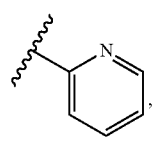

substituted with a spiro bicycle. In certain embodiments, R¹ is pyridyl substituted with one of:

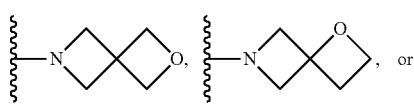

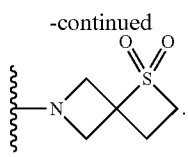

Each of the following embodiments, unless otherwise indicated or outside the scope of the structural formulae, may apply to any one of formulas (I), (II), (III), (IV), (V), or (VI). In those cases where the structure requires a particular substituent (e.g., the spiro bicycle on $R^1$ in formula (VI)), it should be understood that the groups below represent suitable moieties to which the particular substituent would be attached, and therefore retained in the compound as required by the formula.

In certain embodiments, W is —O—, —NH—, —N($C_1$-$C_4$ alkyl) or —C($R^6$)($R^6$)—. In certain embodiments, W is selected from —N($C_1$-$C_4$ alkyl)-, —S—, —S(O)—, —S(O)$_2$— and —C($R^6$)($R^6$)—.

In certain embodiments, $R^1$ is selected from a heterocycle and an an aliphatic carbocycle. In certain embodiments, $R^1$ is selected from aryl other than phenyl, e.g., naphthyl. In certain embodiments, $R^1$ is selected from a heterocycle, such as heteroaryl.

In certain embodiments, $Z^1$ and $Z^2$ are each CR, particularly CH.

In certain embodiments, $R^6$ is —H or —$CH_3$ or two $R^6$ taken together are =O. In particular embodiments, each $R^6$ is —H.

In particular embodiments, W, $Z^1$, $Z^2$ and $R^6$ are chosen such that the compound is selected from any one of the following Structural Formulae:

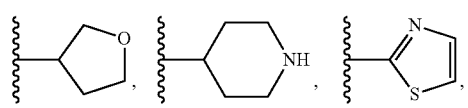

In certain embodiments, $R^1$ is selected from:

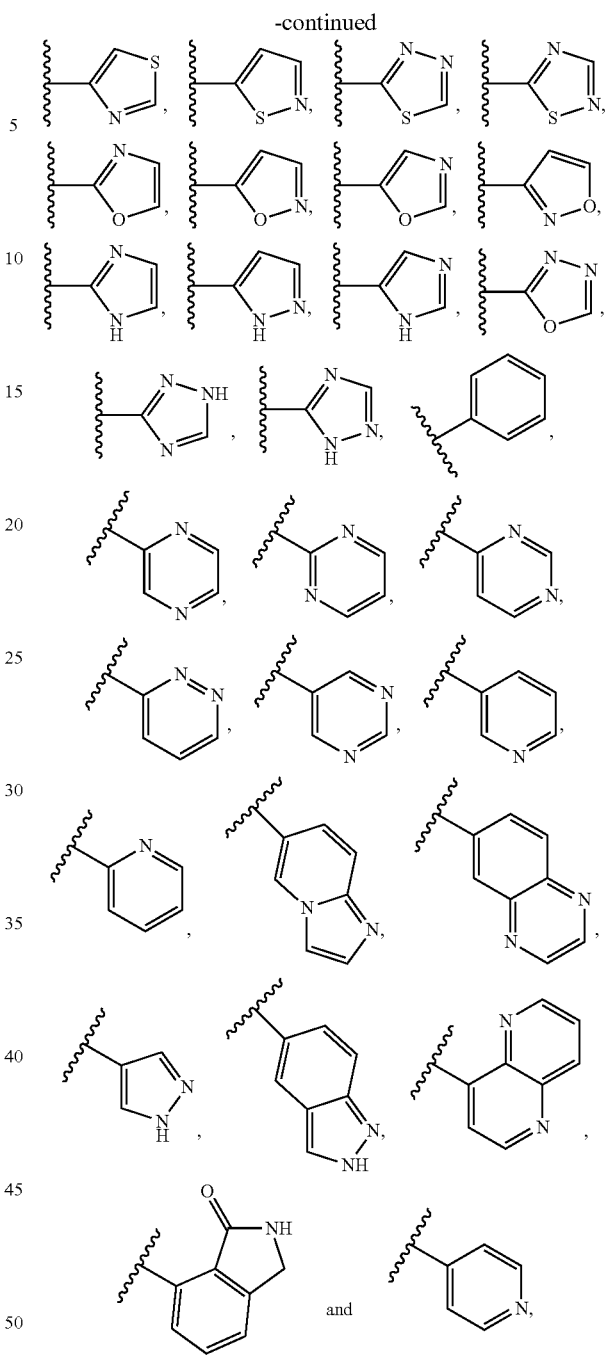

wherein $R^1$ is optionally substituted with one or more substituents independently selected from halo, $C_1$-$C_4$ alkyl, fluoro-substituted $C_1$-$C_2$ alkyl, —($C_1$-$C_4$ alkyl)-N($R^3$)($R^3$), —N($R^3$)($R^3$), —C(O)—N($R^3$)($R^3$), =O, and —O—$R^3$. In certain such embodiments, $R^1$ is substituted with one or more groups independently selected from —F, —Cl, —$CH_3$, —$OCH_3$,

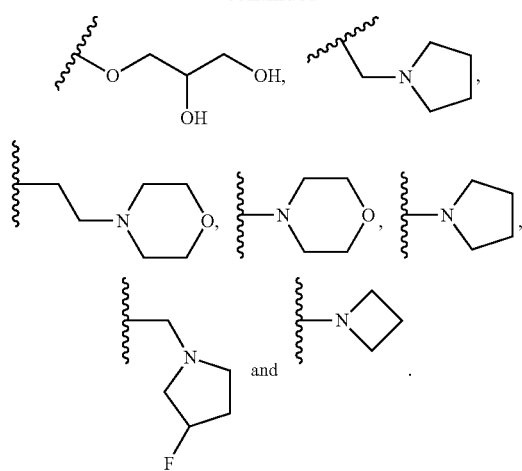
In particular embodiments of a compound of Structural Formula (I), $R^1$ is selected from:
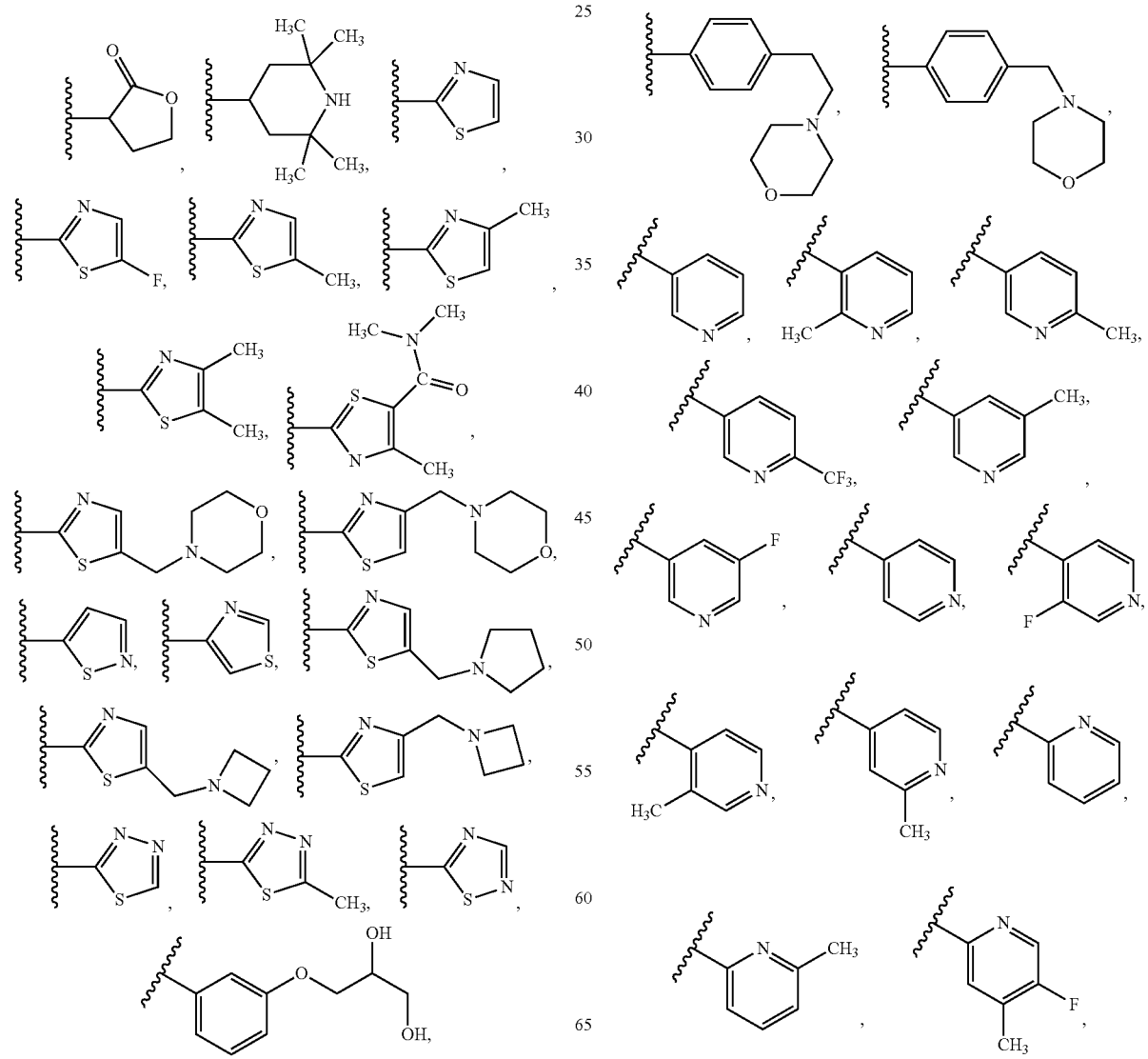
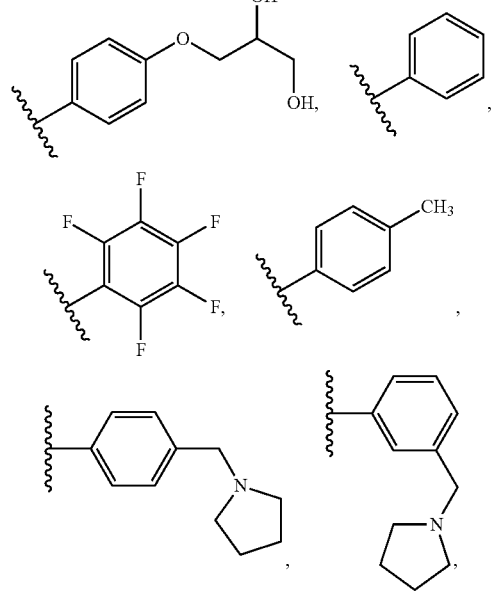

21
-continued
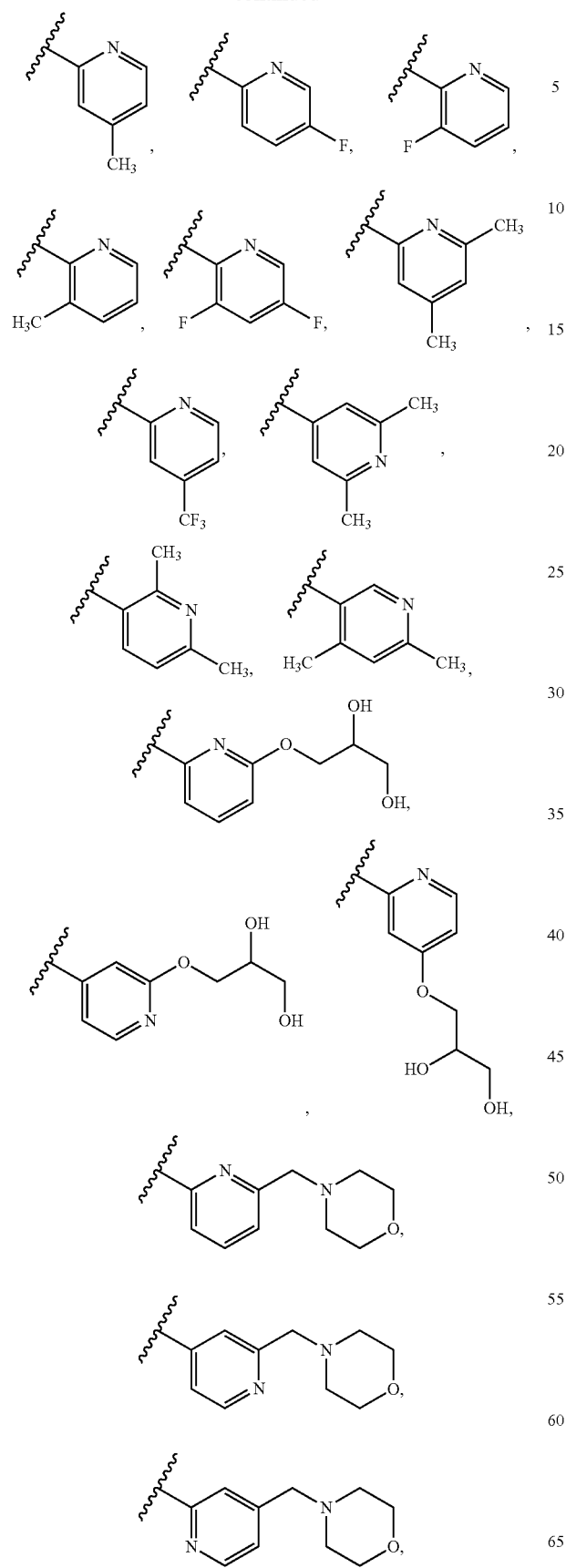
22
-continued
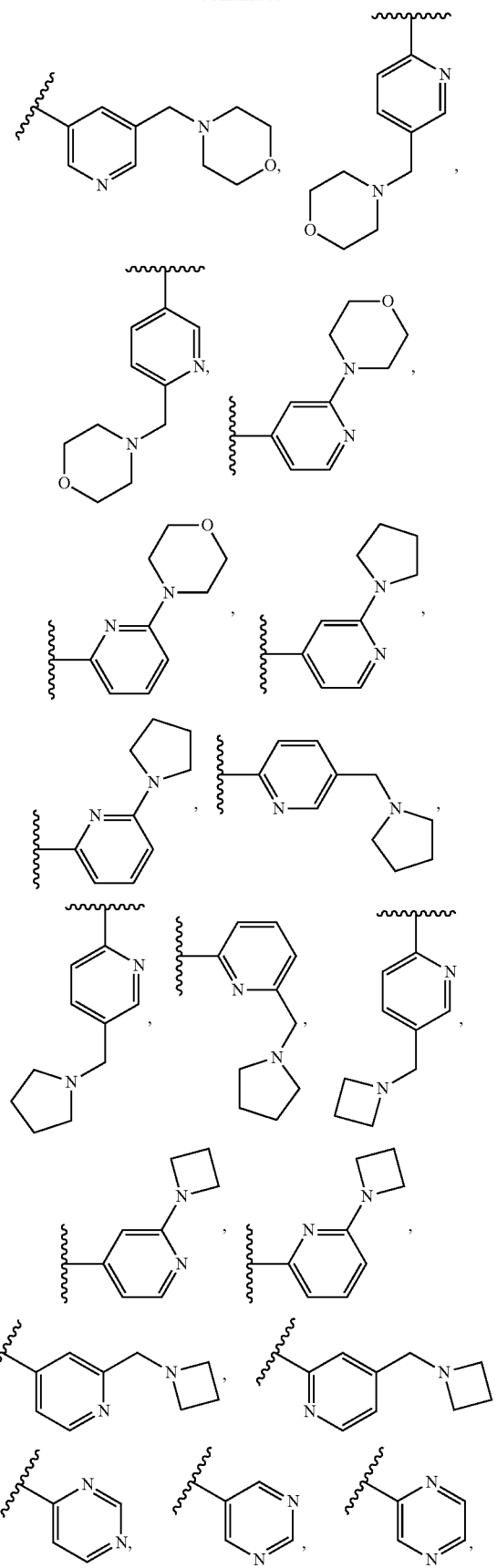

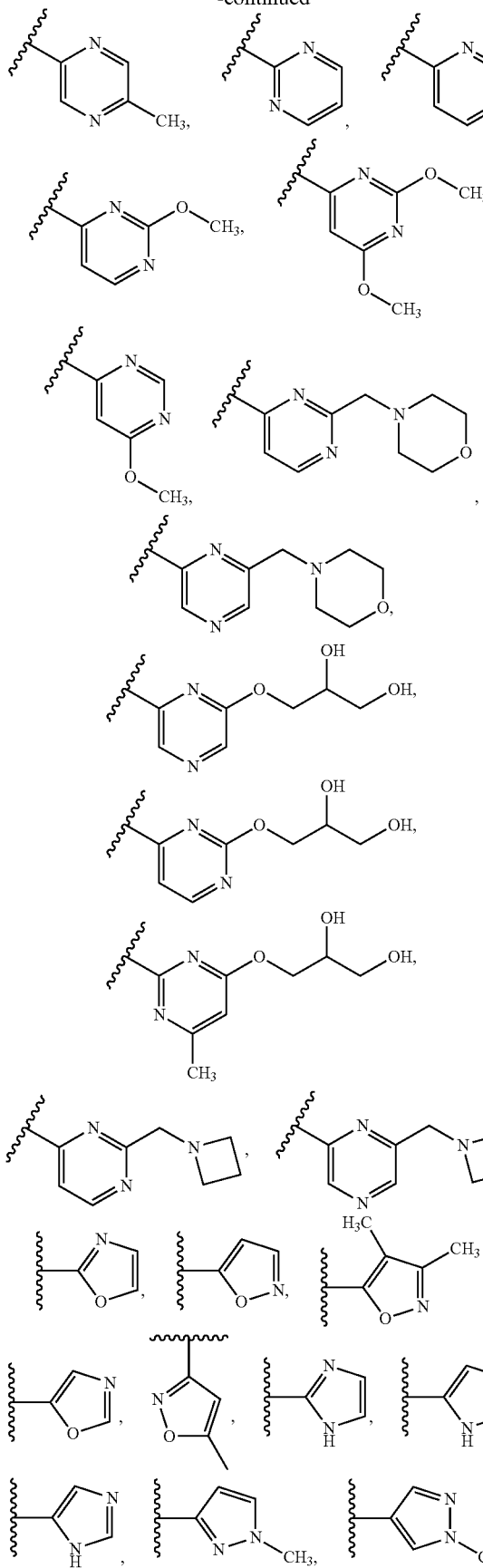
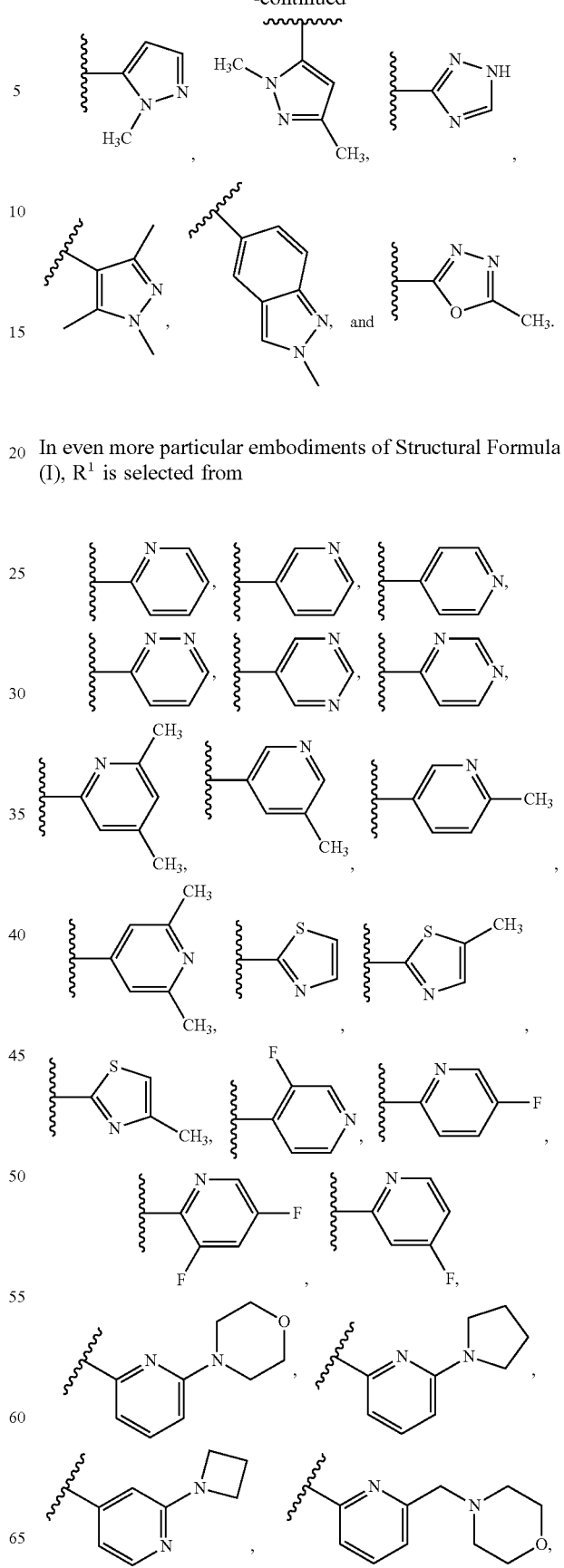
In even more particular embodiments of Structural Formula (I), R¹ is selected from -continued

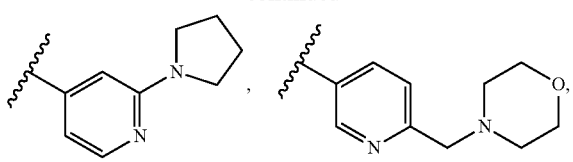

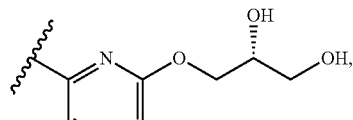

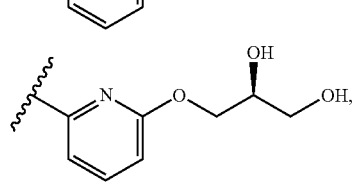

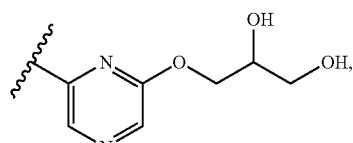

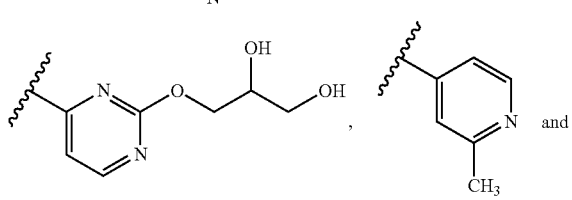

In certain embodiments of a compound of Structural Formula (I), R² is selected from:

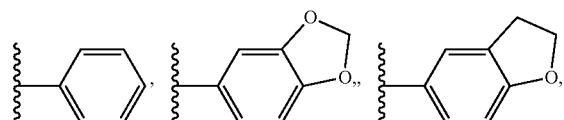

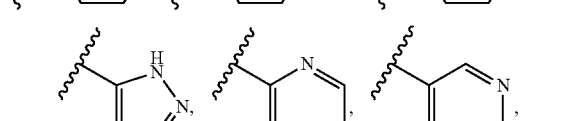

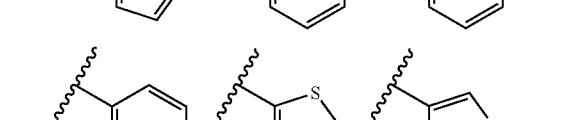

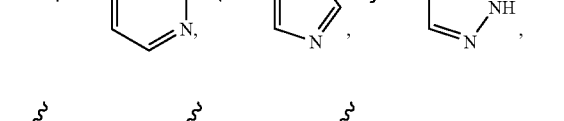

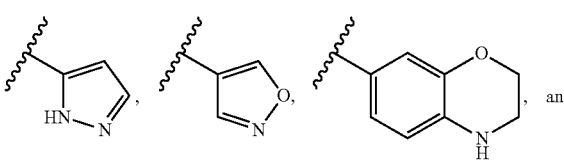

-continued

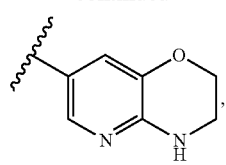

wherein R² is optionally substituted with one or more groups independently selected from halo, $C_1$-$C_4$ alkyl, —($C_1$-$C_4$ alkyl)-N(R³)(R³), $C_1$-$C_2$ fluoro-substituted alkyl, —O—R³, —SO₂—R³, —N(R³)(R³), and —O—($C_1$-$C_4$ alkyl)-N(R³)(R³). In certain such embodiments, R² is optionally substituted with one or more groups independently selected from =O, —F, —Cl, —CN, —CH₃, —OCH₃, —CF₂H, —N(CH₃)₂, —CH₂N(CH₃)₂,

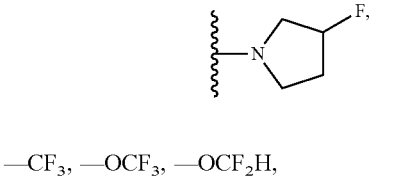

—CF₃, —OCF₃, —OCF₂H,

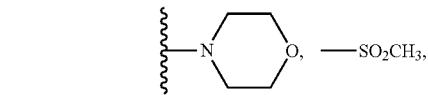

—SO₂CH₃,

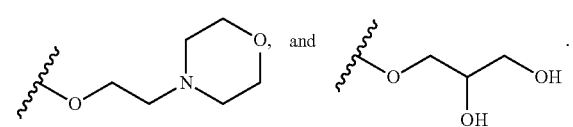

In particular embodiments, R² is selected from:

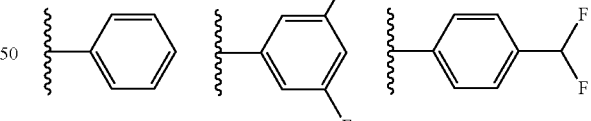

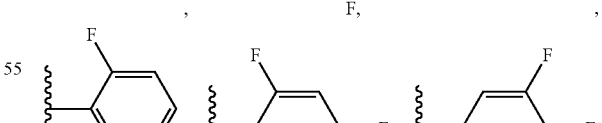

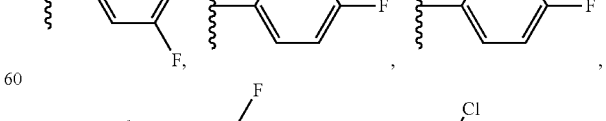

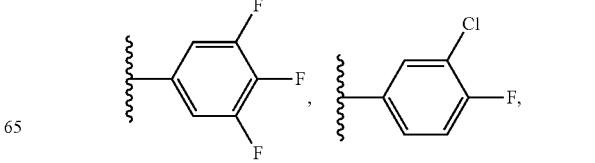

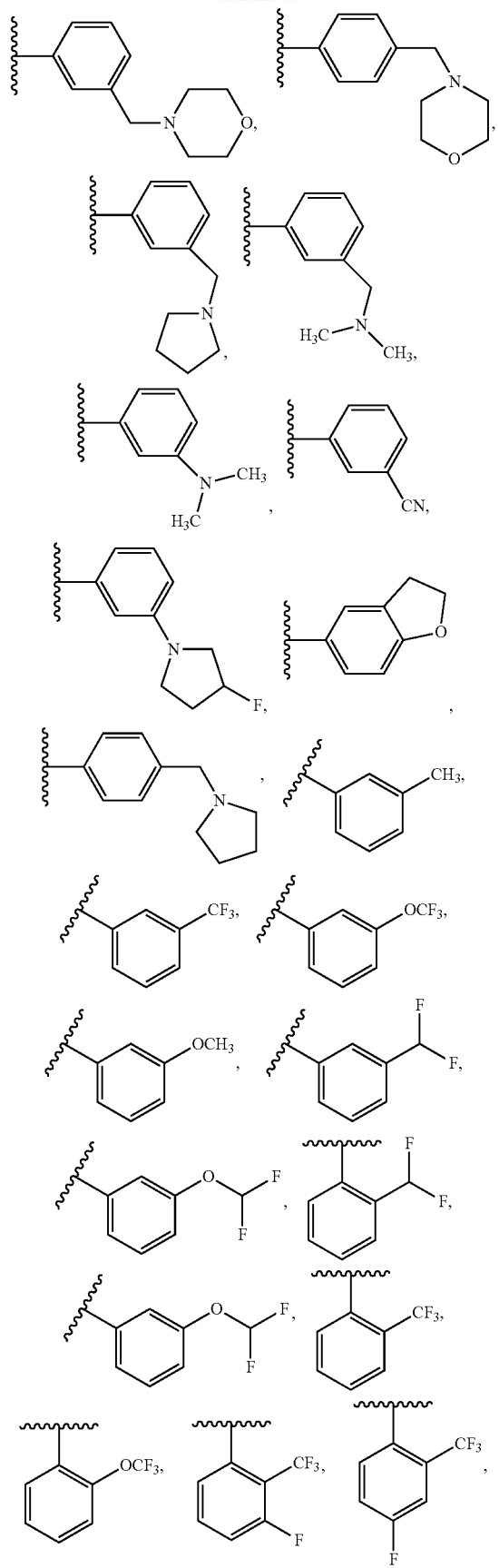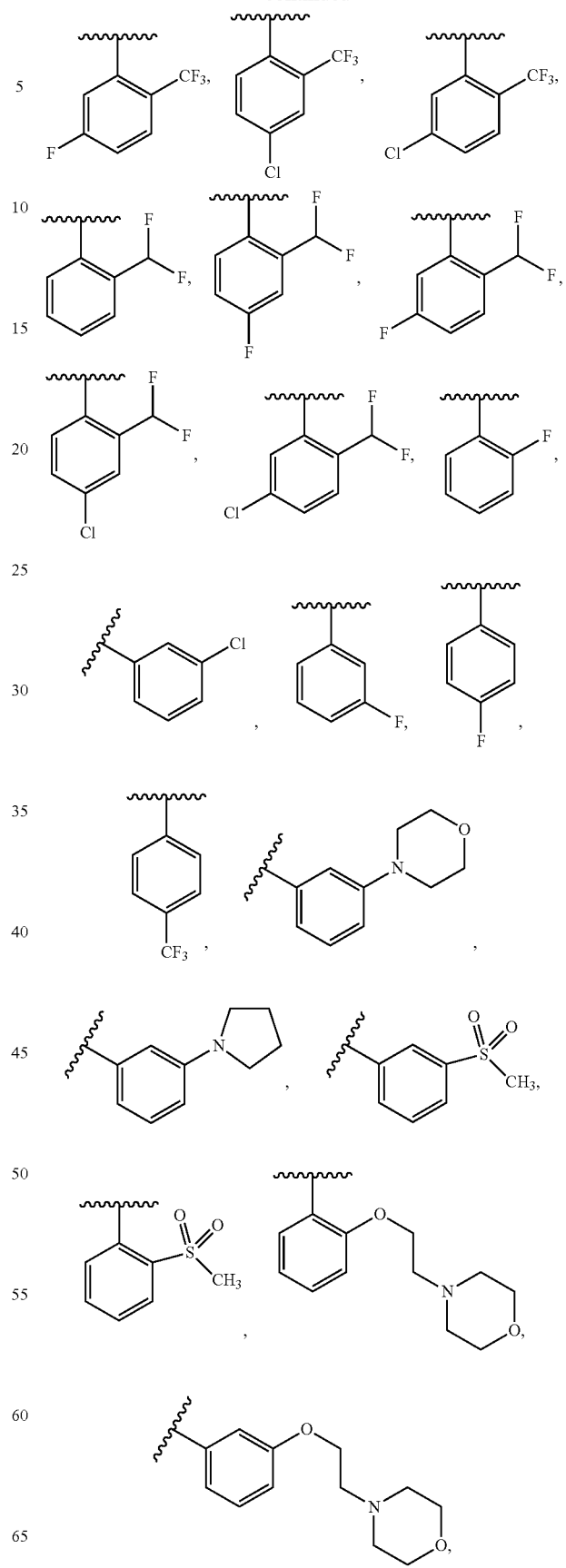

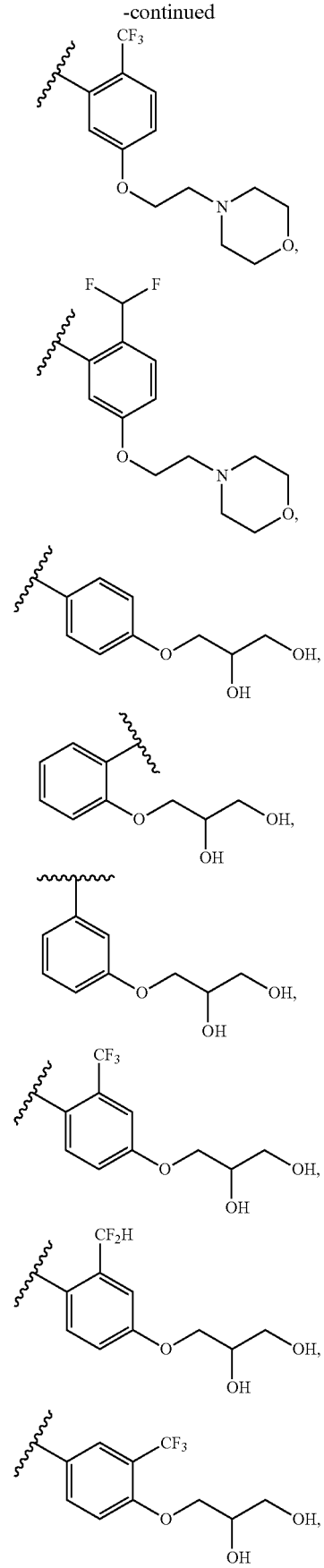
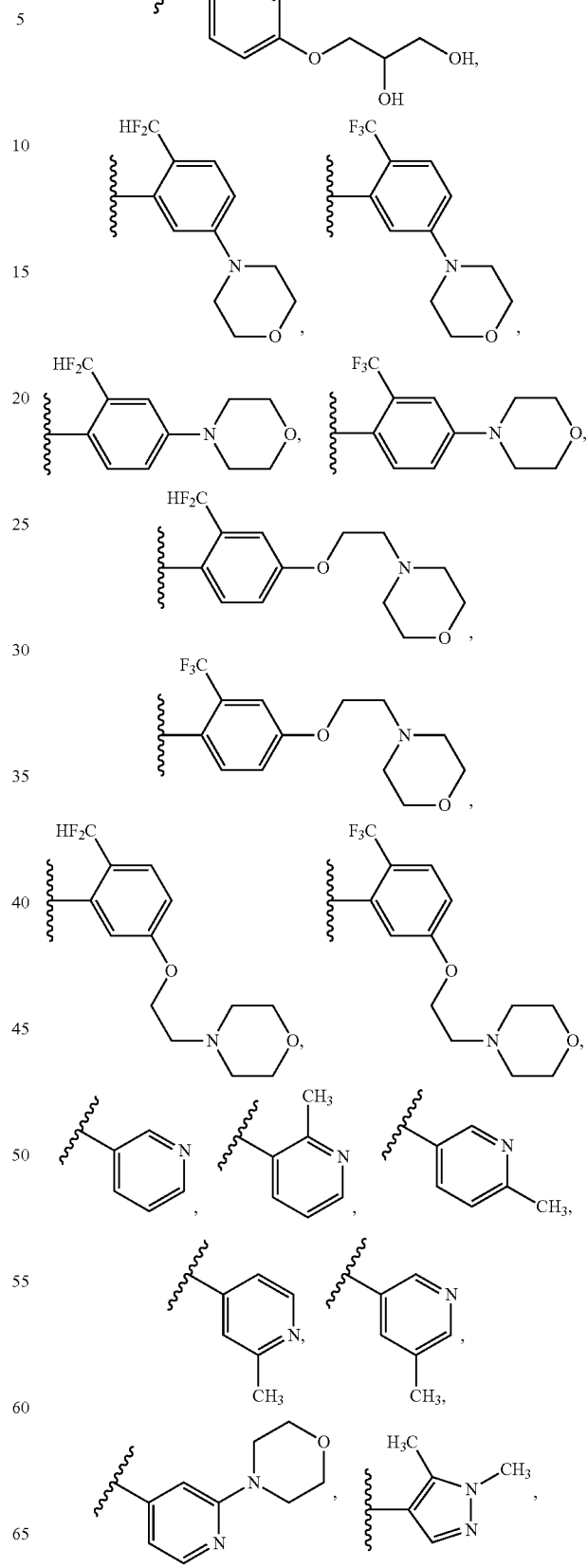

-continued

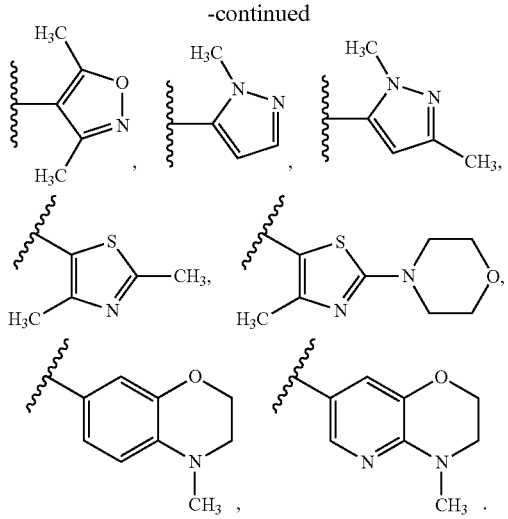

In even more particular embodiments, R is selected from

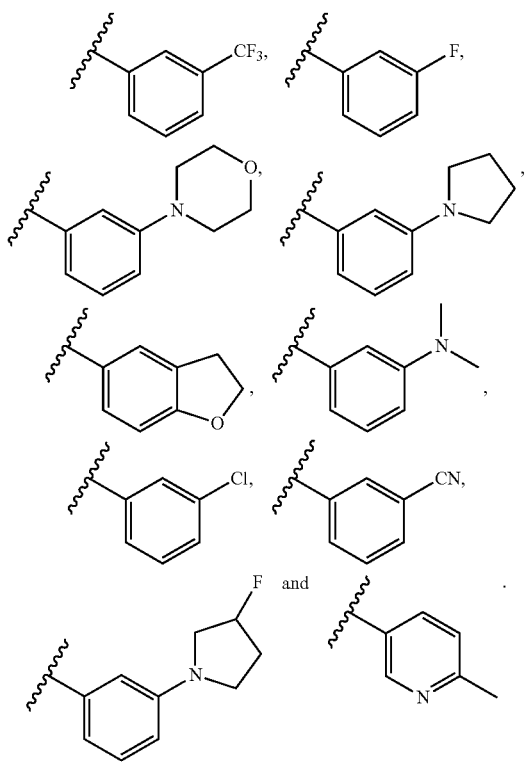

In certain embodiments, X² is —C(=O)—NH-†.

In certain embodiments, R¹, R², W, X², Z¹ and Z² are chosen to have one, two, three, four, five or six of the particular values described above. For example, W, R⁶, Z¹ and Z² may be chosen to have one of the six specific structural formulae shown above in combination with X² as —C(=O)—NH-† and any of the particular structures shown for R¹ and R² above.

The embodiments described below apply to compounds of any of Structural Formulas (I)-(VI).

Compounds of the invention, including novel compounds of the invention, can also be used in the methods described herein.

The compounds and salts thereof described herein can also be present as the corresponding hydrates (e.g., hemihydrate, monohydrate, dihydrate, trihydrate, tetrahydrate) and solvates. Suitable solvents for preparation of solvates and hydrates can generally be selected by a skilled artisan.

The compounds and salts thereof can be present in amorphous or crystalline (including co-crystalline and polymorph) forms.

Sirtuin-modulating compounds of the invention advantageously modulate the level and/or activity of a sirtuin protein, particularly the deacetylase activity of the sirtuin protein.

Separately or in addition to the above properties, certain sirtuin-modulating compounds of the invention do not substantially have one or more of the following activities: inhibition of PI3-kinase, inhibition of aldoreductase, inhibition of tyrosine kinase, transactivation of EGFR tyrosine kinase, coronary dilation, or spasmolytic activity, at concentrations of the compound that are effective for modulating the deacetylation activity of a sirtuin protein (e.g., such as a SIRT1 and/or a SIRT3 protein).

An alkyl group is a straight chained or branched hydrocarbon which is completely saturated. Typically, a straight chained or branched alkyl group has from 1 to about 20 carbon atoms, preferably from 1 to about 10. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_4$ straight chained or branched alkyl group is also referred to as a "lower alkyl" group.

The terms "carbocycle", and "carbocyclic", as used herein, refers to a saturated or unsaturated ring in which each atom of the ring is carbon. Carbocyclic includes 5-7 membered monocyclic and 8-12 membered bicyclic rings. Each ring of a bicyclic carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl and naphthyl.

A cycloalkyl group is a carbocycle which is completely saturated. Exemplary cycloalkyl groups include cyclopentyl, cyclohexyl, bicyclo[2,2,1]heptanyl and adamantyl.

The terms "heterocycle", and "heterocyclic", as used herein, refers to a saturated or unsaturated ring comprising one or more heteroatoms selected from, for example, N, O, and S atoms. Heterocycles include 4-7 membered monocyclic and 8-12 membered bicyclic rings. Each ring of a bicyclic heterocycle may be selected from saturated, unsaturated and aromatic rings. In an exemplary embodiment, an aromatic ring, e.g., pyridyl, may be fused to a saturated or unsaturated ring, e.g., cyclohexane, cyclopentane, or cyclohexene. The terms "heterocyclyl" and "heterocyclic" also include polycyclic ring systems having two or more cyclic rings in which two or more carbons or heteroatoms are common to two adjoining rings wherein at least one of the rings is heterocyclic, e.g., the other cyclic rings can be cycloalkyls, cycloalkenyls, cycloalkynyls, aryls, heteroaryls, and/or heterocycloalkyls. Heterocyclyl groups include, for example, piperidine, piperazine, pyrrolidine, morpholine, lactones, and lactams.

The term "heteroaryl" includes substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" also includes polycyclic ring systems having two or more cyclic rings in which two or more carbons or heteroatoms are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

Monocyclic rings include 5-7 membered aryl or heteroaryl, 3-7 membered cycloalkyl, and 5-7 membered non-aromatic heterocyclyl. Exemplary monocyclic groups include substituted or unsubstituted heterocycles or carbocycles such as thiazolyl, oxazolyl, oxazinyl, thiazinyl, dithianyl, dioxanyl, isoxazolyl, isothiazolyl, triazolyl, furanyl, tetrahydrofuranyl, dihydrofuranyl, pyranyl, tetrazolyl, pyrazolyl, pyrazinyl, pyridazinyl, imidazolyl, pyridinyl, pyrrolyl, dihydropyrrolyl, pyrrolidinyl, piperidinyl, piperazinyl, pyrimidinyl, morpholinyl, tetrahydrothiophenyl, thiophenyl, cyclohexyl, cyclopentyl, cyclopropyl, cyclobutyl, cycloheptenyl, azetidinyl, oxetanyl, thiiranyl, oxiranyl, aziridinyl, and thiomorpholinyl.

Aromatic (aryl) groups include carbocyclic aromatic groups such as phenyl, naphthyl, and anthracyl, and heteroaryl groups such as imidazolyl, thienyl, furyl, pyridyl, pyrimidyl, pyranyl, pyrazolyl, pyrrolyl, pyrazinyl, thiazolyl, oxazolyl, and tetrazolyl. Aromatic groups also include fused polycyclic aromatic ring systems in which a carbocyclic aromatic ring or heteroaryl ring is fused to one or more other heteroaryl rings. Examples include benzothienyl, benzofuryl, indolyl, quinolinyl, benzothiazole, benzoxazole, benzimidazole, quinolinyl, isoquinolinyl and isoindolyl.

"Spiro bicycle" refers to a bicycle in which exactly one atom is common to each ring of the bicycle. Each of the two rings of a spiro bicycle may be selected from 3- to 7-membered rings. For example, a spiro bicycle may have two rings each of which have 4 members, i.e., 4-4 spiro bicycle. Exemplary structures in this category include

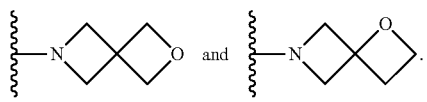 [SMILES: *N1CC2(COC2)C1 ; "and" ; *N1CC2(CCO2)C1 ; "."]

In other examples, the spiro bicycle has two rings of different number of members, e.g., 4-6, 5-6, 6-7. A spiro bicycle may include one or more heteroatoms such as O, N or S, which can be present in the spiro bicycle. A spiro bicycle may be substituted with one or more substituent groups. Exemplary substituents include =O, halo, and alkyl or another of the substituents listed for other groups described herein. Unless otherwise indicated, a spiro bicycle is saturated.

Fluoro-substituted includes from one fluoro substituent up to per-fluoro-substitution. Exemplary fluoro-substituted $C_1$-$C_2$ alkyl includes —$CFH_2$, $CF_2H$, —$CF_3$, —$CH_2CH_2F$, —$CH_2CHF_2$, —$CHFCH_3$, and —$CF_2CHF_2$. Per-fluoro-substituted $C_1$-$C_2$ alkyl, for example, includes —$CF_3$ and —$CF_2CF_3$.

Combinations of substituents and variables envisioned by this invention are only those that result in the formation of stable compounds. As used herein, the term "stable" refers to compounds that possess stability sufficient to allow manufacture and that maintain the integrity of the compound for a sufficient period of time to be useful for the purposes detailed herein.

The compounds disclosed herein also include partially and fully deuterated variants. In certain embodiments, deuterated variants may be used for kinetic studies. One of ordinary skill in the art can select the sites at which such deuterium atoms are present.

Also included in the present invention are salts, particularly pharmaceutically acceptable salts, of the sirtuin-modulating compounds described herein. The compounds of the present invention that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion (e.g., a halide such as bromide, chloride, or fluoride, particularly bromide).

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

According to another embodiment, the present invention provides methods of producing the above-defined sirtuin-modulating compounds. The compounds may be synthesized using conventional techniques. Advantageously, these compounds are conveniently synthesized from readily available starting materials.

Synthetic chemistry transformations and methodologies useful in synthesizing the sirtuin-modulating compounds described herein are known in the art and include, for example, those described in R. Larock, *Comprehensive Organic Transformations* (1989); T. W. Greene and P. G. M. Wuts, *Protective Groups in Organic Synthesis*, 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995). In an exemplary embodiment, a sirtuin-modulating compound may traverse the cytoplasmic membrane of a cell. For example, a compound may have a cell-permeability of at least about 20%, 50%, 75%, 80%, 90% or 95%.

Sirtuin-modulating compounds described herein may also have one or more of the following characteristics: the compound may be essentially non-toxic to a cell or subject; the sirtuin-modulating compound may be an organic molecule or a small molecule of 2000 amu or less, 1000 amu or less; a compound may have a half-life under normal atmospheric conditions of at least about 30 days, 60 days, 120 days, 6 months or 1 year; the compound may have a half-life in solution of at least about 30 days, 60 days, 120 days, 6 months or 1 year; a sirtuin-modulating compound may be more stable in solution than resveratrol by at least a factor of about 50%, 2 fold, 5 fold, 10 fold, 30 fold, 50 fold or 100 fold; a sirtuin-modulating compound may promote deacetylation of the DNA repair factor Ku70; a sirtuin-modulating compound may promote deacetylation of RelA/p65; a compound may increase general turnover rates and enhance the sensitivity of cells to TNF-induced apoptosis.

In certain embodiments, a sirtuin-modulating compound does not have any substantial ability to inhibit a histone deacetylase (HDACs) class I, a HDAC class II, or HDACs I and II, at concentrations (e.g., in vivo) effective for modulating the deacetylase activity of the sirtuin. For instance, in preferred embodiments the sirtuin-modulating compound is a sirtuin-activating compound and is chosen to have an $EC_{50}$ for activating sirtuin deacetylase activity that is at least 5 fold less than the $EC_{50}$ for inhibition of an HDAC I and/or HDAC II, and even more preferably at least 10 fold, 100 fold or even 1000 fold less. Methods for assaying HDAC I and/or HDAC II activity are well known in the art and kits to perform such assays may be purchased commercially. See e.g., BioVision, Inc. (Mountain View, Calif.; world wide web at biovision.com) and Thomas Scientific (Swedesboro, N.J.; world wide web at tomassci-.com).

In certain embodiments, a sirtuin-modulating compound does not have any substantial ability to modulate sirtuin homologs. In one embodiment, an activator of a human sirtuin protein may not have any substantial ability to activate a sirtuin protein from lower eukaryotes, particularly yeast or human pathogens, at concentrations (e.g., in vivo) effective for activating the deacetylase activity of human sirtuin. For example, a sirtuin-activating compound may be chosen to have an $EC_{50}$ for activating a human sirtuin, such as SIRT1 and/or SIRT3, deacetylase activity that is at least 5 fold less than the $EC_{50}$ for activating a yeast sirtuin, such as Sir2 (such as *Candida, S. cerevisiae*, etc.), and even more preferably at least 10 fold, 100 fold or even 1000 fold less. In another embodiment, an inhibitor of a sirtuin protein from lower eukaryotes, particularly yeast or human pathogens, does not have any substantial ability to inhibit a sirtuin protein from humans at concentrations (e.g., in vivo) effective for inhibiting the deacetylase activity of a sirtuin protein from a lower eukaryote. For example, a sirtuin-inhibiting compound may be chosen to have an $IC_{50}$ for inhibiting a human sirtuin, such as SIRT1 and/or SIRT3, deacetylase activity that is at least 5 fold less than the $IC_{50}$ for inhibiting a yeast sirtuin, such as Sir2 (such as *Candida, S. cerevisiae*, etc.), and even more preferably at least 10 fold, 100 fold or even 1000 fold less.

In certain embodiments, a sirtuin-modulating compound may have the ability to modulate one or more sirtuin protein homologs, such as, for example, one or more of human SIRT1, SIRT2, SIRT3, SIRT4, SIRT5, SIRT6, or SIRT7. In one embodiment, a sirtuin-modulating compound has the ability to modulate both a SIRT1 and a SIRT3 protein.

In other embodiments, a SIRT1 modulator does not have any substantial ability to modulate other sirtuin protein homologs, such as, for example, one or more of human SIRT2, SIRT3, SIRT4, SIRT5, SIRT6, or SIRT7, at concentrations (e.g., in vivo) effective for modulating the deacetylase activity of human SIRT1. For example, a sirtuin-modulating compound may be chosen to have an $ED_{50}$ for modulating human SIRT1 deacetylase activity that is at least 5 fold less than the $ED_{50}$ for modulating one or more of human SIRT2, SIRT3, SIRT4, SIRT5, SIRT6, or SIRT7, and even more preferably at least 10 fold, 100 fold or even 1000 fold less. In one embodiment, a SIRT1 modulator does not have any substantial ability to modulate a SIRT3 protein.

In other embodiments, a SIRT3 modulator does not have any substantial ability to modulate other sirtuin protein homologs, such as, for example, one or more of human SIRT1, SIRT2, SIRT4, SIRT5, SIRT6, or SIRT7, at concentrations (e.g., in vivo) effective for modulating the deacetylase activity of human SIRT3. For example, a sirtuin-modulating compound may be chosen to have an $ED_{50}$ for modulating human SIRT3 deacetylase activity that is at least 5 fold less than the $ED_{50}$ for modulating one or more of human SIRT1, SIRT2, SIRT4, SIRT5, SIRT6, or SIRT7, and even more preferably at least 10 fold, 100 fold or even 1000 fold less. In one embodiment, a SIRT3 modulator does not have any substantial ability to modulate a SIRT1 protein.

In certain embodiments, a sirtuin-modulating compound may have a binding affinity for a sirtuin protein of about $10^{-9}$ M, $10^{-10}$ M, $10^{-11}$ M, $10^{-12}$ M or less. A sirtuin-modulating compound may reduce (activator) or increase (inhibitor) the apparent Km of a sirtuin protein for its substrate or NAD+ (or other cofactor) by a factor of at least about 2, 3, 4, 5, 10, 20, 30, 50 or 100. In certain embodiments, Km values are determined using the mass spectrometry assay described herein. Preferred activating compounds reduce the Km of a sirtuin for its substrate or cofactor to a greater extent than caused by resveratrol at a similar concentration or reduce the Km of a sirtuin for its substrate or cofactor similar to that caused by resveratrol at a lower concentration. A sirtuin-modulating compound may increase the Vmax of a sirtuin protein by a factor of at least about 2, 3, 4, 5, 10, 20, 30, 50 or 100. A sirtuin-modulating compound may have an ED50 for modulating the deacetylase activity of a SIRT1 and/or SIRT3 protein of less than about 1 nM, less than about 10 nM, less than about 100 nM, less than about 1 µM, less than about 10 µM, less than about 100 µM, or from about 1-10 nM, from about 10-100 nM, from about 0.1-1 µM, from about 1-10 µM or from about 10-100 µM. A sirtuin-modulating compound may modulate the deacetylase activity of a SIRT1 and/or SIRT3 protein by a factor of at least about 5, 10, 20, 30, 50, or 100, as measured in a cellular assay or in a cell based assay. A sirtuin-activating compound may cause at least about 10%, 30%, 50%, 80%, 2 fold, 5 fold, 10 fold, 50 fold or 100 fold greater induction of the deacetylase activity of a sirtuin protein relative to the same concentration of resveratrol. A sirtuin-modulating compound may have an ED50 for modulating SIRT5 that is at least about 10 fold, 20 fold, 30 fold, 50 fold greater than that for modulating SIRT1 and/or SIRT3.

3. Exemplary Uses

In certain aspects, the invention provides methods for modulating the level and/or activity of a sirtuin protein and methods of use thereof.

In certain embodiments, the invention provides methods for using sirtuin-modulating compounds wherein the sirtuin-modulating compounds activate a sirtuin protein, e.g., increase the level and/or activity of a sirtuin protein. Sirtuin-modulating compounds that increase the level and/or activity of a sirtuin protein may be useful for a variety of therapeutic applications including, for example, increasing the lifespan of a cell, and treating and/or preventing a wide variety of diseases and disorders including, for example, diseases or disorders related to aging or stress, diabetes, obesity, neurodegenerative diseases, cardiovascular disease, blood clotting disorders, inflammation, cancer, and/or flushing, etc. The methods comprise administering to a subject in need thereof a pharmaceutically effective amount of a sirtuin-modulating compound, e.g., a sirtuin-activating compound.

Without wishing to be bound by theory, it is believed that activators of the instant invention may interact with a sirtuin at the same location within the sirtuin protein (e.g., active site or site affecting the Km or Vmax of the active site). It is believed that this is the reason why certain classes of sirtuin activators and inhibitors can have substantial structural similarity.

In certain embodiments, the sirtuin-modulating compounds described herein may be taken alone or in combination with other compounds. In one embodiment, a mixture of two or more sirtuin-modulating compounds may be administered to a subject in need thereof. In another embodiment, a sirtuin-modulating compound that increases the level and/or activity of a sirtuin protein may be administered with one or more of the following compounds: resveratrol, butein, fisetin, piceatannol, or quercetin. In an exemplary embodiment, a sirtuin-modulating compound that increases the level and/or activity of a sirtuin protein may be administered in combination with nicotinic acid. In another embodiment, a sirtuin-modulating compound that decreases the level and/or activity of a sirtuin protein may be administered with one or more of the following compounds: nicotinamide (NAM), suramin; NF023 (a G-protein antagonist); NF279 (a purinergic receptor antagonist); Trolox (6-hydroxy-2,5,7,8,tetramethylchroman-2-carboxylic acid); (−)-epigallocatechin (hydroxy on sites 3,5,7,3',4',5'); (−)-epigallocatechin gallate (Hydroxy sites 5,7,3',4',5' and gallate ester on 3); cyanidin chloride (3,5,7,3',4'-pentahydroxyflavylium chloride); delphinidin chloride (3,5,7,3',4',5'-hexahydroxyflavylium chloride); myricetin (cannabiscetin; 3,5,7,3',4',5'-hexahydroxyflavone); 3,7,3',4',5'-pentahydroxyflavone; gossypetin (3,5,7,8,3',4'-hexahydroxyflavone), sirtinol; and splitomicin. In yet another embodiment, one or more sirtuin-modulating compounds may be administered with one or more therapeutic agents for the treatment or prevention of various diseases, including, for example, cancer, diabetes, neurodegenerative diseases, cardiovascular disease, blood clotting, inflammation, flushing, obesity, aging, stress, etc. In various embodiments, combination therapies comprising a sirtuin-modulating compound may refer to (1) pharmaceutical compositions that comprise one or more sirtuin-modulating compounds in combination with one or more therapeutic agents (e.g., one or more therapeutic agents described herein); and (2) co-administration of one or more sirtuin-modulating compounds with one or more therapeutic agents wherein the sirtuin-modulating compound and therapeutic agent have not been formulated in the same compositions (but may be present within the same kit or package, such as a blister pack or other multi-chamber package; connected, separately sealed containers (e.g., foil pouches) that can be separated by the user; or a kit where the sirtuin modulating compound(s) and other therapeutic agent(s) are in separate vessels). When using separate formulations, the sirtuin-modulating compound may be administered at the same, intermittent, staggered, prior to, subsequent to, or combinations thereof, with the administration of another therapeutic agent.

In certain embodiments, methods for reducing, preventing or treating diseases or disorders using a sirtuin-modulating compound may also comprise increasing the protein level of a sirtuin, such as human SIRT1, SIRT2 and/or SIRT3, or homologs thereof. Increasing protein levels can be achieved by introducing into a cell one or more copies of a nucleic acid that encodes a sirtuin. For example, the level of a sirtuin can be increased in a mammalian cell by introducing into the mammalian cell a nucleic acid encoding the sirtuin, e.g., increasing the level of SIRT1 by introducing a nucleic acid encoding the amino acid sequence set forth in GenBank Accession No. NP_036370 and/or increasing the level of SIRT3 by introducing a nucleic acid encoding the amino acid sequence set forth in GenBank Accession No. AAH01042.

A nucleic acid that is introduced into a cell to increase the protein level of a sirtuin may encode a protein that is at least about 80%, 85%, 90%, 95%, 98%, or 99% identical to the sequence of a sirtuin, e.g., SIRT1 and/or SIRT3 protein. For example, the nucleic acid encoding the protein may be at least about 80%, 85%, 90%, 95%, 98%, or 99% identical to a nucleic acid encoding a SIRT1 (e.g. GenBank Accession No. NM_012238) and/or SIRT3 (e.g., GenBank Accession No. BC001042) protein. The nucleic acid may also be a nucleic acid that hybridizes, preferably under stringent hybridization conditions, to a nucleic acid encoding a wild-type sirtuin, e.g., SIRT1 and/or SIRT3 protein. Stringent hybridization conditions may include hybridization and a wash in 0.2×SSC at 65° C. When using a nucleic acid that encodes a protein that is different from a wild-type sirtuin protein, such as a protein that is a fragment of a wild-type sirtuin, the protein is preferably biologically active, e.g., is capable of deacetylation. It is only necessary to express in a cell a portion of the sirtuin that is biologically active. For example, a protein that differs from wild-type SIRT1 having GenBank Accession No. NP_036370, preferably contains the core structure thereof. The core structure sometimes refers to amino acids 62-293 of GenBank Accession No. NP_036370, which are encoded by nucleotides 237 to 932 of GenBank Accession No. NM_012238, which encompasses the NAD binding as well as the substrate binding domains. The core domain of SIRT1 may also refer to about amino acids 261 to 447 of GenBank Accession No. NP_036370, which are encoded by nucleotides 834 to 1394 of GenBank Accession No. NM_012238; to about amino acids 242 to 493 of GenBank Accession No. NP_036370, which are encoded by nucleotides 777 to 1532 of GenBank Accession No. NM_012238; or to about amino acids 254 to 495 of GenBank Accession No. NP_036370, which are encoded by nucleotides 813 to 1538 of GenBank Accession No. NM_012238. Whether a protein retains a biological function, e.g., deacetylation capabilities, can be determined according to methods known in the art.

In certain embodiments, methods for reducing, preventing or treating diseases or disorders using a sirtuin-modulating compound may also comprise decreasing the protein level of a sirtuin, such as human SIRT1, SIRT2 and/or SIRT3, or homologs thereof. Decreasing a sirtuin protein level can be achieved according to methods known in the art. For example, an siRNA, an antisense nucleic acid, or a ribozyme targeted to the sirtuin can be expressed in the cell. A dominant negative sirtuin mutant, e.g., a mutant that is not capable of deacetylating, may also be used. For example, mutant H363Y of SIRT1, described, e.g., in Luo et al. (2001) Cell 107:137 can be used. Alternatively, agents that inhibit transcription can be used.

Methods for modulating sirtuin protein levels also include methods for modulating the transcription of genes encoding sirtuins, methods for stabilizing/destabilizing the corresponding mRNAs, and other methods known in the art.

Aging/Stress

In one embodiment, the invention provides a method extending the lifespan of a cell, extending the proliferative capacity of a cell, slowing aging of a cell, promoting the survival of a cell, delaying cellular senescence in a cell, mimicking the effects of calorie restriction, increasing the resistance of a cell to stress, or preventing apoptosis of a cell, by contacting the cell with a sirtuin-modulating compound of the invention that increases the level and/or activity of a sirtuin protein. In an exemplary embodiment, the methods comprise contacting the cell with a sirtuin-activating compound.

The methods described herein may be used to increase the amount of time that cells, particularly primary cells (i.e., cells obtained from an organism, e.g., a human), may be kept alive in a cell culture. Embryonic stem (ES) cells and pluripotent cells, and cells differentiated therefrom, may also be treated with a sirtuin-modulating compound that increases the level and/or activity of a sirtuin protein to keep the cells, or progeny thereof, in culture for longer periods of time. Such cells can also be used for transplantation into a subject, e.g., after ex vivo modification.

In one embodiment, cells that are intended to be preserved for long periods of time may be treated with a sirtuin-modulating compound that increases the level and/or activity of a sirtuin protein. The cells may be in suspension (e.g., blood cells, serum, biological growth media, etc.) or in tissues or organs. For example, blood collected from an individual for purposes of transfusion may be treated with a sirtuin-modulating compound that increases the level and/or activity of a sirtuin protein to preserve the blood cells for longer periods of time. Additionally, blood to be used for forensic purposes may also be preserved using a sirtuin-modulating compound that increases the level and/or activity of a sirtuin protein. Other cells that may be treated to extend their lifespan or protect against apoptosis include cells for consumption, e.g., cells from non-human mammals (such as meat) or plant cells (such as vegetables).

Sirtuin-modulating compounds that increase the level and/or activity of a sirtuin protein may also be applied during developmental and growth phases in mammals, plants, insects or microorganisms, in order to, e.g., alter, retard or accelerate the developmental and/or growth process.

In another embodiment, sirtuin-modulating compounds that increase the level and/or activity of a sirtuin protein may be used to treat cells useful for transplantation or cell therapy, including, for example, solid tissue grafts, organ transplants, cell suspensions, stem cells, bone marrow cells, etc. The cells or tissue may be an autograft, an allograft, a syngraft or a xenograft. The cells or tissue may be treated with the sirtuin-modulating compound prior to administration/implantation, concurrently with administration/implantation, and/or post administration/implantation into a subject. The cells or tissue may be treated prior to removal of the cells from the donor individual, ex vivo after removal of the cells or tissue from the donor individual, or post implantation into the recipient. For example, the donor or recipient individual may be treated systemically with a sirtuin-modulating compound or may have a subset of cells/tissue treated locally with a sirtuin-modulating compound that increases the level and/or activity of a sirtuin protein. In certain embodiments, the cells or tissue (or donor/recipient individuals) may additionally be treated with another therapeutic agent useful for prolonging graft survival, such as, for example, an immunosuppressive agent, a cytokine, an angiogenic factor, etc.

In yet other embodiments, cells may be treated with a sirtuin-modulating compound that increases the level and/or activity of a sirtuin protein in vivo, e.g., to increase their lifespan or prevent apoptosis. For example, skin can be protected from aging (e.g., developing wrinkles, loss of elasticity, etc.) by treating skin or epithelial cells with a sirtuin-modulating compound that increases the level and/or activity of a sirtuin protein. In an exemplary embodiment, skin is contacted with a pharmaceutical or cosmetic composition comprising a sirtuin-modulating compound that increases the level and/or activity of a sirtuin protein. Exemplary skin afflictions or skin conditions that may be treated in accordance with the methods described herein include disorders or diseases associated with or caused by inflammation, sun damage or natural aging. For example, the compositions find utility in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including pemphigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In another embodiment, sirtuin-modulating compounds that increase the level and/or activity of a sirtuin protein may be used for the treatment of wounds and/or burns to promote healing, including, for example, first-, second- or third-degree burns and/or thermal, chemical or electrical burns. The formulations may be administered topically, to the skin or mucosal tissue.

Topical formulations comprising one or more sirtuin-modulating compounds that increase the level and/or activity of a sirtuin protein may also be used as preventive, e.g., chemopreventive, compositions. When used in a chemopreventive method, susceptible skin is treated prior to any visible condition in a particular individual.

Sirtuin-modulating compounds may be delivered locally or systemically to a subject. In one embodiment, a sirtuin-modulating compound is delivered locally to a tissue or organ of a subject by injection, topical formulation, etc.

In another embodiment, a sirtuin-modulating compound that increases the level and/or activity of a sirtuin protein may be used for treating or preventing a disease or condition induced or exacerbated by cellular senescence in a subject; methods for decreasing the rate of senescence of a subject, e.g., after onset of senescence; methods for extending the lifespan of a subject; methods for treating or preventing a disease or condition relating to lifespan; methods for treating or preventing a disease or condition relating to the proliferative capacity of cells; and methods for treating or preventing a disease or condition resulting from cell damage or death. In certain embodiments, the method does not act by decreasing the rate of occurrence of diseases that shorten the lifespan of a subject. In certain embodiments, a method does not act by reducing the lethality caused by a disease, such as cancer.

In yet another embodiment, a sirtuin-modulating compound that increases the level and/or activity of a sirtuin protein may be administered to a subject in order to generally increase the lifespan of its cells and to protect its cells against stress and/or against apoptosis. It is believed that treating a subject with a compound described herein is similar to subjecting the subject to hormesis, i.e., mild stress that is beneficial to organisms and may extend their lifespan.

Sirtuin-modulating compounds that increase the level and/or activity of a sirtuin protein may be administered to a subject to prevent aging and aging-related consequences or diseases, such as stroke, heart disease, heart failure, arthritis, high blood pressure, and Alzheimer's disease. Other conditions that can be treated include ocular disorders, e.g., associated with the aging of the eye, such as cataracts, glaucoma, and macular degeneration. Sirtuin-modulating compounds that increase the level and/or activity of a sirtuin protein can also be administered to subjects for treatment of diseases, e.g., chronic diseases, associated with cell death, in order to protect the cells from cell death. Exemplary diseases include those associated with neural cell death, neuronal dysfunction, or muscular cell death or dysfunction, such as Parkinson's disease, Alzheimer's disease, multiple sclerosis, amyotrophic lateral sclerosis, and muscular dystrophy; AIDS; fulminant hepatitis; diseases linked to degeneration of the brain, such as Creutzfeld-Jakob disease, retinitis pigmentosa and cerebellar degeneration; myelodysplasia such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections. Cell death can also be caused by surgery, drug therapy, chemical exposure or radiation exposure.

Sirtuin-modulating compounds that increase the level and/or activity of a sirtuin protein can also be administered to a subject suffering from an acute disease, e.g., damage to an organ or tissue, e.g., a subject suffering from stroke or myocardial infarction or a subject suffering from a spinal cord injury. Sirtuin-modulating compounds that increase the level and/or activity of a sirtuin protein may also be used to repair an alcoholic's liver.

Cardiovascular Disease

In another embodiment, the invention provides a method for treating and/or preventing a cardiovascular disease by administering to a subject in need thereof a sirtuin-modulating compound that increases the level and/or activity of a sirtuin protein.

Cardiovascular diseases that can be treated or prevented using the sirtuin-modulating compounds that increase the level and/or activity of a sirtuin protein include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable or preventable using compounds and methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated or prevented include those related to platelet aggregation, the retinal arterioles, the glomerular arterioles, the vasa nervorum, cardiac arterioles, and associated capillary beds of the eye, the kidney, the heart, and the central and peripheral nervous systems. The sirtuin-modulating compounds that increase the level and/or activity of a sirtuin protein may also be used for increasing HDL levels in plasma of an individual.

Yet other disorders that may be treated with sirtuin-modulating compounds that increase the level and/or activity of a sirtuin protein include restenosis, e.g., following coronary intervention, and disorders relating to an abnormal level of high density and low density cholesterol.

In one embodiment, a sirtuin-modulating compound that increases the level and/or activity of a sirtuin protein may be administered as part of a combination therapeutic with another cardiovascular agent. In one embodiment, a sirtuin-modulating compound that increases the level and/or activity of a sirtuin protein may be administered as part of a combination therapeutic with an anti-arrhythmia agent. In another embodiment, a sirtuin-modulating compound that increases the level and/or activity of a sirtuin protein may be administered as part of a combination therapeutic with another cardiovascular agent.

Cell Death/Cancer

Sirtuin-modulating compounds that increase the level and/or activity of a sirtuin protein may be administered to subjects who have recently received or are likely to receive a dose of radiation or toxin. In one embodiment, the dose of radiation or toxin is received as part of a work-related or medical procedure, e.g., administered as a prophylactic measure. In another embodiment, the radiation or toxin exposure is received unintentionally. In such a case, the compound is preferably administered as soon as possible after the exposure to inhibit apoptosis and the subsequent development of acute radiation syndrome.

Sirtuin-modulating compounds may also be used for treating and/or preventing cancer. In certain embodiments, sirtuin-modulating compounds that increase the level and/or activity of a sirtuin protein may be used for treating and/or preventing cancer. Calorie restriction has been linked to a reduction in the incidence of age-related disorders including cancer. Accordingly, an increase in the level and/or activity of a sirtuin protein may be useful for treating and/or preventing the incidence of age-related disorders, such as, for example, cancer. Exemplary cancers that may be treated using a sirtuin-modulating compound are those of the brain and kidney; hormone-dependent cancers including breast, prostate, testicular, and ovarian cancers; lymphomas, and leukemias. In cancers associated with solid tumors, a modulating compound may be administered directly into the tumor. Cancer of blood cells, e.g., leukemia, can be treated by administering a modulating compound into the blood stream or into the bone marrow. Benign cell growth, e.g., warts, can also be treated. Other diseases that can be treated include autoimmune diseases, e.g., systemic lupus erythematosus, scleroderma, and arthritis, in which autoimmune cells should be removed. Viral infections such as herpes, HIV, adenovirus, and HTLV-1 associated malignant and benign disorders can also be treated by administration of sirtuin-modulating compound. Alternatively, cells can be obtained from a subject, treated ex vivo to remove certain undesirable cells, e.g., cancer cells, and administered back to the same or a different subject.

Chemotherapeutic agents may be co-administered with modulating compounds described herein as having anti-cancer activity, e.g., compounds that induce apoptosis, compounds that reduce lifespan or compounds that render cells sensitive to stress. Chemotherapeutic agents may be used by themselves with a sirtuin-modulating compound described herein as inducing cell death or reducing lifespan or increasing sensitivity to stress and/or in combination with other chemotherapeutics agents. In addition to conventional chemotherapeutics, the sirtuin-modulating compounds described herein may also be used with antisense RNA, RNAi or other polynucleotides to inhibit the expression of the cellular components that contribute to unwanted cellular proliferation.

Combination therapies comprising sirtuin-modulating compounds and a conventional chemotherapeutic agent may be advantageous over combination therapies known in the art because the combination allows the conventional chemotherapeutic agent to exert greater effect at lower dosage. In a preferred embodiment, the effective dose ($ED_{50}$) for a chemotherapeutic agent, or combination of conventional chemotherapeutic agents, when used in combination with a sirtuin-modulating compound is at least 2 fold less than the $ED_{50}$ for the chemotherapeutic agent alone, and even more preferably at 5 fold, 10 fold or even 25 fold less. Conversely, the therapeutic index (TI) for such chemotherapeutic agent or combination of such chemotherapeutic agent when used in combination with a sirtuin-modulating compound described herein can be at least 2 fold greater than the TI for conventional chemotherapeutic regimen alone, and even more preferably at 5 fold, 10 fold or even 25 fold greater.

Neuronal Diseases/Disorders

In certain aspects, sirtuin-modulating compounds that increase the level and/or activity of a sirtuin protein can be used to treat patients suffering from neurodegenerative diseases, and traumatic or mechanical injury to the central nervous system (CNS), spinal cord or peripheral nervous system (PNS). Neurodegenerative disease typically involves reductions in the mass and volume of the human brain, which may be due to the atrophy and/or death of brain cells, which are far more profound than those in a healthy person that are attributable to aging. Neurodegenerative diseases can evolve gradually, after a long period of normal brain function, due to progressive degeneration (e.g., nerve cell dysfunction and death) of specific brain regions. Alternatively, neurodegenerative diseases can have a quick onset, such as those associated with trauma or toxins. The actual onset of brain degeneration may precede clinical expression by many years. Examples of neurodegenerative diseases include, but are not limited to, Alzheimer's disease (AD), Parkinson's disease (PD), Huntington's disease (HD), amyotrophic lateral sclerosis (ALS; Lou Gehrig's disease), diffuse Lewy body disease, chorea-acanthocytosis, primary lateral sclerosis, ocular diseases (ocular neuritis), chemotherapy-induced neuropathies (e.g., from vincristine, paclitaxel, bortezomib), diabetes-induced neuropathies and Friedreich's ataxia. Sirtuin-modulating compounds that increase the level and/or activity of a sirtuin protein can be used to treat these disorders and others as described below.

AD is a CNS disorder that results in memory loss, unusual behavior, personality changes, and a decline in thinking abilities. These losses are related to the death of specific types of brain cells and the breakdown of connections and their supporting network (e.g. glial cells) between them. The earliest symptoms include loss of recent memory, faulty judgment, and changes in personality. PD is a CNS disorder that results in uncontrolled body movements, rigidity, tremor, and dyskinesia, and is associated with the death of brain cells in an area of the brain that produces dopamine. ALS (motor neuron disease) is a CNS disorder that attacks the motor neurons, components of the CNS that connect the brain to the skeletal muscles.

HD is another neurodegenerative disease that causes uncontrolled movements, loss of intellectual faculties, and emotional disturbance. Tay-Sachs disease and Sandhoff disease are glycolipid storage diseases where GM2 ganglioside and related glycolipids substrates for β-hexosaminidase accumulate in the nervous system and trigger acute neurodegeneration.

It is well-known that apoptosis plays a role in AIDS pathogenesis in the immune system. However, HIV-1 also induces neurological disease, which can be treated with sirtuin-modulating compounds of the invention.

Neuronal loss is also a salient feature of prion diseases, such as Creutzfeldt-Jakob disease in human, BSE in cattle (mad cow disease), Scrapie Disease in sheep and goats, and feline spongiform encephalopathy (FSE) in cats. Sirtuin-modulating compounds that increase the level and/or activity of a sirtuin protein may be useful for treating or preventing neuronal loss due to these prior diseases.

In another embodiment, a sirtuin-modulating compound that increases the level and/or activity of a sirtuin protein may be used to treat or prevent any disease or disorder involving axonopathy. Distal axonopathy is a type of peripheral neuropathy that results from some metabolic or toxic derangement of peripheral nervous system (PNS) neurons. It is the most common response of nerves to metabolic or toxic disturbances, and as such may be caused by metabolic diseases such as diabetes, renal failure, deficiency syndromes such as malnutrition and alcoholism, or the effects of toxins or drugs. Those with distal axonopathies usually present with symmetrical glove-stocking sensori-motor disturbances. Deep tendon reflexes and autonomic nervous system (ANS) functions are also lost or diminished in affected areas.

Diabetic neuropathies are neuropathic disorders that are associated with diabetes mellitus. Relatively common conditions which may be associated with diabetic neuropathy include third nerve palsy; mononeuropathy; mononeuritis multiplex; diabetic amyotrophy; a painful polyneuropathy; autonomic neuropathy; and thoracoabdominal neuropathy.

Peripheral neuropathy is the medical term for damage to nerves of the peripheral nervous system, which may be caused either by diseases of the nerve or from the side-effects of systemic illness. Major causes of peripheral neuropathy include seizures, nutritional deficiencies, and HIV, though diabetes is the most likely cause.

In an exemplary embodiment, a sirtuin-modulating compound that increases the level and/or activity of a sirtuin protein may be used to treat or prevent multiple sclerosis (MS), including relapsing MS and monosymptomatic MS, and other demyelinating conditions, such as, for example, chromic inflammatory demyelinating polyneuropathy (CIDP), or symptoms associated therewith.

In yet another embodiment, a sirtuin-modulating compound that increases the level and/or activity of a sirtuin protein may be used to treat trauma to the nerves, including, trauma due to disease, injury (including surgical intervention), or environmental trauma (e.g., neurotoxins, alcoholism, etc.).

Sirtuin-modulating compounds that increase the level and/or activity of a sirtuin protein may also be useful to prevent, treat, and alleviate symptoms of various PNS disorders. The term "peripheral neuropathy" encompasses a wide range of disorders in which the nerves outside of the brain and spinal cord—peripheral nerves—have been damaged. Peripheral neuropathy may also be referred to as peripheral neuritis, or if many nerves are involved, the terms polyneuropathy or polyneuritis may be used.

PNS diseases treatable with sirtuin-modulating compounds that increase the level and/or activity of a sirtuin protein include: diabetes, leprosy, Charcot-Marie-Tooth disease, Guillain-Barré syndrome and Brachial Plexus Neuropathies (diseases of the cervical and first thoracic roots, nerve trunks, cords, and peripheral nerve components of the brachial plexus.

In another embodiment, a sirtuin activating compound may be used to treat or prevent a polyglutamine disease.

Exemplary polyglutamine diseases include Spinobulbar muscular atrophy (Kennedy disease), Huntington's Disease (HD), Dentatorubral-pallidoluysian atrophy (Haw River syndrome), Spinocerebellar ataxia type 1, Spinocerebellar ataxia type 2, Spinocerebellar ataxia type 3 (Machado-Joseph disease), Spinocerebellar ataxia type 6, Spinocerebellar ataxia type 7, and Spinocerebellar ataxia type 17.

In certain embodiments, the invention provides a method to treat a central nervous system cell to prevent damage in response to a decrease in blood flow to the cell. Typically the severity of damage that may be prevented will depend in large part on the degree of reduction in blood flow to the cell and the duration of the reduction. In one embodiment, apoptotic or necrotic cell death may be prevented. In still a further embodiment, ischemic-mediated damage, such as cytoxic edema or central nervous system tissue anoxemia, may be prevented. In each embodiment, the central nervous system cell may be a spinal cell or a brain cell.

Another aspect encompasses administrating a sirtuin activating compound to a subject to treat a central nervous system ischemic condition. A number of central nervous system ischemic conditions may be treated by the sirtuin activating compounds described herein. In one embodiment, the ischemic condition is a stroke that results in any type of ischemic central nervous system damage, such as apoptotic or necrotic cell death, cytoxic edema or central nervous system tissue anoxia. The stroke may impact any area of the brain or be caused by any etiology commonly known to result in the occurrence of a stroke. In one alternative of this embodiment, the stroke is a brain stem stroke. In another alternative of this embodiment, the stroke is a cerebellar stroke. In still another embodiment, the stroke is an embolic stroke. In yet another alternative, the stroke may be a hemorrhagic stroke. In a further embodiment, the stroke is a thrombotic stroke.

In yet another aspect, a sirtuin activating compound may be administered to reduce infarct size of the ischemic core following a central nervous system ischemic condition. Moreover, a sirtuin activating compound may also be beneficially administered to reduce the size of the ischemic penumbra or transitional zone following a central nervous system ischemic condition.

In one embodiment, a combination drug regimen may include drugs or compounds for the treatment or prevention of neurodegenerative disorders or secondary conditions associated with these conditions. Thus, a combination drug regimen may include one or more sirtuin activators and one or more anti-neurodegeneration agents.

Blood Coagulation Disorders

In other aspects, sirtuin-modulating compounds that increase the level and/or activity of a sirtuin protein can be used to treat or prevent blood coagulation disorders (or hemostatic disorders). As used interchangeably herein, the terms "hemostasis", "blood coagulation," and "blood clotting" refer to the control of bleeding, including the physiological properties of vasoconstriction and coagulation. Blood coagulation assists in maintaining the integrity of mammalian circulation after injury, inflammation, disease, congenital defect, dysfunction or other disruption. Further, the formation of blood clots does not only limit bleeding in case of an injury (hemostasis), but may lead to serious organ damage and death in the context of atherosclerotic diseases by occlusion of an important artery or vein. Thrombosis is thus blood clot formation at the wrong time and place.

Accordingly, the present invention provides anticoagulation and antithrombotic treatments aiming at inhibiting the formation of blood clots in order to prevent or treat blood coagulation disorders, such as myocardial infarction, stroke, loss of a limb by peripheral artery disease or pulmonary embolism.

As used interchangeably herein, "modulating or modulation of hemostasis" and "regulating or regulation of hemostasis" includes the induction (e.g., stimulation or increase) of hemostasis, as well as the inhibition (e.g., reduction or decrease) of hemostasis.

In one aspect, the invention provides a method for reducing or inhibiting hemostasis in a subject by administering a sirtuin-modulating compound that increases the level and/or activity of a sirtuin protein. The compositions and methods disclosed herein are useful for the treatment or prevention of thrombotic disorders. As used herein, the term "thrombotic disorder" includes any disorder or condition characterized by excessive or unwanted coagulation or hemostatic activity, or a hypercoagulable state. Thrombotic disorders include diseases or disorders involving platelet adhesion and thrombus formation, and may manifest as an increased propensity to form thromboses, e.g., an increased number of thromboses, thrombosis at an early age, a familial tendency towards thrombosis, and thrombosis at unusual sites.

In another embodiment, a combination drug regimen may include drugs or compounds for the treatment or prevention of blood coagulation disorders or secondary conditions associated with these conditions. Thus, a combination drug regimen may include one or more sirtuin-modulating compounds that increase the level and/or activity of a sirtuin protein and one or more anti-coagulation or anti-thrombosis agents.

Weight Control

In another aspect, sirtuin-modulating compounds that increase the level and/or activity of a sirtuin protein may be used for treating or preventing weight gain or obesity in a subject. For example, sirtuin-modulating compounds that increase the level and/or activity of a sirtuin protein may be used, for example, to treat or prevent hereditary obesity, dietary obesity, hormone related obesity, obesity related to the administration of medication, to reduce the weight of a subject, or to reduce or prevent weight gain in a subject. A subject in need of such a treatment may be a subject who is obese, likely to become obese, overweight, or likely to become overweight. Subjects who are likely to become obese or overweight can be identified, for example, based on family history, genetics, diet, activity level, medication intake, or various combinations thereof.

In yet other embodiments, sirtuin-modulating compounds that increase the level and/or activity of a sirtuin protein may be administered to subjects suffering from a variety of other diseases and conditions that may be treated or prevented by promoting weight loss in the subject. Such diseases include, for example, high blood pressure, hypertension, high blood cholesterol, dyslipidemia, type 2 diabetes, insulin resistance, glucose intolerance, hyperinsulinemia, coronary heart disease, angina pectoris, congestive heart failure, stroke, gallstones, cholecystitis and cholelithiasis, gout, osteoarthritis, obstructive sleep apnea and respiratory problems, some types of cancer (such as endometrial, breast, prostate, and colon), complications of pregnancy, poor female reproductive health (such as menstrual irregularities, infertility, irregular ovulation), bladder control problems (such as stress incontinence); uric acid nephrolithiasis; psychological disorders (such as depression, eating disorders, distorted body image, and low self esteem). Finally, patients with AIDS can develop lipodystrophy or insulin resistance in response to combination therapies for AIDS.

In another embodiment, sirtuin-modulating compounds that increase the level and/or activity of a sirtuin protein may be used for inhibiting adipogenesis or fat cell differentiation, whether in vitro or in vivo. Such methods may be used for treating or preventing obesity.

In other embodiments, sirtuin-modulating compounds that increase the level and/or activity of a sirtuin protein may be used for reducing appetite and/or increasing satiety, thereby causing weight loss or avoidance of weight gain. A subject in need of such a treatment may be a subject who is overweight, obese or a subject likely to become overweight or obese. The method may comprise administering daily or, every other day, or once a week, a dose, e.g., in the form of a pill, to a subject. The dose may be an "appetite reducing dose."

In an exemplary embodiment, sirtuin-modulating compounds that increase the level and/or activity of a sirtuin protein may be administered as a combination therapy for treating or preventing weight gain or obesity. For example, one or more sirtuin-modulating compounds that increase the level and/or activity of a sirtuin protein may be administered in combination with one or more anti-obesity agents.

In another embodiment, sirtuin-modulating compounds that increase the level and/or activity of a sirtuin protein may be administered to reduce drug-induced weight gain. For example, a sirtuin-modulating compound that increases the level and/or activity of a sirtuin protein may be administered as a combination therapy with medications that may stimulate appetite or cause weight gain, in particular, weight gain due to factors other than water retention.

Metabolic Disorders/Diabetes

In another aspect, sirtuin-modulating compounds that increase the level and/or activity of a sirtuin protein may be used for treating or preventing a metabolic disorder, such as insulin-resistance, a pre-diabetic state, type II diabetes, and/or complications thereof. Administration of a sirtuin-modulating compound that increases the level and/or activity of a sirtuin protein may increase insulin sensitivity and/or decrease insulin levels in a subject. A subject in need of such a treatment may be a subject who has insulin resistance or other precursor symptom of type II diabetes, who has type II diabetes, or who is likely to develop any of these conditions. For example, the subject may be a subject having insulin resistance, e.g., having high circulating levels of insulin and/or associated conditions, such as hyperlipidemia, dyslipogenesis, hypercholesterolemia, impaired glucose tolerance, high blood glucose sugar level, other manifestations of syndrome X, hypertension, atherosclerosis and lipodystrophy.

In an exemplary embodiment, sirtuin-modulating compounds that increase the level and/or activity of a sirtuin protein may be administered as a combination therapy for treating or preventing a metabolic disorder. For example, one or more sirtuin-modulating compounds that increase the level and/or activity of a sirtuin protein may be administered in combination with one or more anti-diabetic agents.

Inflammatory Diseases

In other aspects, sirtuin-modulating compounds that increase the level and/or activity of a sirtuin protein can be used to treat or prevent a disease or disorder associated with inflammation. Sirtuin-modulating compounds that increase the level and/or activity of a sirtuin protein may be administered prior to the onset of, at, or after the initiation of inflammation. When used prophylactically, the compounds are preferably provided in advance of any inflammatory response or symptom. Administration of the compounds may prevent or attenuate inflammatory responses or symptoms.

In another embodiment, sirtuin-modulating compounds that increase the level and/or activity of a sirtuin protein may be used to treat or prevent allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). The compounds may be used to treat chronic hepatitis infection, including hepatitis B and hepatitis C.

Additionally, sirtuin-modulating compounds that increase the level and/or activity of a sirtuin protein may be used to treat autoimmune diseases, and/or inflammation associated with autoimmune diseases, such as arthritis, including rheumatoid arthritis, psoriatic arthritis, and ankylosing spondylitis, as well as organ-tissue autoimmune diseases (e.g., Raynaud's syndrome), ulcerative colitis, Crohn's disease, oral mucositis, scleroderma, myasthenia gravis, transplant rejection, endotoxin shock, sepsis, psoriasis, eczema, dermatitis, multiple sclerosis, autoimmune thyroiditis, uveitis, systemic lupus erythematosis, Addison's disease, autoimmune polyglandular disease (also known as autoimmune polyglandular syndrome), and Grave's disease.

In certain embodiments, one or more sirtuin-modulating compounds that increase the level and/or activity of a sirtuin protein may be taken alone or in combination with other compounds useful for treating or preventing inflammation.

Flushing

In another aspect, sirtuin-modulating compounds that increase the level and/or activity of a sirtuin protein may be used for reducing the incidence or severity of flushing and/or hot flashes which are symptoms of a disorder. For instance, the subject method includes the use of sirtuin-modulating compounds that increase the level and/or activity of a sirtuin protein, alone or in combination with other agents, for reducing incidence or severity of flushing and/or hot flashes in cancer patients. In other embodiments, the method provides for the use of sirtuin-modulating compounds that increase the level and/or activity of a sirtuin protein to reduce the incidence or severity of flushing and/or hot flashes in menopausal and post-menopausal woman.

In another aspect, sirtuin-modulating compounds that increase the level and/or activity of a sirtuin protein may be used as a therapy for reducing the incidence or severity of flushing and/or hot flashes which are side-effects of another drug therapy, e.g., drug-induced flushing. In certain embodiments, a method for treating and/or preventing drug-induced flushing comprises administering to a patient in need thereof a formulation comprising at least one flushing inducing compound and at least one sirtuin-modulating compound that increases the level and/or activity of a sirtuin protein. In other embodiments, a method for treating drug induced flushing comprises separately administering one or more compounds that induce flushing and one or more sirtuin-modulating compounds, e.g., wherein the sirtuin-modulating compound and flushing inducing agent have not been formulated in the same compositions. When using separate formulations, the sirtuin-modulating compound may be administered (1) at the same as administration of the flushing inducing agent, (2) intermittently with the flushing inducing agent, (3) staggered relative to administration of the flushing inducing agent, (4) prior to administration of the flushing inducing agent, (5) subsequent to administration of the flushing inducing agent, and (6) various combination thereof. Exemplary flushing inducing agents include, for example, niacin, raloxifene, antidepressants, anti-psychotics, chemotherapeutics, calcium channel blockers, and antibiotics.

In one embodiment, sirtuin-modulating compounds that increase the level and/or activity of a sirtuin protein may be used to reduce flushing side effects of a vasodilator or an antilipemic agent (including anticholesteremic agents and lipotropic agents). In an exemplary embodiment, a sirtuin-modulating compound that increases the level and/or activity of a sirtuin protein may be used to reduce flushing associated with the administration of niacin.

In another embodiment, the invention provides a method for treating and/or preventing hyperlipidemia with reduced flushing side effects. In another representative embodiment, the method involves the use of sirtuin-modulating compounds that increase the level and/or activity of a sirtuin protein to reduce flushing side effects of raloxifene. In another representative embodiment, the method involves the use of sirtuin-modulating compounds that increase the level and/or activity of a sirtuin protein to reduce flushing side effects of antidepressants or anti-psychotic agent. For instance, sirtuin-modulating compounds that increase the level and/or activity of a sirtuin protein can be used in conjunction (administered separately or together) with a serotonin reuptake inhibitor, or a 5HT2 receptor antagonist.

In certain embodiments, sirtuin-modulating compounds that increase the level and/or activity of a sirtuin protein may be used as part of a treatment with a serotonin reuptake inhibitor (SRI) to reduce flushing. In still another representative embodiment, sirtuin-modulating compounds that increase the level and/or activity of a sirtuin protein may be used to reduce flushing side effects of chemotherapeutic agents, such as cyclophosphamide and tamoxifen.

In another embodiment, sirtuin-modulating compounds that increase the level and/or activity of a sirtuin protein may be used to reduce flushing side effects of calcium channel blockers, such as amlodipine.

In another embodiment, sirtuin-modulating compounds that increase the level and/or activity of a sirtuin protein may be used to reduce flushing side effects of antibiotics. For example, sirtuin-modulating compounds that increase the level and/or activity of a sirtuin protein can be used in combination with levofloxacin.

Ocular Disorders

One aspect of the present invention is a method for inhibiting, reducing or otherwise treating vision impairment by administering to a patient a therapeutic dosage of sirtuin modulator selected from a compound disclosed herein, or a pharmaceutically acceptable salt, prodrug or a metabolic derivative thereof.

In certain aspects of the invention, the vision impairment is caused by damage to the optic nerve or central nervous system. In particular embodiments, optic nerve damage is caused by high intraocular pressure, such as that created by glaucoma. In other particular embodiments, optic nerve damage is caused by swelling of the nerve, which is often associated with an infection or an immune (e.g., autoimmune) response such as in optic neuritis.

In certain aspects of the invention, the vision impairment is caused by retinal damage. In particular embodiments, retinal damage is caused by disturbances in blood flow to the eye (e.g., arteriosclerosis, vasculitis). In particular embodiments, retinal damage is caused by disruption of the macula (e.g., exudative or non-exudative macular degeneration).

Exemplary retinal diseases include Exudative Age Related Macular Degeneration, Nonexudative Age Related Macular Degeneration, Retinal Electronic Prosthesis and RPE Transplantation Age Related Macular Degeneration, Acute Multifocal Placoid Pigment Epitheliopathy, Acute Retinal Necrosis, Best Disease, Branch Retinal Artery Occlusion, Branch Retinal Vein Occlusion, Cancer Associated and Related Autoimmune Retinopathies, Central Retinal Artery Occlusion, Central Retinal Vein Occlusion, Central Serous Chorioretinopathy, Eales Disease, Epimacular Membrane, Lattice Degeneration, Macroaneurysm, Diabetic Macular Edema, Irvine-Gass Macular Edema, Macular Hole, Subretinal Neovascular Membranes, Diffuse Unilateral Subacute Neuroretinitis, Nonpseudophakic Cystoid Macular Edema, Presumed Ocular Histoplasmosis Syndrome, Exudative Retinal Detachment, Postoperative Retinal Detachment, Proliferative Retinal Detachment, Rhegmatogenous Retinal Detachment, Tractional Retinal Detachment, Retinitis Pigmentosa, CMV Retinitis, Retinoblastoma, Retinopathy of Prematurity, Birdshot Retinopathy, Background Diabetic Retinopathy, Proliferative Diabetic Retinopathy, Hemoglobinopathies Retinopathy, Purtscher Retinopathy, Valsalva Retinopathy, Juvenile Retinoschisis, Senile Retinoschisis, Terson Syndrome and White Dot Syndromes.

Other exemplary diseases include ocular bacterial infections (e.g. conjunctivitis, keratitis, tuberculosis, syphilis, gonorrhea), viral infections (e.g. Ocular Herpes Simplex Virus, Varicella Zoster Virus, Cytomegalovirus retinitis, Human Immunodeficiency Virus (HIV)) as well as progressive outer retinal necrosis secondary to HIV or other HIV-associated and other immunodeficiency-associated ocular diseases. In addition, ocular diseases include fungal infections (e.g. *Candida choroiditis*, histoplasmosis), protozoal infections (e.g. toxoplasmosis) and others such as ocular toxocariasis and sarcoidosis.

One aspect of the invention is a method for inhibiting, reducing or treating vision impairment in a subject undergoing treatment with a chemotherapeutic drug (e.g., a neurotoxic drug, a drug that raises intraocular pressure such as a steroid), by administering to the subject in need of such treatment a therapeutic dosage of a sirtuin modulator disclosed herein.

Another aspect of the invention is a method for inhibiting, reducing or treating vision impairment in a subject undergoing surgery, including ocular or other surgeries performed in the prone position such as spinal cord surgery, by administering to the subject in need of such treatment a therapeutic dosage of a sirtuin modulator disclosed herein. Ocular surgeries include cataract, iridotomy and lens replacements.

Another aspect of the invention is the treatment, including inhibition and prophylactic treatment, of age related ocular diseases include cataracts, dry eye, age-related macular degeneration (AMD), retinal damage and the like, by administering to the subject in need of such treatment a therapeutic dosage of a sirtuin modulator disclosed herein.

Another aspect of the invention is the prevention or treatment of damage to the eye caused by stress, chemical insult or radiation, by administering to the subject in need of such treatment a therapeutic dosage of a sirtuin modulator disclosed herein. Radiation or electromagnetic damage to the eye can include that caused by CRT's or exposure to sunlight or UV.

In one embodiment, a combination drug regimen may include drugs or compounds for the treatment or prevention of ocular disorders or secondary conditions associated with these conditions. Thus, a combination drug regimen may include one or more sirtuin activators and one or more therapeutic agents for the treatment of an ocular disorder.

In one embodiment, a sirtuin modulator can be administered in conjunction with a therapy for reducing intraocular pressure. In another embodiment, a sirtuin modulator can be administered in conjunction with a therapy for treating and/or preventing glaucoma. In yet another embodiment, a sirtuin modulator can be administered in conjunction with a therapy for treating and/or preventing optic neuritis. In one embodiment, a sirtuin modulator can be administered in conjunction with a therapy for treating and/or preventing CMV Retinopathy. In another embodiment, a sirtuin modulator can be administered in conjunction with a therapy for treating and/or preventing multiple sclerosis.

Mitochondrial-Associated Diseases and Disorders

In certain embodiments, the invention provides methods for treating diseases or disorders that would benefit from increased mitochondrial activity. The methods involve administering to a subject in need thereof a therapeutically effective amount of a sirtuin activating compound. Increased mitochondrial activity refers to increasing activity of the mitochondria while maintaining the overall numbers of mitochondria (e.g., mitochondrial mass), increasing the numbers of mitochondria thereby increasing mitochondrial activity (e.g., by stimulating mitochondrial biogenesis), or combinations thereof. In certain embodiments, diseases and disorders that would benefit from increased mitochondrial activity include diseases or disorders associated with mitochondrial dysfunction.

In certain embodiments, methods for treating diseases or disorders that would benefit from increased mitochondrial activity may comprise identifying a subject suffering from a mitochondrial dysfunction. Methods for diagnosing a mitochondrial dysfunction may involve molecular genetic, pathologic and/or biochemical analyses. Diseases and disorders associated with mitochondrial dysfunction include diseases and disorders in which deficits in mitochondrial respiratory chain activity contribute to the development of pathophysiology of such diseases or disorders in a mammal. Diseases or disorders that would benefit from increased mitochondrial activity generally include for example, diseases in which free radical mediated oxidative injury leads to tissue degeneration, diseases in which cells inappropriately undergo apoptosis, and diseases in which cells fail to undergo apoptosis.

In certain embodiments, the invention provides methods for treating a disease or disorder that would benefit from increased mitochondrial activity that involves administering to a subject in need thereof one or more sirtuin activating compounds in combination with another therapeutic agent such as, for example, an agent useful for treating mitochondrial dysfunction or an agent useful for reducing a symptom associated with a disease or disorder involving mitochondrial dysfunction.

In exemplary embodiments, the invention provides methods for treating diseases or disorders that would benefit from increased mitochondrial activity by administering to a subject a therapeutically effective amount of a sirtuin activating compound. Exemplary diseases or disorders include, for example, neuromuscular disorders (e.g., Friedreich's Ataxia, muscular dystrophy, multiple sclerosis, etc.), disorders of neuronal instability (e.g., seizure disorders, migraine, etc.), developmental delay, neurodegenerative disorders (e.g., Alzheimer's Disease, Parkinson's Disease, amyotrophic lateral sclerosis, etc.), ischemia, renal tubular acidosis, age-related neurodegeneration and cognitive decline, chemotherapy fatigue, age-related or chemotherapy-induced menopause or irregularities of menstrual cycling or ovulation, mitochondrial myopathies, mitochondrial damage (e.g., calcium accumulation, excitotoxicity, nitric oxide exposure, hypoxia, etc.), and mitochondrial deregulation.

Muscular dystrophy refers to a family of diseases involving deterioration of neuromuscular structure and function, often resulting in atrophy of skeletal muscle and myocardial dysfunction, such as Duchenne muscular dystrophy. In certain embodiments, sirtuin activating compounds may be used for reducing the rate of decline in muscular functional capacities and for improving muscular functional status in patients with muscular dystrophy.

In certain embodiments, sirtuin modulating compounds may be useful for treatment mitochondrial myopathies. Mitochondrial myopathies range from mild, slowly progressive weakness of the extraocular muscles to severe, fatal infantile myopathies and multisystem encephalomyopathies. Some syndromes have been defined, with some overlap between them. Established syndromes affecting muscle include progressive external ophthalmoplegia, the Kearns-Sayre syndrome (with ophthalmoplegia, pigmentary retinopathy, cardiac conduction defects, cerebellar ataxia, and sensorineural deafness), the MELAS syndrome (mitochondrial encephalomyopathy, lactic acidosis, and stroke-like episodes), the MERFF syndrome (myoclonic epilepsy and ragged red fibers), limb-girdle distribution weakness, and infantile myopathy (benign or severe and fatal).

In certain embodiments, sirtuin activating compounds may be useful for treating patients suffering from toxic damage to mitochondria, such as, toxic damage due to calcium accumulation, excitotoxicity, nitric oxide exposure, drug induced toxic damage, or hypoxia.

In certain embodiments, sirtuin activating compounds may be useful for treating diseases or disorders associated with mitochondrial deregulation.

Muscle Performance

In other embodiments, the invention provides methods for enhancing muscle performance by administering a therapeutically effective amount of a sirtuin activating compound. For example, sirtuin activating compounds may be useful for improving physical endurance (e.g., ability to perform a physical task such as exercise, physical labor, sports activities, etc.), inhibiting or retarding physical fatigues, enhancing blood oxygen levels, enhancing energy in healthy individuals, enhance working capacity and endurance, reducing muscle fatigue, reducing stress, enhancing cardiac and cardiovascular function, improving sexual ability, increasing muscle ATP levels, and/or reducing lactic acid in blood. In certain embodiments, the methods involve administering an amount of a sirtuin activating compound that increase mitochondrial activity, increase mitochondrial biogenesis, and/or increase mitochondrial mass.

Sports performance refers to the ability of the athlete's muscles to perform when participating in sports activities. Enhanced sports performance, strength, speed and endurance are measured by an increase in muscular contraction strength, increase in amplitude of muscle contraction, shortening of muscle reaction time between stimulation and contraction. Athlete refers to an individual who participates in sports at any level and who seeks to achieve an improved level of strength, speed and endurance in their performance, such as, for example, body builders, bicyclists, long distance runners, short distance runners, etc. Enhanced sports performance in manifested by the ability to overcome muscle fatigue, ability to maintain activity for longer periods of time, and have a more effective workout.

In the arena of athlete muscle performance, it is desirable to create conditions that permit competition or training at higher levels of resistance for a prolonged period of time.

It is contemplated that the methods of the present invention will also be effective in the treatment of muscle related pathological conditions, including acute sarcopenia, for example, muscle atrophy and/or cachexia associated with burns, bed rest, limb immobilization, or major thoracic, abdominal, and/or orthopedic surgery.

In certain embodiments, the invention provides novel dietary compositions comprising sirtuin modulators, a method for their preparation, and a method of using the compositions for improvement of sports performance. Accordingly, provided are therapeutic compositions, foods and beverages that have actions of improving physical endurance and/or inhibiting physical fatigues for those people involved in broadly-defined exercises including sports requiring endurance and labors requiring repeated muscle exertions. Such dietary compositions may additional comprise electrolytes, caffeine, vitamins, carbohydrates, etc.

Other Uses

Sirtuin-modulating compounds that increase the level and/or activity of a sirtuin protein may be used for treating or preventing viral infections (such as infections by influenza, herpes or papilloma virus) or as antifungal agents. In certain embodiments, sirtuin-modulating compounds that increase the level and/or activity of a sirtuin protein may be administered as part of a combination drug therapy with another therapeutic agent for the treatment of viral diseases. In another embodiment, sirtuin-modulating compounds that increase the level and/or activity of a sirtuin protein may be administered as part of a combination drug therapy with another anti-fungal agent.

Subjects that may be treated as described herein include eukaryotes, such as mammals, e.g., humans, ovines, bovines, equines, porcines, canines, felines, non-human primate, mice, and rats. Cells that may be treated include eukaryotic cells, e.g., from a subject described above, or plant cells, yeast cells and prokaryotic cells, e.g., bacterial cells. For example, modulating compounds may be administered to farm animals to improve their ability to withstand farming conditions longer.

Sirtuin-modulating compounds that increase the level and/or activity of a sirtuin protein may also be used to increase lifespan, stress resistance, and resistance to apoptosis in plants. In one embodiment, a compound is applied to plants, e.g., on a periodic basis, or to fungi. In another embodiment, plants are genetically modified to produce a compound. In another embodiment, plants and fruits are treated with a compound prior to picking and shipping to increase resistance to damage during shipping. Plant seeds may also be contacted with compounds described herein, e.g., to preserve them.

In other embodiments, sirtuin-modulating compounds that increase the level and/or activity of a sirtuin protein may be used for modulating lifespan in yeast cells. Situations in which it may be desirable to extend the lifespan of yeast cells include any process in which yeast is used, e.g., the making of beer, yogurt, and bakery items, e.g., bread. Use of yeast having an extended lifespan can result in using less yeast or in having the yeast be active for longer periods of time. Yeast or other mammalian cells used for recombinantly producing proteins may also be treated as described herein.

Sirtuin-modulating compounds that increase the level and/or activity of a sirtuin protein may also be used to increase lifespan, stress resistance and resistance to apoptosis in insects. In this embodiment, compounds would be applied to useful insects, e.g., bees and other insects that are involved in pollination of plants. In a specific embodiment, a compound would be applied to bees involved in the production of honey. Generally, the methods described herein may be applied to any organism, e.g., eukaryote, which may have commercial importance. For example, they can be applied to fish (aquaculture) and birds (e.g., chicken and fowl).

Higher doses of sirtuin-modulating compounds that increase the level and/or activity of a sirtuin protein may also be used as a pesticide by interfering with the regulation of silenced genes and the regulation of apoptosis during development. In this embodiment, a compound may be applied to plants using a method known in the art that ensures the compound is bioavailable to insect larvae, and not to plants.

At least in view of the link between reproduction and longevity, sirtuin-modulating compounds that increase the level and/or activity of a sirtuin protein can be applied to affect the reproduction of organisms such as insects, animals and microorganisms.

4. Assays

Yet other methods contemplated herein include screening methods for identifying compounds or agents that modulate sirtuins. An agent may be a nucleic acid, such as an aptamer. Assays may be conducted in a cell based or cell free format. For example, an assay may comprise incubating (or contacting) a sirtuin with a test agent under conditions in which a sirtuin can be modulated by an agent known to modulate the sirtuin, and monitoring or determining the level of modulation of the sirtuin in the presence of the test agent relative to the absence of the test agent. The level of modulation of a sirtuin can be determined by determining its ability to deacetylate a substrate. Exemplary substrates are acetylated peptides which can be obtained from BIOMOL (Plymouth Meeting, Pa.). Preferred substrates include peptides of p53, such as those comprising an acetylated K382. A particularly preferred substrate is the Fluor de Lys-SIRT1 (BIOMOL), i.e., the acetylated peptide Arg-His-Lys-Lys (SEQ ID NO:2). Other substrates are peptides from human histones H3 and H4 or an acetylated amino acid. Substrates may be fluorogenic. The sirtuin may be SIRT1, Sir2, SIRT3, or a portion thereof. For example, recombinant SIRT1 can be obtained from BIOMOL. The reaction may be conducted for about minutes and stopped, e.g., with nicotinamide. The HDAC fluorescent activity assay/drug discovery kit (AK-500, BIOMOL Research Laboratories) may be used to determine the level of acetylation. Similar assays are described in Bitterman et al. (2002) J. Biol. Chem. 277: 45099. The level of modulation of the sirtuin in an assay may be compared to the level of modulation of the sirtuin in the presence of one or more (separately or simultaneously) compounds described herein, which may serve as positive or negative controls. Sirtuins for use in the assays may be full length sirtuin proteins or portions thereof. Since it has been shown herein that activating compounds appear to interact with the N-terminus of SIRT1, proteins for use in the assays include N-terminal portions of sirtuins, e.g., about amino acids 1-176 or 1-255 of SIRT1; about amino acids 1-174 or 1-252 of Sir2.

In one embodiment, a screening assay comprises (i) contacting a sirtuin with a test agent and an acetylated substrate under conditions appropriate for the sirtuin to deacetylate the substrate in the absence of the test agent; and (ii) determining the level of acetylation of the substrate, wherein a lower level of acetylation of the substrate in the presence of the test agent relative to the absence of the test agent indicates that the test agent stimulates deacetylation by the sirtuin, whereas a higher level of acetylation of the substrate in the presence of the test agent relative to the absence of the test agent indicates that the test agent inhibits deacetylation by the sirtuin.

Methods for identifying an agent that modulates, e.g., stimulates, sirtuins in vivo may comprise (i) contacting a cell with a test agent and a substrate that is capable of entering a cell in the presence of an inhibitor of class I and class II HDACs under conditions appropriate for the sirtuin to deacetylate the substrate in the absence of the test agent; and (ii) determining the level of acetylation of the substrate, wherein a lower level of acetylation of the substrate in the presence of the test agent relative to the absence of the test agent indicates that the test agent stimulates deacetylation by the sirtuin, whereas a higher level of acetylation of the substrate in the presence of the test agent relative to the absence of the test agent indicates that the test agent inhibits deacetylation by the sirtuin. A preferred substrate is an acetylated peptide, which is also preferably fluorogenic, as further described herein. The method may further comprise lysing the cells to determine the level of acetylation of the substrate. Substrates may be added to cells at a concentration ranging from about 1 μM to about 10 mM, preferably from about 10 μM to 1 mM, even more preferably from about 100 μM to 1 mM, such as about 200 μM. A preferred substrate is an acetylated lysine, e.g., ε-acetyl lysine (Fluor de Lys, FdL) or Fluor de Lys-SIRT1. A preferred inhibitor of class I and class II HDACs is trichostatin A (TSA), which may be used at concentrations ranging from about 0.01 to 100 μM, preferably from about 0.1 to 10 μM, such as 1 μM. Incubation of cells with the test compound and the substrate may be conducted for about minutes to 5 hours, preferably for about 1-3 hours. Since TSA inhibits all class I and class II HDACs, and that certain substrates, e.g., Fluor de Lys, is a poor substrate for SIRT2 and even less a substrate for SIRT3-7, such an assay may be used to identify modulators of SIRT1 in vivo.

5. Pharmaceutical Compositions

The sirtuin-modulating compounds described herein may be formulated in a conventional manner using one or more physiologically or pharmaceutically acceptable carriers or excipients. For example, sirtuin-modulating compounds and their pharmaceutically acceptable salts and solvates may be formulated for administration by, for example, injection (e.g. SubQ, IM, IP), inhalation or insufflation (either through the mouth or the nose) or oral, buccal, sublingual, transdermal, nasal, parenteral or rectal administration. In one embodiment, a sirtuin-modulating compound may be administered locally, at the site where the target cells are present, i.e., in a specific tissue, organ, or fluid (e.g., blood, cerebrospinal fluid, etc.).

Sirtuin-modulating compounds can be formulated for a variety of modes of administration, including systemic and topical or localized administration. Techniques and formulations generally may be found in Remington's Pharmaceutical Sciences, Meade Publishing Co., Easton, Pa. For parenteral administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets, lozenges, or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation (e.g., pulmonary delivery), sirtuin-modulating compounds may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

Sirtuin-modulating compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle; e.g., sterile pyrogen-free water, before use.

Sirtuin-modulating compounds may also be formulated in rectal compositions such as suppositories or retention enemas, e.g., containing conventional suppository bases such as cocoa butter or other glycerides.

In addition to the formulations described previously, sirtuin-modulating compounds may also be formulated as a depot preparation. Such long acting formulations may be administered by implantation (for example subcutaneously or intramuscularly) or by intramuscular injection. Thus, for example, sirtuin-modulating compounds may be formulated with suitable polymeric or hydrophobic materials (for example as an emulsion in an acceptable oil) or ion exchange resins, or as sparingly soluble derivatives, for example, as a sparingly soluble salt. Controlled release formula also includes patches.

In certain embodiments, the compounds described herein can be formulated for delivery to the central nervous system (CNS) (reviewed in Begley, Pharmacology & Therapeutics 104: 29-45 (2004)). Conventional approaches for drug delivery to the CNS include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

Liposomes are a further drug delivery system which is easily injectable. Accordingly, in the method of invention the active compounds can also be administered in the form of a liposome delivery system. Liposomes are well-known by a person skilled in the art. Liposomes can be formed from a variety of phospholipids, such as cholesterol, stearylamine of phosphatidylcholines. Liposomes being usable for the method of invention encompass all types of liposomes including, but not limited to, small unilamellar vesicles, large unilamellar vesicles and multilamellar vesicles.

Another way to produce a formulation, particularly a solution, of a sirtuin modulator such as resveratrol or a derivative thereof, is through the use of cyclodextrin. By cyclodextrin is meant $\alpha$-, $\beta$-, or $\gamma$-cyclodextrin. Cyclodextrins are described in detail in Pitha et al., U.S. Pat. No. 4,727,064, which is incorporated herein by reference. Cyclodextrins are cyclic oligomers of glucose; these compounds form inclusion complexes with any drug whose molecule can fit into the lipophile-seeking cavities of the cyclodextrin molecule.

Rapidly disintegrating or dissolving dosage forms are useful for the rapid absorption, particularly buccal and sublingual absorption, of pharmaceutically active agents. Fast melt dosage forms are beneficial to patients, such as aged and pediatric patients, who have difficulty in swallowing typical solid dosage forms, such as caplets and tablets. Additionally, fast melt dosage forms circumvent drawbacks associated with, for example, chewable dosage forms, wherein the length of time an active agent remains in a patient's mouth plays an important role in determining the amount of taste masking and the extent to which a patient may object to throat grittiness of the active agent.

Pharmaceutical compositions (including cosmetic preparations) may comprise from about 0.00001 to 100% such as from 0.001 to 10% or from 0.1% to 5% by weight of one or more sirtuin-modulating compounds described herein. In other embodiments, the pharmaceutical composition comprises: (i) 0.05 to 1000 mg of the compounds of the invention, or a pharmaceutically acceptable salt thereof, and (ii) 0.1 to 2 grams of one or more pharmaceutically acceptable excipients.

In one embodiment, a sirtuin-modulating compound described herein, is incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Formulations may be colorless, odorless ointments, lotions, creams, microemulsions and gels.

Sirtuin-modulating compounds may be incorporated into ointments, which generally are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing.

Sirtuin-modulating compounds may be incorporated into lotions, which generally are preparations to be applied to the skin surface without friction, and are typically liquid or semiliquid preparations in which solid particles, including the active agent, are present in a water or alcohol base. Lotions are usually suspensions of solids, and may comprise a liquid oily emulsion of the oil-in-water type.

Sirtuin-modulating compounds may be incorporated into creams, which generally are viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington's, supra, is generally a nonionic, anionic, cationic or amphoteric surfactant.

Sirtuin-modulating compounds may be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology (New York: Marcel Dekker, 1992), volume 9).

Sirtuin-modulating compounds may be incorporated into gel formulations, which generally are semisolid systems consisting of either suspensions made up of small inorganic particles (two-phase systems) or large organic molecules distributed substantially uniformly throughout a carrier liquid (single phase gels). Although gels commonly employ aqueous carrier liquid, alcohols and oils can be used as the carrier liquid as well.

Other active agents may also be included in formulations, e.g., other anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate).

In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Conditions of the eye can be treated or prevented by, e.g., systemic, topical, intraocular injection of a sirtuin-modulating compound, or by insertion of a sustained release device that releases a sirtuin-modulating compound. A sirtuin-modulating compound that increases the level and/or activity of a sirtuin protein may be delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material. Alternatively, the compounds of the invention may be injected directly into the vitreous and aqueous humour. In a further alternative, the compounds may be administered systemically, such as by intravenous infusion or injection, for treatment of the eye.

Sirtuin-modulating compounds described herein may be stored in oxygen free environment. For example, resveratrol or analog thereof can be prepared in an airtight capsule for oral administration, such as Capsugel from Pfizer, Inc.

Cells, e.g., treated ex vivo with a sirtuin-modulating compound, can be administered according to methods for administering a graft to a subject, which may be accompanied, e.g., by administration of an immunosuppressant drug, e.g., cyclosporin A. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000.

Toxicity and therapeutic efficacy of sirtuin-modulating compounds can be determined by standard pharmaceutical procedures in cell cultures or experimental animals. The $LD_{50}$ is the dose lethal to 50% of the population. The ED50 is the dose therapeutically effective in 50% of the population. The dose ratio between toxic and therapeutic effects ($LD_{50}/ED_{50}$) is the therapeutic index. Sirtuin-modulating compounds that exhibit large therapeutic indexes are preferred. While sirtuin-modulating compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

6. Kits

Also provided herein are kits, e.g., kits for therapeutic purposes or kits for modulating the lifespan of cells or modulating apoptosis. A kit may comprise one or more sirtuin-modulating compounds, e.g., in premeasured doses. A kit may optionally comprise devices for contacting cells with the compounds and instructions for use. Devices include syringes, stents and other devices for introducing a sirtuin-modulating compound into a subject (e.g., the blood vessel of a subject) or applying it to the skin of a subject.

In yet another embodiment, the invention provides a composition of matter comprising a sirtuin modulator of this invention and another therapeutic agent (the same ones used in combination therapies and combination compositions) in separate dosage forms, but associated with one another. The term "associated with one another" as used herein means that the separate dosage forms are packaged together or otherwise attached to one another such that it is readily apparent that the separate dosage forms are intended to be sold and administered as part of the same regimen. The agent and the sirtuin modulator are preferably packaged together in a blister pack or other multi-chamber package, or as connected, separately sealed containers (such as foil pouches or the like) that can be separated by the user (e.g., by tearing on score lines between the two containers).

In still another embodiment, the invention provides a kit comprising in separate vessels, a) a sirtuin modulator of this invention; and b) another therapeutic agent such as those described elsewhere in the specification.

The practice of the present methods will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

EXEMPLIFICATION

The invention now being generally described, it will be more readily understood by reference to the following examples which are included merely for purposes of illustration of certain aspects and embodiments of the present invention, and are not intended to limit the invention in any way.

Example 1

Preparation of N-(pyridin-4-yl)-6-(3-(trifluoromethyl)phenyl)-2H-pyrido[3,2-b][1,4]oxazine-4(3H)-carboxamide (Compound 500)

Step 1. Synthesis of 6-bromo-2-nitropyridin-3-ol (2)

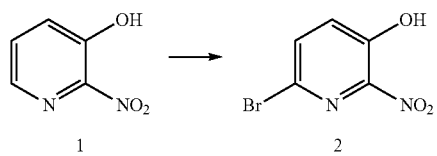 [SMILES: O=[N+]([O-])c1ncccc1O ; O=[N+]([O-])c1nc(Br)ccc1O]

At 0° C., Br$_2$ was slowly added to a mixture of 2-nitropyridin-3-ol (1; 80.0 g, 570 mmol) and NaOCH$_3$ (30.8 g, 570 mmol) in methanol (600 mL) and stirred at this temperature for 30 min. AcOH (1.5 mL) was added to the mixture and stirred again for 10 min. The crude reaction mixture was then concentrated in vacuo to afford a yellow solid, which was triturated in mixed petroleum ether/EtOAc to give 6-bromo-2-nitropyridin-3-ol (2; 35.0 g, 28%). MS (ESI) calcd for C$_5$H$_3$BrN$_2$O$_3$ (m/z): 217.93.

Step 2. Synthesis of 6-bromo-3-(2-bromoethoxy)-2-nitropyridine (3)

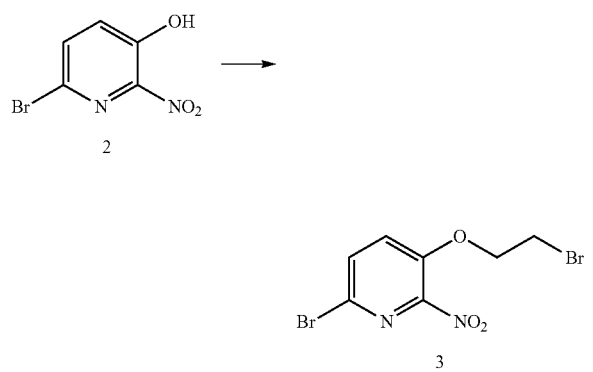 [SMILES: O=[N+]([O-])c1nc(Br)ccc1O ; O=[N+]([O-])c1nc(Br)ccc1OCCBr]

PPh$_3$ (900 mg, 3.4 mmol) was dissolved in THF (10 mL). The diisopropylazodicarboxylate (DIAD) (688 mg, 3.4 mmol) was added dropwise to the solution at 0° C. The mixture was stirred at 0° C. for 30 min. White solid appeared. Then 2-bromoethan-1-ol (427 mg, 3.4 mmol) and 6-bromo-2-nitropyridin-3-ol (2; 500 mg, 2.29 mmol) in THF were added dropwise at 0° C. The white solid disappeared and the resulting mixture was stirred at room temp for 2 h. In general, the solvent was concentrated and the mixture was purified by silica gel chromatography to afford 6-bromo-3-(2-bromoethoxy)-2-nitropyridine (3; 600 mg, 80%). MS (ESI) calcd for C$_7$H$_6$Br$_2$N$_2$O$_3$ (m/z): 323.87.

Step 3. Synthesis of 6-bromo-3,4-dihydro-2H-pyrido[3,2-b][1,4]oxazine (5)

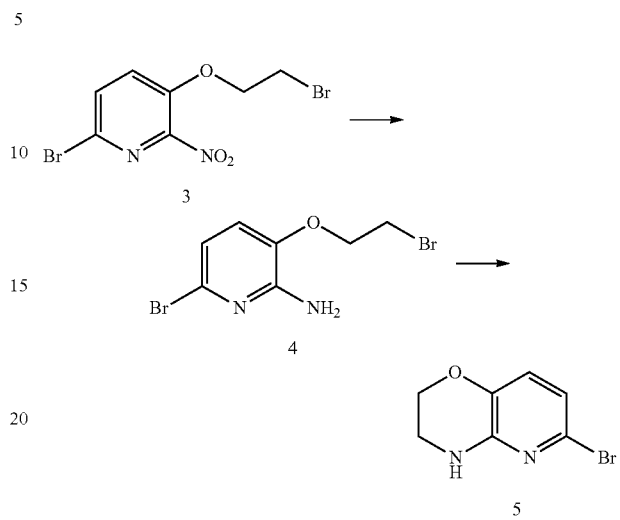

Prepared in a similar manner as 6-bromo-4H-pyrido[3,2-b][1,4]oxazin-3-one referenced in WO 2007/118130. To a solution of 6-bromo-3-(2-bromoethoxy)-2-nitropyridine (3; 560 mg, 1.73 mmol) in glacial acetic acid (6 mL) was added Fe (387 mg, 6.91 mmol) in one portion. The reaction mixture was heated at 90° C. for 5 h, then cooled down, diluted in EtOAc and filtered through a silica plug using EtOAc as the eluent. After evaporation of the AcOH, the residue 4 was dissolved in DMF (5 mL), K$_2$CO$_3$ (716 mg, 5.19 mmol) was added and the mixture was heated to 90° C. overnight. In general, the solvent was concentrated and the mixture was purified by silica gel chromatography to afford 6-bromo-3,4-dihydro-2H-pyrido[3,2-b][1,4]oxazine (5; 185 mg, 50%). MS (ESI) calcd for C$_7$H$_7$BrN$_2$O (m/z): 213.97.

Step 4. Synthesis of 6-(3-(trifluoromethyl)phenyl)-3,4-dihydro-2H-pyrido[3,2-b][1,4]oxazine (6)

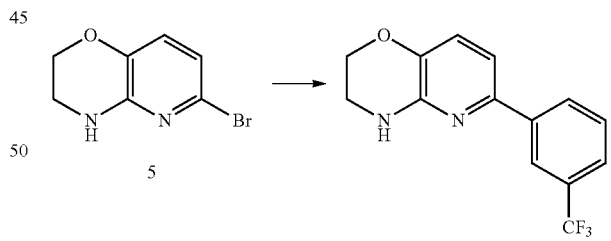

6-bromo-3,4-dihydro-2H-pyrido[3,2-b][1,4]oxazine (5; 2.0 g, 9.30 mmol), 3-(trifluoromethyl)-phenylboronic acid (2.65 g, 13.95 mmol), Pd(Ph$_3$)$_4$ (215 mg, 0.186 mmol) and CsCO$_3$ (6.0 g, 18.6 mmol) were all dissolved in dioxane: H$_2$O mixture (45 mL:1 mL) and heated to 50° C. overnight. Product peak seen by LCMS, but some starting material remained, added more boronic acid and stirred at 50° C. overnight. The starting material peak was unchanged, cooled to room temp and some precipitates started to crash out. Diluted with water (40 mL), extracted with EtOAc (3×40 mL), washed with brine, dried over MgSO$_4$, filtered, concentrated and purified through ISCO silica column (0 to 100% EtOAc/pentanes) to collect mixed fractions of 6-(3-(trifluoromethyl)phenyl)-3,4-dihydro-2H-pyrido[3,2-b][1,4]oxazine (6) MS (ESI) calcd for $C_{14}H_{11}F_3N_2O$ (m/z) 280.08. found 281 [M+H].

This general coupling procedure could be used to prepare a variety of 6-aryl-3,4-dihydro-2H-pyrido[3,2-b][1,4]oxazine derivatives by substituting the appropriate boronic acid for 3-(trifluoromethyl)-phenylboronic acid.

Step 5. Synthesis of N-(thiazol-2-yl)-6-(3-(trifluoromethyl)phenyl)-2H-pyrido[3,2-b][1,4]oxazine-4(3H)-carboxamide (Compound 500)

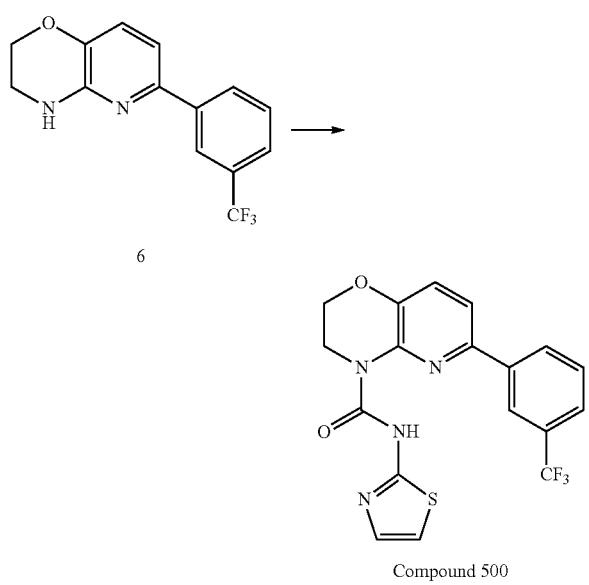

Compound 500

Prepared according to a similar literature procedure as Gool et al *Tet Lett,* 2008, 49, 7171-7173. Dissolved starting material 6-(3-(trifluoromethyl)phenyl)-3,4-dihydro-2H-pyrido[3,2-b][1,4]oxazine (6; 50 mg, 0.18 mmol) in $CH_2Cl_2$ (approx. 3 mL) added triethylamine (0.06 mL, 0.43 mmol), stirred and then added triphosgene (21.13 mg, 0.07 mmol) in 1 mL of $CH_2Cl_2$. Allowed the reaction to stir for approximately 10 min., then added 2-aminothiazole (28.52 mg, 0.29 mmol) and allowed to run for 30 min. Still a bit of starting material remained so added 1 more equivalent of 2-aminothiazole and allowed to stir for 30 min. The reaction was diluted with $CH_2Cl_2$, washed with 10% $NH_4Cl$ and the organic layers extracted and subjected to column chromatography ($CH_2Cl_2$:MeOH (0-3%)). Recrystallization in MeOH afforded the desired N-(thiazol-2-yl)-6-(3-(trifluoromethyl)phenyl)-2H-pyrido[3,2-b][1,4]oxazine-4(3H)-carboxamide (Compound 500) in approximately 90% purity by UV. MS (ESI) calcd for $C_{14}H_{13}F_3N_4O_2S$ (m/z) 406.07. found 407 [M+H].

This general procedure could be used to prepare a variety of 6-aryl-3,4-dihydro-2H-pyrido[3,2-b][1,4]oxazine-4(3H)-carboxamide derivatives by substituting the appropriate amine for 2-aminothiazole.

Example 2

Preparation of 6-(3-chlorophenyl)-N-(pyridin-4-yl)-2H-pyrido[3,2-b][1,4]oxazine-4(3H)-carboxamide (Compound 541)

Step 1. Synthesis of 6-bromo-N-(pyridin-4-yl)-2H-pyrido[3,2-b][3,4]oxazine-4(3H)-carboxamide (7)

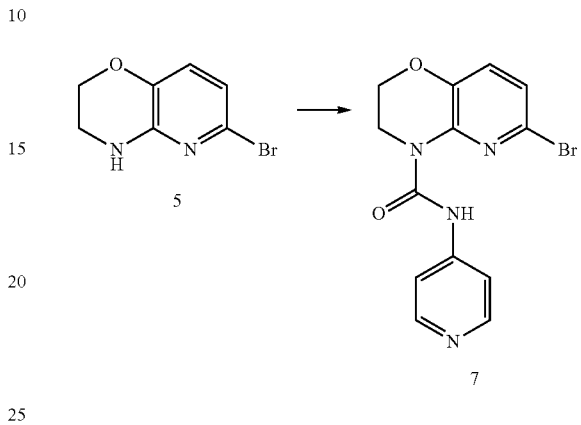

Prepared according to a similar literature procedure as Gool et al *Tet Lett,* 2008, 49, 7171-7173. 6-bromo-3,4-dihydro-2H-pyrido[3,2-b][1,4]oxazine (5) and 4-aminopyridine were subjected to the general urea formation conditions outlined herein and purified by column chromatography eluding with EtOAc:pentanes to afford 6-bromo-N-(pyridin-4-yl)-2H-pyrido[3,2-b][1,4]oxazine-4(3H)-carboxamide (7; 62 mg, 62%). MS (ESI) calcd for $C_{13}H_{11}BrN_4O_2$ (m/z) 335.16. found 336[M+H].

Step 2. Synthesis of 6-(3-chlorophenyl)-N-(pyridin-4-yl)-2H-pyrido[3,2-b][1,4]oxazine-4(3)-carboxamide (Compound 541)

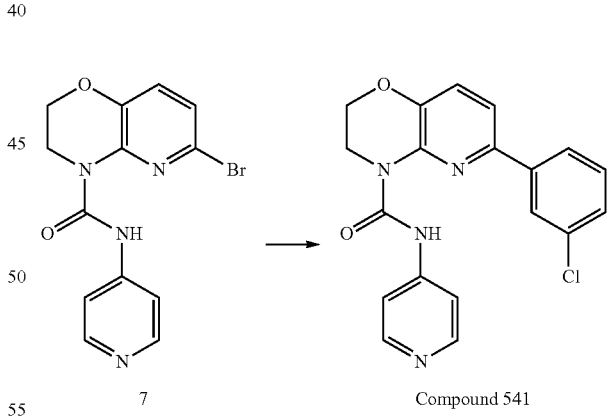

Following the general coupling procedure described above, the 6-bromo-N-(pyridin-4-yl)-2H-pyrido[3,2-b][1,4]oxazine-4(3H)-carboxamide (7; 275.5 mg, 0.822 mmol), 3-(trifluoromethyl)-phenyl boronic acid (160.2 mg, 1.03 mmol), and $CsCO_3$ (0725 mg, 2.1 mmol) were all dissolved in dioxane:$H_2O$ mixture (15 mL: 1.5 mL) and heated to 60° C. overnight. Monitored reaction by TLC. Diluted crude reaction mixture with water (8 mL), extracted with $CH_2Cl_2$ (3×10 mL), washed with brine, dried over $Na_2SO_4$, filtered, concentrated and purified by column chromatography eluding with EtOAc:pentanes to afford 6-(3-chlorophenyl)-N-(pyridin-4-yl)-2H-pyrido[3,2-b][1,4]oxazine-4(3H)-carboxamide (Compound 541; 110 mg, 36%). MS (ESI) calcd for $C_{19}H_{15}ClN_4O_2$ (m/z) 366.8. found 368[M+H].

Example 3

Preparation of N-(5-(pyrrolidin-1-ylmethyl)thiazol-2-yl)-6-(3-(trifluoromethyl)phenyl)-2H-pyrido[3,2-b][1,4]oxazine-4(3H)-carboxamide (Compound 505)

Step 1. Synthesis of tert-butyl 5-(hydroxymethyl)thiazol-2-ylcarbamate (10)

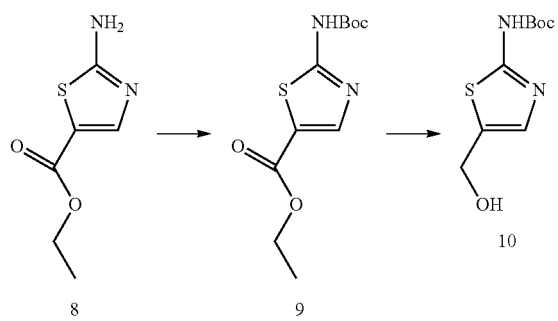 [SMILES: CCOC(=O)c1cnc(N)s1 ; CCOC(=O)c1cnc(NC(=O)OC(C)(C)C)s1 ; CC(C)(C)OC(=O)Nc1ncc(CO)s1]

A slurry of ethyl 2-aminothiazole-5-carboxylate (8; 145 g, 840 mmol), di-tert-butyl dicarbonate (275 g, 1260 mmol) and 4-Dimethylaminopyridine (DMAP) (5 mg, catalytic) in THF (2175 mL) was stirred at 30° C. for 5.5 h. The reaction mixture was concentrated to dryness and EtOAc (1450 mL) was added. The organic solvent was washed with water (2×435 mL) and brine (2×145 mL), dried over $MgSO_4$ and concentrated to give ethyl 2-(tertbutoxycarbonylamino)thiazole-5-carboxylate (9; 227 g, 99.23%) as a crude product, which was used for the next step without any further purification. MS (ESI) calcd for $C_{11}H_{16}N_2O_4S$ (m/z) 272.32.

A stirred solution of ethyl 2-(tert-butoxycarbonylamino)thiazole-5-carboxylate (9; 227 g, 830 mmol) in anhydrous THF (1512 mL) was cooled to −45° C. A solution of superhydride in THF (1.0 M, 1877 mL) was added over 1 hr, and then the reaction mixture was stirred at −45° C. for 2 h, warmed to room temp for 20 h. The reaction was quenched was brine, and warmed to room temp. The mixture was concentrated, taken up in EtOAc and washed with brine, dried over $Na_2SO_4$, concentrated and purified by column chromatography on silica gel (petroleum ether/ethyl acetate=1:1) to give tert-butyl 5-(hydroxymethyl)thiazol-2-ylcarbamate (10; 95 g, 49%). MS (ESI) calcd for $C_9H_{14}N_2O_3S$ (m/z) 230.28.

Step 2. Synthesis of 5-(pyrrolidin-1-ylmethyl)thiazol-2-amine—hydrochloride salt (12)

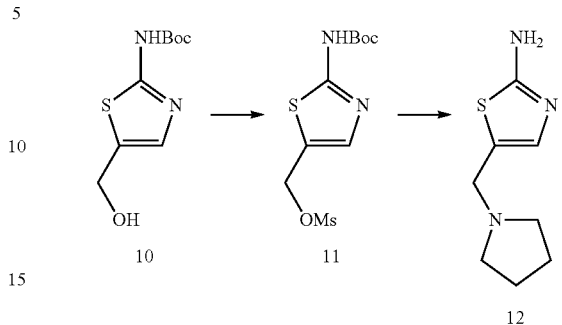

A solution of tert-butyl 5-(hydroxymethyl)thiazol-2-ylcarbamate (10; 37 g, 160 mmol), triethylamine (24.2 g, 240 mmol) in $CH_2Cl_2$ (231 mL) was cooled to 0° C. Mesyl chloride (23.16 g, 200 mmol) was added and the mixture was extracted with $CH_2Cl_2$ (2×93 mL). The combined organic layers were dried over $Na_2SO_4$ and concentrated in vacuo to give 2-(tert-butoxycarbonylamino)thiazol-5-yl)methyl methanesulfonate (11; 40 g, 75%). MS (ESI) calcd for $C_{10}H_{16}N_2O_5S_2$ (m/z) 308.37.

To a stirred solution of 2-(tert-butoxycarbonylamino)thiazol-5-yl)methyl methanesulfonate (11; g, 0.13 mol) in $CH_2Cl_2$ (140 mL) was added pyrrolidine (37.69 g, 530 mmol) at 0° C. and warmed to room temp. The mixture was washed with saturated $NaHCO_3$, and brine (93 mL). The organic solvent was dried over $Na_2SO_4$, concentrated and purified by column chromatography on silica gel (petroleum ether:ethyl acetate=1:1) to give 5-(pyrrolidin-1-ylmethyl)thiazol-2-amine (as the free amine)(12; 34 g, 75%). MS (ESI) calcd for $C_8H_{13}N_3S$ (m/z) 183.27.

A stirred solution of 5-(pyrrolidin-1-ylmethyl)thiazol-2-amine (12; 34 g, 190 mmol) in methanol (121 mL) was bubbled with HCl(gas) and monitored by TLC until all material consumed. The solvent was removed and EtOAc (121 mL) was added to form a precipitate. The mixture was filtered and the filter cake was washed successively with EtOAc to give 5-(pyrrolidin-1-ylmethyl)thiazol-2-amine (as the HCl salt) (12; 20.6 g, 67%) as a white solid. MS (ESI) calcd for $C_8H_{13}N_3S.HCl$ (m/z) 219.73. found 184 [M+H].

Step 3. Synthesis of N-(5-(pyrrolidin-1-ylmethyl)thiazol-2-yl)-6-(3-(trifluoromethyl)phenyl)-2H-pyrido[3,2-b][1,4]oxazine-4(3H)-carboxamide (Compound 505)

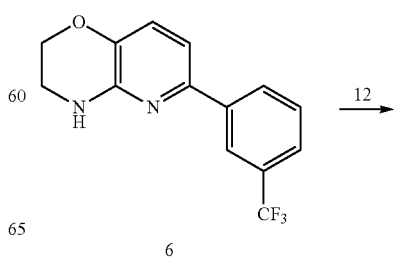

-continued

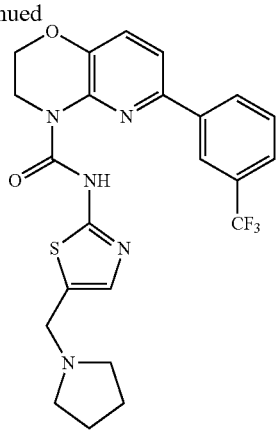

Compound 505

Prepared according to the general procedure described above to afford N-(5-(pyrrolidin-1-ylmethyl)thiazol-2-yl)-6-(3-(trifluoromethyl)phenyl)-2H-pyrido[3,2-b][1,4]oxazine-4(3H)-carboxamide (Compound 505), which was purified by column chromatography eluding with (EtOAc:pentanes) afforded N-(5-(pyrrolidin-1-ylmethyl)thiazol-2-yl)-6-(3-(trifluoromethyl)phenyl)-2H-pyrido[3,2-b][1,4]oxazine-4(3H)-carboxamide 505 (64.3 mg, 53%). MS (ESI) calcd for $C_{23}H_{22}F_3N_5O_2S$ (m/z) 489.51. found 491 [M+H].

Example 4

Preparation of N-(6-morpholinopyridin-2-yl)-6-(3-(trifluoromethyl)phenyl)-2H-pyrido[3,2-b][1,4]oxazine-4(3H)-carboxamide—trifluoracetate salt (Compound 506)

Step 1. Synthesis of 6-morpholinopyridin-2-amine (14) $NH_2NH_2$

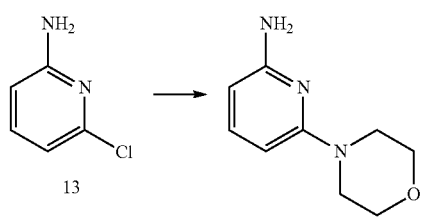

A mixture of 4-chloro-2-aminopyridine (13; 19.3 g, 150 mmol), $K_2CO_3$ (41.7 g, 0.30 mol) and morpholine (38.9 mL, 450 mmol) in DMSO (150 mL) was stirred at 190° C. (oil bath) for 10 h. After cooling to room temperature, water (300 mL) was added and extracted with ethyl acetate (4×150 mL). The combined organic layers were washed with water (3×25 mL), dried over $Na_2SO_4$ and concentrated in vacuo. The residue was purified by silica gel chromatography (10:1 petroleum ether:ethyl acetate) to give 6-morpholinopyridin-2-amine as a white solid (14; 9.0 g, 54.8 mmol). MS (ESI) calcd for $C_9H_{13}N_3O$ (m/z): 179.11. found 180 [M+H].

2-(pyrrolidin-1-yl)pyridin-4-amine

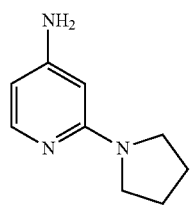

15 was prepared by the same sequence above, starting from 2-chloropyridin-4-amine.

Step 2. Synthesis of N-(6-morpholinopyridin-2-yl)-6-(3-(trifluoromethyl)phenyl)-2H-pyrido[3,2-b][1,4]oxazine-4(3H)-carboxamide—trifluoroacetate salt (Compound 505)

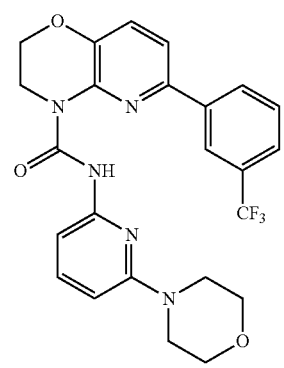

Compound 506

Prepared according to the general procedure described above to afford N-(6-morpholinopyridin-2-yl)-6-(3-(trifluoromethyl)phenyl)-2H-pyrido[3,2-b][1,4]oxazine-4(3H)-carboxamide (506), which was purified by column chromatography (EtOAc:pentanes), subsequent purification by HPLC eluding with MeOH and 0.1% TFA afforded the TFA salt (68.2 mg, 32%). MS (ESI) calcd for $C_{24}H_{22}F_3N_5O_3 \cdot C_2HO_2F_3$ (m/z) 599.48. found 486 [M+H].

Example 5

Preparation of N-(6-(morpholinomethyl)pyridin-3-yl)-6-(3-(trifluoromethyl)phenyl)-2H-pyrido[3,2-b][1,4]oxazine-4(3H)-carboxamide (Compound 507)

Step 1. Synthesis of ethyl 5-(tert-butoxycarbonylamino)picolinate (18)

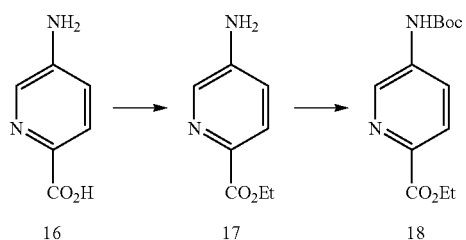 [SMILES: Nc1ccc(C(=O)O)nc1 ; CCOC(=O)c1ccc(N)cn1 ; CCOC(=O)c1ccc(NC(=O)OC(C)(C)C)cn1]

To a solution of 5-aminopyridiencarboxylic acid (16; 8.4 g, 60.8 mmol) inethanol (100 mL) was added $SOCl_2$ (14.5 g, 120 mmol) at 0° C. The mixture was refluxed for 12 h. The solvent was removed and saturated $Na_2CO_3$ solution was added to adjust pH=9 and filtrated to give a solid. Dried in vacuo to give ethyl 5-aminopicolinate (17; 7.5 g, 75%). MS (ESI) calcd for $C_8H_{10}N_2O_2$ (m/z) 166.18.

To a solution of ethyl 5-aminopicolinate (17; 7.5 g, 45 mmol) in t-BuOH (60 mL) and acetone (20 mL) was added DMAP (0.10 g, 0.9 mmol) and di-t-butyl dicarbonate (19.6 g, 90 mmol). The reaction was stirred at room temp overnight. The solvent was removed and hexane (150 mL) was added and cooled to −20° C. for 2 h. The mixture was filtered and the solid was dried in vacuo to give ethyl 5-(tert-butoxycarbonylamino)picolinate (18; 8.9 g, 53%). MS (ESI) calcd for $C_{13}H_{18}N_2O_4$ (m/z) 266.29.

Step 2. Synthesis of tert-butyl 6-(hydroxymethyl)pyridin-3-ylcarbamate (19)

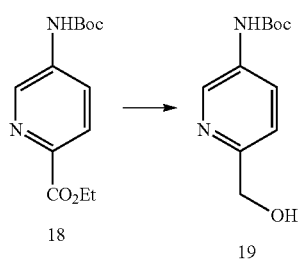 [SMILES: CCOC(=O)c1ccc(NC(=O)OC(C)(C)C)cn1 ; CC(C)(C)OC(=O)Nc1ccc(CO)nc1]

To a stirred solution of ethyl 5-(tert-butoxycarbonylamino)picolinate (18; 8.9 g, 24 mmol) in ethyl ether (200 mL) under nitrogen was added lithium aluminum hydride (LAH) (1.8 g, 48 mmol) in ethyl ether (100 mL) over a period of 30 min at 0° C. The reaction mixture was stirred for 3 h, water (1 mL) and 10% NaOH solution (2 mL) was added and the mixture was filtered and the filtrate was dried over $Na_2SO_4$ and concentrated under reduced pressure to give compound tert-butyl 6-(hydroxymethyl)pyridin-3-ylcarbamate (19; 4.2 g, 78%). MS (ESI) calcd for $C_1H_{16}N_2O_3$ (m/z) 224.26.

Step 3. Synthesis of tert-butyl 6-(morpholinomethyl)pyridin-3-ylcarbamate (21)

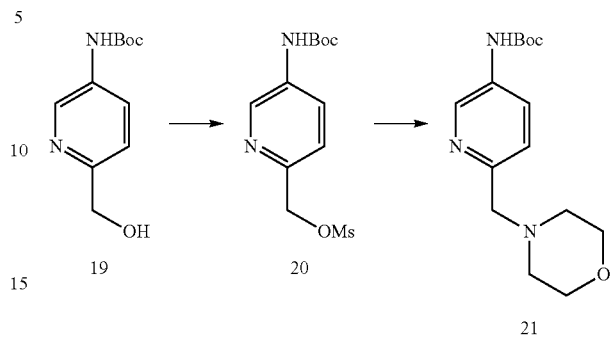

To a solution of tert-butyl 6-(hydroxymethyl)pyridin-3-ylcarbama (19; 4.2 g, 18.8 mmol) and DIPEA (7.0 g, 56.4 mmol) in THF (20 mL) was added MSCl (2.8 g, 24.4 mmol) over a period of 30 min at 0° C. and the mixture was stirred for 1 h. The reaction was quenched by adding saturated aqueous $NaHCO_3$ and extracted with EtOAc (3×60 mL). The combined organic layer was washed with brine and dried over $Na_2SO_4$. The organic solvent was removed to give compound (5-(tert-butoxycarbonylamino)pyridin-2-yl) methyl methanesulfonate (20; 5.5 g) without further purification for next step.

A mixture of (5-(tert-butoxycarbonylamino)pyridin-2-yl) methyl methanesulfonate (20; 1.70 g), morpholine (1.0 g, 11.3 mmol) and $K_2CO_3$ (2.30 g, 16.9 mmol) acenitrile (30 mL) was stirred at room temperature for 12 h. Water (30 mL) was added and the mixture was extracted with ethyl acetate (3×30 mL) and dried over $MgSO_4$, concentrated in vacuo and purified by chromatography on silica gel (petroleum ether:ethyl acetate=1:1 to 1:3) to give tert-butyl 6-(morpholinomethyl)pyridin-3-ylcarbamate (21; 1.20 g, 71% for two steps). MS (ESI) calcd for $C_{15}H_{23}N_3O_3$ (m/z) 293.36.

Step 4. Synthesis of 6-(morpholinomethyl)pyridin-3-amine (22)

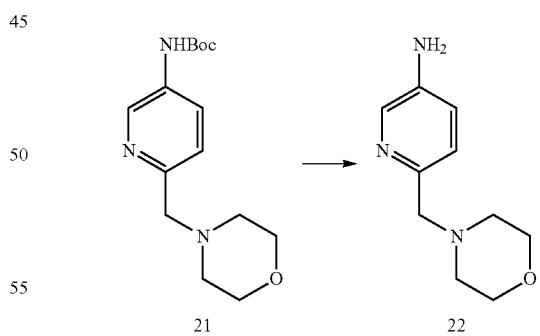

To a solution of tert-butyl 6-(morpholinomethyl)pyridin-3-ylcarbamate (21; 1.20 g, 4.1 mmol) in $CH_2Cl_2$ (20 mL) was added TFA (6 mL). The mixture was stirred for 12 h at room temperature. The solvent was removed in vacuo and the solid was basified to pH=9 with saturated $Na_2CO_3$, The mixture was concentrated to dryness and acidified to pH=1, basified to pH=9 and concentrated to dryness. The residue was washed with ethyl acetate (3×25 mL), the combined organic layers were concentrated to give 6-(morpholinomethyl)pyridin-3-amine (22; 450 mg, 56%). MS (ESI) calcd for $C_{10}H_{15}N_3O$ (m/z) 193.25. found 194[M+H].

6-(morpholinomethyl)pyridin-2-amine

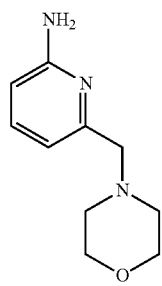

23 was prepared by the same sequence above, starting from 6-aminopicolinic acid.

Step 5. Synthesis of N-(6-(morpholinomethyl)pyridin-3-yl)-6-(3-(triluoromethyl)phenyl)-2H-pyrido[3,2-b][1,4]oxazine-4(3H)-carboxamide (Compound 507)

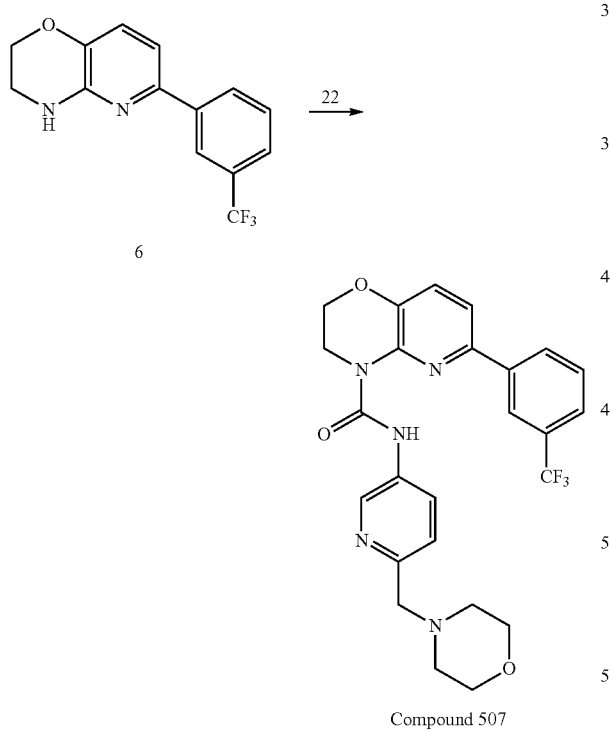

Compound 507

Prepared according to the general procedure described above to afford N-(6-(morpholinomethyl)pyridin-3-yl)-6-(3-(trifluoromethyl)phenyl)-2H-pyrido[3,2-b][1,4]oxazine-4(3H)-carboxamide (Compound 507), which was purified by column chromatography (EtOAc:pentanes), subsequent purification by HPLC eluding with MeOH and 0.1% TFA afforded the TFA salt (112.3 mg, 51%). MS (ESI) calcd for $C_{25}H_{24}F_3N_5O_3 \cdot C_2HO_2F_3$ (m/z) 613.5. found 500[M+H].

Example 6

Preparation of N-(6-(azetidin-1-yl)pyridin-2-yl)-6-(3-(trifluoromethyl)phenyl)-2H-pyrido[3,2-b][1,4]oxazine-4(3H)-carboxamide—trifluoroacetate salt (Compound 512)

Step 1. Synthesis of 2-(azetidin-1-yl)-6-chloropyridine (25)

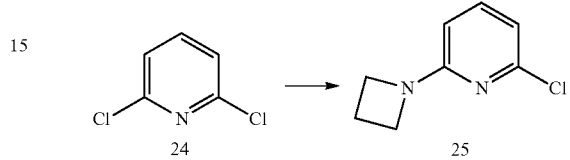

A mixture of 2,6-dichloropyridine (24; 10.0 g, 67.6 mmol), azetidine hydrochloride (6.3 g, 67.6 mmol) and $K_2CO_3$ (23.3 g, 169 mmol) in DMSO (100 mL) was stirred at 110° C. for 12 h. Water (150 mL) was added and the mixture was extracted with ethyl acetate (100 mL×3). The combined organic layers were washed with brine (1.00 mL×3) and dried over $Na_2SO_4$, concentrated to dryness to afford 2-(azetidin-1-yl)-6-chloropyridine (25; 10.5 g), which was used for next step without further purification. MS (ESI) calcd for $C_8H_9ClN_2$ (m/z): 168.05.

Step 2. Synthesis of 6-(azetidin-1-yl)-N-(4-methoxybenzyl)pyridin-2-amine (26)

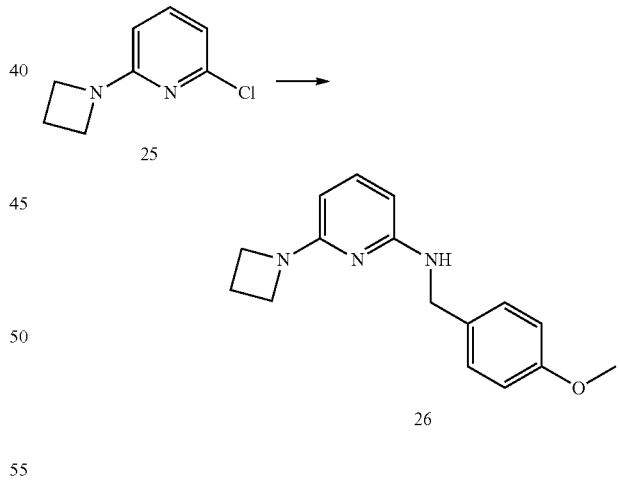

A mixture of 2-(azetidin-1-yl)-6-chloropyridine (25; 1.68 g, 10.0 mmol), 4-methoxylbenzylamine 1.35 g, 10.0 mmol), $Pd_2(dba)_3$ (0.27 g, 0.29 mmol), BINAP (0.37 g, 0.60 mmol) and t-BuONa (1.12 g, 10.0 mmol) in $CH_2Cl_2$ (20 mL) was stirred at 110° C. under $N_2$ for 12 h. The mixture was diluted with water (100 mL), washed with water (3×50 mL), dried over $Na_2SO_4$ and concentrated in vacuo. The residue was purified by silica gel chromatography on (5:1 petroleum ether:ethyl acetate) to afford 6-(azetidin-1-yl)-N-(4-methoxybenzyl)pyridin-2-amine as an yellow oil (26; 2.60 g, 9.67 mmol). MS (ESI) calcd for $C_{16}H_{19}N_3O$ (m/z): 269.15.

Step 3. Synthesis of 6-(azetidin-1-yl)pyridin-2-amine (27)

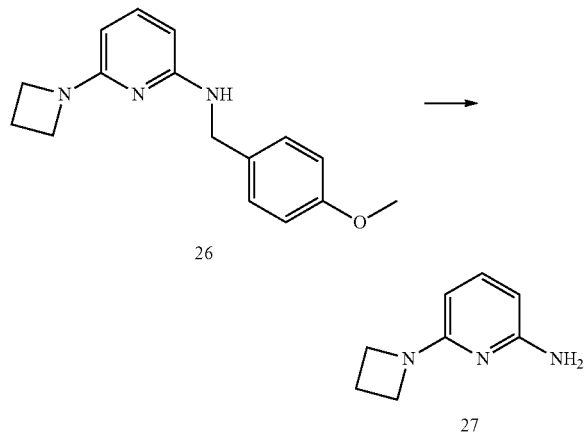

A solution of 6-(azetidin-1-yl)-N-(4-methoxybenzyl)pyridin-2-amine (26; 2.5 g, 9.3 mmol) and TFA (20.0 mL) in dichloromethane (40 mL) was stirred at room temp for 3 h. The pH was adjusted to 9 by $Na_2CO_3$ and extracted with EtOAc (3×50 mL). The combined organic layers were washed with brine (2×50 mL), dried over anhydrous $Na_2SO_4$, concentrated in vacuo and purified by silica gel chromatography (1:1 petroleum ether:ethyl acetate) to afford 6-(azetidin-1-yl)pyridin-2-amine as a white solid (27; 50 mg, 0.33 mmol). MS (ESI) calcd for $C_8H_{11}N_3$ (m/z): 149.10. found 150 [M+H].

2-(azetidin-1-yl)pyridin-4-amine

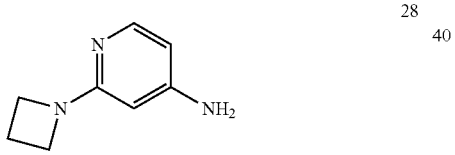

28 was prepared by the same sequence as above starting from 2,4-dichloropyridine.

Step 4. Synthesis of N-(6-(azetidin-1-yl)pyridin-2-yl)-6-(3-(trifluoromethyl)phenyl)-2H-pyrido[3,2-b][1,4]oxazine-4(3H)-carboxamide—trifluoroacetate salt (Corn pound 512)

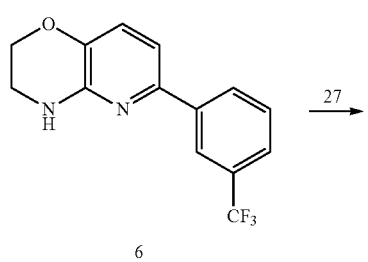

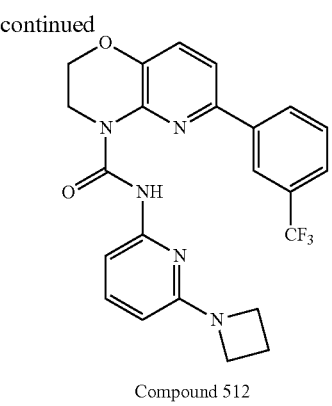

Compound 512

Prepared according to the general procedure described above to afford N-(6-(azetidin-1-yl)pyridin-2-yl)-6-(3-(trifluoromethyl)phenyl)-2H-pyrido[3,2-b][1,4]oxazine-4(3H)-carboxamide (Compound. 512), which was purified by HPLC eluding with MeOH and 0.1% TFA afforded as the TFA salt (Compound 512; 47.4 mg, 47%). MS (ESI) calcd for $C_{23}H_{20}F_3N_5O_2 \cdot C_2HO_2F_3$ (m/z) 569.45. found 456[M+H].

Example 7

Preparation of (R)—N-(6-(2,3-dihydroxypropoxy)pyridin-2-yl)-6-(3-(trifluoromethyl)phenyl)-2H-pyrido[3,2-b][1,4]oxazine-4(3H)-carboxamide (Compound 570)

Step 1. Synthesis of (S)-6-((2,2-dimethyl-1,3-dioxolan-4-yl)methoxy)pyridin-2-amine (30)

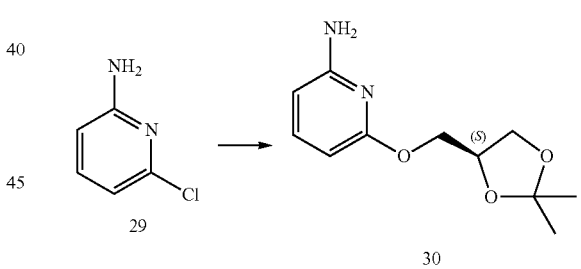

To a solution of (S)-(2,2-dimethyl-1,3-dioxolan-4-yl)methanol (19.5 g, 150 mmol) in dioxane (250 mL) was added NaH (6.0 g, 60%) at room temperature and stirred for 30 min. then 2-amino-6-chloropyridine (29; 6.43 g, 50 mmol) was added and the mixture was stirred under reflux for 48 h. Water was added and extracted with ethyl acetate (3×100 mL). The combined organic layers were washed with water (6×50 mL), dried over $Na_2SO_4$, concentrated in vacuo and purified by silica gel chromatography (20:1 dichloromethane:methanol) to afford (S)-6-((2,2-dimethyl-1,3-dioxolan-4-yl)methoxy)pyridin-2-amine as an oil (30; 5.7 g, 25.4 mmol, 51%). MS (ESI) calcd for $C_{11}H_{16}N_2O_3$ (m/z) 224.12. found 225 [M+H].

(R)-6-((2,2-dimethyl-1,3-dioxolan-4-yl)methoxy)pyridin-2-amine was prepared by the same sequence above, using (R)-(2,2-dimethyl-1,3-dioxolan-4-yl)methanol. Similarly, 6-((2,2-dimethyl-1,3-dioxolan-4-yl)methoxy)pyridin- 2-amine was prepared by the same sequence above, using (2,2-dimethyl-1,3-dioxolan-4-yl)methanol.

Step 2. Synthesis of (S)—N-(6-((2,2-dimethyl-1,3-dioxolan-4-yl)methoxy)pyridin-2-yl)-6-(3-(trifluoromethyl)phenyl)-2H-pyrido[3,2-b][1,4]oxazine-4(3H)-carboxamide (31)

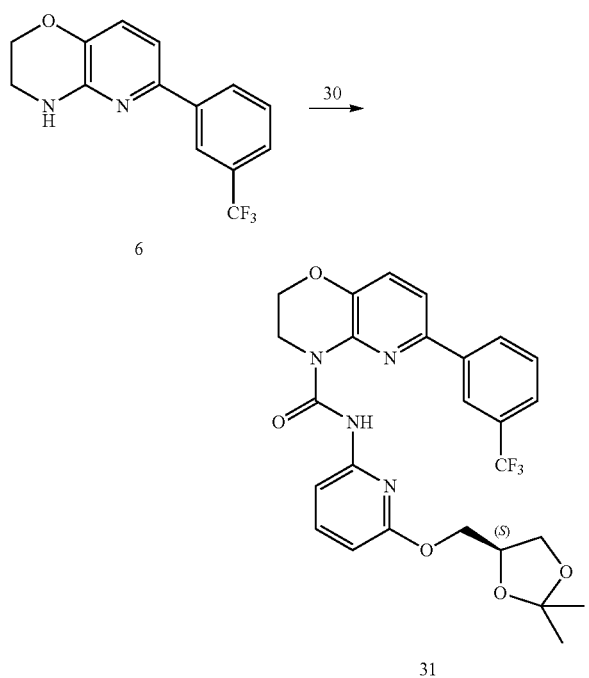

Prepared according to the general procedure described above to afford (S)—N-(6-((2,2-dimethyl-1,3-dioxolan-4-yl)methoxy)pyridin-2-yl)-6-(3-(trifluoromethyl)phenyl)-2H-pyrido[3,2-b][1,4]oxazine-4(3H)-carboxamide (31). MS (ESI) calcd for $C_{26}H_{25}F_3N_4O_5$ (m/z) 530.18.

Step 3. Synthesis of (R)—N-(6-(2,3-dihydroxypropoxy)pyridin-2-yl)-6-(3-(trifluoromethyl)phenyl)-2H-pyrido[3,2-b][1,4]oxazine-4(3H)-carboxamide (Compound 570)

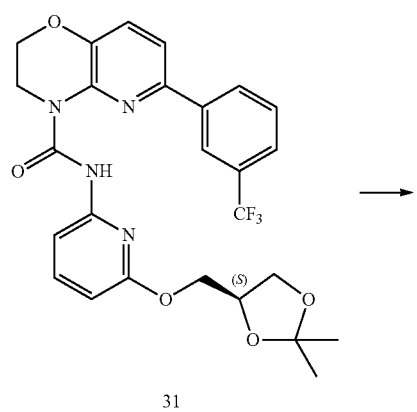

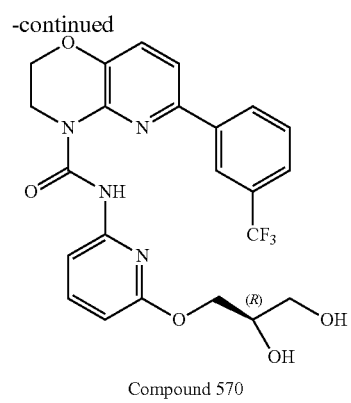

Compound 570

(S)—N-(6-((2,2-dimethyl-1,3-dioxolan-4-yl)methoxy)pyridin-2-yl)-6-(3-(trifluoromethyl)phenyl)-2H-pyrido[3,2-b][1,4]oxazine-4(3H)-carboxamide (31; 109 mg, 0.21 mmol) was taken up in MeOH (12 mL) along with 10 drops of concentrated HCl. The reaction mixture was stirred at room temperature for 1 h and then concentrated under reduced pressure. Purification by silica gel chromatography afforded (R)—N-(6-(2,3-dihydroxypropoxy)pyridin-2-yl)-6-(3-(trifluoromethyl)phenyl)-2H-pyrido[3,2-b][1,4]oxazine-4(3H)-carboxamide (Compound 570; 75 mg, 75%). MS (ESI) calcd for $C_{23}H_{21}F_3N_4O_5$ (m/z) 490.15. found: 491 [M+H].

The use of (R)-6-((2,2-dimethyl-1,3-dioxolan-4-yl)methoxy)pyridin-2-amine in Step 2, followed by the procedures of Step 3 results in the production of Compound 571.

Example 8

Preparation of N-(1-(pyridin-2-yl)cyclopropyl)-6-(3-(trifluoromethyl)phenyl)-2H-pyrido[3,2-b][1,4]oxazine-4(3H)-carboxamide (Compound 633)

Step 1. Synthesis of 2-(pyridin-2-yl)cyclopropanamine (33)

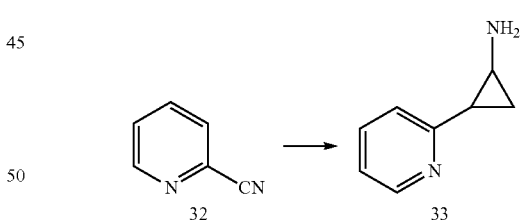

Prepared according to a similar literature preparation as Bertus et al JOC, 2002, 67, 3965-3968. To a stirred solution of picolinonitrile (4.0 g, 38.42 mmol) and Ti(O-iPr)$_4$ (13 mL, 43.31 mmol) in THF (64 mL) was added EtMgBr (26 mL, 3M in THF, 78.74 mm#1) at 50° C. The mixture stirred for 2 h and BF$_3$—.Et$_2$O (10 mL, 78.74 mmol) was added at 50° C. The mixture stirred overnight. The mixture was adjusted to pH=9 with aqueous NaOH and extracted with ethyl acetate (39 mL×2). The combined organic layer were washed with water (79 mL×2), dried over Na$_2$SO$_4$, purified by chromatography on silica gel (CH$_2$Cl$_2$:methanol=10:1) to give an oil. The oil was dissolved in CH$_2$Cl$_2$ (79 mL). Oxalic acid (1.4 g; 11.1 mmol) in methanol (8 mL) was added and stirred for 1.5 h to give a solid. The solid was collected by filtration and washed with CH₂Cl₂/MeOH (39 mL, v/v=10:1) and ethyl ether (16 mL), dried in vacuo to give 2-(pyridin-2-yl)cyclopropanamine (33; 1.2 g, 13.6%) as a solid. MS (ESI) calcd for $C_8H_{10}N_2$ (m/z) 134.08.

Step 2. Synthesis of N-(1-(pyridin-2-yl)cyclopropyl)-6-(3-(trifluoromethyl)phenyl)-2H-pyrido[3,2-b][1,4]oxazine-4(3H)-carboxamide (Compound 633)

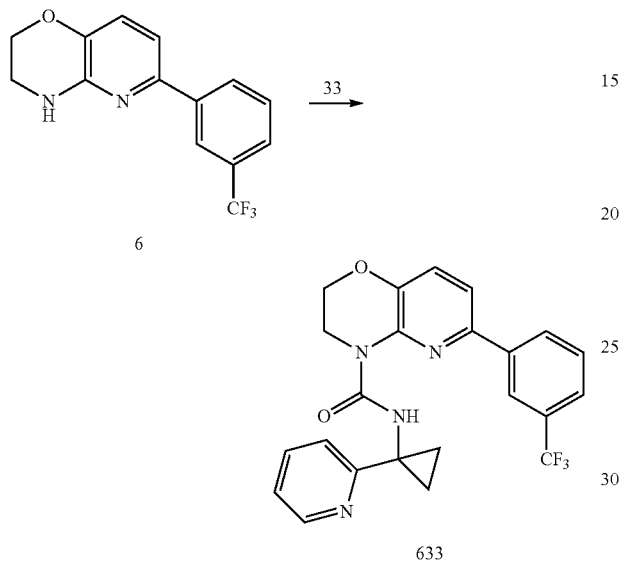

Prepared according to the general procedure described above to afford N-(1-(pyridin-2-yl)cyclopropyl)-6-(3-(trifluoromethyl)phenyl)-2H-pyrido[3,2-b][1,4]oxazine-4(3H)-carboxamide (Compound 633; 126.2 mg, 43%). MS (ESI) calcd for $C_{23}H_{19}F_3N_4O_2$ (m/z) 440.42. found: 441 [M+H].

Example 9

Preparation of N-(6-(2,3-dihydroxypropoxy)pyrazin-2-yl)-6-(3-(trifluoromethyl)phenyl)-2H-pyrido[3,2-b][1,4]oxazine-4(3H)-carboxamide (Compound 696)

Step 1. Synthesis of 6-((2,2-dimethyl-, 3-dioxolan-4-yl)methoxy)pyrazin-2-amine (35)

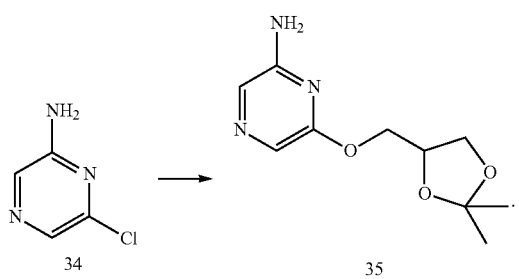 [SMILES: Nc1cncc(Cl)n1 ; CC1(C)OCC(COc2cncc(N)n2)O1]

To a solution of solketal (48.7 g, 0.369 mol) in 1,4-dioxane (1500 mL) was added NaH (14.8 g, 369 mmol) at room temp and stirred for 2 h. Then 6-chloropyrazin-2-amine (34; 16.0 g, 123 mmol) was added and the mixture was stirred at 120° C. for 12 h. The solvent was removed and ethyl acetate (1000 mL) was added. The mixture was washed with brine (1000 mL×3), The organic solvent was dried over Na₂SO₄, concentrated in vacuo and purified by chromatography on silica gel (dichloromethane:methanol=30:1-10:1) to give 6-((2,2-dimethyl-1,3-dioxolan-4-yl)methoxy)pyrazin-2-amine (35; 13.8 g, 61.3 mmol, 50%) as a yellow solid. MS (ESI) calcd for $C_{10}H_{15}N_3O_3$ (m/z) 225.24. found: 226 [M+H].

2-((2,2-dimethyl-1,3-dioxolan-4-yl)methoxy)pyridin-4-amine 36

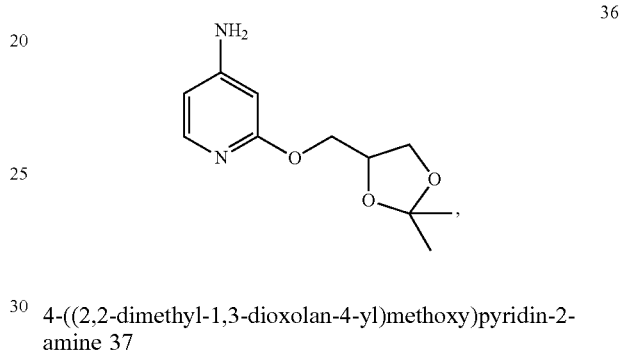

4-((2,2-dimethyl-1,3-dioxolan-4-yl)methoxy)pyridin-2-amine 37

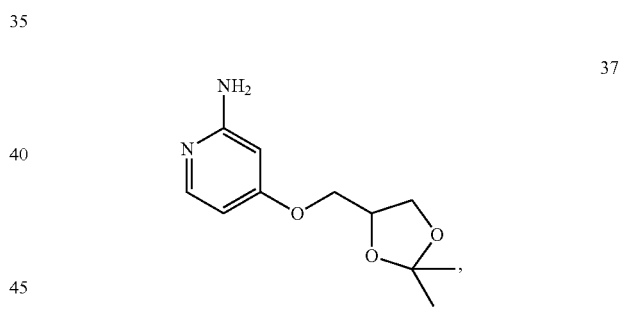

4-((2,2-dimethyl-1,3-dioxolan-4-yl)methoxy)-6-methylpyrimidin-2-amine 38

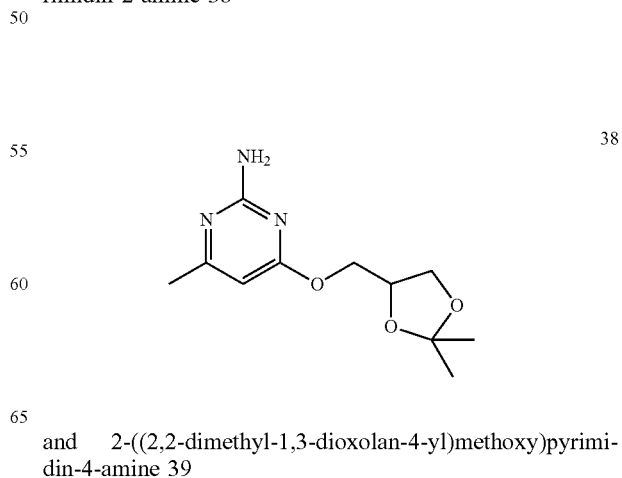

and 2-((2,2-dimethyl-1,3-dioxolan-4-yl)methoxy)pyrimidin-4-amine 39

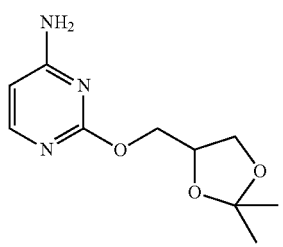

39 were all made following the sequence described above, starting from 2-bromopyridin-4-amine, 4-chloropyridin-2-amine, 4-chloro-6-methylpyrimidin-2-amine and 2-chloropyrimidin-4-amine respectively.

Step 2. Synthesis of N-(6-((2,2-dimethyl-, 3-dioxolan-4-yl)methoxy)pyrazin-2-yl)-6-(3-(trifluoromethyl)phenyl)-2H-pyrido[3,2-b][1,4]oxazine-4(3H)-carboxamide (40)

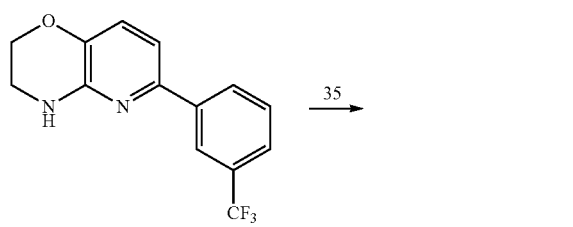

6

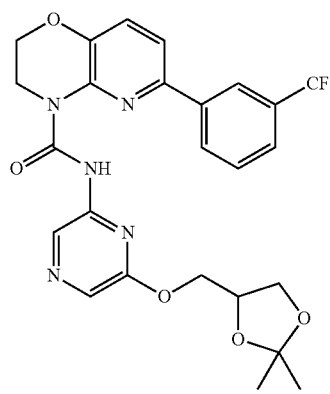

40

Prepared according to the general procedure described to afford N-(6-((2,2-dimethyl-1,3-dioxolan-4-yl)methoxy)pyrazin-2-yl)-6-(3-(trifluoromethyl)phenyl)-2H-pyrido[3,2-b][1,4]oxazine-4(3H)-carboxamide (40; 21.6 mg, 42%). MS (ESI) calcd for $C_{25}H_{24}F_3N_5O_5$ (m/z) 531.48. found: 532 [M+H].

Step 3. Synthesis of N-(6-(2,3-dihydroxypropoxy)pyrazin-2-yl)-6-(3-(trifluoromethyl)phenyl)-2H-pyrido[3,2-b][1,4]oxazine-4(3H)-carboxamide (Compound 696)

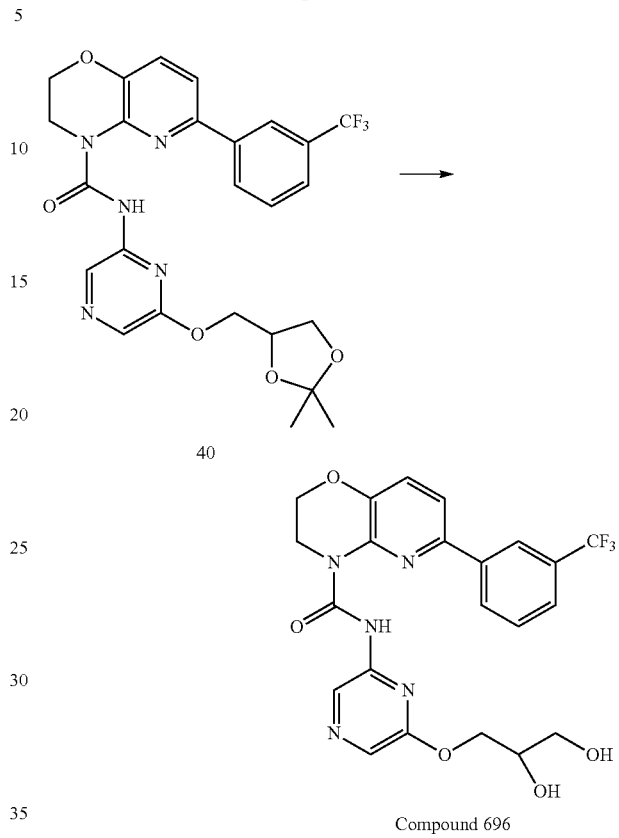

Compound 696

Compound 696 prepared using the same deprotection sequence that afforded Compound 570, N-(6-((2,2-dimethyl-1,3-dioxolan-4-yl)methoxy)pyrazin-2-yl)-6-(3-(trifluoromethyl)phenyl)-2H-pyrido[3,2-b][1,4]oxazine-4(3H)-carboxamide was dissolved in MeOH, 10 drops of concentrated HCl was added and stirred at room temp for 1 h, purified by HPLC to afford N-(6-(2,3-dihydroxypropoxy)pyrazin-2-yl)-6-(3-(trifluoromethyl)phenyl)-2H-pyrido[3,2-b][1,4]oxazine-4(3H)-carboxamide (Compound 696, 21.6 mg, 36%). MS (ESI) calcd for $C_{22}H_{20}F_3N_5O_5$ (m/z) 491.42. found: 492 [M+H].

Example 10

Preparation of N-(6-(1-oxa-6-azaspiro[3.3]heptan-6-yl)pyridin-2-yl)-6-(3-(trifluoromethyl)phenyl)-2H-pyrido[3,2-b][1,4]oxazine-4(3H)-carboxamide (Compound 823)

Step 1. Synthesis of tert-butyl 1-oxa-6-azaspiro[3.3]heptane-6-carboxylate (42)

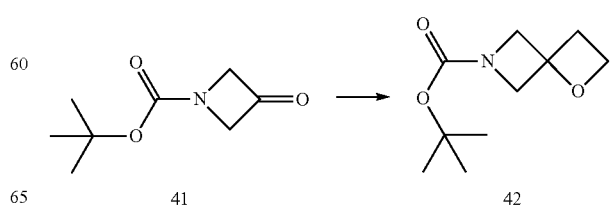

41                              42

To a suspension of trimethylsulfoxonium iodide (80 g, 370 mmol) in dry tert-BuOH (1.4 L) was added at 50° C. potassium tert-butoxide (41.3 g, 0.37 mmol), upon which the mixture turned to a cloudy suspension. The mixture was stirred at that temperature for 1.5 h, after which was added tert-butyl 3-oxoazetidine-1-carboxylate (41; 25 g, 150 mmol). The suspension was stirred at 50° C. for 48 h. It was cooled to room temperature and the mixture was partitioned between saturated aqueous NH$_4$Cl (30 ml) and EtOAc (50 ml). The phases were separated and the aqueous phase was extracted with EtOAc (50 ml). The combined organic phases were dried (Na$_2$SO$_4$), filtered, and concentrated in vacuo. Tert-butyl 1-oxa-6-azaspiro[3.3]heptane-6-carboxylate was obtained (42; 8 g, 28%) after purification by flash chromatography on silica gel hexanes:EtOAc 2:1→0:1 gradient). MS (ESI) calcd for C$_{24}$H$_{19}$F$_3$N$_6$O$_2$ 199.1.

Step 2. Synthesis of 1-oxa-6-azaspiro[3.3]heptanes TFA salt (43)

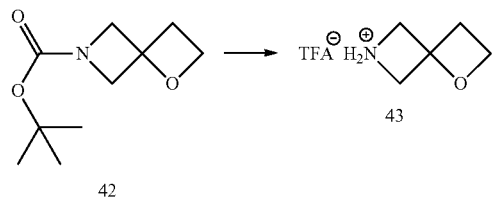

To a solution of tert-butyl 1-oxa-6-azaspiro[3.3]heptane-6-carboxylate (42; 3 g, 15.06 mmol) in CH$_2$Cl$_2$ (10 ml) was added at 20° C. 2,2,2-trifluoroacetic acid (34.3 g, 301 mmol) was added and the mixture was stirred at 20° C. for 30 min, when the volatiles were removed in vacuo. The residue 1-oxa-6-azaspiro[3.3]heptanes TFA salt was used without further purification (43; 2.5 g, 85%). MS (ESI) calcd for C$_5$H$_{10}$NO—C$_2$F$_3$O 197.16.

Step 3. Synthesis of tert-butyl (6-(1-oxa-6-azaspiro [3.3]heptan-6-yl)pyridin-2-yl)carbamate (45)

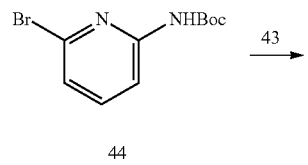

A mixture of tert-butyl 6-bromopyridin-2-ylcarbamate (44; 8.18 g, 30.0 mmol), 1-oxa-6-azoniaspiro[3.3]heptane (43; 3 g, 30.0 mmol), 1,1'-bis(diphenylphosphino)ferrocene (DPPF) (1.663 g, 3.00 mmol), Pd(OAc)$_2$ (0.34 g, 1.5 mmol), and Cs$_2$CO$_3$ (19.5 g, 59.9 mmol) in 50 ml of toluene was heated to 120° C. for 5 h in a sealed tube and cooled. After evaporation of the solvent tert-butyl (6-(1-oxa-6-azaspiro [3.3]heptan-6-yl)pyridin-2-yl) carbamate was obtained by flash column chromatography (45; 2.7 g, 23%). MS (ESI) calcd for C$_{15}$H$_{21}$N$_3$O$_3$ 291.2.

Step 4. Synthesis of 6-(1-oxa-6-azaspiro[3.3]heptan-6-yl)pyridin-2-amine (46)

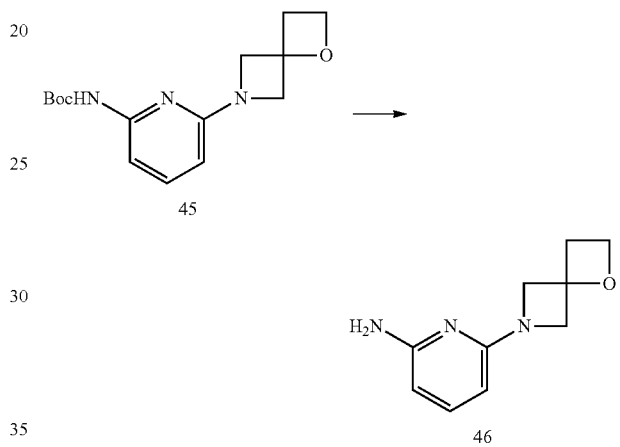

To a solution of tert-butyl 6-(1-oxa-6-azaspiro[3.3]heptan-6-yl)pyridin-2-ylcarbamate (45; 2 g, 6.86 mmol) in 20 ml of methylene chloride was added 2,2,2-trifluoroacetic acid (7.83 g, 68.6 mmol) at room temperature. The mixture was stirred for further 1 h and 50 ml of saturated aq. Na$_2$CO$_3$ was added. The organic phase was separated and concentrated. 6-(1-oxa-6-azaspiro[3.3]heptan-6-yl)pyridin-2-amine was obtained by flash column chromatography (46; 900 mg, 69%). MS (ESI) calcd for C$_{10}$H$_{13}$N$_3$O 191.1. found 192.2.

Step 5. Synthesis of N-(6-(1-oxa-6-azaspiro[3.3] heptan-6-yl)pyridin-2-yl)-6-(3-(trifluoromethyl)phenyl)-2H-pyrido[3,2-b][1,4]oxazine-4 (3-H)-carboxamide (Compound 823)

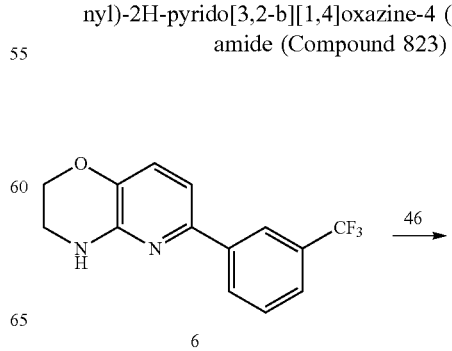

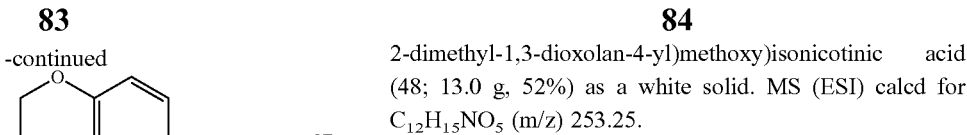

Compound 823

Prepared according to the general procedure described above to afford N-(6-(1-oxa-6-azaspiro[3.3]heptan-6-yl)pyridin-2-yl)-6-(3-(trifluoromethyl)phenyl)-2H-pyrido[3,2-b][1,4]oxazine-4(3H)-carboxamide (Compound 823; 50 mg, 38%). MS (ESI) calcd for $C_{25}H_{22}F_3N_5O_3$: 497.17. found: 498 [M+H].

Example 11

Synthesis of (2-(2,3-dihydroxypropoxy)pyridin-4-yl)(6-(3-(trifluoromethyl)phenyl)-2H-pyrido[3,2-b][1,4]oxazin-4(3H)-yl)methanone-trifluoroacetate salt (Compound 518)

Step 1. Synthesis of 2-((2,2-dimethyl-1,3-dioxolan-4-yl)methoxy)isonicotinic acid (48)

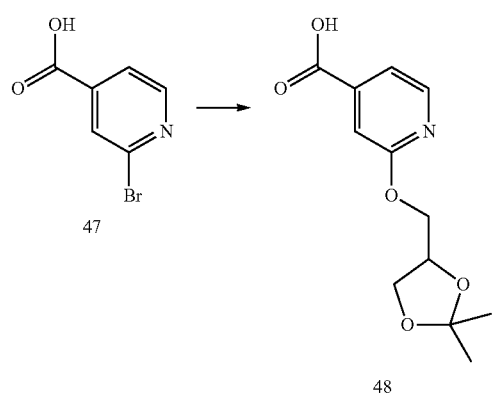 [SMILES: O=C(O)c1ccnc(Br)c1 ; CC1(C)OCC(COc2cc(C(=O)O)ccn2)O1]

To a mixture of NaH (11.95 g, 300 mmol, 60% with oil) in anhydrous THF (667 mL) was added 2,2-dimethyl-1,3-dioxolan-4-yl (solketal) (39.65 g, 300 mmol) at 0° C. The mixture was stirred for 1 hour. 2-bromoisonicotinic acid (47; 20.0 g, 100 mmol) was added and stirred under reflux for 1.5 h. Water (83 mL) was added and adjusted pH to 2-3. The mixture was extracted with EtOAc (83 mL×4). The combined organic layers were washed with water (42 mL×3), dried over Na$_2$SO$_4$ and concentrated in vacuo to give 2-((2, 2-dimethyl-1,3-dioxolan-4-yl)methoxy)isonicotinic acid (48; 13.0 g, 52%) as a white solid. MS (ESI) calcd for $C_{12}H_{15}NO_5$ (m/z) 253.25.

Step 2. Synthesis of (2-((2,2-dimethyl-1,3-dioxolan-4-yl)methoxy)pyridin-4-yl)(6-(3-(trifluoromethyl)phenyl)-2H-pyrido[3,2-b][1,4]oxazin-4(3H)-yl)methanone (49)

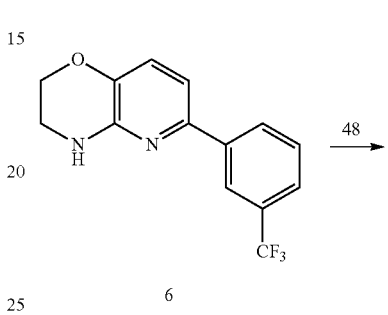

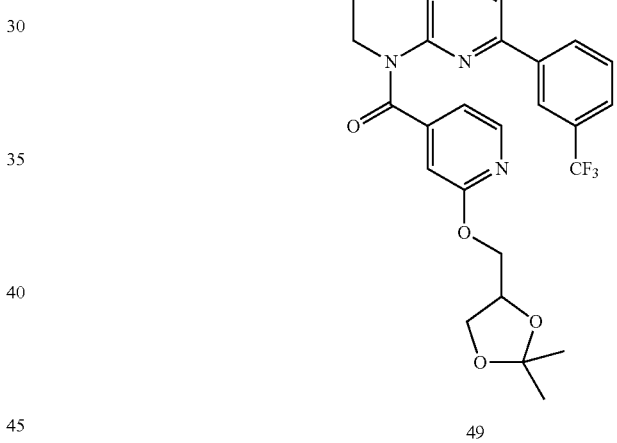

6-(3-(trifluoromethyl)phenyl)-3,4-dihydro-2H-pyrido[3,2-b][1,4]oxazine (6; 70 mg, 0.25 mmol) was taken up in 2 mL of DMF along with 2-((2,2-dimethyl-1,3-dioxolan-4-yl)methoxy)isonicotinic acid (48; 155.24 mg, 0.61 mmol), 2-(7-Aza-1H-benzotriazole-1-yl)-1,1,3,3-tetramethyluronium hexafluorophosphate (HATU) (284.83 mg, 0.75 mmol) and Hunig's (0.10 mL, 0.75 mmol). The reaction mixture was stirred overnight at 50° C. It was diluted with CH$_2$Cl$_2$ (10 mL) and washed with water (3×5 mL). The combine dorgnaic layers were dried over Na$_2$SO$_4$, filtered and concentrated under vacuum. The crude reaction mixture was purified by column chromatography eluding with EtOAc: pentanes to afford (2-((2,2-dimethyl-1,3-dioxolan-4-yl)methoxy)pyridin-4-yl)(6-(3-(trifluoromethyl)phenyl)-2H-pyrido[3,2-b][1,4]oxazin-4(3H)-yl)methanone (49; 69.3 mg, 54%). MS (ESI) calcd for $C_{26}H_{24}F_3N_3O_5$ (m/z) 515.48.

Step 3. Synthesis of (2-(2,3-dihydroxypropoxy)pyridin-4-yl)(6-(3-(trifluoromethyl)phenyl)-2H-pyrido[3,2-b][1,4]oxazin-4(3H)-yl)methanone—TFA salt (Compound 518)

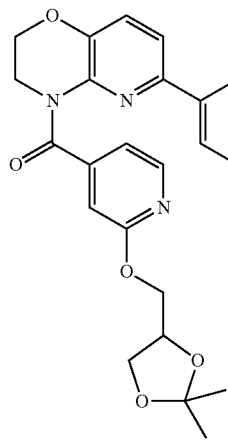

49

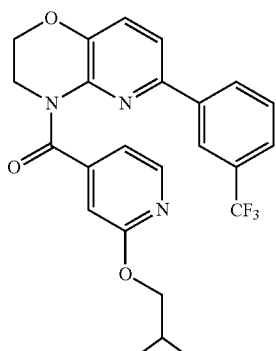

Compound 518

(2-((2,2-dimethyl-1,3-dioxolan-4-yl)methoxy)pyridin-4-yl)(6-(3-(trifluoromethyl)phenyl)-2H-pyrido[3,2-b][1,4]oxazin-4(3H)-yl)methanone (49; 69.3 mg, 0.13 mmol) was taken up in MeOH (10 mL) along with 10 drops of concentrated HCl. The reaction mixture was stirred at room temperature for 1 h and then concentrated under vacuum. Purified by HPLC eluding with MeOH and 0.1% TFA to afford (2-(2,3-dihydroxypropoxy)pyridin-4-yl)(6-(3-(trifluoromethyl)phenyl)-2H-pyrido[3,2-b][1,4]oxazin-4(3H)-yl)methanone as the trifluoroacetate salt (Compound 518; 46.8 mg, 59%). MS (ESI) calcd for $C_{23}H_{20}F_3N_3O_5$ (m/z) 589.44. found 590[M+H].

Example 12

Preparation of pyridin-4-yl 6-(3-(trifluoromethyl)phenyl)-2H-pyrido[3,2-b][1,4]oxazine-4(3H)-carboxylate (Compound 562)

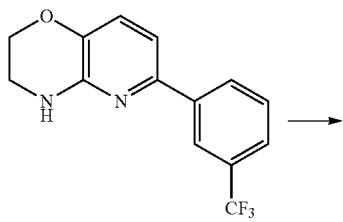

6

-continued

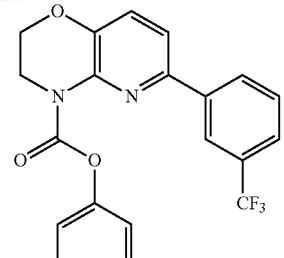

Compound 562

Dissolved 6-(3-(trifluoromethyl)phenyl)-3,4-dihydro-2H-pyrido[3,2-b][1,4]oxazine (6; 100 mg, 0.357 mmol) in 5 mL of THF, added triphosgene in 3 mL of TH-F and TEA (0.73 mL, 1.43 mmol). Allowed the reaction to stir at room temp for 30 min. Added 3-hydroxypyridine (84.87 mg, 0.89 mmol) and monitored reaction by LCMS, after 40 min no starting material was observed. The crude reaction mixture was diluted with $CH_2Cl_2$ (8 mL), washed with 10% $NH_4Cl$, organic layer extracted, dried over $Na_2SO_4$, filtered and condensed under reduced pressure. Purification by HPLC eluding with MeOH and 0.1% TFA afforded pyridin-4-yl 6-(3-(trifluoromethyl)phenyl)-2H-pyrido[3,2-b][1,4]oxazine-4(3H)-carboxylate (Compound 562; 72.5 mg, 39%). MS (ESI) calcd for $C_{20}H_{14}F_3N_3O_3 \cdot C_2HO_2F_3$ (m/z) 515.36. found 402[M+H].

Example 13

Preparation of 8-methyl-N-(4-methylthiazol-2-yl)-6-(3-(trifluoromethyl)phenyl)-2H-pyrido[3,2-b][1,4]oxazine-4(31)-carboxamide (Compound 668)

Step 1. Synthesis of 3-acetoxy-4-methylpyridine 1-oxide

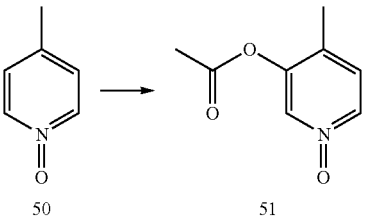

50                          51

4-Methylpyridine N-oxide (50; 39.0 g, 365 mmol) was added in portions to acetic anhydride (80 mL). After the addition was complete (1.5 h), the resulting reaction mixture was refluxed for 30 min. Then the solvent was removed under vacuum, the residue was stirred with a saturated aqueous solution of sodium bicarbonate. The mixture was extracted with $CH_2Cl_2$. The $CH_2Cl_2$ extracts were combined, dried and concentrated. The residue was purified by column chromatography (5:1 $CH_2Cl_2$/EtOAc) to afford 3-acetoxy-4-methylpyridine 1-oxide (51; 15.0 g, 28% yield) as a pale-yellow oil. MS (ESI) calcd for $C_8H_9NO_3$ (m/z) 167.16.

Step 2. Synthesis of 4-methylpyridin-3-ol (52)

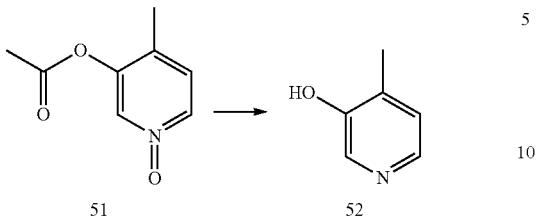

To a solution of KOH (7.0 g) in methanol (50 ml) was added 3-acetoxy-4-methylpyridine 1-oxide (51; 15.0 g, 106 mmol). The mixture was stirred at room temperature overnight. The methanol was removed under vacuum and the residue was dissolved in water. The solution was neutralized to pH 7 with conc. HCl and extracted with $CH_2Cl_2$ and EtOAc. The extracts were combined, dried and concentrated to obtain 4-methylpyridin-3-ol (52; 8.40 g, 80% yield) as an oil. MS (ESI) calcd for $C_6H_7NO$ (m/z) 109.13.

Step 3. Synthesis of 4-methyl-2-nitropyridin-3-ol (53)

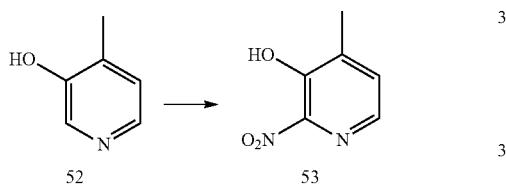

4-Methylpyridin-3-ol (52; 8.4 g, 78.5 mmol) was added to ice cold conc. $H_2SO_4$ (42 mL). Fuming nitric acid (4 mL) was added dropwise while maintaining the temperature below 10° C. and the mixture was stirred at 10-20° C. for 2 hours. The mixture was poured onto crushed ice and adjusted to pH 2 with 8N NaOH and extracted with EtOAc. The extracts were combined, dried, and concentrated. The residue was purified by column chromatography to obtain 4-methyl-2-nitropyridin-3-ol (53; 8.0 g, 67% yield). MS (ESI) calcd for $C_6H_6N_2O_3$ (m/z) 154.12.

Step 4. Synthesis of 6-bromo-4-methyl-2-nitropyridin-3-ol (54)

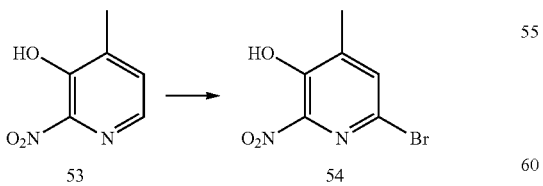

To a solution of 4-methyl-2-nitropyridin-3-ol (53; 8.0 g, 52 mmol) in methanol (150 mL) was added NaOMe (10.4 mL, 28% w/w soln. in MeOH). The solution was stirred at room temp for 15 min. and then cooled on an ice-bath. A solution of bromine (2.64 mL) in methanol (25 mL) was added dropwise and the reaction mixture was stirred at 0° C. for 2 h. The solvent was removed and the residue was purified by column chromatography (1:80 $MeOH/CH_2Cl_2$) to obtain 6-bromo-4-methyl-2-nitropyridin-3-ol (54; 7.0 g, 58% yield). MS (ESI) calcd for $C_6H_5BrN_2O_3$ (m/z) 233.02.

Step 5. Synthesis of ethyl 2-(6-bromo-4-methyl-2-nitropyridin-3-yloxy)acetate (55)

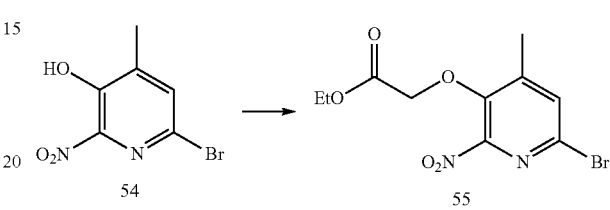

A solution of 6-bromo-4-methyl-2-nitropyridin-3-ol (54; 7.0 g, 30 mmol), $K_2CO_3$ (12.4 g, 90 mmol) and ethyl bromoacetate (4.4 mL, 39 mmol) in DMSO (80 mL) was stirred at 30° C. for 24 h. The mixture was poured into water and was extracted with $CH_2Cl_2$. The extracts were combined, dried and the solvent was removed under vacuum. The residue was purified by column chromatography to obtain ethyl 2-(6-bromo-4-methyl-2-nitropyridin-3-yloxy)acetate (55; 8.0 g, 84% yield). MS (ESI) calcd for $C_{10}H_{11}BrN_2O_5$ (m/z) 319.11. found 320.

Step 6. Synthesis of 6-bromo-8-methyl-2H-pyrido[3,2-b][1,4]oxazin-3(4H)-on (56)

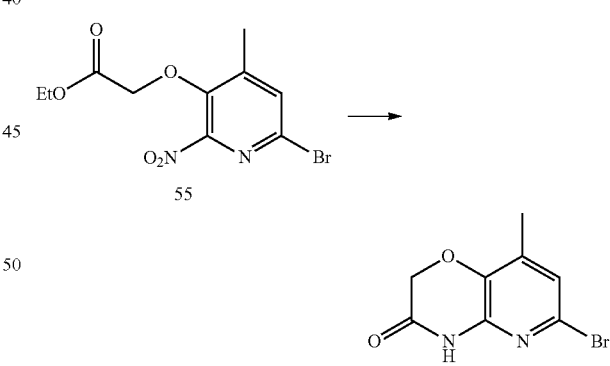

Ethyl 2-(6-bromo-4-methyl-2-nitropyridin-3-yloxy)acetate (55; 8.0 g, 25 mmol) was taken up in a 9:2 $EtOH/H_2O$ mixture (120 mL) along with iron (7.0 g, 125 mmol) and $CaCl_2$ (1.41 mg, 12.5 mmol). The resulting reaction mixture was refluxed for 8 h. The insoluble material was filtered off and the filtrate was concentrated under vacuum. The residue was purified by column chromatography to obtain 6-bromo-8-methyl-2H-pyrido[3,2-b][1,4]oxazin-3(4H)-one (56; 2.5 g, 41% yield). MS (ESI) calcd for $C_8H_7BrN_2O_2$ (m/z) 243.06.

Step 7. Synthesis of 6-bromo-8-methyl-3,4-dihydro-2H-pyrido[3,2-b][1,4]oxazine (57)

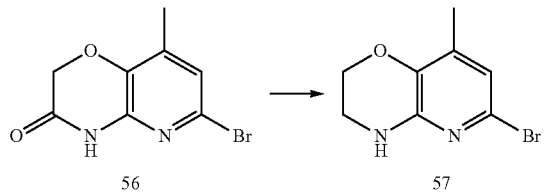

6-Bromo-8-methyl-2H-pyrido[3,2-b][1,4]oxazin-3(4H)-one (56; 2.7 g, 11.1 mmol) was taken up in THF (40 mL) along with 9.8 M BH$_3$-Me$_2$S (11.4 mL, 11.1 mmol). The resulting reaction mixture was refluxed overnight. After cooling, methanol (8 mL) was added dropwise and the reaction mixture was refluxed for 30 min. The solvent was removed in vacuo and the residue was purified by column chromatography (1:15 EtOAc/petroleum ether) to afford 6-bromo-8-methyl-3,4-dihydro-2H-pyrido[3,2-b][1,4]oxazine (57; 2.24 g, 88% yield). MS (ESI) calcd for C$_8$H$_9$BrN$_2$O (m/z) 229.07. found 230.

Step 8. Synthesis of 8-methyl-6-(3-(trifluoromethyl)phenyl)-3,4-dihydro-2H-pyrido[3,2-b][1,4]oxazine (58)

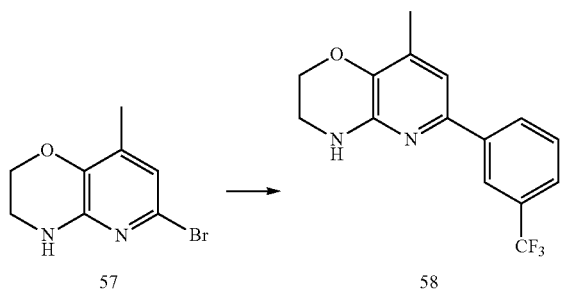 [SMILES: Cc1cc(Br)nc2c1OCCN2 ; Cc1cc(-c2cccc(C(F)(F)F)c2)nc2c1OCCN2]

6-Bromo-8-methyl-3,4-dihydro-2H-pyrido[3,2-b][1,4]oxazine (57; 1.5 g, 6.55 mmol), 3-(trifluoromethyl)phenylboronic acid (1.49 g, 7.86 mmol), Pd(PPh$_3$)$_4$ (379 mg, 0.33 mmol), Na$_2$CO$_3$ (1.67 g, 15.72 mmol) and 4:1 dioxane/water (30 mL) were added to a sealed tube and flushed with nitrogen. The mixture was heated to 120° C. for 12 h. After cooling, CH$_2$Cl$_2$ (100 mL) was added and the mixture was filtered through a pad of Na$_2$SO$_4$. The solvent was removed in vacuo and the residue was purified by column chromatography (1:15 EtOAc/petroleum ether,) to afford 8-methyl-6-(3-(trifluoromethyl)phenyl)-3,4-dihydro-2H-pyrido[3,2-b][1,4]oxazine (58; 1.64 g, 85% yield). MS (ESI) calcd for C$_{15}$H$_{13}$F$_3$N$_2$O (m/z) 294.27. found 295.

This general coupling procedure could be used to prepare a variety of 8-methyl-6-aryl-3,4-dihydro-2H-pyrido[3,2-b][1,4]oxazine derivatives by substituting the appropriate boronic acid for 3-(trifluoromethyl)phenylboronic acid.

Step 9. Synthesis of 8-methyl-N-(4-methylthiazol-2-yl)-6-(3-(trifluormethyl)phenyl)-2H-pyrido[3,2-b][1,4]oxazine-4(3H)-carboxamide (Compound 668)

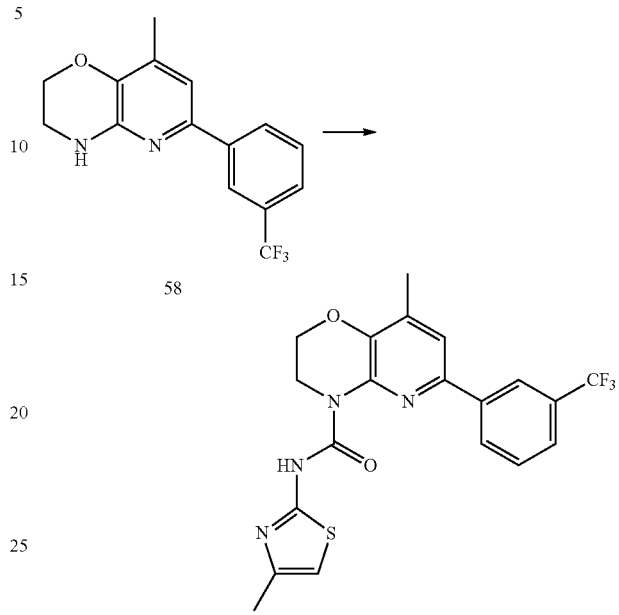

Compound 668

To a solution of 8-methyl-6-(3-(trifluoromethyl)phenyl)-3,4-dihydro-2H-pyrido[3,2-b][1,4]oxazine (58; 80 mg, 0.272 mmol) and triethylamine (96 mg, 0.952 mmol) in CH$_2$Cl$_2$ (4 mL) was added triphosgene (40 mg, 0.136 mmol). The reaction mixture was stirred at room temp for 30 min, and then 4-methylthiazol-2-amine (93 mg, 0.816 mmol) was added and the reaction mixture was stirred overnight. The solvent was removed and the residue was purified by column chromatography to afford 8-methyl-N-(4-methylthiazol-2-yl)-6-(3-(trifluoromethyl)phenyl)-2H-pyrido[3,2-b][1,4]oxazine-4(3H)-carboxamide (Compound 668; 78 mg, 66.1% yield). MS (ESI) calcd for C$_{20}$H$_{17}$F$_3$N$_4$O$_2$S: 434.10. found: 435 [M+H].

This general procedure could be used to prepare a variety of 8-methyl-N-(substituted)-6-aryl-2H-pyrido[3,2-b][1,4]oxazine-4(3H)-carboxamide derivatives by substituting the appropriate amine for 4-methylthiazol-2-amine. Alternatively, derivatives can also be prepared by reacting the appropriate phenyl carbamate with 8-methyl-6-aryl-3,4-dihydro-2H-pyrido[3,2-b][1,4]oxazine in the presence of DIEA at room temp to 50° C.

Example 14

N-(4-methylthiazol-2-yl)-6-(3-(trifluoromethyl)phenyl)-2H-pyrazino[2,3-b][1,4]oxazine-4(3H)-carboxamide (Compound 740)

Step 1. Synthesis of 3-Bromo-6-chloropyrazin-2-amine (60)

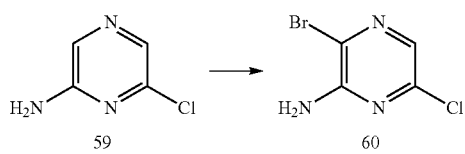 [SMILES: Nc1cncc(Cl)n1 ; Nc1nc(Cl)cnc1Br]

1-Bromopyrrolidine-2,5-dione (27.5 g, 154 mmol) was added portionwise over 30 min. to a solution of 6-chloropyrazin-2-amine (59; 20 g, 154 mmol) in chloroform (200 mL) heated under reflux. After the addition was complete, the reaction mixture was allowed to cool, washed with water and concentrated. The residue was purified by silica gel chromatography eluting with $CH_2Cl_2$ to obtain a 3-bromo-6-chloropyrazin-2-amine (60; 8 g, 25% yield). MS (ESI) calcd for $C_4H_3BrClN_3$: 208.44. found.

Step 2. Synthesis of
6-chloro-3-methoxypyrazin-2-amine (61)

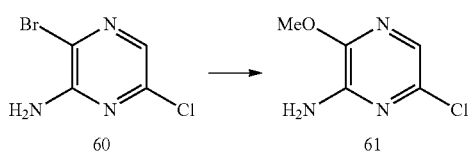 [SMILES: Nc1nc(Cl)cnc1Br ; COc1ncc(Cl)nc1N]

3-Bromo-6-chloro-2-pyrazinamine (60; 1.0 g), sodium methoxide (3 mL, 25% w/w in MeOH) and MeOH (10 mL) were heated at reflux for 3 h. The solvent was evaporated and the residue was dissolved in EtOAc and brine. The organic layer was separated, dried ($MgSO_4$) and concentrated. The residue was purified by silica gel chromatography eluting with dichloromethane to afford 6-chloro-3-methoxypyrazin-2-amine (61; 2.0 g, 33% yield). MS (ESI) calcd for $C_5H_6ClN_3O$: 159.57.

Step 3. Synthesis of 3-amino-5-chloropyrazin-2-ol (62)

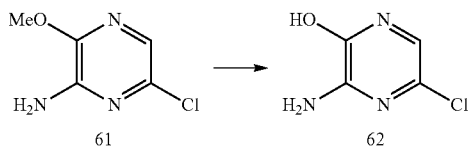 [SMILES: COc1ncc(Cl)nc1N ; Nc1nc(Cl)cnc1O]

To a solution of 6-chloro-3-methoxypyrazin-2-amine (61; 2 g, 12.53 mmol) in $CH_2Cl_2$ (300 mL) was added tribromoborane (3.14 g, 12.53 mmol) dropwise, and the mixture was stirred overnight. MeOH was added and the mixture was dissolved into water. The solution was adjusted to pH 8-9 with aqueous $NaHCO_3$, and then extracted with EtOAc. The organic phase was concentrated to and the residue was purified by silica gel chromatography to afford 3-amino-5-chloropyrazin-2-ol (62; 0.9 g, 50% yield). MS (ESI) calcd for $C_4H_4ClN_3O$: 145.55.

Step 4. 6-chloro-3,4-dihydro-2H-pyrazino[2,3-b][1,4]oxazine (63)

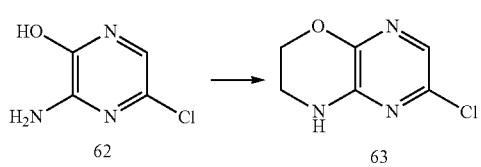 [SMILES: Nc1nc(Cl)cnc1O ; Clc1cnc2c(n1)NCCO2]

To a solution of 3-amino-5-chloropyrazin-2-ol (62; 0.9 g, 6.18 mmol) in $CH_3CN$ (100 mL) was added 1,2-dibromoethane (1.16 g, 6.18 mmol) and $K_2CO_3$ (1.71 g, 12.37 mmol). The mixture was refluxed overnight. After cooling to room temp, the mixture was concentrated, dissolved in water and then extracted with EtOAc. The combined organic phase was concentrated and the residue was purified by silica gel chromatography to obtain 6-chloro-3,4-dihydro-2H-pyrazino[2,3-b][1,4]oxazine (63; 0.8 g, 75% yield). MS (ESI) calcd for $C_6H_6ClN_3O$: 171.58. found: 173 [M+H].

Step 5. Synthesis of 6-(3-(trifluoromethyl)phenyl)-3,4-dihydro-2H-pyrazino[2,3-b][1,4]oxazine (64)

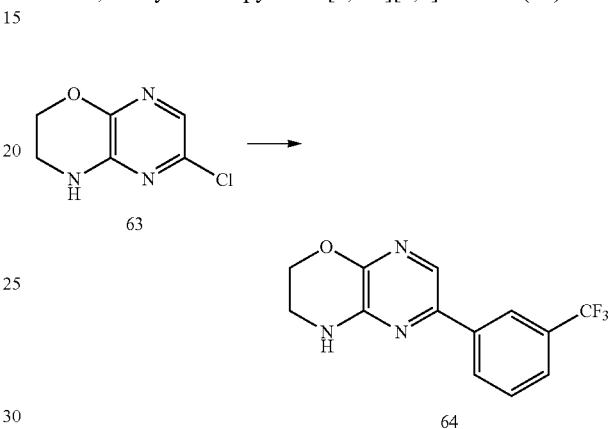

3-(Trifluoromethyl)phenylboronic acid (886 mg, 4.66 mmol) was added to a solution of 6-chloro-3,4-dihydro-2H-pyrazino[2,3-b][1,4]oxazine (63; 0.8 g, 4.66 mmol) in 4:1 dioxane/water (25 mL). The mixture was deoxygenated in vacuo and backfilled with nitrogen. After the mixture was stirred under nitrogen for 30 min, $Pd(PPh_3)_4$ (539 mg, 0.466 mmol) and $K_2CO_3$ (1.29 g, 9.32 mmol) was added. The solution was heated to 100° C. until the reaction was complete. The reaction mixture was then extracted with water and the organic layer was dried and concentrated to yield a crude oil that was purified by silica gel chromatography to afford 6-(3-(trifluoromethyl)phenyl)-3,4-dihydro-2H-pyrazino[2,3-b][1,4]oxazine (64; 0.35 g, 27% yield). MS (ESI) calcd for $C_{13}H_{10}F_3N_3O$: 281.23. found: 282 [M+H].

This general coupling procedure could be used to prepare a variety of 6-aryl-3,4-dihydro-2H-pyrazino[2,3-b][1,4]oxazine derivatives by substituting the appropriate boronic acid for 3-(trifluoromethyl)-phenylboronic acid.

Step 6. Synthesis of N-(4-methylthiazol-2-yl)-6-(3-(trifluoromethyl)phenyl)-2H-pyrazino[2,3-b][1,4]oxazine-4(3H)-carboxamide (Compound 740)

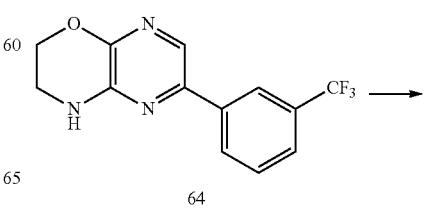

93

-continued

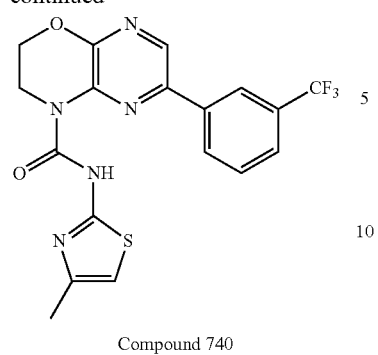

Compound 740

To a solution of 6-(3-(trifluoromethyl)phenyl)-3,4-dihydro-2H-pyrazino[2,3-b][1,4]oxazine (64; 100 mg, 0.356 mmol) and triethylamine (126 mg, 1.245 mmol) in CH$_{12}$Cl$_2$ (10 mL) was added bis(trichloromethyl) carbonate (52.8 mg, 0.178 mmol). The reaction mixture was stirred at room temperature for 30 min, and then 4-methylthiazol-2-amine (122 mg, 1.067 mmol) was added and the mixture was stirred overnight. The solvent was removed and the residue was purified by column chromatography to afford N-(4-methylthiazol-2-yl)-6-(3-(trifluoromethyl)phenyl)-2H-pyrazino[2,3-b][1,4]oxazine-4(3H)-carboxamide (Compound 740; mg, 27% yield). MS (ESI) calcd for C$_{18}$H$_{14}$F$_3$N$_5$O$_2$S: 421.08. found 422 [M+H].

This general procedure could be used to prepare a variety of N-substituted-6-aryl-2H-pyrazino[2,3-b][1,4]oxazine-4(3H)-carboxamide derivatives by substituting the appropriate amine for 4-methylthiazol-2-amine. Alternatively, derivatives can also be prepared by reacting the appropriate phenyl carbamate with 6-aryl-3,4-dihydro-2H-pyrazino[2,3-b][1,4]oxazine in the presence of DIEA at room temp to 50° C.

Example 15

Preparation of N-(4-methylthiazol-2-yl)-2-(3-(trifluoromethyl)phenyl)-6H-pyrimido[5,4-b][1,4]oxazine-8(7H)-carboxamide (Compound 709)

Step 1. Synthesis of 2-Chloro-5-methoxypyrimidin-4-amine (66)

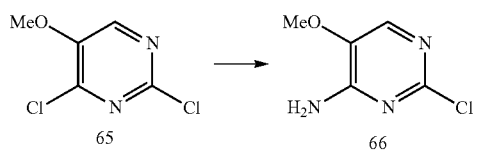 [SMILES: COc1cnc(Cl)nc1Cl ; COc1cnc(Cl)nc1N]

To 2,4-dichloro-5-methoxypyrimidine (65; 9.8 g, 55 mmol) in dioxane (20 mL) was added 25% ammonium hydroxide (25 mL). The resulting reaction mixture was heated to 100° C. for 21 h in a sealed tube. After cooling, the solvent was removed under vacuum and the residue was purified by column chromatography to obtain 2-chloro-5-methoxypyrimidin-4-amine (66; 8.31 g, 95% yield). MS (ESI) calcd for C$_5$H$_6$ClN$_3$O: 159.57.

94

Step 2. Synthesis of 4-Amino-2-chloropyrimidin-5-ol (67)

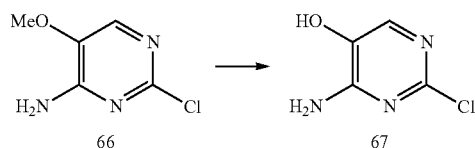 [SMILES: COc1cnc(Cl)nc1N ; Nc1nc(Cl)ncc1O]

To a solution of 2-chloro-5-methoxypyrimidin-4-amine (66; 8.3 g, 52 mmol) in CH$_2$Cl$_2$ (1.5 L) was added boron tribromide (75 mL) dropwise. The mixture was stirred at room temp overnight. MeOH was cautiously added until the solution was homogenous. The solvent was removed under vacuum, and aqueous NaHCO$_3$ was added. The mixture was extracted with CH$_2$Cl$_2$, and the organic layers were dried and concentrated. The residue was purified by column chromatography to afford 4-amino-2-chloropyrimidin-5-ol (67; 4.1 g, 54% yield). MS (ESI) calcd for C$_4$H$_4$ClN$_3$O: 145.55.

Step 3. Synthesis of 2-chloro-7,8-dihydro-6H-pyrimido[5,4-b][1,4]oxazine (68)

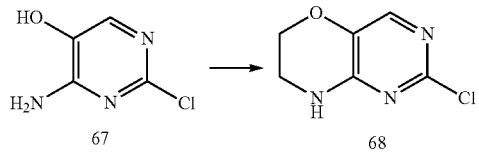 [SMILES: Nc1nc(Cl)ncc1O ; Clc1ncc2c(n1)NCCO2]

4-Amino-2-chloropyrimidin-5-ol (67; 3.75 g, 25.8 mmol) was taken up in CH$_2$Cl$_2$ (2500 mL) along with 1,2-dibromoethane (4.85 g, 25.8 mmol) and K$_2$CO$_3$ (10.68 g, 77.4 mmol). The resulting reaction mixture was refluxed for 4 h. The solid in the mixture was removed by filtration. The filtrate was concentrated, and the residue was purified by column chromatography to obtain 2-chloro-7,8-dihydro-6H-pyrimido[5,4-b][1,4]oxazine (68; 3.18 g, 72% yield). MS (ESI) calcd for C$_6$H$_6$ClN$_3$O: 171.58. found 173 [M+H].

Step 4. Synthesis of 2-(3-(trifluoromethyl)phenyl)-7,8-dihydro-6H-pyrimido[5,4-b][1,4]oxazine (69)

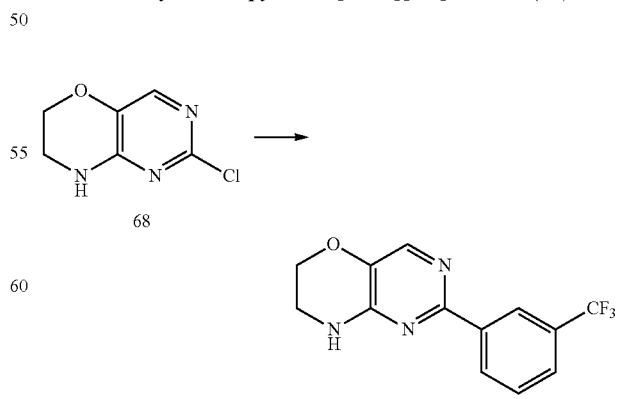

2-Chloro-7,8-dihydro-6H-pyrimido[5,4-b][1,4]oxazine (68; 1.41 g, 8.22 mmol), 3-(trifluoromethyl)phenylboronic acid (1.87 g, 9.86 mmol), Pd(PPh$_3$)$_4$ (475 mg, 0.411 mmol), Na$_2$CO$_3$ (2.09 g, 19.7 mmol) and dioxane/water (4:1, 35 ml) were added to a sealed tube and filled with nitrogen. Then the mixture was heated to 120° C. for 12 hours. After cooling, CH$_2$Cl$_2$ (100 mL) was added and the mixture was passed through a pad of Na$_2$SO$_4$. The solvent was removed under vacuum and the residue was purified by column chromatography (1:15 EtOAc/petroleum ether) to afford 2-(3-(trifluoromethyl)phenyl)-7,8-dihydro-6H-pyrimido[5,4-b][1,4]oxazine (69; 1.20 g, 52% yield). MS (ESI) calcd for C$_{13}$H$_{10}$F$_3$N$_3$O: 281.23. found 282[M+H].

This general coupling procedure could be used to prepare a variety of 2-aryl-7,8-dihydro-6H-pyrimido[5,4-b][1,4]oxazine derivatives by substituting the appropriate boronic acid for 3-(trifluoromethyl)-phenylboronic acid.

Step 5. Synthesis of N-(4-methylthiazol-2-yl)-2-(3-(trifluoromethyl)phenyl)-6H-pyrimido[5,4-b][1,4]oxazine-8(7H)-carboxamide (Compound 709)

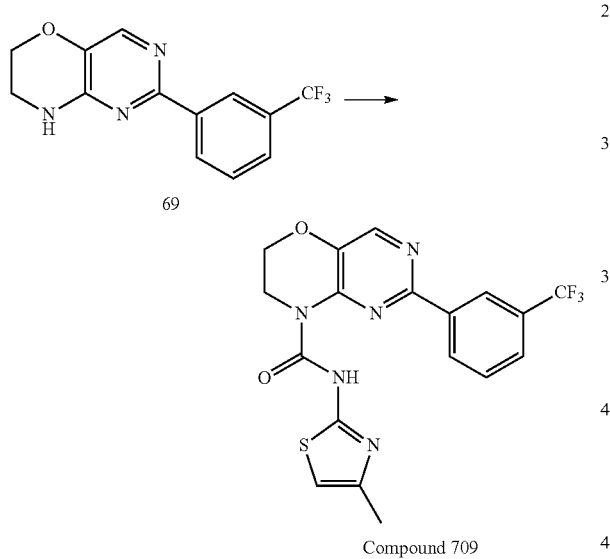

Compound 709

To a solution of 2-(3-(trifluoromethyl)phenyl)-7,8-dihydro-6H-pyrimido[5,4-b][1,4]oxazine (84 mg, 0.3 mmol) and triethylamine (69; 106 mg, 1.05 mmol) in CH$_2$Cl$_2$ (6 mL) was added triphosgene (44.5 mg, 0.15 mmol). The reaction mixture was stirred at room temp for 30 min, and then 4-methylthiazol-2-amine (103 mg, 0.9 mmol) was added and the reaction mixture was stirred overnight. The solvent was removed and the residue was purified by column chromatography to afford N-(4-methylthiazol-2-yl)-2-(3-(trifluoromethyl)phenyl)-6H-pyrimido[5,4-b][1,4]oxazine-8 (7H)-carboxamide (Compound 709; 56 mg, 44% yield). MS (ESI) calcd for C$_{18}$H$_{14}$F$_3$N$_5$O$_2$S: 421.08. found 422 [M+H].

This general procedure could be used to prepare a variety of N-substituted-2-aryl-6H-pyrimido[5,4-b][1,4]oxazine-8 (7H)-carboxamide derivatives by substituting the appropriate amine for 4-methylthiazol-2-amine. Alternatively, derivatives can also be prepared by reacting the appropriate phenyl carbamate with 2-aryl-7,8-dihydro-6H-pyrimido[5,4-b][1,4]oxazine in the presence of DIEA at room temp to 50° C.

Example 16

Preparation of 4-(dimethylamino)-2-(3-fluorophenyl)-N-(pyridin-4-yl)-6H-pyrimido[5,4-b][1,4]oxazine-8(7H)-carboxamide (Compound 736)

Step 1. Synthesis of Ethyl 3-fluorobenzimidate hydrochloride (71)

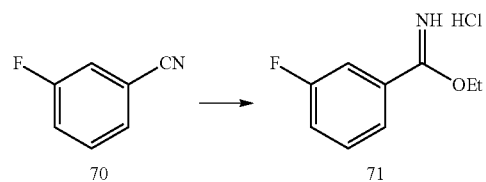 [SMILES: Cl ; N#Cc1cccc(F)c1 ; CCOC(=N)c1cccc(F)c1]

A solution of 3-fluorobenzonitrile (70; 20.0 g, 165 mmol) and EtOH (50 mL) and was cooled with an ice-bath. HCl gas was bubbled through the solution until saturation and the reaction mixture was stirred overnight. The solid was collected by filtration and was washed with cold ether to obtain ethyl-3-fluorobenzimidate hydrochloride as a solid (71; 33.5 g, 99% yield). MS (ESI) calcd for C$_9$H$_{10}$FNO—HCl: 203.64.

Step 2. Synthesis of 3-Fluorobenzimidamide hydrochloride (72)

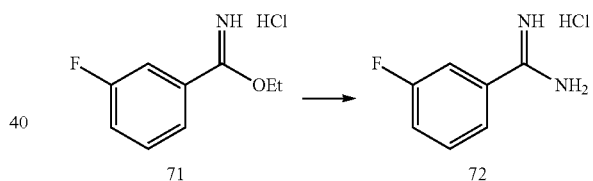

A solution of ethyl-3-fluorobenzimidate hydrochloride (71; 33.5 g, 164 mmol) in (150 mL) of EtOH and was cooled to −5 to −10° C. Ammonia gas was bubbled to saturate the solution and the reaction mixture was stirred overnight. The solid was collected by filtration and was washed with cold ether to afford 3-fluorobenzimidamide hydrochloride (72; 27.2 g, 95% yield). MS (ESI) calcd for C$_7$H$_{17}$FN$_2$—HCl: 138.14.

Step 3. Synthesis of 2-(3-Fluorophenyl)-5-methoxypyrimidine-4,6-diol (73)

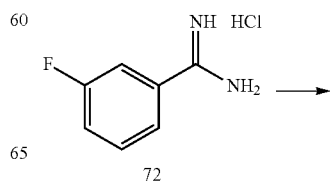

Step 5. Synthesis of 6-Chloro-2-(3-fluorophenyl)-5-methoxypyrimidin-4-amine (75)

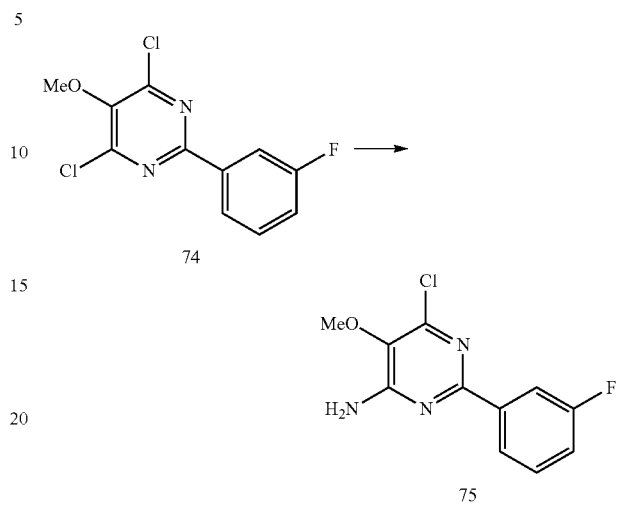

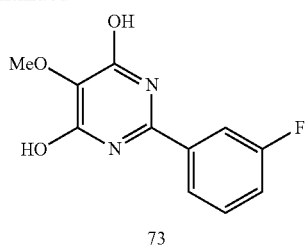

Sodium (2.05 g, 89.3 mmol) was added to anhydrous methanol (60 mL) at 0° C. After the sodium completely dissolved, 3-fluorobenzimidamide hydrochloride (72; 5.0 g, 28.8 mmol) was added to the cold solution. Dimethyl 2-methoxymalonate (4.67 g, 28.8 mmol) was then added dropwise over 30 min. at 0° C. The resulting reaction mixture was refluxed for 1.5 h. After cooling, the solution was neutralized with HCl. The solvent was removed under vacuum, and the residue was purified by column chromatography to obtain 2-(3-fluorophenyl)-5-methoxypyrimidine-4,6-diol (73; 3.57 g, 53% yield). MS (ESI) calcd for $C_{11}H_9FN_2O_3$: 236.20.

4,6-Dichloro-2-(3-fluorophenyl)-5-methoxypyrimidine (74; 4.1 g, 15 mmol) and 25% ammonium hydroxide (50 mL) was heated to 100° C. for 21 h in a sealed tube. After cooling, the solvent was removed under vacuum, and the residue was purified by column chromatography to obtain 6-chloro-2-(3-fluorophenyl)-5-methoxypyrimidin-4-amine (75; 2.7 g, 71% yield). MS (ESI) calcd for $C_{11}H_9ClFN_3O$: 253.66.

Step 4. Synthesis of 4,6-Dichloro-2-(3-fluorophenyl)-5-methoxypyrimidine (74)

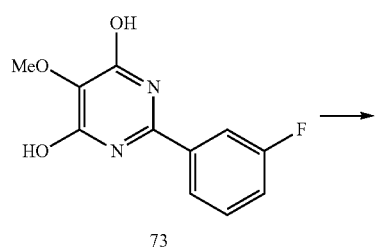

Step 6. Synthesis of 4-Amino-6-chloro-2-(3-fluorophenyl)pyrimidin-5-ol (76)

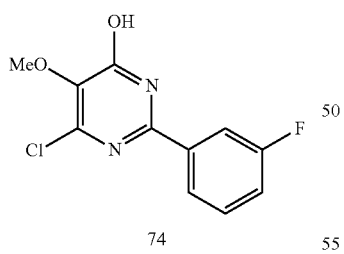

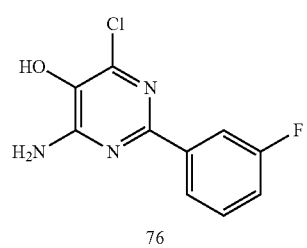

A solution of 2-(3-fluorophenyl)-5-methoxypyrimidine-4,6-diol (73; 3.57 g, 15.1 mmol) in POCl₃ (20 mL) was refluxed for 22 hours. The excessive POCl₃ was removed under vacuum and the residue was partitioned between water and CH₂Cl₂. The organic layer was dried, concentrated and purified by column chromatography to obtain 4,6-dichloro-2-(3-fluorophenyl)-5-methoxypyrimidine (74; 4.10 g, 99% yield). MS (ESI) calcd for $C_{11}H_7Cl_2FN_2O$: 273.09.

To a solution of 6-chloro-2-(3-fluorophenyl)-5-methoxypyrimidin-4-(75; 2.7 g, 10.6 mmol) in CH₂Cl₂ (50 mL) was added dropwise boron tribromide (10.2 mL). The resulting reaction mixture was stirred at room temperature for 24 h. MeOH was cautiously added until the solution was homogenous. The solvent was removed under vacuum, and aqueous NaHCO₃ was added. The mixture was extracted with CH₂Cl₂ and the organic layer was dried and concentrated. The residue was purified by column chromatography to obtain 4-amino-6-chloro-2-(3-fluorophenyl)pyrimidin-5-ol (76; 1.07 g, 42% yield). MS (ESI) calcd for $C_{10}H_7ClFN_3O$: 239.63.

Step 7. Synthesis of 4-Chloro-2-(3-fluorophenyl)-6H-pyrimido[5,4-b][1,4]oxazin-7(8H)-one

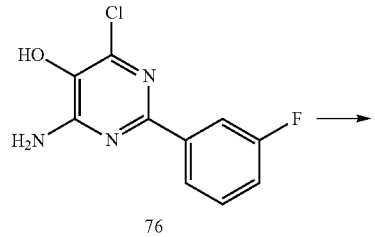

76

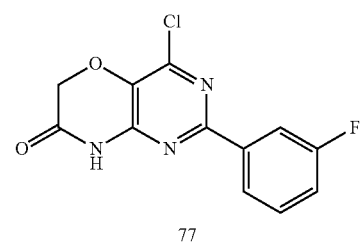

77

4-Amino-6-chloro-2-(3-fluorophenyl)pyrimidin-5-ol (76; 5.3 g, 22.1 mmol) was dissolved in THF (2200 mL) along with $K_2CO_3$ (15.2 g, 110 mmol). 2-Chloroacetyl chloride (2.50 g, 22.1 mmol) was added dropwise and the reaction mixture was stirred at room temp for 2 h. The reaction mixture was refluxed for 24 h. The solvent was removed under vacuum, and the residue was purified by column chromatography to obtain 4-chloro-2-(3-fluorophenyl)-6H-pyrimido[5,4-b][1,4]oxazin-7(8H)-one (77; 3.4 g, 55% yield). MS (ESI) calcd for $C_{12}H_7ClFN_3O_2$: 279.65.

Step 8. Synthesis of 4-Chloro-2-(3-fluorophenyl)-7,8-dihydro-6H-pyrimido[5,4-b][1,4]oxazine (78)

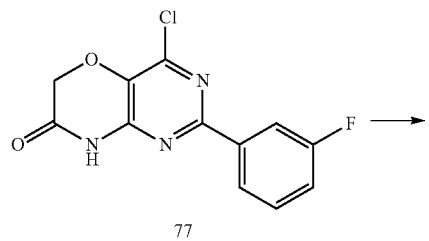

77

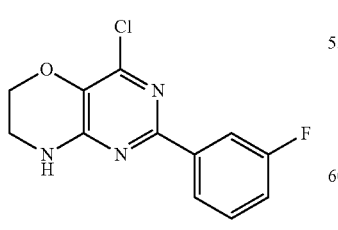

78

To a solution of 4-Chloro-2-(3-fluorophenyl)-6H-pyrimido[5,4-b][1,4]oxazin-7(8H)-one (77; 3.4 g, 12.1 mmol) in THF (40 mL) was added 9.8 M $BH_3$-$Me_2S$ (12.4 mL, 121 mmol). The reaction mixture was refluxed overnight. After cooling, methanol (8 mL) was added dropwise to the solution and the reaction mixture was refluxed for 30 min. The solvent was removed under vacuum, and the residue was purified by column chromatography to obtain 4-chloro-2-(3-fluorophenyl)-7,8-dihydro-6H-pyrimido[5,4-b][1,4]oxazine (78; 2.16 g, 67% yield). MS (ESI) calcd for $C_{12}H_9ClFN_3O$: 265.67.

Step 9. Synthesis of 2-(3-Fluorophenyl)-N,N-dimethyl-7,8-dihydro-6H-pyrimido[5,4-b][1,4]oxazin-4-amine (79)

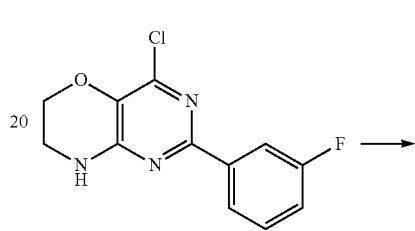

79

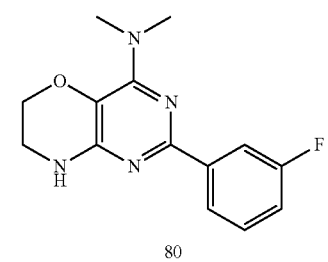

80

A mixture of 4-chloro-2-(3-fluorophenyl)-7,8-dihydro-6H-pyrimido[5,4-b][1,4]oxazine (79; 550 mg, 2.07 mmol), 33% dimethylamine solution (35 mL) in dioxane (70 ml) was heated at 90° C. for 24 h in a sealed tube. The solvent was removed and the residue was purified by column chromatography to afford 2-(3-Fluorophenyl)-N,N-dimethyl-7,8-dihydro-6H-pyrimido[5,4-b][1,4]oxazin-4-amine. (80; 420 mg, 74% yield). MS (ESI) calcd for $C_{14}H_{15}FN_4O$: 274.29. found 275.

The general protocol described above was used to synthesize the analogous 2-(3-fluorophenyl)-4-(pyrrolidin-1-yl)-7,8-dihydro-6H-pyrimido[5,4-b][1,4]oxazine

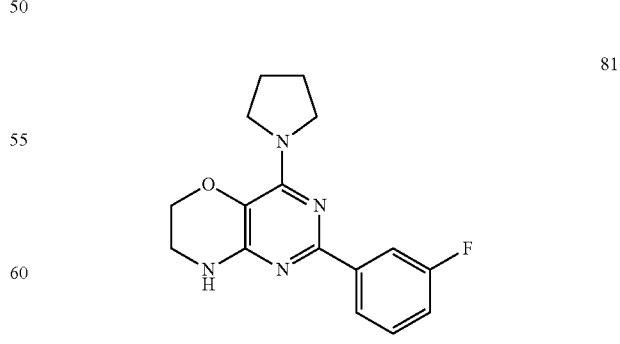

81 by substituting pyrroline for dimethylamine and 2-(3-fluorophenyl)-4-morpholino-7,8-dihydro-6H-pyrimido[5,4-b][1,4]oxazine 82

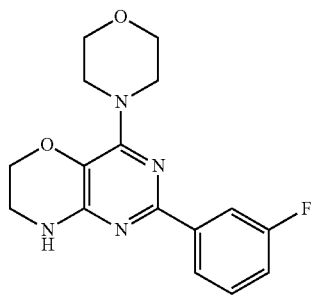

by substituting morpholine for dimethylamine.

Step 10. Synthesis of 4-(dimethylamino)-2-(3-fluorophenyl)-N-(pyridin-4-yl)-6H-pyrimido[5,4-b][1,4]oxazine-8(7H)-carboxamide (Compound 736)

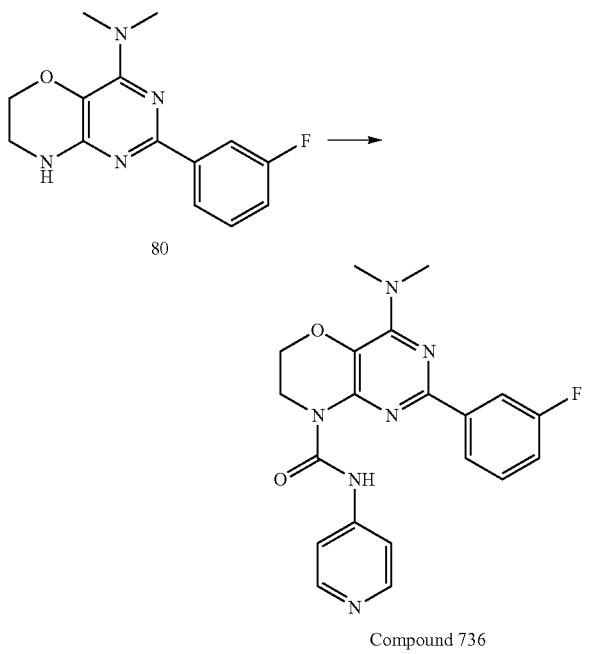

To a solution of 2-(3-fluorophenyl)-N,N-dimethyl-7,8-dihydro-6H-pyrimido[5,4-b][1,4]oxazin-4-amine (80; 90 mg, 0.328 mmol) and triethylamine (116 mg, 1.15 mmol) in CH$_2$Cl$_2$ (5 mL) was added triphosgene (49 mg, 0.164 mmol). The reaction mixture was stirred at room temp for 2 h, and then pyridin-4-amine (93 mg, 0.984 mmol) was added and the reaction mixture was stirred for 24 h. The solvent was removed and the residue was purified by column chromatography to afford 4-(dimethylamino)-2-(3-fluorophenyl)-N-(pyridin-4-yl)-6H-pyrimido[5,4-b][1,4]oxazine-8(7H)-carboxamide. (Compound 736; 24 mg, 19% yield). MS (ESI) calcd for C$_{20}$H$_{19}$FN$_6$O$_2$: 394.16. found 395 [M+H].

This general procedure could be used to prepare a variety of 4-substituted-2-aryl-N-substituted-6H-pyrimido[5,4-b][1,4]oxazine-8(7H)-carboxamide derivatives by substituting the appropriate amine for pyridine-4-amine. Alternatively, derivatives can also be prepared by reacting the appropriate phenyl carbamate with 2-aryl-substituted-7,8-dihydro-6H-pyrimido[5,4-b][1,4]oxazin-4-amine in the presence of DIEA at room temp to 50° C.

Example 17

Preparation of 2-(3-fluorophenyl)-4-(piperazin-1-yl)-N-(pyridin-4-yl)-6H-pyrimido[5,4-b][1,4]oxazine-8(7H)-carboxamide (Compound 738)

Step 1. Synthesis of tert-butyl 4-(2-(3-fluorophenyl)-7,8-dihydro-6H-pyrimido[5,4-b][1,4]oxazin-4-yl)piperazine-1-carboxylate (83)

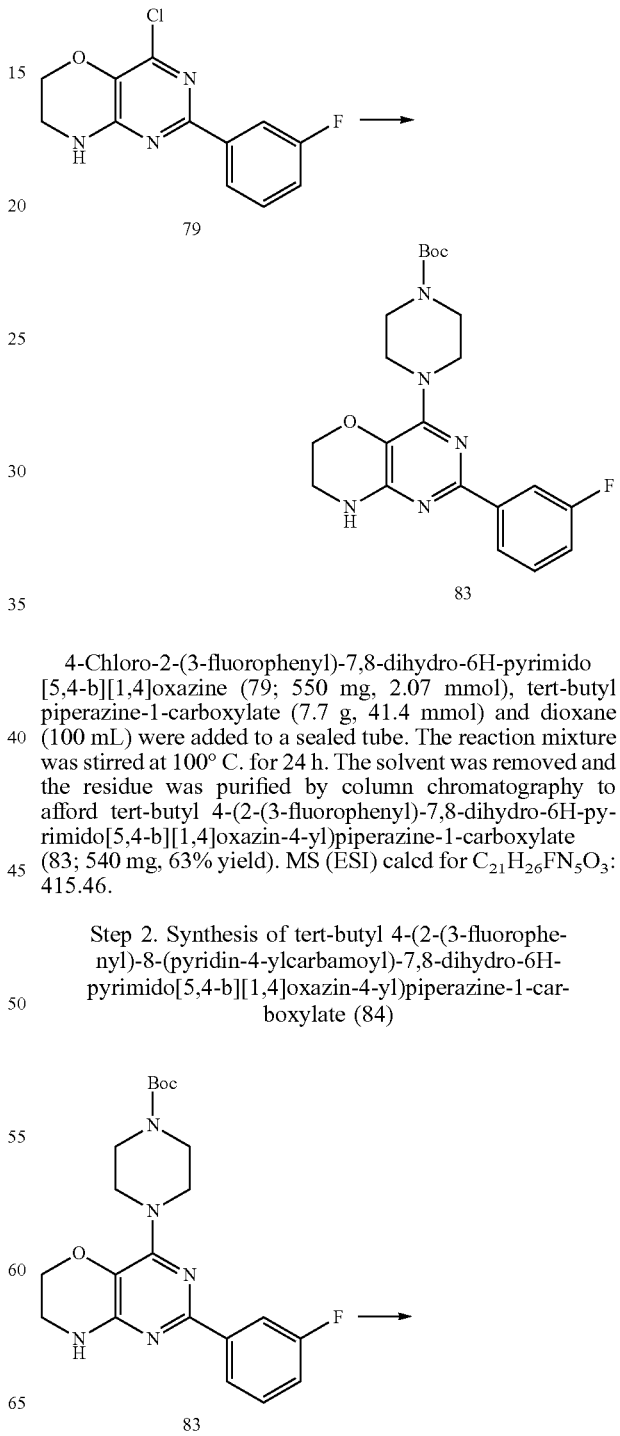

4-Chloro-2-(3-fluorophenyl)-7,8-dihydro-6H-pyrimido[5,4-b][1,4]oxazine (79; 550 mg, 2.07 mmol), tert-butyl piperazine-1-carboxylate (7.7 g, 41.4 mmol) and dioxane (100 mL) were added to a sealed tube. The reaction mixture was stirred at 100° C. for 24 h. The solvent was removed and the residue was purified by column chromatography to afford tert-butyl 4-(2-(3-fluorophenyl)-7,8-dihydro-6H-pyrimido[5,4-b][1,4]oxazin-4-yl)piperazine-1-carboxylate (83; 540 mg, 63% yield). MS (ESI) calcd for C$_{21}$H$_{26}$FN$_5$O$_3$: 415.46.

Step 2. Synthesis of tert-butyl 4-(2-(3-fluorophenyl)-8-(pyridin-4-ylcarbamoyl)-7,8-dihydro-6H-pyrimido[5,4-b][1,4]oxazin-4-yl)piperazine-1-carboxylate (84)

-continued

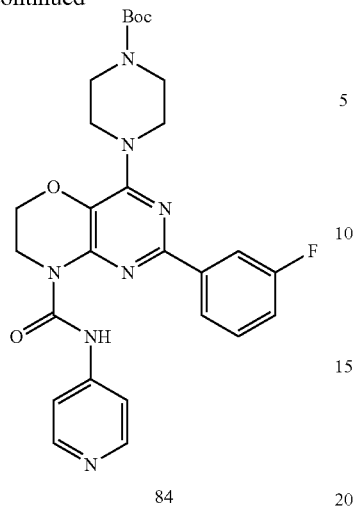

84

To a solution of tert-butyl 4-(2-(3-fluorophenyl)-7,8-dihydro-6H-pyrimido[5,4-b][1,4]oxazin-4-yl)piperazine-1-carboxylate (83; 120 mg, 0.289 mmol) and triethylamine (102 mg, 1.01 mmol) in $CH_2Cl_2$ (7 mL) was added triphosgene (43 mg, 0.144 mmol). The reaction mixture was stirred at room temperature for 2 h. Pyridin-4-amine (82 mg, 0.867 mmol) was added and the reaction mixture was stirred for 24 h. The solvent was removed and the residue was purified by column chromatography to afford tert-butyl 4-(2-(3-fluorophenyl)-8-(pyridin-4-ylcarbamoyl)-7,8-dihydro-6H-pyrimido[5,4-b][1,4]oxazin-4-yl)piperazine-1-carboxylate. (84; 85 mg, 55% yield). MS (ESI) calcd for $C_{27}H_{30}FN_7O_4$: 535.57.

This general procedure could be used to prepare a variety of 4-aryl-8-substituted-7,8-dihydro-6H-pyrimido[5,4-b][1,4]oxazin-4-yl) substituted-1-carboxylate derivatives by substituting the appropriate amine for pyridine-4-amine. Alternatively, derivatives can also be prepared by reacting the appropriate phenyl carbamate with 4-aryl-7,8-dihydro-6H-pyrimido[5,4-b][1,4]oxazin-4-yl) substituted-1-carboxylate in the presence of DIEA at room temp to 50° C.

Step 3. Synthesis of 2-(3-fluorophenyl)-4-(piperazin-1-yl)-N-(pyridin-4-yl)-6H-pyrimido[5,4-b][1,4]oxazine-8(7H)-carboxamide (Compound 738)

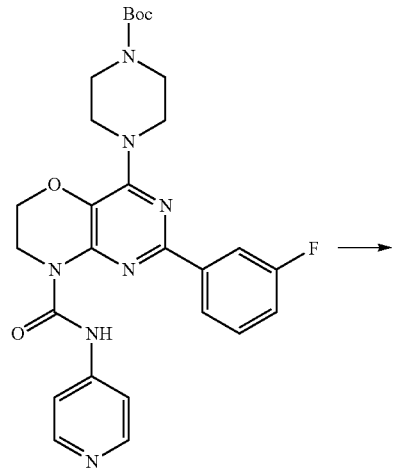

84

-continued

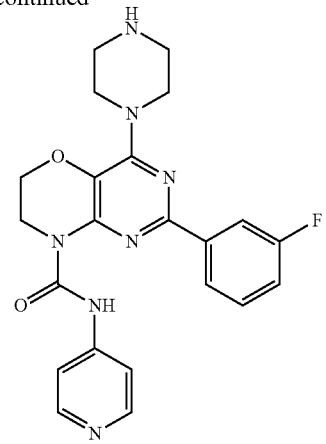

Compound 738

Tert-butyl 4-(2-(3-fluorophenyl)-8-(pyridin-4-ylcarbamoyl)-7,8-dihydro-6H-pyrimido[5,4-b][1,4]oxazin-4-yl)piperazine-1-carboxylate (84; 85 mg, 0.159 mmol) was added to 1N HCl (20 mL) and the mixture was stirred at room temp overnight. The solution was neutralized with sat. $NaHCO_3$ and extracted with EtOAc. The organic layers were combined, dried and concentrated. The residue was purified by column chromatography to afford 2-(3-fluorophenyl)-4-(piperazin-1-yl)-N-(pyridin-4-yl)-6H-pyrimido[5,4-b][1,4]oxazine-8(7H)-carboxamide (Compound 738; 0 mg, 58% yield). MS (ESI) calcd for $C_{22}H_{22}FN_7O_2$: 435.18. found 436 [M+H].

Example 18

Preparation of 2,2-dimethyl-N-(pyridin-4-yl)-6-(3-(trifluoromethyl)phenyl)-2H-pyrido[3,2-b][1,4]oxazine-4(3H)-carboxamide (Compound 560)

Step 1. Synthesis of ethyl 2-((6-bromo-2-nitropyridin-3-yl)oxy)-2-methylpropanoate (86)

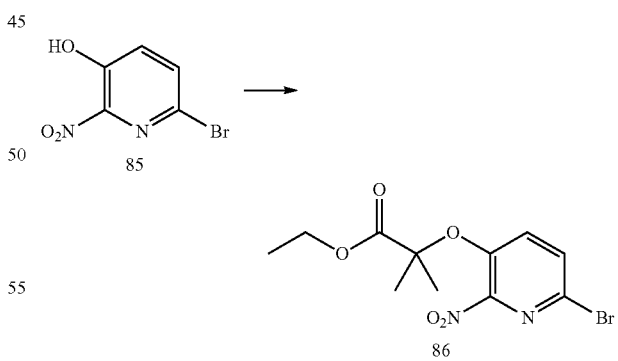

A mixture of 6-bromo-2-nitropyridin-3-ol (85; 3.28 g, 15 mmol), ethyl 2-bromo-2-methylpropanoate (3.51 g, 18 mmol), and $K_2CO_3$ in dimethylformamide (30 mL) was stirred at room temp for 48 h. Water was added and the mixture was extracted with EtOAc. The combined organic layers were washed with water and brine, dried, concentrated and purified with column chromatography, eluting with petroleum ether:EtOAc to afford ethyl 2-((6-bromo-2- nitropyridin-3-yl)oxy)-2-methylpropanoate (86; 1.3 g, 36%) as a yellow solid. MS (ESI) calcd for $C_{11}H_{13}BrN_2O_5$: 333.14.

Step 2. Synthesis of 6-bromo-2,2-dimethyl-2H-pyrido[3,2-b][1,4]oxazin-3(4H)-one (87)

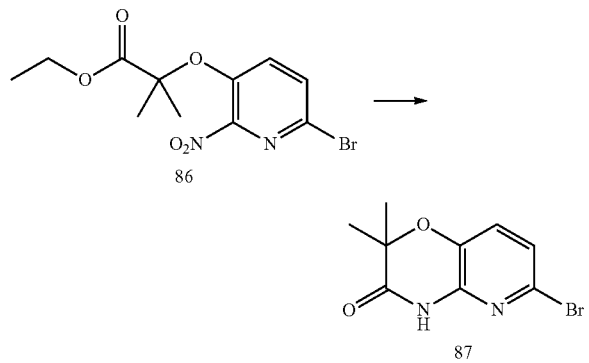

A mixture of ethyl 2-((6-bromo-2-nitropyridin-3-yl)oxy)-2-methylpropanoate (86; 5.5 g, 17.2 mmol) and iron powder (5.2 g, 92 mmol) in HOAc (50 mL) was heated at 90° C. for 2 h. The hot solution was filtered though a pad of celite and concentrated. The residue was treated with saturated aq. NaHCO and extracted with EtOAc. The combined organic layers were washed with brine concentrated to give 6-bromo-2,2-dimethyl-2H-pyrido[3,2-b][1,4]oxazin-3(4H)-one (87; 4.1 g, 92%) as a white solid. MS (ESI) calcd for $C_9H_9BrN_2O_2$: 257.08.

Step 3. Synthesis of 6-bromo-2,2-dimethyl-3,4-dihydro-2H-pyrido[3,2-b][1,4]oxazine (88)

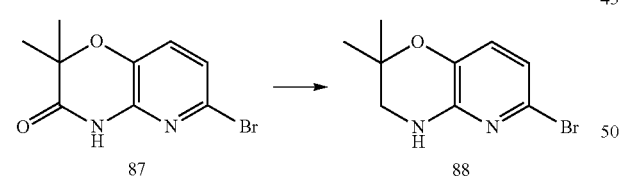

A solution of 6-bromo-2,2-dimethyl-2H-pyrido[3,2-b][1,4]oxazin-3(4H)-one (87; 4.4 g, 17.1 mmol) and $BH_3 \cdot Me_2S$ (2.5 M in THF, 64 mL, 160 mmol) was heated at reflux 24 h. After cooling, MeOH (10 mL) was added portionwise to the solution and the reaction mixture was refluxed for 30 min. The reaction mixture was then concentrated, water was added, and the mixture was extracted with ethyl acetate. The combined organic layers were washed with brine, dried ($Na_2SO_4$), filtered, and concentrated, and purified by column chromatography eluting with ethyl acetate:petroleum ether to give 6-bromo-2,2-dimethyl-3,4-dihydro-2H-pyrido[3,2-b][1,4]oxazine (88; 2.5 g, 57%) as a yellow oil. MS (ESI) calcd for $C_9H_{11}BrN_2O$: 243.10. found 245 [M+H].

Step 4. Synthesis of 2,2-dimethyl-6-(3-(trifluoromethyl)phenyl)-3,4-dihydro-2H-pyrido[3,2-b][1,4]oxazine (89)

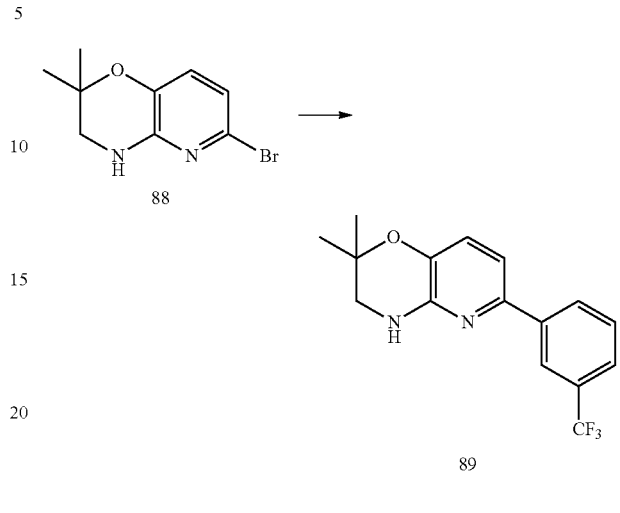

A mixture of compound 6-bromo-2,2-dimethyl-3,4-dihydro-2H-pyrido[3,2-b][1,4]oxazine (88; 1.0 g, 4.11 mmol), (3-(trifluoromethyl)phenyl)boronic acid (1.2 g, 6.17 mmol), $Pd(PPh_3)_4$ (250 mg, 0.21 mmol) and cesium carbonate (2.7 g, 8.22 mmol) in 1,2-dimethoxyethane (20 mL) and water (2 mL) was stirred at 100° C. for 18 h. The solid was filtered and the filtrate was concentrated to give a dark residue, which was purified by column chromatography eluting with ethyl acetate:petroleum ether to afford 2,2-dimethyl-6-(3-(trifluoromethyl)phenyl)-3,4-dihydro-2H-pyrido[3,2-b][1,4]oxazine (89; 1.13 g, 89%) as an off-white solid. MS (ESI) calcd for $C_{16}H_{15}F_3N_2O$: 308.30. found 309 [M+H].

This general coupling procedure could be used to prepare a variety of 2,2-dimethyl-6-aryl-3,4-dihydro-2H-pyrido[3,2-b][1,4]oxazine derivatives by substituting the appropriate boronic acid for 3-(trifluoromethyl)-phenylboronic acid.

Step 5. Synthesis of 2,2-dimethyl-N-(pyridin-4-yl)-6-(3-(trifluoromethyl)phenyl)-2H-pyrido[3,2-b][1,4]oxazine-4(3H)-carboxamide (Compound 560)

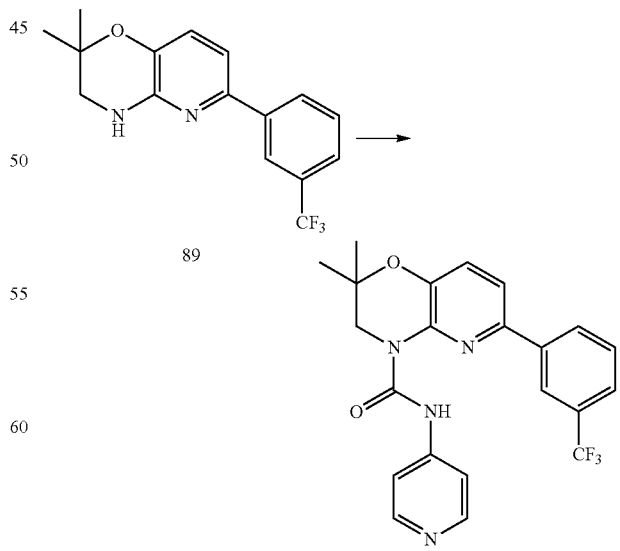

To a solution of 2,2-dimethyl-6-(3-(trifluoromethyl)phenyl)-3,4-dihydro-2H-pyrido[3,2-b][1,4]oxazine (89; 100 mg, 0.32 mmol) and triethylamine (0.16 mL, 1.13 mmol) in CH$_2$Cl$_2$ (5 mL) was added triphosgene (48 mg, 0.16 mmol), and the mixture was stirred at room temperature for 30 min. Then pyridine-4-amine (92 mg, 0.97 mmol) was added and the mixture was stirred at room temperature overnight. The reaction mixture was diluted with CH$_2$Cl$_2$, and washed with water and brine, dried (MgSO$_4$), filtered, and concentrated. The residue was purified by chromatography to give 2,2-dimethyl-N-(pyridin-4-yl)-6-(3-(trifluoromethyl)phenyl)-2H-pyrido[3,2-b][1,4]oxazine-4(3H)-carboxamide (Compound 560; mg, 29%). MS (ESI) calcd for C$_{22}$H$_{19}$F$_3$N$_4$O$_2$: 428.15. found: 429 [M+H].

This general procedure could be used to prepare a variety of 2,2-dimethyl-N-substituted-6-aryl-2H-pyrido[3,2-b][1,4]oxazine-4(3H)-carboxamide derivatives by substituting the appropriate amine for pyridine-4-amine. Alternatively, derivatives can also be prepared by reacting the appropriate phenyl carbamate with 2,2-dimethyl-6-aryl-3,4-dihydro-2H-pyrido[3,2-b][1,4]oxazine in the presence of DIEA at room temp to 50° C.

Example 19

Preparation of (S)-6-(3-(3-fluoropyrrolidin-1-yl)phenyl)-2,2-dimethyl-N-(5-methylpyridin-3-yl)-2H-pyrido[3,2-b][1,4]oxazine-4(3H)-carboxamide (Compound 660)

Step 1. Synthesis of (S)-1-(3-bromophenyl)-3-fluoropyrrolidin (91)

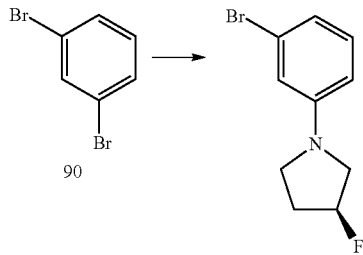

To a solution of 1,3-dibromobenzene (90; 5 g, 21.20 mmol) and (S)-3-fluoropyrrolidin hydrochloride (2.93 g, 23.31 mmol) in toluene (100 mL) were added BINAP (1.32 g, 2.12 mmol), Pd$_2$(dba)$_3$ (0.97 g, 1.06 mmol), and Cs$_2$CO$_3$ (6.93 g, 50.9 mmol). The reaction was stirred at 121° C. for 10 h. The mixture was concentrated and purified by column chromatography to give (S)-1-(3-bromophenyl)-3-fluoropyrrolidine (91; 3.5 g, 68%). MS (ESI) calcd for C$_{10}$H$_{11}$BrFN: 244.10.

Step 2. Synthesis of (S)-(3-(3-fluoropyrrolidin-1-yl)phenyl)boronic acid (92)

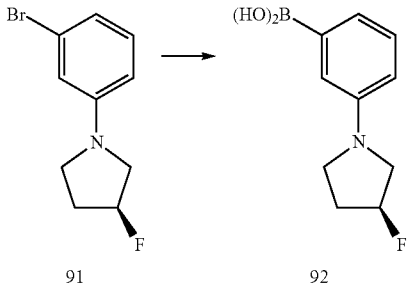 [SMILES: F[C@H]1CCN(c2cccc(Br)c2)C1 ; OB(O)c1cccc(N2CC[C@H](F)C2)c1]

To a solution of (S)-1-(3-bromophenyl)-3-fluoropyrrolidine (91; 3.5 g, 14.34 mmol) in THF (70 mL) was added n-BuLi (2.5 M solution in hexane, 12 mL, 28.68 mmol) at −78° C., the reaction mixture was stirred at the same temperature for 1 h and was added trimethylborate (1.79 g, 17.21 mmol) dropwise. After stirring the mixture at −78° C. for an additional 30 min, MeOH was added and the mixture was extracted with EtOAc. The organic layer was dried (Na$_2$SO$_4$) and concentrated. The residue was purified by column chromatography to afford (S)-(3-(3-fluoropyrrolidin-1-yl)phenyl)boronic acid (92; 940 mg, 31%). MS (ESI) calcd for C$_{10}$H$_{13}$BFNO$_2$: 209.03. found: 210 [M+H].

Step 3. Synthesis of (S)-6-(3-(3-fluoropyrrolidin-1-yl)phenyl)-2,2-dimethyl-3,4-dihydro-2H-pyrido[3,2-b][1,4]oxazine (93)

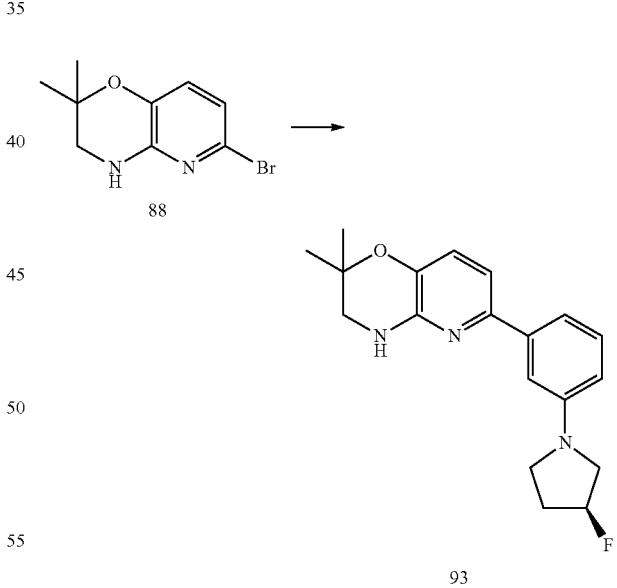

A mixture of compound 6-bromo-2,2-dimethyl-3,4-dihydro-2H-pyrido[3,2-b][1,4]oxazine (88; 350 mg, 1.44 mmol), (S)-(3-(3-fluoropyrrolidin-1-yl)phenyl)boronic acid (330 mg, 1.58 mmol), Pd(dppf)Cl$_2$ (60 mg, 0.072 mmol) and cesium carbonate (0.94 g, 2.88 mmol) in 1,2-dimethoxyethane (10 mL) was stirred at 95° C. overnight. The reaction mixture was purified by column chromatography, eluting with EtOAc:petroleum ether, to afford (S)-6-(3-(3-fluoropyrrolidin-1-yl)phenyl)-2,2-dimethyl-3,4-dihydro-2H-pyrido

[3,2-b][1,4]oxazine (93; 290 mg, 62%). MS (ESI) calcd for $C_{19}H_{22}FN_3O$: 327.40. found: 328 [M+H].

Step 4. Synthesis of (S)-6-(3-(3-fluoropyrrolidin-1-yl)phenyl)-2,2-dimethyl-N-(5-methylpyridin-3-yl)-2H-pyrido[3,2-b][1,4]oxazine-4(3H)-carboxamide (Compound 660)

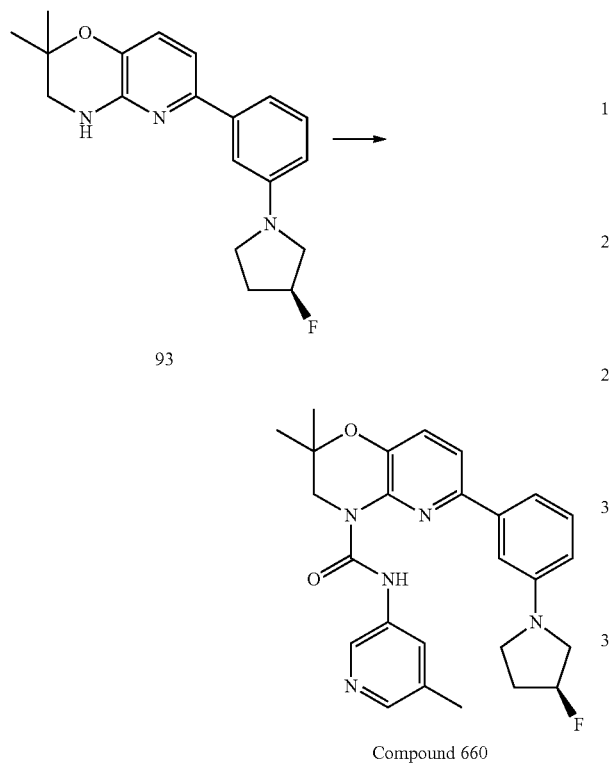

To a mixture of (S)-6-(3-(3-fluoropyrrolidin-1-yl)phenyl)-2,2-dimethyl-3,4-dihydro-2H-pyrido[3,2-b][1,4]oxazine (93; 65 mg, 0.2 mmol) and triethylamine (61 mg, 0.6 mmol) in THF (3 mL) was added triphosgene (24 mg, 0.08 mmol). The reaction mixture was stirred at room temperature for 1.5 h. 5-Methylpyridin-3-amine (43 mg, 0.4 mmol) was added and the reaction mixture was stirred at 60° C. for 18 h. The reaction mixture was then washed with saturated sodium bicarbonate solution and water. The organic layer was concentrated and purified by chromatography to give (S)-6-(3-(3-fluoropyrrolidin-1-yl)phenyl)-2,2-dimethyl-N-(5-methylpyridin-3-yl)-2H-pyrido[3,2-b][1,4]oxazine-4(3H)-carboxamide (Compound 660; 34 mg, 31%) as a yellow solid. MS (ESI) calcd for $C_{26}H_{28}FN_5O_2$: 461.22. found: 462 [M+H].

(R)-6-(3-(3-fluoropyrrolidin-1-yl)phenyl)-2,2-dimethyl-N-(5-methylpyridin-3-yl)-2H-pyrido[3,2-b][1,4]oxazine-4(3H)-carboxamide (Compound 701) was prepared using a procedure analogous to that described above for (S)-6-(3-(3-fluoropyrrolidin-1-yl)phenyl)-2,2-dimethyl-N-(5-methylpyridin-3-yl)-2H-pyrido[3,2-b][1,4]oxazine-4(3H)-carboxamide, starting from the enantiomer (S)-3-fluoropyrrolidine hydrochloride Example 20

Preparation of 2,2-dimethyl-N-(5-methylpyridin-3-yl)-6-(3-(pyrrolidin-1-ylmethyl)phenyl)-2H-pyrido[3,2-b][1,4]oxazine-4(3H)-carboxamide (Compound 629)

Step 1. Synthesis of methyl 3-(2,2-dimethyl-3,4-dihydro-2H-pyrido[3,2-b][1,4]oxazin-6-yl)benzoate (94)

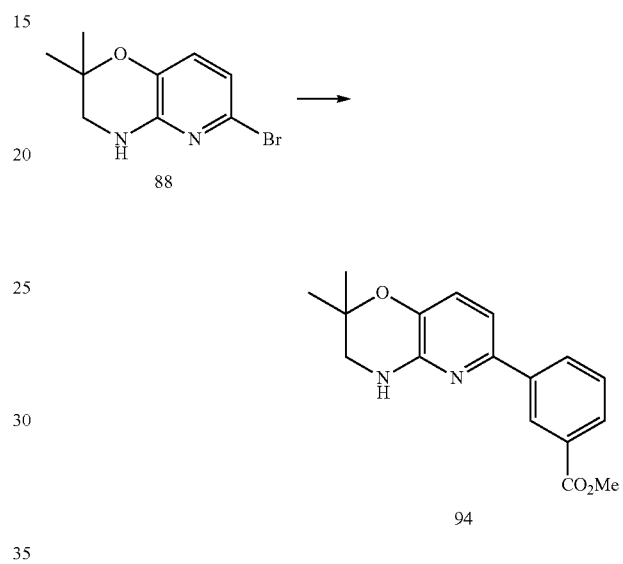

Under a nitrogen atmosphere, a mixture of 6-bromo-2,2-dimethyl-3,4-dihydro-2H-pyrido[3,2-b][1,4]oxazine (88; 1.5 g, 6.2 mmol), (3-(methoxycarbonyl)phenyl)boronic acid (1.45 g, 8.0 mmol), Pd(dppf)Cl$_2$ (260 mg, 0.31 mmol,), and cesium carbonate (4.0 g, 12.34 mmol) in dimethoxyethane (50 mL) was stirred at 90° C. overnight. The reaction mixture was concentrated and was purified by chromatography, eluting with EtOAc:petroleum ether, to give methyl 3-(2,2-dimethyl-3,4-dihydro-2H-pyrido[3,2-b][1,4]oxazin-6-yl)benzoate (94; 1.7 g, 92%) as a yellow solid. MS (ESI) calcd for $C_{17}H_{18}N_2O_3$: 298.34.

Step 2. Synthesis of methyl 3-(2,2-dimethyl-3,4-dihydro-2H-pyrido[3,2-b][1,4]oxazin-6-yl)benzoic acid (95)

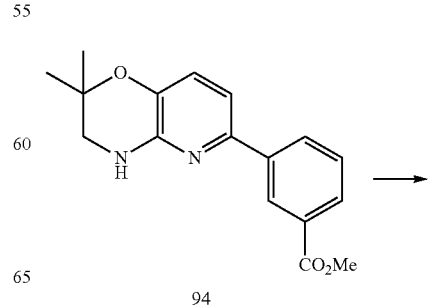

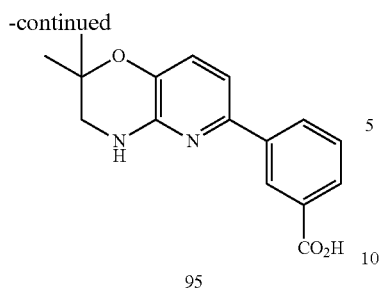

95

To the solution of compound methyl 3-(2,2-dimethyl-3,4-dihydro-2H-pyrido[3,2-b][1,4]oxazin-6-yl)benzoate (94; 700 mg, 2.35 mmol) in the solvent mixture MeOH:THF:H₂O (5 mL:5 mL:3 mL) was added LiOH.H₂O (200 mg, 4.7 mmol) and the mixture was stirred at ambient temperature for 1 hour. The reaction mixture was concentrated, water (25 mL) was added, and the pH was adjusted to 3-4 with concentrated hydrochloric acid. The precipitate was filtered and dried to give methyl 3-(2,2-dimethyl-3,4-dihydro-2H-pyrido[3,2-b][1,4]oxazin-6-yl)benzoic acid (95; 0.59 g, 84%) as a white solid. MS (ESI) calcd for $C_{16}H_{16}N_2O_3$: 284.31.

Step 3. Synthesis of (3-(2,2-dimethyl-3,4-dihydro-2H-pyrido[3,2-b][1,4]oxazin-6-yl)phenyl)(pyrrolidin-1-yl)methanone (96)

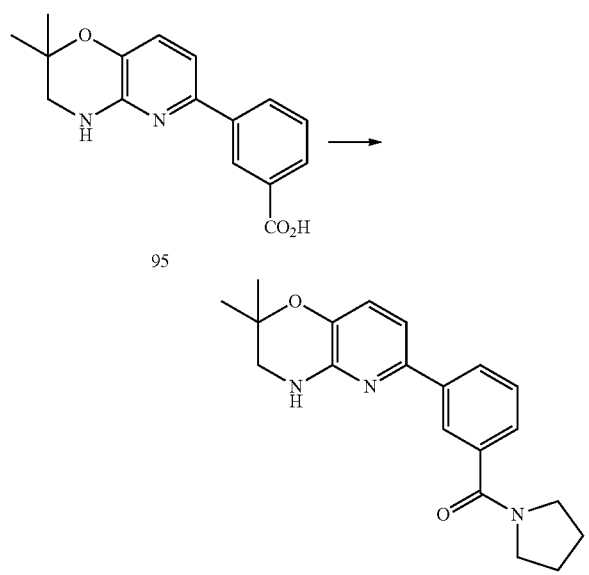

Methyl 3-(2,2-dimethyl-3,4-dihydro-2H-pyrido[3,2-b][1,4]oxazin-6-yl)benzoic acid (95; 0.59 g, 2.1 mmol), pyrrolidine (300 mg, 4.2 mmol), and 2-(7-Aza-1H-benzotriazole-1-yl)-1,1,3,3-tetramethyluronium hexafluorophosphate (HATU) (1.6 g, 4.2 mmol) were dissolved in N,N-Dimethylformamide (DMF) (10 mL). Then diisopropylethylamine (0.8 ml, 4.2 mmol) was added and stirred at room temp overnight. Then the reaction mixture was dilute with water and extracted with EtOAc and the combined organic layers were washed with saturated sodium bicarbonate and water and brine, dried (Na₂SO₄), and concentrated. The residue was triturated with EtOAc:petroleum ether to give (3-(2,2-dimethyl-3,4-dihydro-2H-pyrido[3,2-b][1,4]oxazin-6-yl)phenyl)(pyrrolidin-1-yl)methanone (96; 0.49 g, 72%) as yellow solid. MS (ESI) calcd for $C_{20}H_{23}N_3O_2$: 337.42. found: 338 [M+H].

Step 4. Synthesis of 2,2-dimethyl-6-(3-(pyrrolidin-1-ylmethyl)phenyl)-3,4-dihydro-2H-pyrido[3,2-b][1,4]oxazine (97)

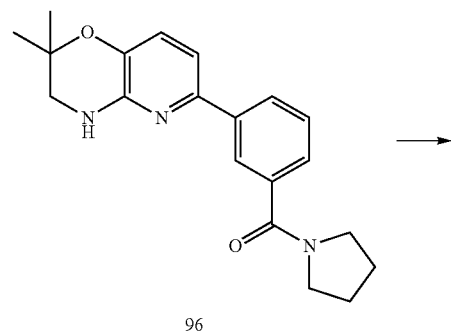

A mixture of (3-(2,2-dimethyl-3,4-dihydro-2H-pyrido[3,2-b][1,4]oxazin-6-yl)phenyl)(pyrrolidin-1-yl)methanone (96; 0.49 g, 1.45 mmol) and BH₃.Me₂S (10 M in THF, 1.5 mL, 15 mmol) in THF (7.5 mL) was heated to reflux for 18 h. After cooling, MeOH (10 mL) was added to the solution and continued to reflux for 1 h. The reaction mixture was concentrated and the residue was purified by column chromatography, eluting with MeOH:CH₂Cl₂, to give 2,2-dimethyl-6-(3-(pyrrolidin-1-ylmethyl)phenyl)-3,4-dihydro-2H-pyrido[3,2-b][1,4]oxazine (97; 0.36 g, 76%) as semi-solid. MS (ESI) calcd for $C_{20}H_{25}N_3O$: 323.43. found: 324 [M+H].

Step 5. Synthesis of 2,2-dimethyl-N-(5-methylpyridin-3-yl)-6-(3-(pyrrolidin-1-ylmethyl)phenyl)-2H-pyrido[3,2-b][1,4]oxazine-4(3H)-carboxamide (Compound 629)

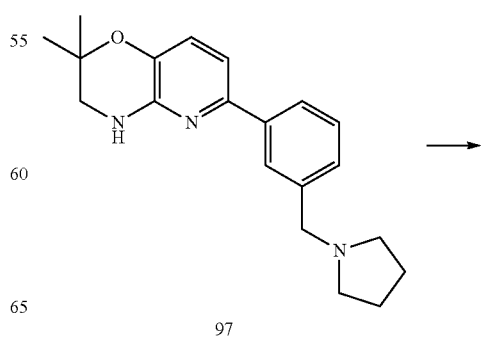

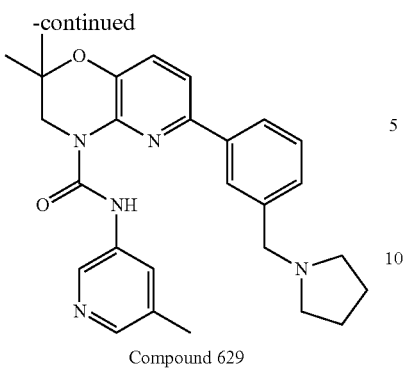

Compound 629

To a solution of 2,2-dimethyl-6-(3-(pyrrolidin-1-ylmethyl)phenyl)-3,4-dihydro-2H-pyrido[3,2-b][1,4]oxazine (97; 50 mg, 0.15 mmol) and triethylamine (50 mg, 0.46 mmol) in THF (3 mL) was added triphosgene (19 mg, 0.062 mmol), and the mixture was stirred at room temperature for 30 min. Then 5-methylpyridine-3-amine (25 mg, 0.23 mmol) was added and the mixture was stirred at 60° C. overnight. The reaction mixture was purified by chromatography to give 2,2-dimethyl-N-(5-methylpyridin-3-yl)-6-(3-(pyrrolidin-1-ylmethyl)phenyl)-2H-pyrido[3,2-b][1,4]oxazine-4(3H)-carboxamide (Compound 629; 15 mg, 20%). MS (ESI) calcd for $C_{27}H_{31}N_5O_2$: 457.25. found: 458 [M+H].

This general procedure could be used to prepare a variety of 2,2-dimethyl-N-substituted-6-(3-(pyrrolidin-1-ylmethyl)phenyl)-2H-pyrido[3,2-b][1,4]oxazine-4(3H)-carboxamide derivatives by substituting the appropriate amine for 5-methylpyridine. Alternatively, derivatives can also be prepared by reacting the appropriate phenyl carbamate with 2,2-dimethyl-6-(3-(pyrrolidin-1-ylmethyl)phenyl)-3,4-dihydro-2H-pyrido[3,2-b][1,4]oxazine in the presence of DIEA at room temp to 50° C.

Example 21

Preparation of 6-(3-((dimethylamino)methyl)phenyl)-2,2-dimethyl-N-(pyridin-3-yl)-2H-pyrido[3,2-b][1,4]oxazine-4(3H)-carboxamide (Compound 677)

Step 1. Synthesis of 3-(2,2-dimethyl-3,4-dihydro-2H-pyrido[3,2-b][1,4]oxazin-6-yl)-N,N-dimethylbenzamide (98)

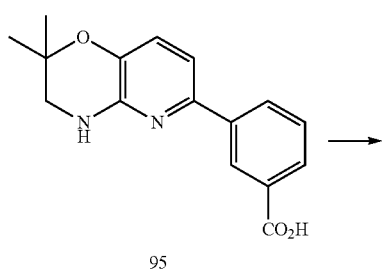

95

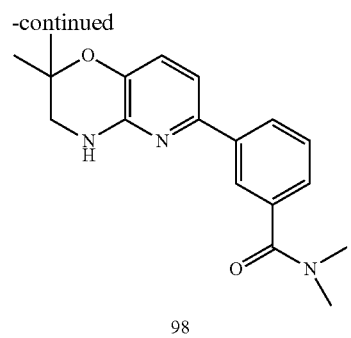

98

Methyl 3-(2,2-dimethyl-3,4-dihydro-2H-pyrido[3,2-b][1,4]oxazin-6-yl)benzoic acid (0.50 g, 1.74 mmol), dimethylamine hydrochloride (95; 710 mg, 8.71 mmol), and HATU (1.3 g, 3.42 mmol) were dissolved in DMF (10 mL). Then diisopropylethylamine (562 mg, 4.36 mmol) was added and stirred at 30° C. overnight. Then the reaction mixture was dilute with water and extracted with EtOAc and the combined organic layers were washed with saturated sodium bicarbonate and water and brine, dried ($Na_2SO_4$), and concentrated. The residue was triturated with EtOAc:petroleum ether to give 3-(2,2-dimethyl-3,4-dihydro-2H-pyrido[3,2-b][1,4]oxazin-6-yl)-N,N-dimethylbenzamide (98; 493 mg, 90%). MS (ESI) calcd for $C_{18}H_{21}N_3O_2$: 311.38. found: 312 [M+H].

Step 2. Synthesis of 1-(3-(2,2-dimethyl-3,4-dihydro-2H-pyrido[3,2-b][1,4]oxazin-6-yl)phenyl)-N,N-dimethylmethanamine (99)

98

99

A mixture of 3-(2,2-dimethyl-3,4-dihydro-2H-pyrido[3,2-b][1,4]oxazin-6-yl)-N,N-dimethylbenzamide (98; 0.49 g, 1.56 mmol) and $BH_3·Me_2S$ (10 M in THF, 1.56 mL, 15.6 mmol) in THF (10 mL) was heated to reflux for 18 h. After cooling, MeOH was added to the solution and continued to reflux for 1 h. The reaction mixture was concentrated and the residue was purified by column chromatography, eluting with MeOH:CH$_2$Cl$_2$, to give 1-(3-(2,2-dimethyl-3,4-dihydro-2H-pyrido[3,2-b][1,4]oxazin-6-yl)phenyl)-N,N-dimethylmethanamine (99; 0.2 g, 43%). MS (ESI) calcd for C$_{18}$H$_{23}$N$_3$O: 297.39. found: 298 [M+H].

Step 3. Synthesis of 6-(3-((dimethylamino)methyl)phenyl)-2,2-dimethyl-N-(pyridin-3-yl)-2H-pyrido[3,2-b][1,4]oxazine-4(3H)-carboxamide (Compound 677)

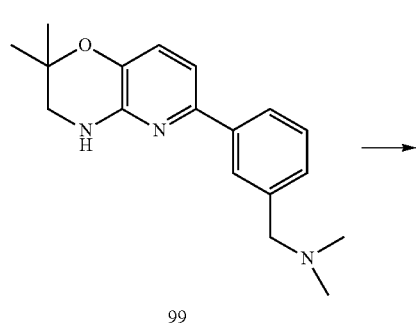

99

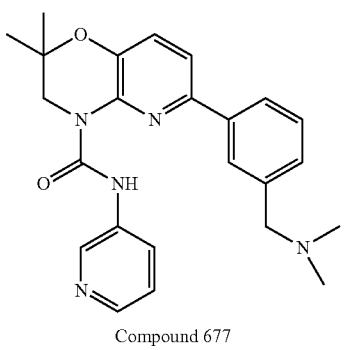

Compound 677

To a solution of 1-(3-(2,2-dimethyl-3,4-dihydro-2H-pyrido[3,2-b][1,4]oxazin-6-yl)phenyl)-N,N-dimethylmethanamine (99; 50 mg, 0.15 mmol) and triethylamine (50 mg, 0.46 mmol) in THF (3 mL) was added triphosgene (18 mg, 0.062 mmol), and the mixture was stirred at room temperature for 30 min. Then pyridin-3-amine (42 mg, 0.46 mmol) was added and the mixture was stirred at 60° C. overnight. The reaction mixture was purified by chromatography to give 6-(3-((dimethylamino)methyl)phenyl)-2,2-dimethyl-N-(pyridin-3-yl)-2H-pyrido[3,2-b][1,4]oxazine-4(3H)-carboxamide (Compound 677; 15 mg, 23%). MS (ESI) calcd for C$_{24}$H$_{27}$N$_5$O$_2$: 417.22. found: 418 [M+H].

This general procedure could be used to prepare a variety of 6-(3-((dimethylamino)methyl)phenyl)-2,2-dimethyl-N-substituted-2H-pyrido[3,2-b][1,4]oxazine-4(3H)-carboxamide derivatives by substituting the appropriate amine for pyridine-3-amine. Alternatively, derivatives can also be prepared by reacting the appropriate phenyl carbamate with 1-(3-(2,2-dimethyl-3,4-dihydro-2H-pyrido[3,2-b][1,4]oxazin-6-yl)phenyl)-N,N-dimethylmethanamine in the presence of N,N-Diisopropylethylamine (DIEA) at room temp to 50° C.

Example 22

Preparation of 1-methyl-2-oxo-N-(thiazol-2-yl)-6-(3-(trifluoromethyl)phenyl)-2,3-dihydropyrido[2,3-b]pyrazine-4(1H)-carboxamide—trifluoracetate salt (Compound 520)

Step 1. Synthesis of ethyl 2-(6-chloro-3-nitropyridin-2-ylamino)acetate (101)

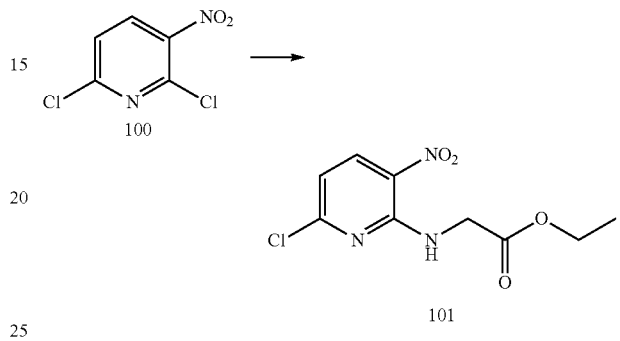

Prepared according to a similar literature procedure in *Bioorganic and Med. Chem. Letters,* 2006, 16, 839-844. Under a nitrogen atmosphere, a mixture of 2,6-dichloro-3-nitropyridine (100; 50 g, 259 mmol) and ethyl 2-aminoacetate (29.34 g, 285 mmol), N,N-Diisopropylethylamine (100.43 g, 777 mmol) in N,N-dimethylformamide (~0.1 M of 2,6-dichloro-3-nitropyridine) was stirred at room temperature for 3 h, the reaction progress was monitored by TLC. Saturated sodium hydrocarbonate solution was added to the reaction mixture and extracted with ethyl acetate (2 times) and the combined organic layers were washed with water and brine, then concentrated in vacuuo to give a brown residue, which was purified by column chromatography to give ethyl 2-(6-chloro-3-nitropyridin-2-ylamino)acetate (101; 42 g from 50 g of S. M, 66%) as a yellow solid. MS (ESI) calcd for C$_9$H$_{10}$ClN$_3$O$_4$ (m/z) 259.65.

Step 2. Synthesis of ethyl 2-(3-nitro-6-(3-(trifluoromethyl)phenyl)pyridin-2-ylamino)acetate (102)

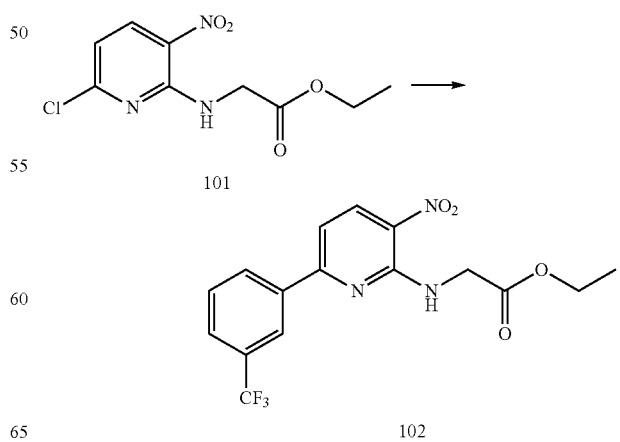

At nitrogen atmosphere, the mixture of ethyl 2-(6-chloro-3-nitropyridin-2-ylamino)acetate (101; 25 g, 93 mmol), 3-(trifluoromethyl)-phenylboronic acid (19.6 g, 111.6 mmol), Pd(PPh₃)₄ (3.8 g, 4.65 mmol) and cesium carbonate (66 g, 186 mmol) in 500 ml of 1,2-dimethoxyethane and 32 ml of water was stirred at 65° C. for 2 h. The solid was filtered and the filtrate was concentrated in vacuuo to give a dark residue, which was purified by column chromatography eluting with ethyl acetate/petroleum ether=1:10 to afford ethyl 2-(3-nitro-6-(3-(trifluoromethyl)phenyl)pyridin-2-ylamino)acetate (102; 31 g, 93.5%) as a white solid. MS (ESI) calcd for $C_{16}H_{14}F_3N_3O_4$ (m/z) 369.30.

Step 3. Synthesis of 6-(3-(trifluoromethyl)phenyl)-3,4-dihydropyrido[2,3-b]pyrazin-2(1H)-one (104)

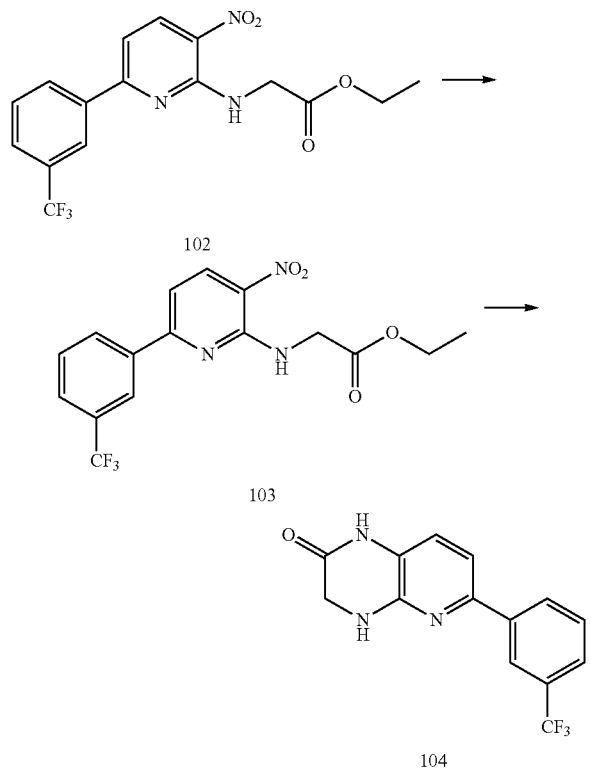

A suspension of ethyl 2-(3-nitro-6-(3-(trifluoromethyl) phenyl)pyridin-2-ylamino)acetate (102; 31 g, 9.54 mmol) and 3.0 g of wet Pd—C(wet, 50%) in 300 ml of methanol was hydrogenated under H₂ at ambient temperature for about 6 hours. The black catalyst was removed by filtration through celite and the filtrate was concentrated in vacuuo to give crude off-white solid ethyl 2-(3-nitro-6-(3-(trifluoromethyl)phenyl)pyridin-2-ylamino)acetate (103; 35.6 g.), which was used in the next step without further purification.

Then 2-(3-nitro-6-(3-(trifluoromethyl)phenyl)pyridin-2-ylamino)acetate (103; 35.6 g.) was dissolved in 300 ml of EtOH and stirred at reflux for 22 h. The solvent was removed in reduced pressure and the residue was loading on flash chromatography using ethyl acetate/petroleum ether=1:8 as eluent to give 6-(3-(trifluoromethyl)phenyl)-3,4-dihydropyrido[2,3-b]pyrazin-2(1H)-one (104; 23 g, 83%) as a yellow solid. MS (ESI) calcd for $C_{14}H_{10}F_3N_3O$ (m/z) 293.24. found 294[M+H].

Step 4. Synthesis of 1-methyl-6-(3-(trifluoromethyl) phenyl)-3,4-dihydropyrido[2,3-b]pyrazin-2(1H)-one (105)

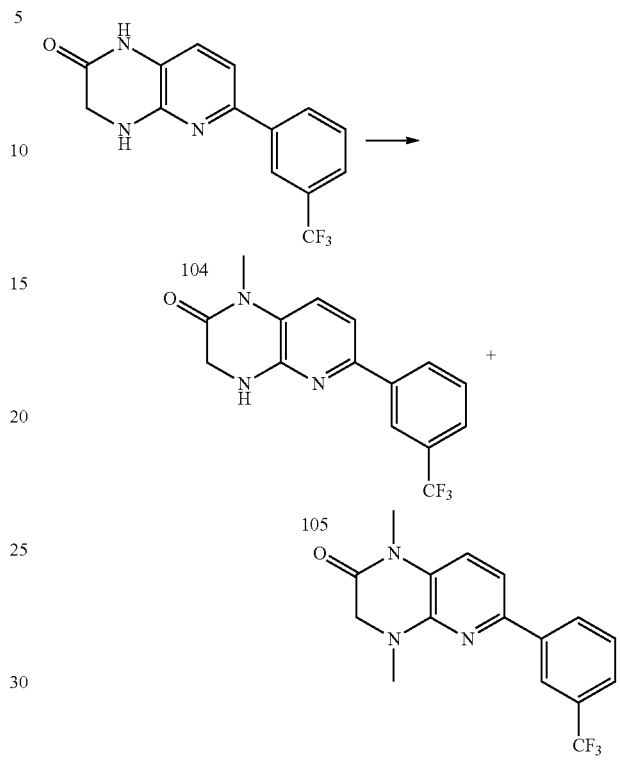

Sodium Hexamethyldisilazide, (NaHMDS) (53.4 ml, 40% in THF, 103.2 mmol) was added to a solution of 6-(3-(trifluoromethyl)phenyl)-3,4-dihydropyrido[2,3-b] pyrazin-2(1H)-one (104; 25.2 g, 86.0 mmol) in 400 ml of dry THF at 0° C. After addition, the mixture was stirred at the same temperature for 0.5 h. CH₃I was added to the red-black solution and the mixture was stirred at room temperature overnight. 100 ml of saturated NH₄Cl and 500 ml of water was added to the reaction mixture and extracted with EtOAc (300 ml×2), the combined organic layers were washed with water, brine and dried, concentrated to give a crude residue, which was purified by column chromatography to give 1-methyl-6-(3-(trifluoromethyl)phenyl)-3,4-dihydropyrido[2,3-b]pyrazin-2(1H)-one (105; 13.8 g, 52%) as a white solid. MS (ESI) calcd for $C_{15}H_{12}F_3N_3O$ (m/z) 307.27. found 308[M+H].

Step 5. Synthesis of 1-methyl-2-oxo-N-(thiazol-2-yl)-6-(3-(trifluoromethyl)phenyl)-2,3-dihydropyrido [2,3-b]pyrazine-4(1H)-carboxamide-trifluoroacetate salt (Compound 520)

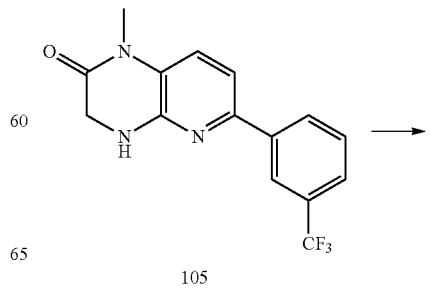

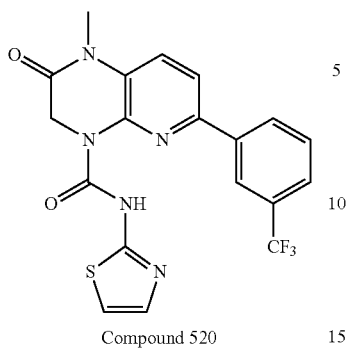

Compound 520

Prepared according to a literature procedure, Gool et al Tet Lett, 2008, 49, 7171-7173. 1-methyl-6-(3-(trifluoromethyl)phenyl)-3,4-dihydropyrido[2,3-b]pyrazin-2(1H)-one 105 and 2-aminothiazole were subjected to the general urea formation conditions outlined herein and purified by HPLC eluding with MeOH and 0.1% TFA to afford 1-methyl-2-oxo-N-(thiazol-2-yl)-6-(3-(trifluoromethyl)phenyl)-2,3-dihydropyrido[2,3-b]pyrazine-4(1H)-carboxamide as the TFA salt (Compound 520; 59.6 mg, 33%). MS (ESI) calcd for $C_{19}H_{14}F_3N_5O_2S.C_2HO_2F_3$ (m/z) 547.43. found 434[M+H].

This general procedure could be used to prepare a variety of 1-methyl-2-oxo-N-substituted-6-aryl-2,3-dihydropyrido[2,3-b]pyrazine-4(1H)-carboxamide derivatives by substituting the appropriate amine for 2-amino thiazole. Alternatively, derivatives can also be prepared by reacting the appropriate phenyl carbamate with 1-methyl-6-aryl-3,4-dihydropyrido[2,3-b]pyrazin-2(1H)-one in the presence of N,N-Diisopropylethylamine (DIEA) at room temp to 50° C.

Example 23

Preparation of 1-methyl-N-(thiazol-2-yl)-6-(3-(trifluoromethyl)phenyl)-2,3-dihydropyrido[2,3-b]pyrazine-4(1H)-carboxamide—TFA salt (Compound 529)

Step 1. Synthesis of 1-methyl-6-(3-(trifluoromethyl)phenyl)-1,2,3,4-tetrahydropyrido[2,3-b]pyrazine (106)

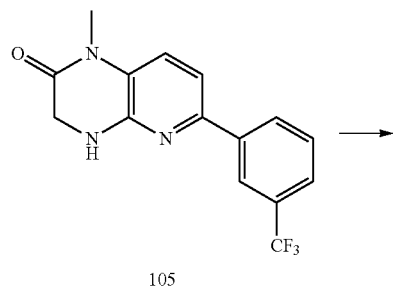

105

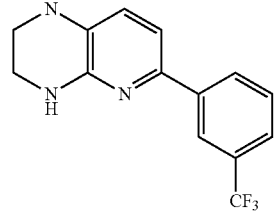

106

A solution of 1-methyl-6-(3-(trifluoromethyl)phenyl)-3,4-dihydropyrido[2,3-b]pyrazin-2(1H)-one (105; 8.8 g, 28.6 mmol) and 9-BBN (32.21 g, 132 mmol) in 265 ml of THF was stirred at reflux for 4 h. The solvent was removed in reduced pressure and the residue was purified by column chromatography to give an oily product (6.4 g, 81%). Then this crude product was triturated with pure petroleum ether to give 1-methyl-6-(3-(trifluoromethyl)phenyl)-1,2,3,4-tetrahydropyrido[2,3-b]pyrazine (106; 2.8 g, 35%) as a white solid and 3.3 g of crude oil contaminated with 9-BBN (42%). MS (ESI) calcd for $C_{15}H_{14}F_3N_3$ (m/z) 293.29. found 294[M+H].

Step 2. Synthesis of 1-methyl-N-(thiazol-2-yl)-6-(3-(trifluoromethyl)phenyl)-2,3-dihydropyrido[2,3-b]pyrazine-4(1H)-carboxamide—TFA salt (Compound 529)

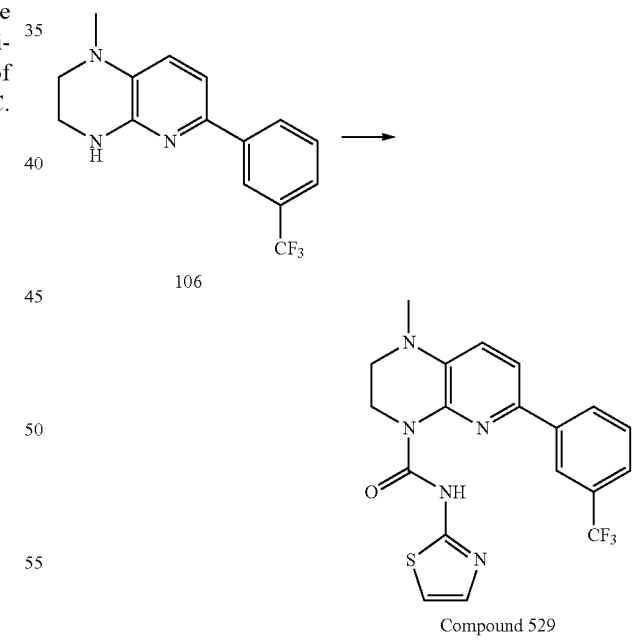

Compound 529

Prepared according to a similar literature procedure, Gool et al Tet Lett, 2008, 49, 7171-7173. 1-methyl-6-(3-(trifluoromethyl)phenyl)-1,2,3,4-tetrahydropyrido[2,3-b]pyrazine 106 and 2-aminothiazole were subjected to the general conditions described above and purified by HPLC eluding with MeOH and 0.1% TFA to afford 1-methyl-N-(thiazol-2-yl)-6-(3-(trifluoromethyl)phenyl)-2,3-dihydropyrido[2,3-b]pyrazine-4(1H)-carboxamide as the TFA salt (Compound 529; 72.4 mg; 39%). MS (ESI) calcd for $C_{19}H_{14}F_3N_5O_2S.C_2HO_2F_3$ (m/z) 547.43. found 434[M+H].

This general procedure could be used to prepare a variety of 1-methyl-N-substituted-6-aryl-2,3-dihydropyrido[2,3-b]pyrazine-4(1H)-carboxamide derivatives by substituting the appropriate amine for 2-amino thiazole. Alternatively, derivatives can also be prepared by reacting the appropriate phenyl carbamate with 1-methyl-6-aryl-1,2,3,4-tetrahydropyrido[2,3-b]pyrazine in the presence of N,N-Diisopropylethylamine (DIEA) at room temp to 50° C.

Example 24

Preparation of N-(5-methylpyridin-3-yl)-7-(3-(trifluoromethyl)phenyl)-3,4-dihydro-1,8-naphthyridine-1(2H)-carboxamide (Compound 585)

Step 1. Synthesis of tert-butyl 6-chloropyridin-2-yl carbamate (108)

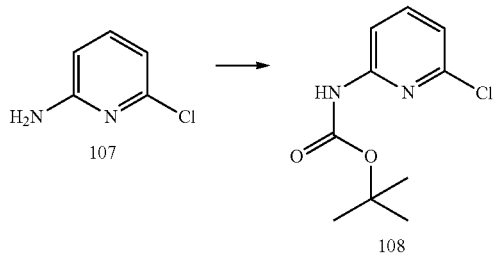

NaHMDS (351 ml, 0.7 mol) in THF (300 ml) was cooled to 0° C., a solution of 2-amino-6-chloropyridine (107; 40 g, 0.311 mol) in THF (300 ml) was added, followed by a solution of di-tert-butyl dicarbonate (68 g, 0.311 mol) in THF, ensuring the internal temperature remained below 0° C. The resulting reaction mixture was aged for 1 h at room temp and then carefully acidified to pH 3 by addition of 1 M hydrochloric acid. extracted with EtOAc, the combined organic layers were then washed sequentially with saturated aqueous NaHCO$_3$ and brine, dried over Na$_2$SO$_4$, filtered, concentrated to afford crude product, Triturated with ether to afforded desired product tert-butyl 6-chloropyridin-2-ylcarbamate (108; 45 g, yield 63.4%). MS (ESI) calcd for $C_{10}H_{13}ClN_2O_2$ (m/z) 228.69.

Step 2. Synthesis of tert-butyl 7-chloro-3,4-dihydro-1,8-naphthyridine-1(2H)-carboxylate (109)

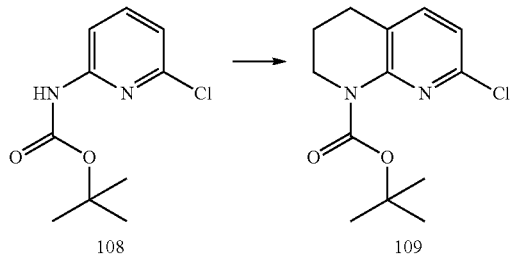 [SMILES: CC(C)(C)OC(=O)Nc1cccc(Cl)n1 ; CC(C)(C)OC(=O)N1CCCc2ccc(Cl)nc21]

To a stirred solution of Tetramethylethylenediamine (TMEDA) (63.84 g, 0.549 mol) in THF (600 mL) at -20° C. was added n-BuLi (220 mL, 0.549 mol, 2.5M in hexanes) over 10 min. Solution stirred between -20 and 10° C. for 30 min and subsequently cooled to -78° C. A solution of tert-butyl 6-chloropyridin-2-ylcarbamate (108; 57.0 g, 0.249 mol) in THF (300 mL) was added over 15 min. The reaction mixture was aged for 1 hour and then CuI (47.6 g, 0.249 mol) was added in one portion. The reaction mixture was allowed to warm to -10° C. for one hour. 1-Chloro-3-iodopropane (76.5 g, 0.374 mol) was added neat over a period of 1 min, the cooling bath was removed and reaction allowed to warm to ambient temp and subsequently refluxed overnight. Upon completion of the reaction, the reaction mixture was cooled and quenched via addition of saturated sodium bicarbonate. The aqueous layer was extracted with EtOAc, The combined organic layers were dried over Na$_2$SO$_4$, filtered through a short silica gel pad, concentrated to afford crude product. Triturated with ether to afforded tert-butyl 7-chloro-3,4-dihydro-1,8-naphthyridine-1(2H)-carboxylate (109; 43 g, yield 67%). MS (ESI) calcd for $C_{13}H_{17}ClN_2O_2$ (m/z) 268.74.

Step 3. Synthesis of 7-chloro-1,2,3,4-tetrahydro-1,8-naphthyridine (110)

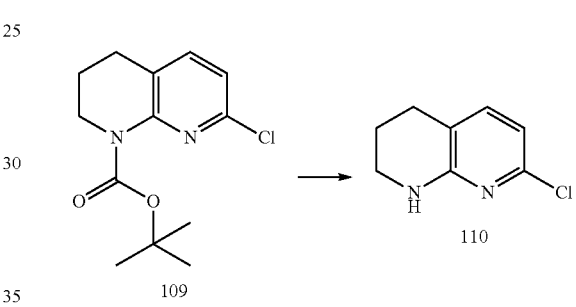

Tert-butyl 7-chloro-3,4-dihydro-1,8-naphthyridine-1(2H)-carboxylate (109; 21 g, 0.078 mol) was added to CF$_3$COOH (100 ml) and stirred at rt. Overnight. The reaction mixture was concentrated and dissolved in EA. Saturated aqueous NaHCO$_3$, was carefully added till the pH=9. The aqueous layer was extracted with EtOAc again and the combined organic layers were dried over Na$_2$SO$_4$, filtered and concentrated to afford 7-chloro-1,2,3,4-tetrahydro-1,8-naphthyridine (110; 12.9 g, yield 98%). MS (ESI) calcd for $C_8H_9ClN_2$ (m/z) 168.62.

Step 4. Synthesis of 7-(3-(trifluoromethyl)phenyl)-1,2,3,4-tetrahydro-1,8-naphthyridine (111)

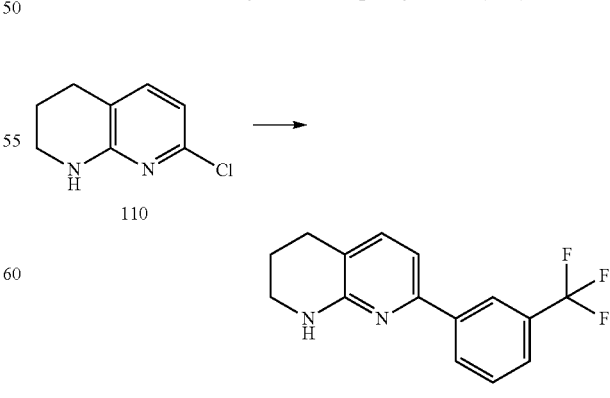

Under a nitrogen atmosphere, 1,2,3,4-tetrahydro-1,8-naphthyridine (110; 1.2 g, 7.12 mmol) was dissolved in DME (40 mL) along with, 3-(trifluoromethyl)-phenylboronic acid (2.03 g, 10.68 mmol), $Cs_2CO_3$ (4.64 g, 14.24 mmol) and $Pd(dppf)Cl_2$ (297 mg, 0.356 mmol). The reaction mixture was stirred at 90° C. overnight. The solid was filtered. The filtration was then diluted with $H_2O$ and extracted with ethyl acetate. The combined organic layers were washed with brine, dried over $Na_2SO_4$ and then concentrated in vacuo. The residue was purified by column chromatography to afford 7-(3-(trifluoromethyl)phenyl)-1,2,3,4-tetrahydro-1,8-naphthyridine (111; 1.25 g, 63%). MS (ESI) calcd for $C_{15}H_{13}F_3N_2$ (m/z) 278.27.

This general coupling procedure could be used to prepare a variety of 7-aryl-1,2,3,4-tetrahydro-1,8-naphthyridine derivatives by substituting the appropriate boronic acid for 3-(trifluoromethyl)-phenylboronic acid.

Step 5. Synthesis of N-(5-methylpyridin-3-yl)-7-(3-(trifluoromethyl)phenyl)-3,4-dihydro-1,8-naphthyridine-1(2H)-carboxamide (Compound 585)

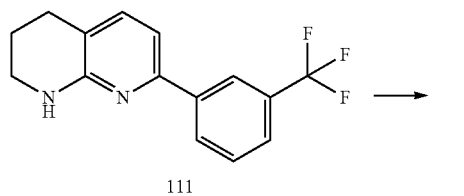

111

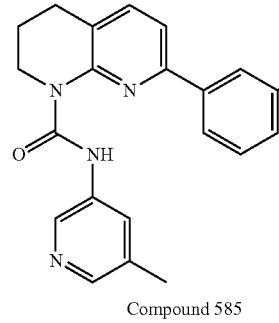

Compound 585

Under a nitrogen atmosphere, to the mixture of 7-(3-(trifluoromethyl)phenyl)-1,2,3,4-tetrahydro-1,8-naphthyridine (111; 0.36 mmol, 1.0 eq.) and TEA (0.15 ml, 1 mmol, 3.0 eq.) in anhydrous THF was added triphosgene (43 mg, 0.144 mmol, 0.4 eq) portion-wise. Then the above mixture was stirred at 30° C. for 30 min until the 7-(3-(trifluoromethyl)phenyl)-1,2,3,4-tetrahydro-1,8-naphthyridine (111) disappeared (monitored by TLC). 5-methylpyridin-3-amine (0.36 mmol, 1.0 eq) was added and the reaction was stirred at 60° C. for 18 hours. Saturated sodium bicarbonate (5 ml) and dichloromethane (10 ml) were added to the reaction mixture. The organic layer was washed with water (10 ml) and brine, then dried over anhydrous $Na_2SO_4$ and concentrated in vacuo. The crude product was purified by prep-TLC to afford N-(5-methylpyridin-3-yl)-7-(3-(trifluoromethyl)phenyl)-3,4-dihydro-1,8-naphthyridine-1(2H)-carboxamide (Compound 585; 40 mg, 27%) as white solids. MS (ESI) calcd for $C_{22}H_{19}F_3N_4O$ (m/z) 412.41.

3-(2,3-dihydroxypropoxy)phenyl 7-(3-(trifluoromethyl)phenyl)-3,4-dihydro-1,8-naphthyridine-1(2H)-carboxylate (Compound 641) and (3-(2,3-dihydroxypropoxy)phenyl)(7-(3-(trifluoromethyl)phenyl)-3,4-dihydro-1,8-naphthyridin-1 (2H)-yl)methanone (Compound 642) were synthesized by routes previously described above for Compounds 562 and 518.

This general procedure could be used to prepare a variety of N-substituted-7-aryl-3,4-dihydro-1,8-naphthyridine-1 (2H)-carboxamide derivatives by substituting the appropriate amine for 5-methylpyridin-3-amine. Alternatively, derivatives can also be prepared by reacting the appropriate phenyl carbamate with 7-aryl-1,2,3,4-tetrahydro-1,8-naphthyridine in the presence of N,N-Diisopropylethylamine (DIEA) at room temp to 50° C.

Example 25

Preparation of 4-oxo-N-(pyridin-4-yl)-7-(3-(trifluoromethyl)phenyl)-3,4-dihydro-1,8-naphthyridine-1 (2H)-carboxamide (Compound 719)

Step 1. Synthesis of tert-butyl 7-chloro-3,4-dihydro-1,8-naphthyridine-1(2H)-carboxylate (112)

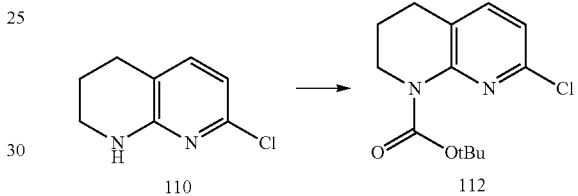

The mixture of 7-chloro-1,2,3,4-tetrahydro-1,8-naphthyridine (110; 6.0 g, 35.7 mmol), $Boc_2O$ (15.6 g, 71.4 mmol) and 4-Dimethylaminopyridine (DMAP) (13.1 g, 107.1 mmol) in THF (200 mL) was stirred under reflux for overnight. TLC showed the reaction was complete and the mixture was poured into water. The organic layer was dried over anhydrous $Na_2SO_4$, filtered and concentrated to give tert-butyl 7-chloro-3,4-dihydro-1,8-naphthyridine-1(2H)-carboxylate (112; 8.74 g, 91%) as a white solid. MS (ESI) calcd for $C_{13}H_{17}ClN_2O_2$ (m/z) 268.74.

Step 2. Synthesis of tert-butyl 7-(3-(trifluoromethyl)phenyl)-3,4-dihydro-1,8-naphthyridine-1(2H)-carboxylate (113)

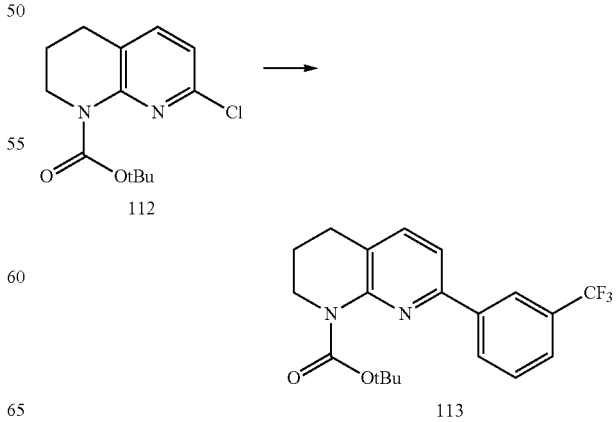

The mixture of tert-butyl 7-chloro-3,4-dihydro-1,8-naphthyridine-1(2H)-carboxylate (112; 7.74 g, 28.77 mmol), (3-(trifluoromethyl)phenyl)boronic acid (10.94 g, 57.54 mmol), Pd(dppf)Cl$_2$ (2.35 g, 2.88 mmol), Cs$_2$CO$_3$ (18.72 g, 57.54 mmol) and dioxane/H$_2$O (10/1, v/v) (165 mL) was stirred at 100° C. for overnight under a nitrogen atmosphere. The solvent was removed and the residue was dissolved in EtOAc (200 mL). The solution was washed with brine and dried over anhydrous Na$_2$SO$_4$, filtered and concentrated. The residue was purified by chromatography on a silica gel column (eluted with petroleum ether/ethyl acetate=10/1) to give tert-butyl 7-(3-(trifluoromethyl)phenyl)-3,4-dihydro-1,8-naphthyridine-1(2H)-carboxylate as a white solid (113; 9.63 g, 89% yield). MS (ESI) calcd for C$_{20}$H$_{21}$F$_3$N$_2$O$_2$: 378.16.

This general coupling procedure could be used to prepare a variety of tert-butyl 7-aryl-3,4-dihydro-1,8-naphthyridine-1(2H)-carboxylate derivatives by substituting the appropriate boronic acid for 3-(trifluoromethyl)-phenylboronic acid.

Step 3. Synthesis of tert-butyl 4-oxo-7-(3-(trifluoromethyl)phenyl)-3,4-dihydro-1,8-naphthyridine-1(2H)-carboxylate (114)

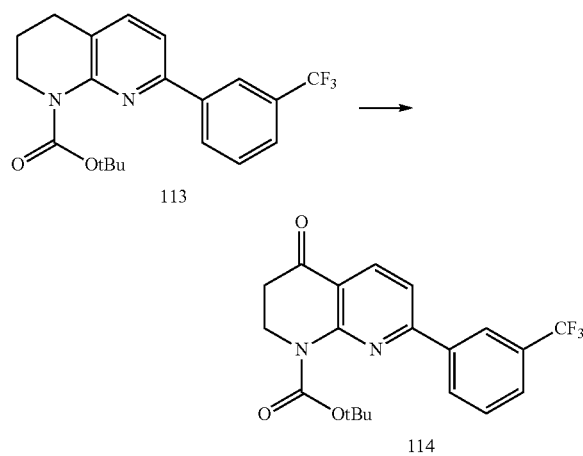

The mixture of tert-butyl 7-(3-(trifluoromethyl)phenyl)-3,4-dihydro-1,8-naphthyridine-1(2H)-carboxylate (113; 10.4 g, 27.51 mmol) and NaH$_2$PO$_4$ (8.254 g, 68.78 mmol) in t-BuOH (38.5 mL) and H$_2$O (35.8 mL) was heated to 50° C., then NaMnO$_4$/H$_2$O (40%) (55.02 g) was added dropwise, keeping the temperature under 60° C. After the addition of permanganate was completed, the reaction was stirred at 50° C. for 7 h (reaction time was determined by TLC plate and LCMS). After the reaction was completed, Na$_2$SO$_3$ solid was added carefully to the cooled reaction mixture until the purple color disappeared. The resulting suspension was filtered to remove manganese dioxide and the filtrate was extracted with EtOAc (3×100 mL), the combined organic layers were washed with aqueous Na$_2$CO$_3$ and brine, dried over anhydrous Na$_2$SO$_4$, filtered and concentrated. The residue was purified by chromatography on a silica gel column (eluted with petroleum ether/ethyl acetate=6/1) to give tert-butyl 4-oxo-7-(3-(trifluoromethyl)phenyl)-3,4-dihydro-1,8-naphthyridine-1(2H)-carboxylate as a yellow solid (114; 8.0 g, 74% yield). MS (ESI) calcd for C$_{20}$H$_{19}$F$_3$N$_2$O$_3$: 392.13.

Step 4. Synthesis of 7-(3-(trifluoromethyl)phenyl)-2,3-dihydro-1,8-naphthyridin-4(1H)-one (115)

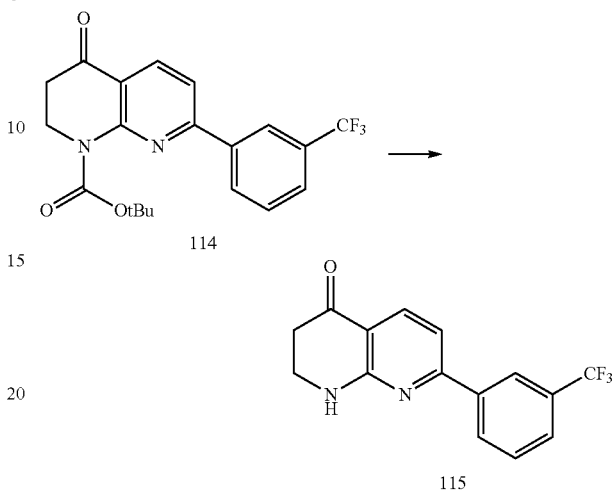

tert-butyl 4-oxo-7-(3-(trifluoromethyl)phenyl)-3,4-dihydro-1,8-naphthyridine-(2H)-carboxylate (114; 1.0 g, 2.55 mmol) was dissolved in HCl/MeOH (10 mL, 3 N), then stirred at room temperature overnight. The reaction mixture was concentrated and brought to pH~10 by adding aqueous Na$_2$CO$_3$. The resulting mixture was extracted with EtOAc. The organic layer was dried over anhydrous Na$_2$SO$_4$, filtered and concentrated to give 7-(3-(trifluoromethyl)phenyl)-2,3-dihydro-1,8-naphthyridin-4(1H)-one (115; 0.85 g, 114% yield) as a yellow solid. MS (ESI) calcd for C$_{15}$H$_{11}$F$_3$N$_2$O: 292.08. found: 293 [M+H].

Step 5. Synthesis of 4-oxo-N-(pyridin-4-yl)-7-(3-(trifluoromethyl)phenyl)-3,4-dihydro-1,8-naphthyridine-1(2H)-carboxamide (Compound 719)

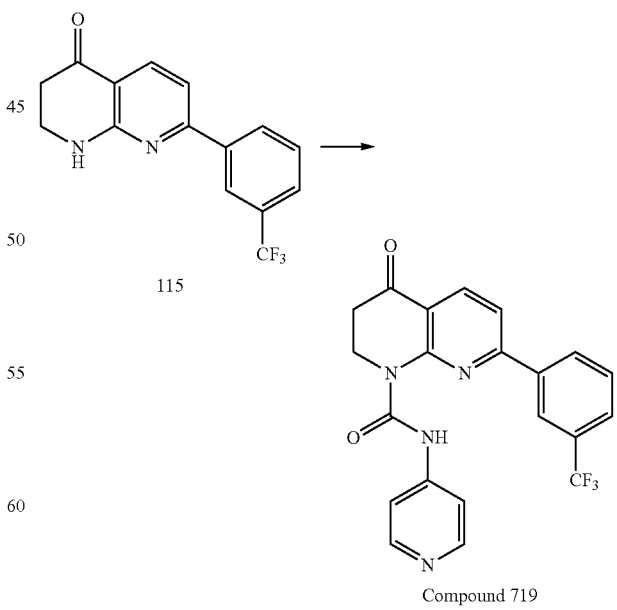

To a solution of 7-(3-(trifluoromethyl)phenyl)-2,3-dihydro-1,8-naphthyridin-4(1-1)-one (115; 150 mg, 0.52 mmol) and triethylamine (0.28 mL, 2.06 mmol) in CH$_2$Cl$_2$ (5 mL) was added triphosgene (152 mg, 0.52 mmol), and the mixture was stirred at room temperature for 30 min. Then pyridine-4-amine (144 mg, 0.15 mmol) was added and the mixture was stirred at room temperature overnight. The reaction mixture concentrated and purified by chromatography to give 4-oxo-N-(pyridin-4-yl)-7-(3-(trifluoromethyl)phenyl)-3,4-dihydro-1,8-naphthyridine-1(2H)-carboxamide (Compound 719; 15 mg, 7%). MS (ESI) calcd for C$_{21}$H$_{15}$F$_3$N$_4$O$_2$: 412.11. found: 413 [M+H].

This general procedure could be used to prepare a variety of 4-oxo-N-substituted-7-aryl-3,4-dihydro-1,8-naphthyridine-1(2H)-carboxamide derivatives by substituting the appropriate amine for 5-pyridin-4-amine. Alternatively, derivatives can also be prepared by reacting the appropriate phenyl carbamate with 7-aryl-2,3-dihydro-1,8-naphthyridin-4(1H)-one in the presence of DIEA at room temp to 50° C.

Example 26

4,4-difluoro-N-(pyridin-4-yl)-7-(3-(trifluoromethyl)phenyl)-3,4-dihydro-1,8-naphthyridine-1(2H)-carboxamide (Compound 743)

Step 1. Synthesis of 4,4-difluoro-7-(3-(trifluoromethyl)phenyl)-1,2,3,4-tetrahydro-1,8-naphthyridine (116)

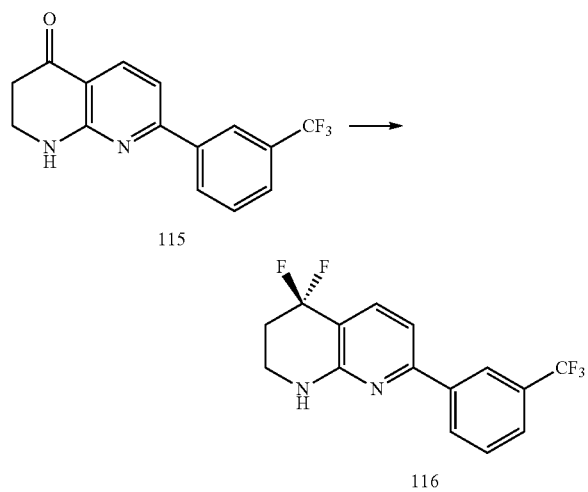

7-(3-(trifluoromethyl)phenyl)-2,3-dihydro-1,8-naphthyridin-4(1H)-one (115; 1.46 g, 5 mmol) was treated with diethylaminosulfur trifluoride (DAST) (10 mL), then stirred at 30° C. for 3 days. The reaction was quenched with water (dropwise), extracted with EtOAc (3×30 mL), the combined organic layers were washed with saturated aqueous NaHCO$_3$, brine, dried over anhydrous Na$_2$SO$_4$, filtered and concentrated. The residue was purified by chromatography on a silica gel column (eluted with petroleum ether/ethyl acetate=10/1) to give 4,4-difluoro-7-(3-(trifluoromethyl)phenyl)-1,2,3,4-tetrahydro-1,8-naphthyridine as a yellow solid (116; 759 mg, 50% yield). MS (ESI) calcd for C$_{15}$H$_{11}$F$_5$N$_2$: 314.08. found: 315 [M+H].

Step 2. Synthesis of 4,4-difluoro-N-(pyridin-4-yl)-7-(3-(trifluoromethyl)phenyl)-3,4-dihydro-1,8-naphthyridine-1(2H)-carboxamide (Compound 743)

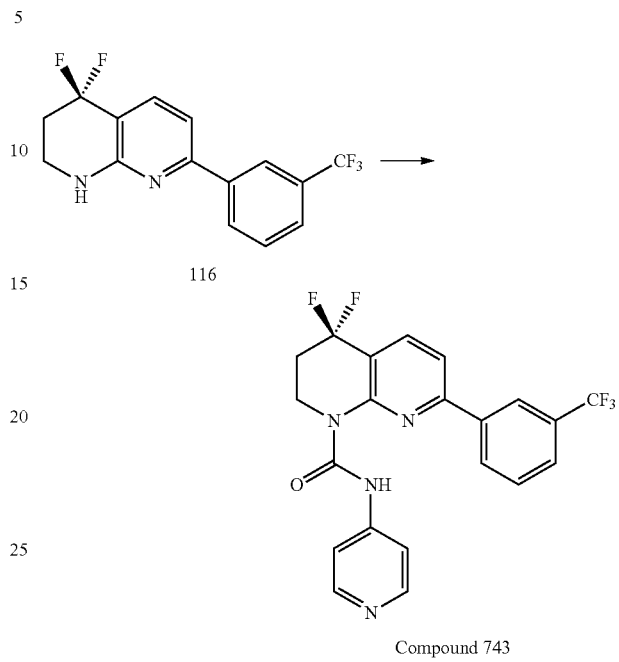

Method A:

To a mixture of 4,4-difluoro-7-(3-(trifluoromethyl)phenyl)-1,2,3,4-tetrahydro-1,8-naphthyridine (116; 50 mg, 0.16 mmol) in 3 mL of dry THF was added in one-portion triethylamine (0.066 mL, 0.48 mmol) followed by triphosgene (19 mg, 0.064 mmol). The above mixture was stirred at 30° C. for 1-2 hours and 4-aminopyridine (30 mg, 0.32 mmol, 2.0 eq) was added to the reaction mixture and stirred for an additional 20 hours. Water and dichloromethane (10 mL) were added to the reaction mixture; the organic layer was successively washed with water (10 mL) and brine, dried with anhydrous sodium sulfate and concentrated in vacuo. The crude product was purified by preparative TLC to afford 4,4-difluoro-N-(pyridin-4-yl)-7-(3-(trifluoromethyl)phenyl)-3,4-dihydro-1,8-naphthyridine-1 (21-1)-carboxamide (Compound 743; mg, 29%) as a pale yellow solid. MS (ESI) calcd for C$_{21}$H$_{15}$F$_5$N$_4$O: 434.12. found: 435 [M+H].

Example 27

Preparation of 4,4-difluoro-N-(pyridin-2-yl)-7-(3-(trifluoromethyl)phenyl)-3,4-dihydro-1,8-naphthyridine-1(2H)-carboxamide (Compound 814)

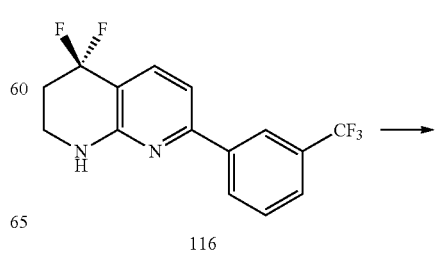

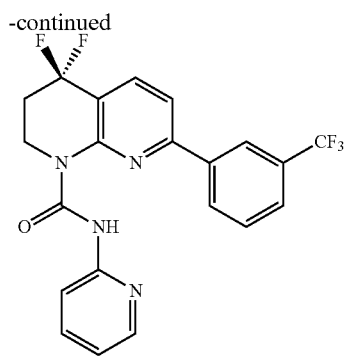

Compound 814

Method B:

A mixture of 4,4-difluoro-7-(3-(trifluoromethyl)phenyl)-1,2,3,4-tetrahydro-1,8-naphthyridine (116; 50 mg, 0.16 mmol), phenyl pyridin-2-ylcarbamate (69 mg, 0.32 mmol) and 4-Dimethylaminopyridine (DMAP) (23 mg, 0.192 mmol) in acetonitrile was heated in a sealed tube at 60° C. for 18 h. The crude product was purified by loading onto a preparative TLC plate eluting with ethyl acetate/petroleum ether (1:8). This afforded 4,4-difluoro-N-(pyridin-2-yl)-7-(3-(trifluoromethyl)phenyl)-3,4-dihydro-1,8-naphthyridine-1(2H)-carboxamide (Compound 814) as a pale yellow solid. Yield: 60%. MS (ESI) calcd for $C_{21}H_{15}F_5N_4O$: 434.12. found: 435 [M+H].

These general procedures could be used to prepare a variety of 4,4-difluoro-N-substituted-7-aryl-3,4-dihydro-1,8-naphthyridine-1(2H)-carboxamide derivatives by selecting the appropriate amine or phenyl carbamate.

Example 28

Preparation of 4,4-dimethyl-N-(pyridin-4-yl)-7-(3-(trifluoromethyl)phenyl)-3,4-dihydro-1,8-naphthyridine-1(2H)-carboxamide (Compound 826)

Step 1. Synthesis of N-(6-aminopyridin-2-yl)-3-methylbut-2-enamide (118)

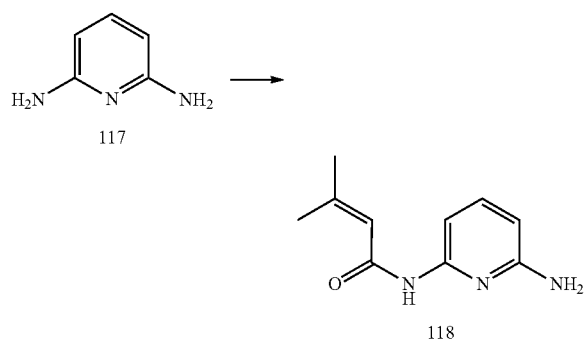

To the solution of 1,4-diaminopyridine (32.7 g, 0.3 mol, 3.0 eq) in dry THF (150 mL) and $Et_3N$ (35 mL, 0.25 mol, 2.5 eq) was added dropwise 3-methylbut-2-enoyl chloride (12 g, 0.10 mol, 1.0 eq) over 10 min at 0° C. After addition, the reaction mixture was stirred at room temperature for one hour. The resulting mixture was poured into aqueous saturated sodium bicarbonate solution and extracted with DCM (80 mL×2). The combined organic layers were washed with water and brine and dried over anhydrous sodium sulfate, filtered and concentrated under reduced pressure. The crude residue, was adsorbed onto silica gel and loaded onto a chromatography column and eluted with ethyl acetate and petroleum ether (1:5) to afford N-(6-aminopyridin-2-yl)-3-methylbut-2-enamide as white solid (10.7 g, 56%). MS (ESI) calcd for $C_{10}H_{13}N_3O$: 191.23.

Step 2. Synthesis of 7-amino-4,4-dimethyl-3,4-dihydro-1,8-naphthyridin-2(1H)-one (119)

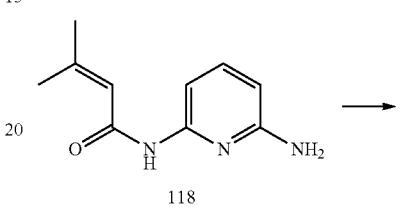

Under a nitrogen atmosphere, $MeSO_3H$ (2.85 g, 30.0 mmol, 3.0 eq) was added to the solution of N-(6-aminopyridin-2-yl)-3-methylbut-2-enamide (118; 1.91 g, 10.0 mmol, 1.0 eq) in 20 mL of dry dichloromethane while maintaining the temperature below 20° C. The above mixture was added dropwise to the suspension of $AlCl_3$ (10.7 g, 80.0 mmol, 8.0 eq) in 60 mL of dry DCM and controlled to maintain the temperature below 10° C. After addition, the reaction mixture was stirred at ambient temperature for overnight. Ice-water (100 mL) was added to the reaction mixture, stirred for 10 min and basified with aqueous NaOH (2N) to pH=8-10. The aqueous layer was extracted with DCM/MeOH (100:10) (2×50 mL), the combined organic layers were washed with water and brine and evaporated under reduced pressure to give a crude residue. The crude product was triturated in ethyl acetate/petroleum ether=1:1 to give a white solid of 7-amino-4,4-dimethyl-3,4-dihydro-1,8-naphthyridin-2(1H)-one (119; 1.25 g, 63%). MS (ESI) calcd for $C_{10}H_{13}N_3O$: 191.23.

Step 3. Synthesis of 7-chloro-4,4-dimethyl-3,4-dihydro-1,8-naphthyridin-2(1H)-one (120)

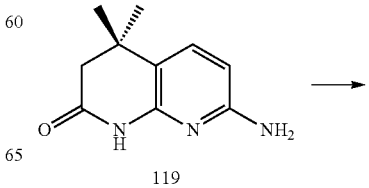

131

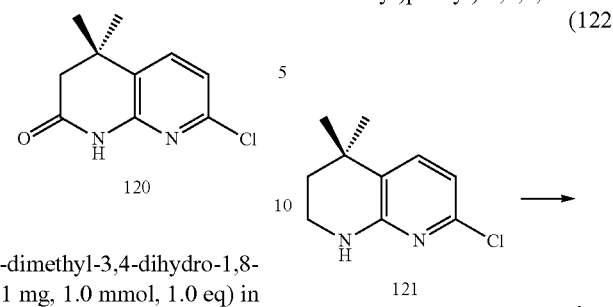

120

To a mixture of 7-amino-4,4-dimethyl-3,4-dihydro-1,8-naphthyridin-2(1H)-one (119; 191 mg, 1.0 mmol, 1.0 eq) in 2 mL of concentrated hydrochloric acid at 0° C. was added a solution of $NaNO_2$ in water (386 mg/0.5 mL). After stirring for 30 min, powdered CuCl (150 mg, 1.5 mmol) was added to the above mixture and stirred for 2 hours. Water (5 mL) was added to the reaction mixture and the pH adjusted to ~9-10 with $NH_4OH$ and then extracted with ethyl acetate (2×). The combined organic layers were washed with water, brine, and concentrated in vacuo to provide a yellow solid. The crude material was loaded onto a silica gel flash column using ethyl acetate/petroleum ether=10:1 as eluent to afford a yellow solid of 7-chloro-4,4-dimethyl-3,4-dihydro-1,8-naphthyridin-2(1H)-one (120; 105 mg, 50%). MS (ESI) calcd for $C_{10}H_{11}ClN_2O$: 210.06.

Step 4. Synthesis of 7-chloro-4,4-dimethyl-1,2,3,4-tetrahydro-1,8-naphthyridine (121)

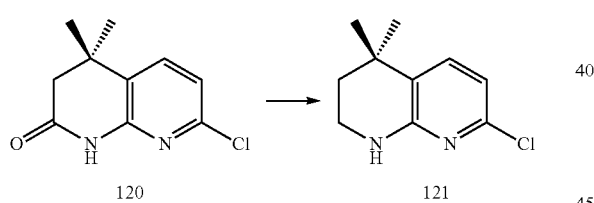

Under a nitrogen atmosphere, to a stirred solution of 7-chloro-4,4-dimethyl-3,4-dihydro-1,8-naphthyridin-2(1H)-one (120; 1.9 g, 9.05 mmoL, 1.0 eq) in 50 mL of dry THF was added, in one-portion, $BF_3.Et_2O$ (2.7 g, 19.0 mmol, 2.1 eq) at 0° C. The mixture was stirred at 0° C. for 10 min then sodium borohydride (0.72 g, 19.0 mmol, 2.1 eq) was added and the reaction stirred at room temperature for 18 hours. Ethyl acetate (20 mL) was added to the reaction mixture, followed by dropwise addition of 9 mL of 1 M HCl and the mixture was poured into saturated sodium bicarbonate solution and extracted with ethyl acetate (2×60 mL). The combined organic layers were washed with water and brine, dried over anhydrous $Na_2SO_4$ and concentrated under reduced pressure to give crude product. The crude product was purified by trituration in petroleum ether to afford 7-chloro-4,4-dimethyl-1,2,3,4-tetrahydro-1,8-naphthyridine (121; 1.74 g, 98%) as yellow solid. MS (ESI) calcd for $C_{10}H_{13}ClN_2$: 196.68.

132

Step 5. Synthesis of 4,4-dimethyl-7-(3-(trifluoromethyl)phenyl)-1,2,3,4-tetrahydro-1,8-naphthyridine (122)

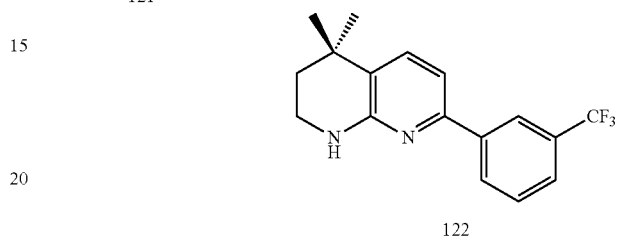

Under a nitrogen atmosphere, the mixture of 7-chloro-4,4-dimethyl-1,2,3,4-tetrahydro-1,8-naphthyridine (121; 1.0 g, 5.1 mmol, 1.0 eq), 3-(trifluoromethyl)-phenyl boronic acid (1.45 g, 7.65 mmol, 1.5 eq.), $Pd(dppf)Cl_2$ (425 mg, 0.51 mmol, 0.10 eq) and cesium carbonate (4.1 g, 12.75 mmol, 2.5 eq) in 20 mL of dimethoxyethane (DME) and 2 mL of water was stirred at 90° C. overnight. The reaction mixture was adsorbed onto silica gel and purified by flash chromatography eluting with ethyl acetate/petroleum ether (1:20) to afford 4,4-dimethyl-7-(3-(trifluoromethyl)phenyl)-1,2,3,4-tetrahydro-1,8-naphthyridine as a yellow solid (122; 1.27 g, 81%). MS (ESI) calcd for $C_{17}H_{17}F_3N_2$: 306.33.

Step 6. Synthesis of 4,4-dimethyl-N-(pyridin-4-yl)-7-(3-(trifluoromethyl)phenyl)-3,4-dihydro-1,8-naphthyridine-1(2H)-carboxamide (Compound 826)

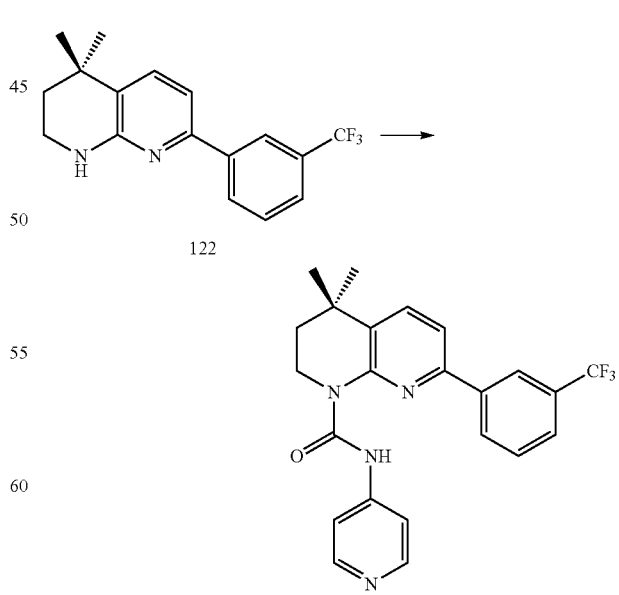

Compound 826

Method A:

A mixture of 4,4-dimethyl-7-(3-(trifluoromethyl)phenyl)-1,2,3,4-tetrahydro-1,8-naphthyridine (122; 61.2 mg, 0.2 mmol), phenyl pyridin-4-ylcarbamate (65 mg, 0.0.3 mmol) and 4-Dimethylaminopyridine (DMAP) (25 mg, 0.2 mmol) in acetonitrile was heated in a sealed tube at 60° C. for 18 h. The crude product was purified by loading onto a preparative TLC plate eluting with ethyl acetate/petroleum ether (1:3). This afforded 4,4-dimethyl-N-(pyridin-4-yl)-7-(3-(trifluoromethyl)phenyl)-3,4-dihydro-1,8-naphthyridine-1(2H)-carboxamide (Compound 826) as a white solid. Yield 74%. MS (ESI) calcd for $C_{23}H_{21}F_3N_4O$: 426.17. found: 427 [M+H].

Example 29

Preparation of 4,4-dimethyl-N-(3-methylpyridin-4-yl)-7-(3-(trifluoromethyl)phenyl)-3,4-dihydro-1,8-naphthyridine-1(2H)-carboxamide (Compound 834)

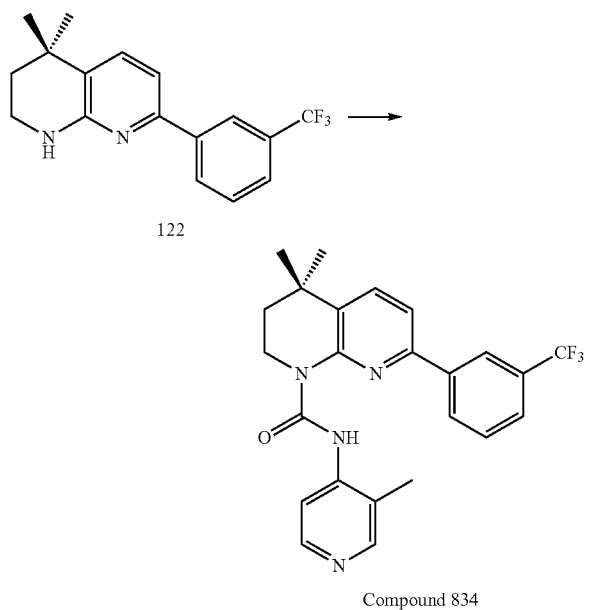

Method B:

To a mixture of 3-methylpyridin-4-amine (122; 43.3 mg, 0.4 mmol) in 3 mL of dry THF was added in one portion triethylamine (0.3 mL) followed by triphosgene (47.5 mg, 0.16 mmol). The above mixture was stirred at 50° C. for 2 hours and 4,4-dimethyl-7-(3-(trifluoromethyl)phenyl)-1,2,3,4-tetrahydro-1,8-naphthyridine (61.2 mg, 0.2 mmol) was added to the reaction mixture and stirred for an additional 20 hours at 60° C. Saturated sodium bicarbonate solution and dichloromethane (10 mL) were added to the reaction mixture; the organic layer was successively washed with water (10 mL) and brine, dried with anhydrous sodium sulfate and concentrated in vacuo. The crude product was purified by preparative TLC to afford 4,4-dimethyl-N-(3-methylpyridin-4-yl)-7-(3-(trifluoromethyl)phenyl)-3,4-dihydro-1,8-aphthyridine-1(2H)-carboxamide (Compound 834) as yellow solid. Yield 23%. MS (ESI) calcd for $C_{24}H_{23}F_3N_4O$: 440.18. found: 441 [M+H].

These general procedures could be used to prepare a variety of 4,4-dimethyl-N-(3-substituted-7-aryl-3,4-dihydro-1,8-aphthyridine-1(2H)-carboxamide derivatives by selecting the appropriate amine or phenyl carbamate.

Example 30

Preparation of 4-methyl-N-(pyridin-4-yl)-7-(3-(trifluoromethyl)phenyl)-3,4-dihydro-1,8-naphthyridine-1(2H)-carboxamide (Compound 786)

Step 1. Synthesis of 4-methyl-7-(3-(trifluoromethyl)phenyl)-1,2-dihydro-1,8-naphthyridine (124)

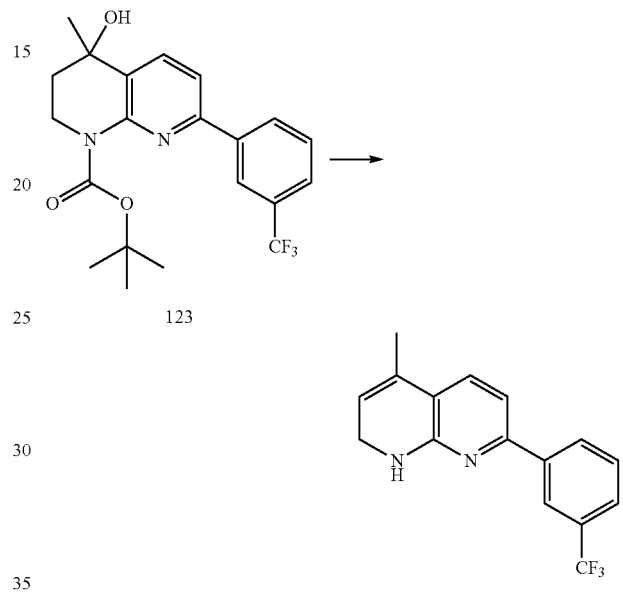

To a solution of tert-butyl 4-hydroxy-4-methyl-7-(3-(trifluoromethyl)phenyl)-3,4-dihydro-1,8-naphthyridine-1 (2H)-carboxylate (123; 0.54 g, 1.32 mmol) in DCM (10 mL) was added Trifluoroacetic acid (TFA) (10 mL). After 40 minutes, TLC showed the starting material had disappeared. TFA and DCM were removed under vacuum. The residue was dissolved in EtOAc which was washed with $H_2O$, saturated aqueous $Na_2CO_3$ solution and brine, dried over anhydrous $Na_2SO_4$, filtered and concentrated to afford 4-methyl-7-(3-(trifluoromethyl)phenyl)-1,2-dihydro-1,8-naphthyridine as a yellow solid (124; 400 mg, quantitative yield). MS (ESI) calcd for $C_{16}H_{13}F_3N_2O$: 290.28.

Step 3. Synthesis of 4-methyl-7-(3-(trifluoromethyl)phenyl)-1,2,3,4-tetrahydro-1,8-naphthyridine (125)

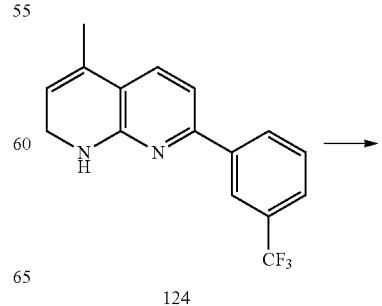

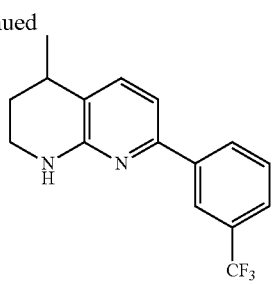

125

A mixture of 4-methyl-7-(3-(trifluoromethyl)phenyl)-1,2-dihydro-1,8-naphthyridine (124; 674 mg, 2.33 mmol), Pd/C (150 mg) in THF (10 mL) was stirred under 1 atmosphere of H₂ for overnight. After TLC showed the reaction was complete, the mixture was filtered and concentrated. The residue was purified by chromatography on a silica gel column (eluting with petroleum ether/ethyl acetate=10/1) to give 4-methyl-7-(3-(trifluoromethyl)phenyl)-1,2,3,4-tetrahydro-1,8-naphthyridine as a white solid (125; 629 mg, 93% yield). MS (ESI) calcd for $C_{16}H_{15}F_3N_2$: 292.12. found: 293 [M+H].

Step 4. Synthesis of 4-methyl-N-(pyridin-4-yl)-7-(3-(trifluoromethyl)phenyl)-3,4-dihydro-1,8-naphthyridine-1(2H)-carboxamide (Compound 786)

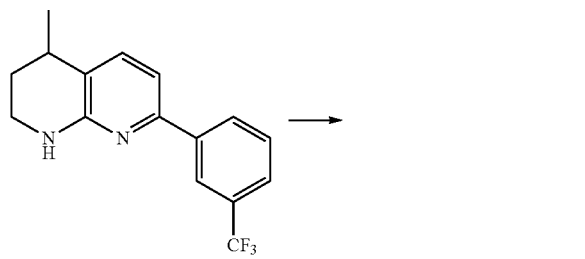

125

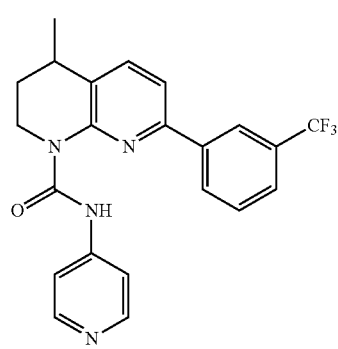

Compound 786

Method A:

To a mixture of 4-aminopyridine (32 mg, 0.34 mmol) in 3 mL of dry THF was added in one-portion triethylamine (0.5 mL) followed by triphosgene (33 mg, 0.11 mmol). The above mixture was stirred at room temp for 3 h and 4-methyl-7-(3-(trifluoromethyl)phenyl)-1,2,3,4-tetrahydro-1,8-naphthyridine (125; 0 mg, 0.17 mmol) was added to the reaction mixture and stirred for an additional 18 h at 60° C. Water was added to the reaction mixture and the aqueous portion extracted with dichloromethane (3×15 mL). The combined organics were washed with aqueous NaHCO₃ solution and brine, dried with anhydrous sodium sulfate and concentrated. The crude product was purified by preparative TLC to afford 4-methyl-N-(pyridin-4-yl)-7-(3-(trifluoromethyl)phenyl)-3,4-dihydro-1,8-naphthyridine-(2H)-carboxamide (Compound 786) as white solid. MS (ESI) calcd for $C_{22}H_{19}F_3N_4O$: 412.15. found: 413 [M+H].

Example 31

Preparation of 4-methyl-N-(pyridin-2-yl)-7-(3-(trifluoromethyl)phenyl)-3,4-dihydro-1,8-naphthyridine-1(2H)-carboxamide (Compound 785)

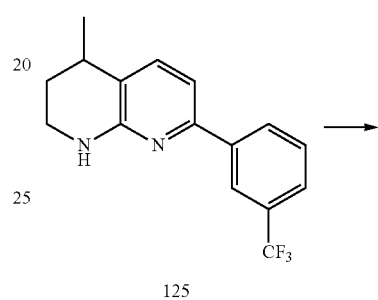

125

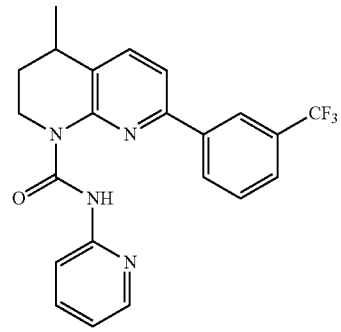

Compound 785

Method B:

A mixture of 4-methyl-7-(3-(trifluoromethyl)phenyl)-1,2,3,4-tetrahydro-1,8-naphthyridine (125; 40 mg, 0.14 mmol), phenyl pyridin-2-ylcarbamate (60 mg, 0.28 mmol) and DMAP (27 mg, 0.22 mmol) in acetonitrile was refluxed overnight. The acetonitrile was removed by evaporation under reduced pressure. The residue was dissolved in dichloromethane and washed with aqueous Na₂CO₃ and brine, dried over anhydrous sodium sulfate and concentrated. The crude product was purified by loading onto a preparative TLC plate to afford 4-methyl-N-(pyridin-2-yl)-7-(3-(trifluoromethyl)phenyl)-3,4-dihydro-1,8-naphthyridine-1(2H)-carboxamide (Compound 785) as a white solid. Yield: 21%. MS (ESI) calcd for C22H19F3N4O: 412.15. found: 413 [M+H].

These general procedures could be used to prepare a variety of 4-methyl-N-substituted-7-aryl-3,4-dihydro-1,8-naphthyridine-1(2H)-carboxamide derivatives by selecting the appropriate amine or phenyl carbamate.

Example 32

Preparation of 2-(3-chlorophenyl)-5-oxo-N-(pyridin-3-yl)-7,8-dihydro-5H-pyrido[2,3-b]azepine-9(6H)-carboxamide (Compound 747)

Step 1. Synthesis of tert-butyl 2-chloro-7,8-dihydro-5H-pyrido[2,3-b]azepine-9(6H)-carboxylate (127)

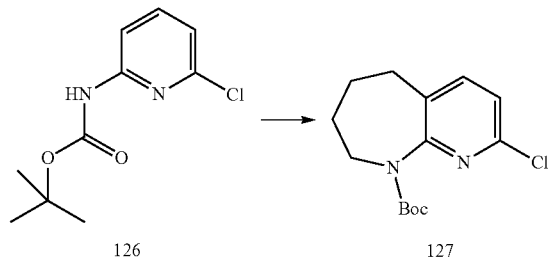 [SMILES: CC(C)(C)OC(=O)Nc1cccc(Cl)n1 ; CC(C)(C)OC(=O)N1CCCCc2ccc(Cl)nc21]

To a stirred solution of tetramethylethylenediamine (TMEDA) (5.6 g, 48.24 mmol) in THF (300 mL) cooled in a dry-ice bath was added n-BuLi (19.3 mL, 2.5M in hexanes, 48.24 mmol) over 5 min. After 20 min, a solution of tert-butyl 6-chloropyridin-2-ylcarbamate (126; 5.0 g, 21.88 mmol) in THF (25 mL) was added dropwise over 5 min. The reaction mixture was stirred for 1 hour and then CuI (4.2 g, 21.88 mmol) was added in one portion. The reaction mixture was allowed to warm to −20° C. for 1 h. 1-Chloro-4-iodobutane (7.2 g, 32.82 mmol) was added and the reaction mixture was allowed to warm to ambient temperature and subsequently refluxed for 18 h. Then the reaction mixture was quenched via addition of saturated sodium bicarbonate solution. The aqueous layer was extracted with EtOAc, washed with water and brine sequentially. The combined organic layers were concentrated to afford crude product, which was triturated with petroleum ether to afford tert-butyl 2-chloro-7,8-dihydro-5H-pyrido[2,3-b]azepine-9(6H)-carboxylate (127; 3.5 g, 56%) as a pale yellow solid. MS (ESI) calcd for $C_{14}H_{19}ClN_2O_2$: 282.77.

Step 2. Synthesis of tert-butyl 2-chloro-5-oxo-7,8-dihydro-5H-pyrido[2,3-b]azepine-9(6H)-carboxylate (128)

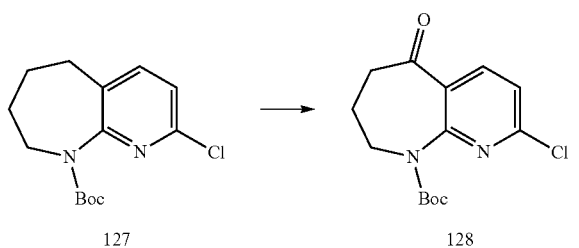 [SMILES: CC(C)(C)OC(=O)N1CCCCc2ccc(Cl)nc21 ; CC(C)(C)OC(=O)N1CCCC(=O)c2ccc(Cl)nc21]

A mixture of tert-butyl 2-chloro-7,8-dihydro-5H-pyrido[2,3-b]azepine-9(6H)-carboxylate (127; 20.0 g, 70.92 mmol) and $NaH_2PO_4 \cdot H_2O$ (16.6 g, 106.4 mmol) in t-BuOH (300 mL) and $H_2O$ (240 mL) was heated to 50° C. $NaMnO_4$ (aqueous 40%) (60 mL) was added and the reaction was stirred at 50° C. Thin-layer chromatography (TLC) was used to monitor the progress of the reaction. The reaction was worked up by careful addition of $Na_2SO_3$ to the cooled reaction mixture until the purple color disappeared, followed by extraction with EtOAc. The combined organic layers were washed with water and brine, dried ($Na_2SO_4$), filtered and concentrated. The residue was purified by chromatography, eluting with ethyl acetate:petroleum ether to give tert-butyl 2-chloro-5-oxo-7,8-dihydro-5H-pyrido[2,3-b]azepine-9(6H)-carboxylate (128; 7.04 g, 37%) as a white solid. MS (ESI) calcd for $C_{14}H_{17}ClN_2O_2$: 296.75.

Step 3. Synthesis of tert-butyl 2-(3-chlorophenyl)-5-oxo-7,8-dihydro-5H-pyrido[2,3-b]azepine-9(6H)-carboxylate (129)

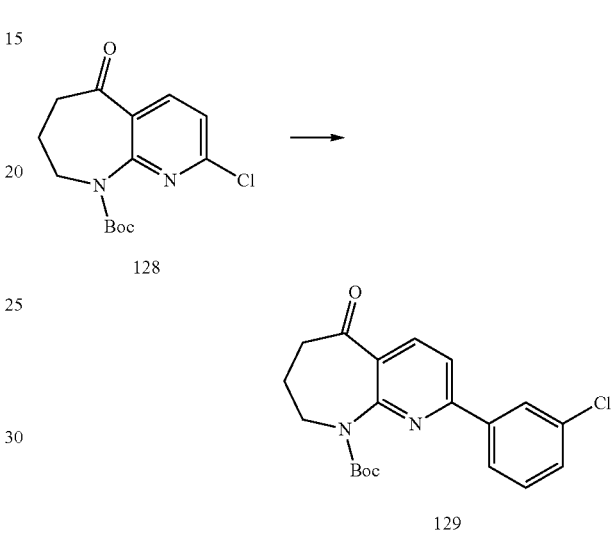

A mixture of tert-butyl 2-chloro-5-oxo-7,8-dihydro-5H-pyrido[2,3-b]azepine-9(6H)-carboxylate (128; 7.0 g, 23.6 mmol), 3-chlorophenyl boronic acid (9.23 g, 59.0 mmol), Pd(dppf)Cl$_2$ (1.97 g, 2.36 mmol), Cs$_2$CO$_3$ (19.2 g, 59.0 mmol) in dioxane:H$_2$O (10:1, v:v) (200 ml) was stirred at reflux for 18 h. Then the reaction was extracted with EtOAc, washed with water, and brine. The combined organic layers were dried (Na$_2$SO$_4$), filtered, and concentrated. The residue was purified by chromatography, eluting with ethyl acetate: petroleum ether to give tert-butyl 2-(3-chlorophenyl)-5-oxo-7,8-dihydro-5H-pyrido[2,3-b]azepine-9(6H)-carboxylate (129; 5.5 g, 63%) as a white solid. MS (ESI) calcd for $C_{20}H_{21}ClN_2O_3$: 372.85.

This general coupling procedure could be used to prepare a variety of tert-butyl 2-aryl-5-oxo-7,8-dihydro-5H-pyrido[2,3-b]azepine-9(6H)-carboxylate derivatives by substituting the appropriate boronic acid for 3-chlorophenyl boronic acid.

Step 4. Synthesis of (3-chlorophenyl)-6,7,8,9-tetrahydro-5H-pyrido[2,3-b]azepin-5-one (130)

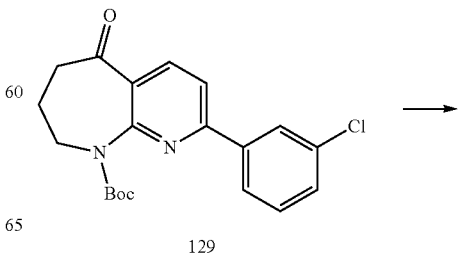

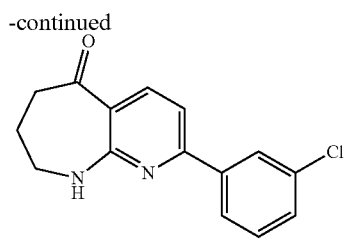

130

Tert-Butyl 2-(3-chlorophenyl)-5-oxo-7,8-dihydro-5H-pyrido[2,3-b]azepine-9(6H)-carboxylate (129; 0.28 g, 0.75 mmol) was dissolved in HCl/MeOH (5 ml, 3 N), then stirred at ambient temperature. The reaction mixture was concentrated to give crude 2-(3-chlorophenyl)-6,7,8,9-tetrahydro-5H-pyrido[2,3-b]azepin-5-one (130; 202 mg, 87%) as an oil. MS (ESI) calcd for $C_{15}H_{13}ClN_2O$: 272.73.

Step 5. Synthesis of 2-(3-chlorophenyl)-5-oxo-N-(pyridin-3-yl)-7,8-dihydro-5H-pyrido[2,3-b]azepine-9(6H)-carboxamide (Compound 747)

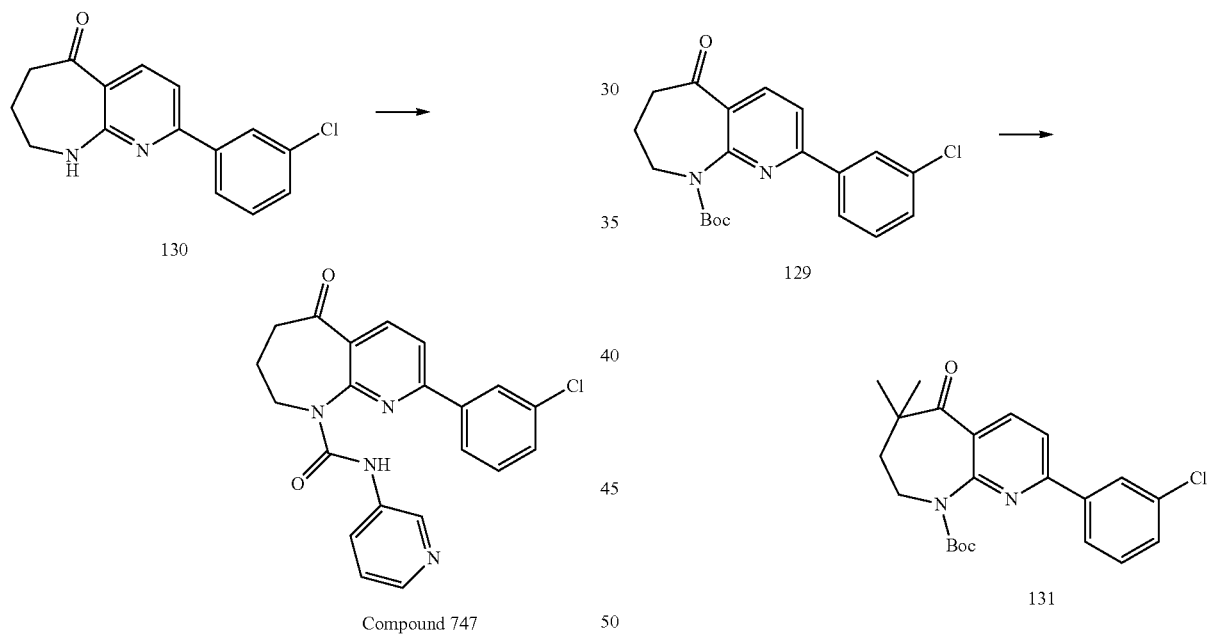

To a solution of 3-aminopyridine (30 mg, 0.32 mmol) and triethylamine (0.3 mL, 2.15 mmol) in THF was added triphosgene (76 mg, 0.26 mmol) under a nitrogen atmosphere, and the mixture was stirred at 60° C. for 2 h. Then 2-(3-chlorophenyl)-6,7,8,9-tetrahydro-5H-pyrido[2,3-b]azepin-5-one (130; 50 mg, 0.16 mmol) was added and the mixture was stirred at 60° C. overnight. Water was added and the mixture was extracted with $CH_2Cl_2$. The combined organic layers were washed with brine and concentrated. The residue was purified by preparative thin layer chromatography to give 2-(3-chlorophenyl)-5-oxo-N-(pyridin-3-yl)-7,8-dihydro-5H-pyrido[2,3-b]azepine-9(6H)-carboxamide (Compound 747; 30 mg, 48%). MS (ESI) calcd for $C_{21}H_{17}ClN_4O_2$: 392.10. found: 393 [M+H].

This general procedure could be used to prepare a variety of 2-aryl-5-oxo-N-substituted-7,8-dihydro-5H-pyrido[2,3-b]azepine-9(6H)-carboxamide derivatives by substituting the appropriate amine for pyridine-3-amine. Alternatively, derivatives can also be prepared by reacting the appropriate phenyl carbamate with 2-aryl-6,7,8,9-tetrahydro-5H-pyrido[2,3-b]azepin-5-one in the presence of DIEA at room temp to 50° C.

Example 33

Preparation of 2-(3-chlorophenyl)-6,6-dimethyl-N-(4-methylthiazol-2-yl)-5-oxo-7,8-dihydro-5H-pyrido[2,3-b]azepine-9(6H)-carboxamide (Compound 836)

Step 1. Synthesis of tert-butyl 2-(3-chlorophenyl)-6,6-dimethyl-5-oxo-7,8-dihydro-5H-pyrido[2,3-b]azepine-9(6H)-carboxylate (131)

To a solution of tert-butyl 2-(3-chlorophenyl)-5-oxo-7,8-dihydro-5H-pyrido[2,3-b]azepine-9(6H)-carboxylate (129; 1.75 g, 4.70 mmol) in THF (63 mL) was added t-BuOK (5.26 g, 47.0 mmol). The mixture was stirred at −40° C. for 1 h. Then $CH_3I$ (2.34 mL, 37.6 mmol) was added and the mixture stirred at −40° C. for 1 h and at room temperature for 2 h. Saturated $NH_4Cl$ solution was added and the aqueous layer was extracted with EtOAc. The combined organic layers were dried ($Na_2SO_4$), filtered, and concentrated. The residue was purified by chromatography, eluting with ethyl acetate:petroleum ether to give tert-butyl 2-(3-chlorophenyl)-6,6-dimethyl-5-oxo-7,8-dihydro-5H-pyrido[2,3-b]azepine-9(6H)-carboxylate (131; 703 mg, 37%) as a yellow oil. MS (ESI) calcd for $C_{22}H_{25}ClN_2O_3$: 400.90.

Step 2. Synthesis of 2-(3-chlorophenyl)-6,6-dimethyl-6,7,8,9-tetrahydro-5H-pyrido[2,3-b]azepin-5-one (132)

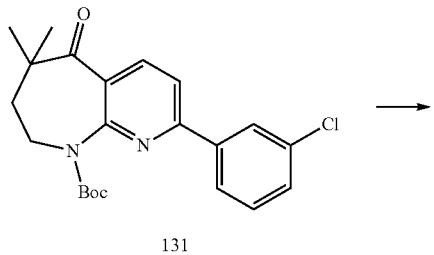

131

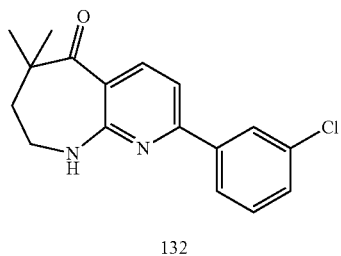

132

Tert-Butyl 2-(3-chlorophenyl)-6,6-dimethyl-5-oxo-7,8-dihydro-5H-pyrido[2,3-b]azepine-9(6H)-carboxylate (131; 1.2 g, 3.0 mmol) was dissolved in HCl/MeOH (30 ml, 3 N), then stirred at room temperature overnight. The reaction mixture was concentrated, followed by addition of aqueous NaHCO$_3$ to make pH=10. The resulting mixture was extracted with EtOAc and washed with brine. The organic layers were dried (Na$_2$SO$_4$), filtered, and concentrated to give 2-(3-chlorophenyl)-6,6-dimethyl-6,7,8,9-tetrahydro-5H-pyrido[2,3-b]azepin-5-one (132; 890 mg, 99%) as a yellow solid. MS (ESI) calcd for C$_{17}$H$_{17}$ClN$_2$O: 300.78. found: 301. [M+H].

Step 3. Synthesis of 2-(3-chlorophenyl)-N-(3-fluoropyridin-4-yl)-6,6-dimethyl-5-oxo-7,8-dihydro-5H-pyrido[2,3-b]azepine-9(6H)-carboxamide (Compound 836)

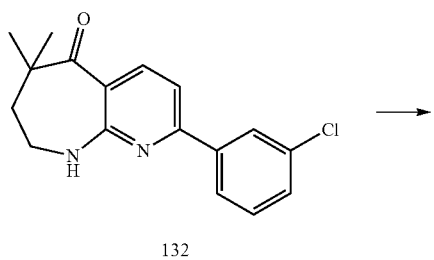

132

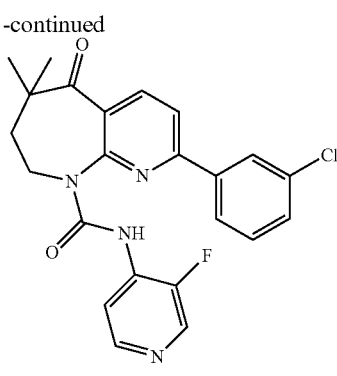

Compound 836

To a solution of 3-fluoropyridin-4-amine (38 mg, 0.33 mmol) and triethylamine (0.3 mL, 2.11 mmol) in THF (5 mL) was added triphosgene (40 mg, 0.13 mmol) under a nitrogen atmosphere, and the mixture was stirred at 50° C. for 2 h. Then 2-(3-chlorophenyl)-6,6-dimethyl-6,7,8,9-tetrahydro-5H-pyrido[2,3-b]azepin-5-one (132; 50 mg, 0.17 mmol) was added and the mixture was stirred at 60° C. for 18 h. Saturated sodium bicarbonate solution and EtOAc was added to the reaction mixture, separated and the aqueous layer was extracted with EtOAc. The combined organic layers were washed with brine and dried (Na$_2$SO$_4$), filtered, and concentrated. The residue was purified by preparative thin layer chromatography to give 2-(3-chlorophenyl)-N-(3-fluoropyridin-4-yl)-6,6-dimethyl-5-oxo-7,8-dihydro-5H-pyrido[2,3-b]azepine-9(6H)-carboxamide (Compound 837; 6.3 mg, 9%) as a white solid. MS (ESI) calcd for C$_{23}$H$_{20}$ClFN$_4$O$_2$: 438.13. found: 439 [M+H].

This general procedure could be used to prepare a variety of 2-aryl-N-substituted-6,6-dimethyl-5-oxo-7,8-dihydro-5H-pyrido[2,3-b]azepine-9(6H)-carboxamide derivatives by substituting the appropriate amine for 3-fluoropyridin-4-amine. Alternatively, derivatives can also be prepared by reacting the appropriate phenyl carbamate with 2-aryl-6,6-dimethyl-6,7,8,9-tetrahydro-5H-pyrido[2,3-b]azepin-5-one in the presence of DIEA at room temp to 50° C.

Example 34

Preparation of 2-(3-chlorophenyl)-N-(pyridin-4-yl)-7,8-dihydro-5H-pyrido[2,3-b]azepine-9(6H)-carboxamide (Compound 728)

Step 1. Synthesis of tert-butyl 2-(3-chlorophenyl)-7,8-dihydro-5H-pyrido[2,3-b]azepine-9(6H)-carboxylate (133)

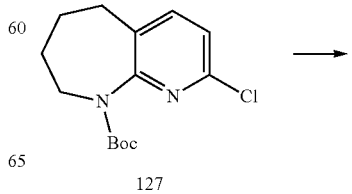

127

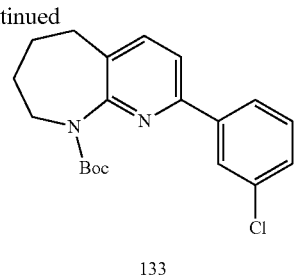

133

A mixture of tert-butyl 2-chloro-7,8-dihydro-5H-pyrido[2,3-b]azepine-9(6H)-carboxylate (127; 1 g, 3.54 mmol), 3-chlorophenyl boronic acid (1.1 g, 7.08 mmol), Pd(dppf)Cl$_2$ (295 mg, 0.35 mmol), Cs$_2$CO$_3$ (2.3 g, 7.08 mmol), in 1,4-dioxane:H$_2$O (10:1, 15 mL) was heated to 110° C. overnight. The reaction mixture was concentrated and purified by chromatography, eluting with ethyl acetate:petroleum ether to give tert-butyl 2-(3-chlorophenyl)-7,8-dihydro-5H-pyrido[2,3-b]azepine-9(6H)-carboxylate (133; 1.15 g, 90%) as a semi-solid. MS (ESI) calcd for C$_{20}$H$_{23}$ClN$_2$O$_2$: 358.86.

This general coupling procedure could be used to prepare a variety of tert-butyl 2-aryl-7,8-dihydro-5H-pyrido[2,3-b]azepine-9(6H)-carboxylate derivatives by substituting the appropriate boronic acid for 3-chlorophenyl boronic acid.

Step 2. Synthesis of 2-(3-chlorophenyl)-6,7,8,9-tetrahydro-5H-pyrido[2,3-b]azepine (134)

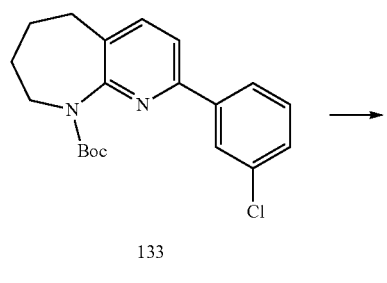

133

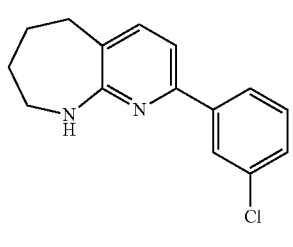

134

A solution of tert-butyl 2-(3-chlorophenyl)-7,8-dihydro-5H-pyrido[2,3-b]azepine-9(6H)-carboxylate (133; 790 mg, 2.2 mmol) in HCl/MeOH (3N, 10 ml) was stirred at room temperature overnight. The reaction mixture was concentrated to give 2-(3-chlorophenyl)-6,7,8,9-tetrahydro-5H-pyrido[2,3-b]azepine (134; 859 mg, 100%) as a white solid. MS (ESI) calcd for C$_{15}$H$_{15}$ClN$_2$: 258.75.

Step 3. Synthesis of 2-(3-chlorophenyl)-N-(pyridin-4-yl)-7,8-dihydro-5H-pyrido[2,3-b]azepine-9(6H)-carboxamide (Compound 728)

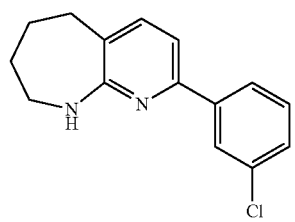

134

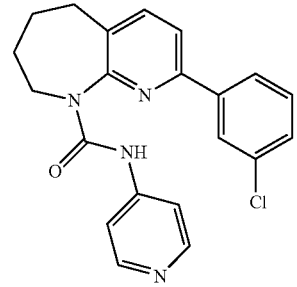

Compound 728

The mixture of 2-(3-chlorophenyl)-6,7,8,9-tetrahydro-5H-pyrido[2,3-b]azepine (134; 75 mg, 0.25 mmol), triphosgene (60 mg, 0.20 mmol) and triethylamine (0.3 mL, 2.15 mmol) in THF (2 mL) was heated to 50° C. for 30 min. Then pyridin-4-amine (28 mg, 0.25 mmol) was added and the mixture was heated to 50° C. for 3 h. The mixture was concentrated and purified by preparative thin layer chromatography to get 2-(3-chlorophenyl)-N-(pyridin-4-yl)-7,8-dihydro-5H-pyrido[2,3-b]azepine-9(6H)-carboxamide (Compound 728; 36.8 mg, 39%) as a yellow solid. MS (ESI) calcd for C$_{21}$H$_{19}$ClN$_4$O: 378.12. found: 379 [M+H].

This general procedure could be used to prepare a variety of 2-aryl-N-substituted-7,8-dihydro-5H-pyrido[2,3-b]azepine-9(6H)-carboxamide derivatives by substituting the appropriate amine for pyridine-4-amine. Alternatively, derivatives can also be prepared by reacting the appropriate phenyl carbamate with 2-aryl-6,7,8,9-tetrahydro-5H-pyrido[2,3-b]azepine in the presence of DIEA at room temp to 50° C.

Example 35

Preparation of 2-(3-chlorophenyl)-5,5-difluoro-N-(pyrimidin-4-yl)-7,8-dihydro-5H-pyrido[2,3-b]azepine-9(6H)-carboxamide (Compound 799)

Step 1. Synthesis of tert-butyl 2-(3-chlorophenyl)-5,5-difluoro-7,8-dihydro-5H-pyrido[2,3-b]azepine-9(6H)-carboxylate (135)

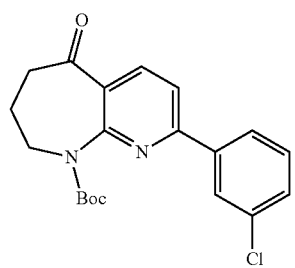

129

-continued

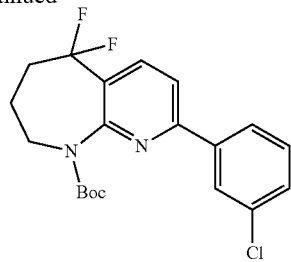

135

A mixture of tert-butyl 2-(3-chlorophenyl)-5-oxo-7,8-dihydro-5-pyrido[2,3-b]azepine-9(6H)-carboxylate (129; 100 mg, 0.27 mmol) and diethylaminosulfur trifluoride (DAST) (2 mL) was stirred at room temperature for 3 days, and then at 44° C. for 3 days. Water was added slowly and the mixture was extracted with $CH_2Cl_2$. Purified by chromatography, eluting with ethyl acetate:petroleum ether to give tert-butyl 2-(3-chlorophenyl)-5,5-difluoro-7,8-dihydro-5H-pyrido[2,3-b]azepine-9(6H)-carboxylate (135; 75 mg, 70%). MS (ESI) calcd for $C_{20}H_{21}ClF_2N_2O_2$: 394.84.

Step 2. Synthesis of 2-(3-chlorophenyl)-5,5-difluoro-6,7,8,9-tetrahydro-5H-pyrido[2,3-b]azepine (136)

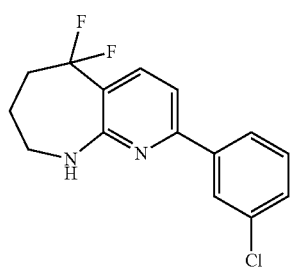

135

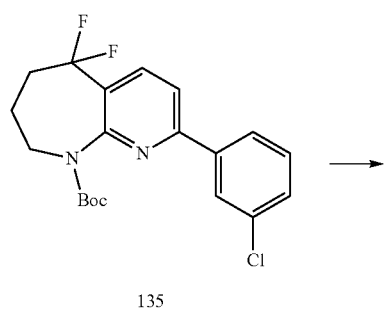

136

A solution of tert-butyl 2-(3-chlorophenyl)-5,5-difluoro-7,8-dihydro-5H-pyrido[2,3-b]azepine-9(6H)-carboxylate (135; 1.16 g, 2.94 mmol) in HCl/MeOH (3N, 25 ml) was stirred at room temperature overnight. The reaction mixture was washed with a NaHCO$_3$ solution, extracted with EtOAc, and concentrated to give 2-(3-chlorophenyl)-5,5-difluoro-6,7,8,9-tetrahydro-5H-pyrido[2,3-b]azepine (136; 808 mg, 93%). MS (ESI) calcd for $C_{15}H_{13}ClF_2N_2$: 294.73.

Step 3. Synthesis of 2-(3-chlorophenyl)-5,5-difluoro-N-(pyrimidin-4-yl)-7,8-dihydro-5H-pyrido[2,3-b]azepine-9(6H)-carboxamide (Compound 799)

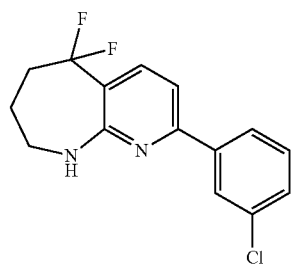

136

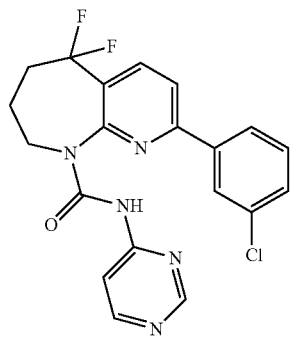

Compound 799

To an ice-cooled solution of pyrimidin-4-amine (5.0 g, 52.6 mmol), triethylamine (15 mL, 107.6 mmol) in THF (100 mL) was added phenyl chloroformate (10.7 g, 68.4 mmol). The reaction mixture was stirred at room temperature for 18 h. Then the reaction was quenched with NaHCO$_3$ solution and extracted with $CH_2Cl_2$. The combined organic layers were washed with water, and brine, dried (Na$_2$SO$_4$), filtered, and concentrated. The residue was triturated in petroleum ether to give crude phenyl pyrimidin-4-ylcarbamate. A solution of phenyl pyrimidin-4-ylcarbamate (73 mg, 0.34 mmol), 2-(3-chlorophenyl)-5,5-difluoro-6,7,8,9-tetrahydro-5H-pyrido[2,3-b]azepine (136; 50 mg, 0.17 mmol) and DMAP (25 mg, 0.20 mmol) in MeCN (5 mL) was stirred at 80° C. for 18 h. The reaction mixture was purified by preparative thin layer chromatography to give 2-(3-chlorophenyl)-5,5-difluoro-N-(pyrimidin-4-yl)-7,8-dihydro-5H-pyrido[2,3-b]azepine-9(6H)-carboxamide (Compound 799; 35 mg, 50%) as a white solid. MS (ESI) calcd for $C_{20}H_{16}ClF_2N_5O$: 415.10. found: 416 [M+H].

This general procedure could be used to prepare a variety of 2-aryl-5,5-difluoro-N-substituted-7,8-dihydro-5H-pyrido[2,3-b]azepine-9(6H)-carboxamide derivatives by substituting for phenyl pyrimidin-4-ylcarbamate an appropriate phenyl carbamate.

Example 36

Preparation of 7-(3-chlorophenyl)-1-ethyl-2-oxo-N-(pyridin-2-yl)-3,4-dihydro-1H-pyrido[2,3-b][1,4]diazepine-5(2H)-carboxamide (Compound 765)

Step 1. Synthesis of ethyl 3-((6-chloro-3-nitropyridin-2-yl)amino)propanoate (138)

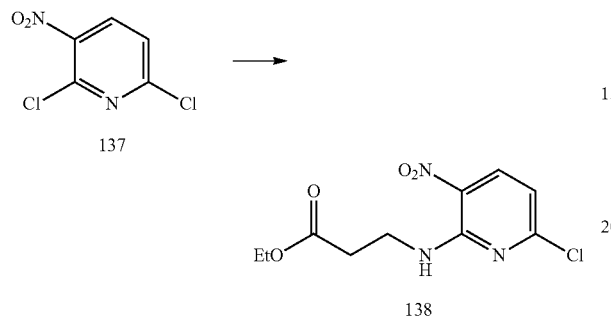

A mixture of 2,6-dichloro-3-nitropyridine (137; 1.92 g, 10 mmol), ethyl 3-aminopropanoate hydrochloride (1.7 g, 11 mmol), and diisopropylethylamine (3.9 g, 30 mmol) in dimethylformamide (10 mL) was stirred at room temperature overnight. The reaction progress was monitored by TLC. Saturated NaHCO$_3$ solution was added to the reaction mixture, which was then extracted with ethyl acetate. The combined organic layers were washed with water and brine, then concentrated to give ethyl 3-((6-chloro-3-nitropyridin-2-yl)amino)propanoate (138; 2.8 g, 100%) as a pale yellow oil. MS (ESI) calcd for $C_{10}H_{12}ClN_3O_4$: 273.67.

Step 2. Synthesis of 7-chloro-4,5-dihydro-1H-pyrido[2,3-b][1,4]diazepin-2(3H)-one (139)

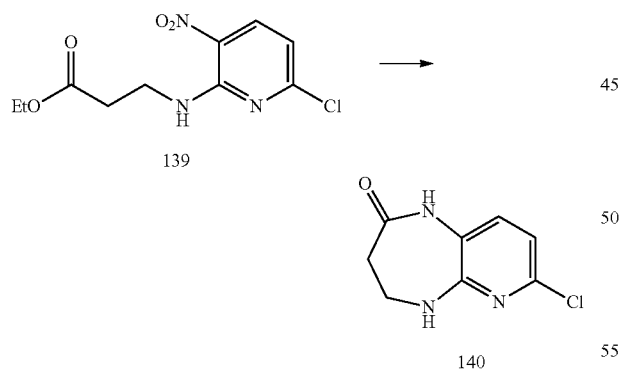

A mixture of ethyl 3-((6-chloro-3-nitropyridin-2-yl)amino)propanoate (139; 39 g, 143 mmol) and Pd/C (3.9 g) in EtOAc (800 mL) was stirred under hydrogen (2.5 atm) for 16 h. The resulting mixture was filtered through a celite pad, concentrated and purified by chromatography to give a dark solid, which was used in the next step without further purification. The dark solid was dissolved in AcOH (1000 mL), and stirred at 130° C. overnight. AcOH was removed under reduced pressure. The residue was dissolved in EtOH, activated carbon was added and stirred at 60° C. for 3 h, then filtered. The crude material was crystallized to give 7-chloro-4,5-dihydro-1H-pyrido[2,3-b][1,4]diazepin-2(3H)-one (140; 6.8 g, 24%) as a gray solid. MS (ESI) calcd for $C_8H_8ClN_3O$: 197.62.

Step 3. Synthesis of 7-(3-chlorophenyl)-4,5-dihydro-1H-pyrido[2,3-b][1,4]diazepin-2(3H)-one (141)

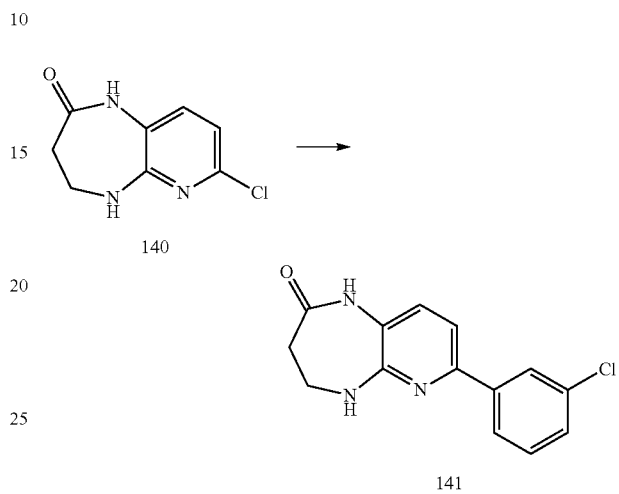

A mixture of compound 7-chloro-4,5-dihydro-1H-pyrido[2,3-b][1,4]diazepin-2(3H)-one (140; 1.97 g, 10 mmol), (3-chlorophenyl)boronic acid (1.88 g, 12 mmol), Pd(PPh$_3$)$_4$ (577 mg, 0.5 mmol) and cesium carbonate (6.5 g, 20 mmol) in 1,2-dimethoxyethane (50 mL) and water (3 mL) was stirred at 65° C. overnight. The solid was filtered and the filtrate was concentrated to give a dark residue, which was taken up in CH$_2$Cl$_2$ and extracted with water. The organic layer was dried (Na$_2$SO$_4$), filtered, and concentrated. The residue was triturated with methanol to give 7-(3-chlorophenyl)-4,5-dihydro-1H-pyrido[2,3-b][1,4]diazepin-2(3H)-one (1.9 g, 62%) as a yellow solid. The supernatant from the trituration was concentrated and purified by chromatography, eluting with ethyl acetate:petroleum ether to afford another 1.1 g of 7-(3-chlorophenyl)-4,5-dihydro-1H-pyrido[2,3-b][1,4]diazepin-2(3H)-one (141). MS (ESI) calcd for $C_{14}H_{12}ClN_3O$: 273.72.

This general coupling procedure could be used to prepare a variety of 7-aryl-4,5-dihydro-1H-pyrido[2,3-b][1,4]diazepin-2(3H)-one derivatives by substituting the appropriate boronic acid for 3-chlorophenyl boronic acid.

Step 4. Synthesis of 7-(3-chlorophenyl)-1-ethyl-4,5-dihydro-1H-pyrido[2,3-b][1,4]diazepin-2(3H)-one (142)

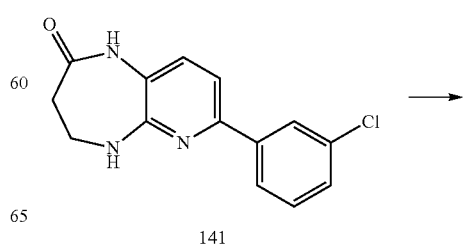

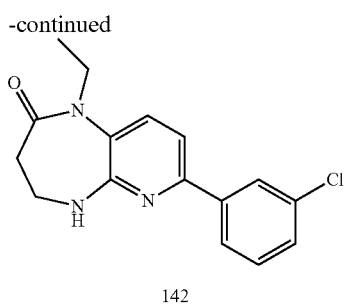

142

To a solution of 7-(3-chlorophenyl)-4,5-dihydro-1H-pyrido[2,3-b][1,4]diazepin-2(3H)-one (141; 168 mg, 0.63 mmol) in THF (3 mL), was added t-BuOK (84 mg, 0.75 mmol) and the reaction mixture was stirred for 1 h. Then EtI (0.055 mL, 0.68 mmol) was added, stirred at room temperature overnight. The reaction mixture was concentrated and the residue was dissolved in EtOAc. The resulting solution was filtered, and the filtrate was concentrated. The residue was purified by preparatory thin layer chromatography to give 7-(3-chlorophenyl)-1-ethyl-4,5-dihydro-1H-pyrido[2,3-b][1,4]diazepin-2(3H)-one (142; 160 mg, 86%) as a yellow semi-solid. MS (ESI) calcd for $C_{16}H_{16}ClN_3O$: 301.77.

Step 5. Synthesis of 7-(3-chlorophenyl)-1-ethyl-2-oxo-N-(pyridin-2-yl)-3,4-dihydro-1H-pyrido[2,3-b][1,4]diazepine-5(2H)-carboxamide (Compound 765)

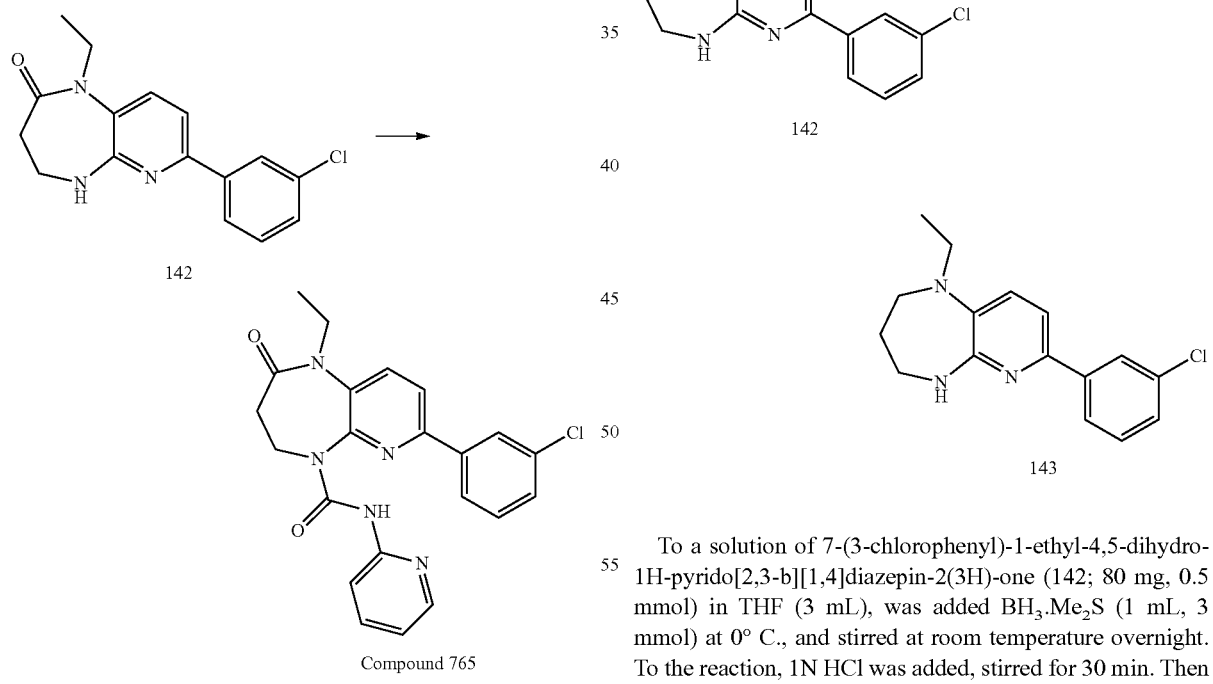

A solution of phenyl pyridin-2-ylcarbamate (71 mg, 0.33 mmol), 7-(3-chlorophenyl)-1-ethyl-4,5-dihydro-1H-pyrido[2,3-b][1,4]diazepin-2(3H)-one (142; 50 mg, 0.17 mmol), and 4-Dimethylaminopyridine (DMAP) (20 mg, 0.17 mmol) in MeCN (3 ml) was stirred at reflux overnight. The reaction mixture was concentrated and purified by preparative thin layer chromatography to give 7-(3-chlorophenyl)-1-ethyl-2-oxo-N-(pyridin-2-yl)-3,4-dihydro-1H-pyrido[2,3-b][1,4]diazepine-5(2H)-carboxamide (Compound 765; 31 mg, 44%) as a white solid. MS (ESI) calcd for $C_{22}H_{20}ClN_5O_2$: 421.13. found: 422 [M+H].

This general procedure could be used to prepare a variety of 7-aryl-1-ethyl-2-oxo-N-substituted-3,4-dihydro-1H-pyrido[2,3-b][1,4]diazepine-5(2H)-carboxamide derivatives by substituting the appropriate phenyl carbamate for phenyl pyridin-2-ylcarbamate.

Example 37

Preparation of 7-(3-chlorophenyl)-ethyl-N-(pyridin-3-yl)-3,4-dihydro-1H-pyrido[2,3-b][1,4]diazepine-5(2H)-carboxamide (Compound 789)

Step 1. Synthesis of 7-(3-chlorophenyl)-1-ethyl-2,3,4,5-tetrahydro-1H-pyrido[2,3-b][1,4]diazepine (143)

To a solution of 7-(3-chlorophenyl)-1-ethyl-4,5-dihydro-1H-pyrido[2,3-b][1,4]diazepin-2(3H)-one (142; 80 mg, 0.5 mmol) in THF (3 mL), was added $BH_3 \cdot Me_2S$ (1 mL, 3 mmol) at 0° C., and stirred at room temperature overnight. To the reaction, 1N HCl was added, stirred for 30 min. Then the pH was adjusted to 8 with saturated $NaHCO_3$ solution, and the mixture was extracted with EtOAc. The organic layer was dried ($Na_2SO_4$), filtered, concentrated, and purified by preparative thin layer chromatography to give 7-(3-chlorophenyl)-1-ethyl-2,3,4,5-tetrahydro-1H-pyrido[2,3-b][1,4]diazepine (143; 48 mg, 64%) as solid. MS (ESI) calcd for $C_{16}H_{18}ClN_3$: 287.79.

Step 2. Synthesis of 7-(3-chlorophenyl)-1-ethyl-N-(pyridin-3-yl)-3,4-dihydro-1H-pyrido[2,3-b][1,4]diazepine-5(2H)-carboxamide (Compound 789)

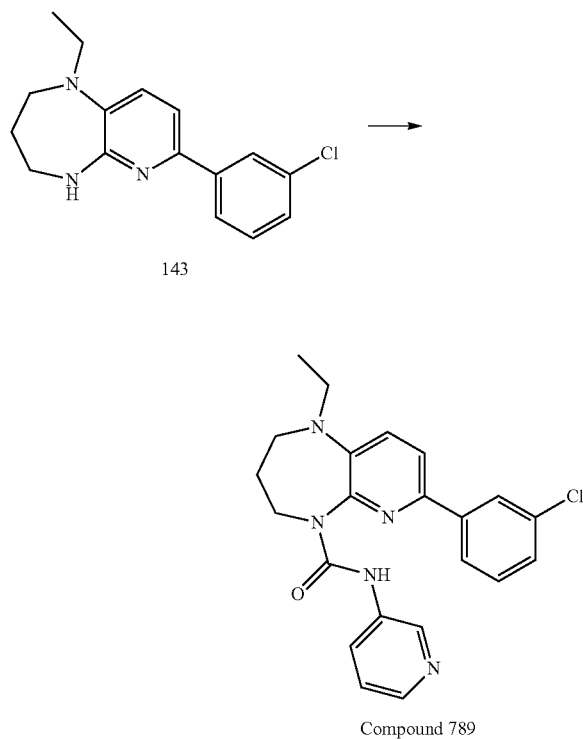

Compound 789

To a solution of pyridine-3-amine (34 mg, 0.36 mmol) and triethylamine (0.1 mL, 0.72 mmol) in THF (3 mL) was added triphosgene (42 mg, 0.14 mmol) under a nitrogen atmosphere, and the mixture was stirred at 60° C. for about 4 hours. Then 7-(3-chlorophenyl)-1-ethyl-2,3,4,5-tetrahydro-1H-pyrido[2,3-b][1,4]diazepine (143; 50 mg, 0.18 mmol) was added and the mixture was stirred at 60° C. overnight. Saturated sodium bicarbonate solution and EtOAc was added to the reaction mixture, separated and the aqueous layer was extracted with EtOAc. The combined organic layers were washed with brine and concentrated. The residue was purified by preparative thin layer chromatography to give 7-(3-chlorophenyl)-1-ethyl-N-(pyridin-3-yl)-3,4-dihydro-1H-pyrido[2,3-b][1,4]diazepine-5(2H)-carboxamide (Compound 789; 34 mg, 47%) as a yellow semi-solid. MS (ESI) calcd for: $C_{22}H_{22}ClN_5O$: 407.15. found: 408 [M+H].

This general procedure could be used to prepare a variety of 7-aryl-1-ethyl-N-substituted-3,4-dihydro-1H-pyrido[2,3-b][1,4]diazepine-5(2H)-carboxamide derivatives by substituting the appropriate amine for pyridine-3-amine. Alternatively, derivatives can also be prepared by reacting the appropriate phenyl carbamate with 7-aryl-1-ethyl-2,3,4,5-tetrahydro-1H-pyrido[2,3-b][1,4]diazepine in the presence of DIEA at room temp to 50° C.

Example 38

Preparation of N-(pyridin-4-yl)-7-(3-(trifluoromethyl)phenyl)-3,4-dihydropyrido[3,2-b][1,4]oxazepine-5(2H)-carboxamide (Compound 558)

Step 1. Synthesis of 6-bromo-3-(3-bromopropoxy)-2-nitropyridine (145)

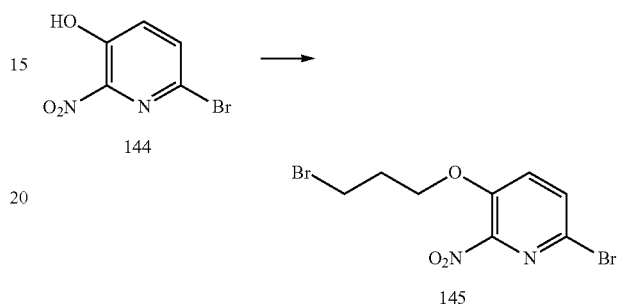

To a cooled (0° C.) solution of triphenylphosphine (3.93 g, 15 mmol) in THF (22 mL) was added DIAD (3.0 g, 15 mmol) dropwise. The reaction mixture was stirred for 30 min, and then to it was added a solution of 6-bromo-2-nitropyridin-3-ol (2.19 g, 10 mmol) and 3-bromopropan-1-ol (2.1 g, 15 mmol) in THF (18 mL). The reaction mixture was allowed to come to room temperature and stirred for about 2 h. Then the reaction mixture was concentrated and the residue was partitioned between EtOAc and water. The organic layer was washed with water and brine, dried ($Na_2SO_4$), filtered, and concentrated. The residue was purified by chromatography, eluting with ethyl acetate:petroleum ether to give 6-bromo-3-(3-bromopropoxy)-2-nitropyridine (1.18 g, 35%) as a yellow oil. MS (ESI) calcd for: $C_8H_8Br_2N_2O_3$: 339.97.

Step 2. Synthesis of 6-bromo-3-(3-bromopropoxy)pyridin-2-amine (146)

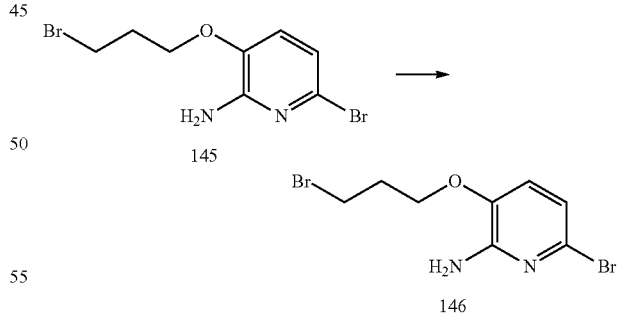

A mixture of 6-bromo-3-(3-bromopropoxy)-2-nitropyridine (145; 1.18 g, 3.47 mmol) and Fe powder (0.78 g, 13.88 mmol) in AcOH (10 mL) was stirred at 90° C. for 2 h. Then the reaction mixture was cooled to room temperature, EtOAc was added, and the mixture was filtered. The filtrate was concentrated and purified by chromatography, eluting with ethyl acetate:petroleum ether to give 6-bromo-3-(3-bromopropoxy)pyridin-2-amine (146; 600 mg, 56%) as a white solid. MS (ESI) calcd for: $C_8H_{10}Br_2N_2O$: 309.99.

Step 3. Synthesis of 7-bromo-2,3,4,5-tetrahydropyrido[3,2-b][1,4]oxazepine (147)

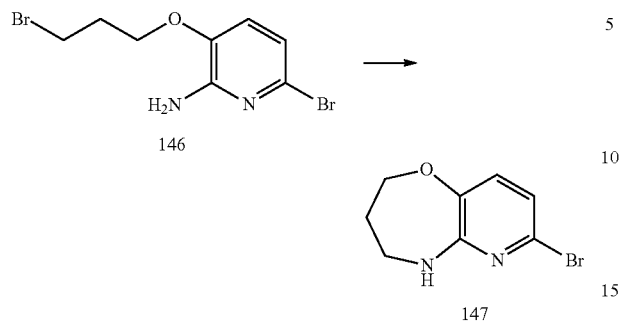

To a stirred solution of 6-bromo-3-(3-bromopropoxy)pyridin-2-amine (146; 5 g, 16.13 mmol) in DMF (500 mL) was added NaH (1.29 g, 32.3 mmol, suspended in mineral oil) at 0° C. The reaction mixture was stirred at 100° C. for 1 h. Saturated NH$_4$Cl solution and water were added and the mixture was extracted with dichloromethane. The combined organic layers were washed with water and brine, dried (Na$_2$SO$_4$), and concentrated. A second batch of the same scale was run and the combined crude materials was purified by chromatography, eluting with ethyl acetate:petroleum ether to give 7-bromo-2,3,4,5-tetrahydropyrido[3,2-b][1,4]oxazepine (147; 5.9 g, 80%) as a white solid. MS (ESI) calcd for: C$_8$H$_9$BrN$_2$O: 229.07.

Step 4. Synthesis of 7-(3-(trifluoromethyl)phenyl)-2,3,4,5-tetrahydropyrido[3,2-b][1,4]oxazepine (148)

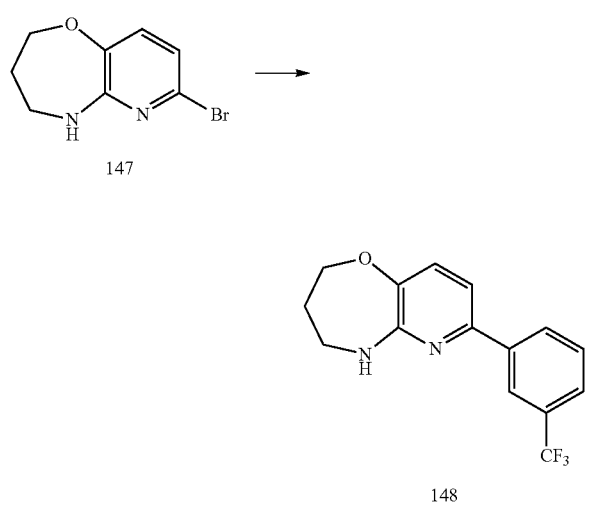 [SMILES: Brc1ccc2c(n1)NCCCO2 ; FC(F)(F)c1cccc(-c2ccc3c(n2)NCCCO3)c1]

A mixture of 7-bromo-2,3,4,5-tetrahydropyrido[3,2-b][1,4]oxazepine (147; 1.2 g, 5.24 mmol), (3-(trifluoromethyl)phenyl)boronic acid (1.5 g, 7.86 mmol), PdCl$_2$ (dppf) (218 mg, 0.26 mmol), and cesium carbonate (3.4 g, 10.5 mmol) in 1,4-dioxane (20 mL) was stirred at 80° C. under a nitrogen atmosphere for 4 h. The reaction mixture was concentrated and purified by chromatography, eluting with ethyl acetate:petroleum ether to give 7-(3-(trifluoromethyl)phenyl)-2,3,4,5-tetrahydropyrido[3,2-b][1,4]oxazepine (148; 1.3 g, 84%). MS (ESI) calcd for: C$_{15}$H$_{13}$F$_3$N$_2$O: 294.27.

This general coupling procedure could be used to prepare a variety of 7-aryl-2,3,4,5-tetrahydropyrido[3,2-b][1,4]oxazepine derivatives by substituting the appropriate boronic acid for (3-(trifluoromethyl)phenyl)boronic acid.

Step 5. Synthesis of N-(pyridin-4-yl)-7-(3-(trifluoromethyl)phenyl)-3,4-dihydropyrido[3,2-b][1,4]oxazepine-5(2H)-carboxamide (Compound 558)

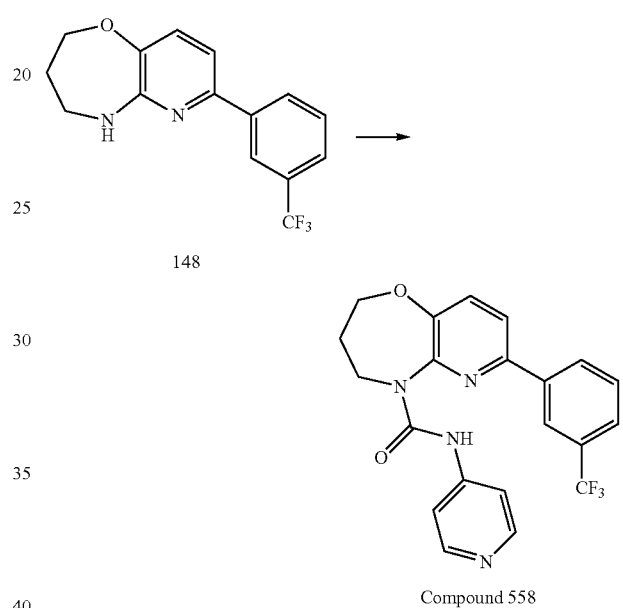

To a solution of 7-(3-(trifluoromethyl)phenyl)-2,3,4,5-tetrahydropyrido[3,2-b][1,4]oxazepine (148; 100 mg, 0.34 mmol) and triethylamine (0.17 mL, 1.19 mmol) in CH$_2$Cl$_2$ (5 mL) was added triphosgene (50 mg, 0.17 mmol), and the mixture was stirred at room temperature for 30 min. Then pyridine-4-amine (96 mg, 1.02 mmol) was added and the mixture was stirred at room temperature overnight. The reaction mixture was diluted with CH$_2$Cl$_2$, and washed with water and brine, dried (MgSO$_4$), filtered, and concentrated. The residue was purified by chromatography to give N-(pyridin-4-yl)-7-(3-(trifluoromethyl)phenyl)-3,4-dihydropyrido[3,2-b][1,4]oxazepine-5(2H)-carboxamide (Compound 558; 10 mg, 7%). MS (ESI) calcd for C$_{21}$H$_{17}$F$_3$N$_4$O$_2$: 414.13. found: 415 [M+H].

This general procedure could be used to prepare a variety of N-substituted-7-aryl-3,4-dihydropyrido[3,2-b][1,4]oxazepine-5(2H)-carboxamide derivatives by substituting the appropriate amine for pyridine-4-amine. Alternatively, derivatives can also be prepared by reacting the appropriate phenyl carbamate with 7-aryl-2,3,4,5-tetrahydropyrido[3,2-b][1,4]oxazepine in the presence of DIEA at room temp to 50° C.

Example 39

Preparation of N-(pyridin-2-yl)-6-(3-(trifluoromethyl)phenyl)-2,3-dihydro-1H-pyrrolo[2,3-b]pyridine-1-carboxamide (Compound 861)

Step 1. Synthesis of 1H-pyrrolo[2,3-b]pyridine 7-oxide (150)

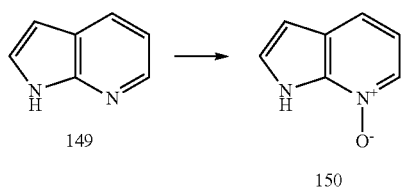 [SMILES: c1cnc2[nH]ccc2c1 ; [O-][n+]1cccc2cc[nH]c21]

To a solution of 1H-pyrrolo[2,3-b]pyridine (149; 20 g, 170 mmol) in $CH_2Cl_2$ (300 mL) was added the suspension of m-CPBA (73 g, 430 mmol) and $CH_2Cl_2$ (20 mL) over 30 min at 0° C. The reaction was warmed to room temperature and stirred for 3 h. TLC plate showed the reaction was completed and the reaction mixture was concentrated. The residue was dissolved in MeOH (200 mL) and saturated aqueous $K_2CO_3$ (100 mL) was added, then stirred for 30 min and filtered, the filtrate was concentrated, the resultant residue was triturated in $CH_2Cl_2/MeOH(10/1)$, filtered, and the solvent was removed. The residue was purified by chromatography on a silica gel column (eluting with $CH_{12}Cl_2/MeOH=10/1$ to 5/1) to give a crude product which was triturated with $Et_2O$ to afford 1H-pyrrolo[2,3-b]pyridine 7-oxide as a yellow solid (150; 9.5 g, purity 80%, yield 35%). MS (ESI) calcd for $C_7H_6N_2O$: 134.14.

Step 2. Synthesis of methyl 6-chloro-1H-pyrrolo[2,3-b]pyridine-1-carboxylate (151)

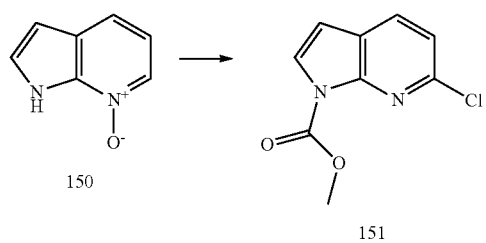

To a solution of 1H-pyrrolo[2,3-b]pyridine 7-oxide (150; 8.9 g, 66 mmol) and hexamethyldisilazane (HMDS) (10.65 mL, 66 mmol) in THF (300 mL) was added $ClCO_2Me$ (15.7 g, 166 mmol) dropwise under $N_2$ atmosphere at room temperature. After stirring for 1 h at the same temperature, the solvent was removed and the residue was dissolved in EtOAc. The EtOAc was washed with saturated aqueous $NaHCO_3$ solution (3×30 mL) and brine, dried over anhydrous $Na_2SO_4$, filtered and concentrated. The crude product was purified by chromatography on a silica gel column (eluting with petroleum ether/ethyl acetate=10/1) to afford methyl 6-chloro-1H-pyrrolo[2,3-b]pyridine-1-carboxylate as a white solid (151; 3.25 g, yield 23%). MS (ESI) calcd for $C_9H_7ClN_2O_2$: 210.67.

Step 3. Synthesis of 6-(3-(trifluoromethyl)phenyl)-1H-pyrrolo[2,3-b]pyridine (152)

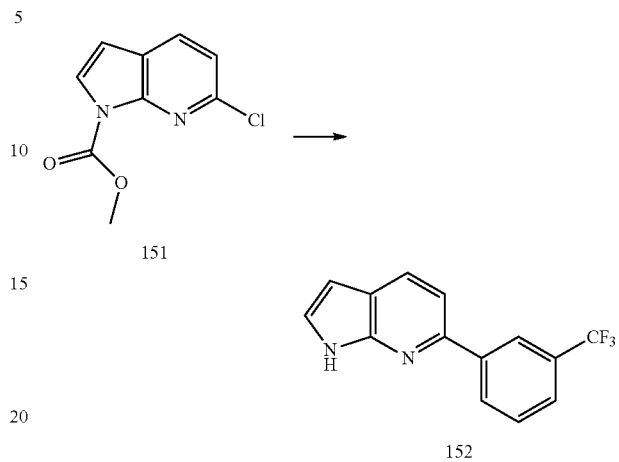

The mixture of methyl 6-chloro-1H-pyrrolo[2,3-b]pyridine-1-carboxylate (151; 3.25 g, 15.5 mmol), (3-(trifluoromethyl)phenyl)boronic acid (5.89 g, 31 mmol), $Pd(dppf)Cl_2$ (1.26 g, 1.55 mmol), $Cs_2CO_3$ (15.11 g, 46.5 mmol) and dioxane/$H_2O$ (10/1, v/v) (50 mL) was stirred at 100° C. for overnight under $N_2$. The solvent was removed and the residue was dissolved in EtOAc (200 mL). The solution was washed with brine and dried over anhydrous $Na_2SO_4$, filtered and concentrated. The residue was purified by chromatography on a silica gel column (eluting with petroleum ether/ethyl acetate=20/1) to afford 6-(3-(trifluoromethyl)phenyl)-1H-pyrrolo[2,3-b]pyridine as a white solid (152; 3.62 g, 89% yield). MS (ESI) calcd for $C_{14}H_9F_3N_2$: 262.23.

This general coupling procedure could be used to prepare a variety of 6-aryl-1H-pyrrolo[2,3-b]pyridine derivatives by substituting the appropriate boronic acid for (3-(trifluoromethyl)phenyl)boronic acid.

Step 4. Synthesis of 6-(3-(trifluoromethyl)phenyl)-2,3-dihydro-1-1H-pyrrolo[2,3-b]pyridine (153)

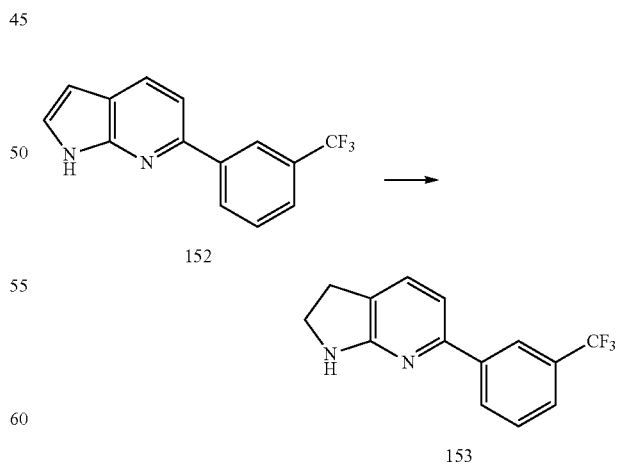

To a stirred solution of 6-(3-(trifluoromethyl)phenyl)-1H-pyrrolo[2,3-b]pyridine (152; 3.62 g, 13.84 mmol) in THF (30 mL) was added borane (13.84 mL, 10 M in $Me_2S$, 138.4 mmol). After 16 h, the solvent was removed and the residue was purified by chromatography on a silica gel column (eluting with petroleum ether/ethyl acetate=10/1) to give the 6-(3-(trifluoromethyl)phenyl)-2,3-dihydro-1H-pyrrolo[2,3-b]pyridine as a yellow solid (153; 886 mg, yield 24%). MS (ESI) calcd for $C_{14}H_{11}F_3N_2$: 264.25.

Step 5. Synthesis of N-(pyridin-2-yl)-6-(3-(trifluoromethyl)phenyl)-2,3-dihydro-1H-pyrrolo[2,3-b]pyridine-1-carboxamide (Compound 861)

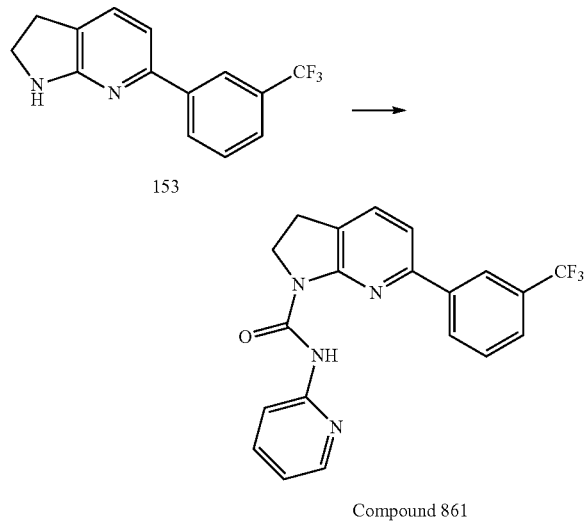

Compound 861

Method A:

To a mixture of 2-aminopyridine (54 mg, 0.19 mmol) in 3 mL of dry THF was added in one-portion triethylamine (0.5 mL) followed by triphosgene (68 mg, 0.23 mmol). The above mixture was stirred at room temperature for 3 hours and 6-(3-(trifluoromethyl)phenyl)-2,3-dihydro-1H-pyrrolo[2,3-b]pyridine (153; 50 mg, 0.19 mmol) was added to the reaction mixture and stirred for an additional 18 hours at 60° C. Water was added to the reaction mixture and the aqueous portion extracted with dichloromethane (3×15 mL). The combined organics were washed with aqueous $NaHCO_3$ solution and brine, dried with anhydrous sodium sulfate and concentrated. The crude product was purified by preparative TLC to afford 4-methyl-N-(pyridin-2-yl)-7-(3-(trifluoromethyl)phenyl)-3,4-dihydro-1,8-naphthyridine-1(2H)-carboxamide (Compound 861) as white solid. MS (ESI) calcd for $C_{22}H_{19}F_3N_4O$: 412.15. found: 413 [M+H].

Preparation of 6-(2-oxa-6-azaspiro[3.3]heptan-6-yl)pyridin-2-amine (160)

Step 1. Synthesis of 6-tosyl-2-oxa-6-azaspiro[3.3]heptane (155)

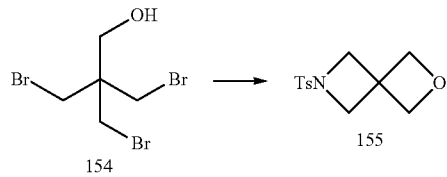 [SMILES: OCC(CBr)(CBr)CBr ; Cc1ccc(S(=O)(=O)N2CC3(COC3)C2)cc1]

To a solution of KOH (33.2 g, 0.59 mol) and p-tosylamide (37.9 g, 0.22 mol) in 600 ml ethanol, 3-Bromo-2,2-bis(bromomethyl)propan-1-ol (154; 60.1 g, 0.19 mol) was added at room temperature and the reaction mixture was heated to reflux for 90 h. The solvent was removed by evaporation, 500 ml 1M KOH was added and the white suspension was left to stir for another 2 hours at room temperature. The mixture was filtered and the white filter cake was rinsed with water until the washing water was neutral. The filter cake was dried under high vacuum to give 6-tosyl-2-oxa-6-azaspiro[3.3]heptane (155; 30.55 g of product containing 10 mol % of tosylamide as a white solid). The overall yield of pure 6-tosyl-2-oxa-6-azaspiro[3.3]heptane was calculated to be (155; 27.4 g, 58%). MS (ESI) calcd for $C_{12}H_{15}NO_3S$ 253.3.

Step 2. Synthesis of 2-oxa-6-azaspiro[3.3]heptane oxalate (156)

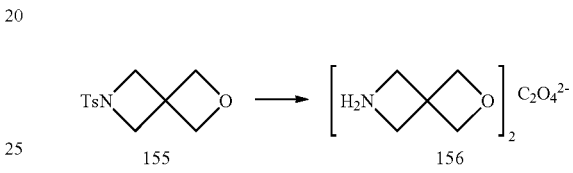

6-tosyl-2-oxa-6-azaspiro[3.3]heptanes (155; 7.30 g, 28.8 mol) and magnesium (4.9 g, 0.2 mol) were sonicated for one hour in methanol (500 ml). Almost all solvent was removed from the grey reaction mixture on a rotary evaporator to give a viscous grey residue. Diethyl ether (500 ml) and sodium sulfate (15.0 g) were added and the resulting light grey mixture was stirred vigorously for 30 min before filtration. The filtrate was dried over anhydrous sodium sulfate and anhydrous oxalic acid (1.3 g, 14.4 mol) dissolved in ethanol (~1 ml) was added to the organic phase. A thick white precipitate formed instantly. It was filtered off and dried under vacuum to give 2-oxa-6-azaspiro[3.3]heptane oxalate (156; 3.37 g, 81%) as amorphous white solid. MS (ESI) calcd for $C_{10}H_{20}N_2O_2$—$C_4O_8$ 376.28.

Step 3. Synthesis of ethyl 6-(2-oxa-6-azaspiro[3.3]heptan-6-yl)picolinate (157)

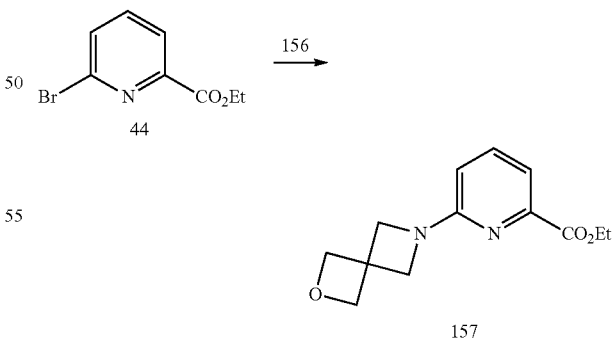

2-oxa-6-azaspiro[3.3]heptane oxalate (156; 20 g, 0.23 mol), ethyl 6-bromopicolinate (44; 56.9 g, 0.25 mol) and $K_2CO_3$ (62 g, 0.454 mol) were dissolved in DMSO (100 ml). The suspension was heated to 140° C. After cooling to room temperature, the reaction was poured into water and extracted with methylene chloride. The organic layer was evaporated to dryness and product was purified on a gel silica to afford ethyl 6-(2-oxa-6-azaspiro[3.3]heptan-6-yl)picolinate (157; 7.2 g, 30%). MS (ESI) calcd for $C_{13}H_{16}N_2O_3$ 248.1.

Step 4. Synthesis of 6-(2-oxa-6-azaspiro[3.3]heptan-6-yl)picolinic acid (158)

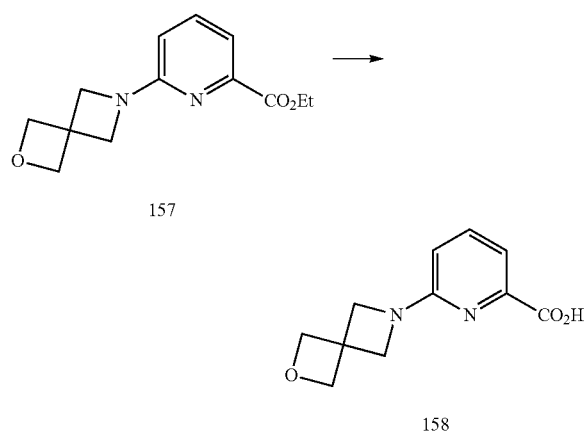

Ethyl 6-(2-oxa-6-azaspiro[3.3]heptan-6-yl)picolinate (157; 7.2 g, 0.03 mol) was dissolved in dioxane (50 ml), and NaOH (2.3 g, 0.06 mol) in water (50 ml) was added. The suspension was stirred at 50° C. for about 2 h. The solvent was removed and water (50 ml) was added. The pH was adjusted 5 to afford 6-(2-oxa-6-azaspiro[3.3]heptan-6-yl)picolinic acid (158; 4.5 g, 70%). MS (ESI) calcd for $C_{11}H_{12}N_2O_3$ 220.1. found 221.2 [M+H].

Step 5. Synthesis of tert-butyl (6-(2-oxa-6-azaspiro[3.3]heptan-6-yl)pyridin-2-yl)carbamate (159)

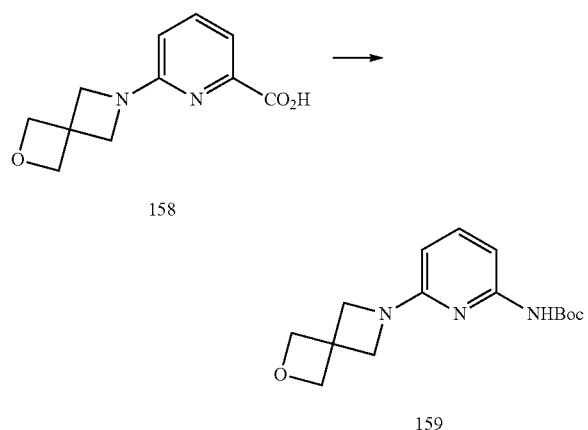

To a solution of 6-(2-oxa-6-azaspiro[3.3]heptan-6-yl)picolinic acid (158; 4.4 g, 0.02 mol) in t-BuOH (50 ml) was added $Et_3N$ (2.4 g, 0.02 mol) and diphenylphosphoryl azide (DPPA) (6.6 g, 0.024 mol). The mixture was refluxed overnight. After cooling to room temperature, the solvent was evaporated and crude product was purified column chromatography to afford tert-butyl (6-(2-oxa-6-azaspiro [3.3]heptan-6-yl)pyridin-2-yl)carbamate (159; 4 g, 70%). MS (ESI) calcd for $C_{15}H_{21}N_3O_3$ 291.35.

Step 6. Synthesis of 6-(2-oxa-6-azaspiro[3.3]heptan-6-yl)pyridin-2-amine (160)

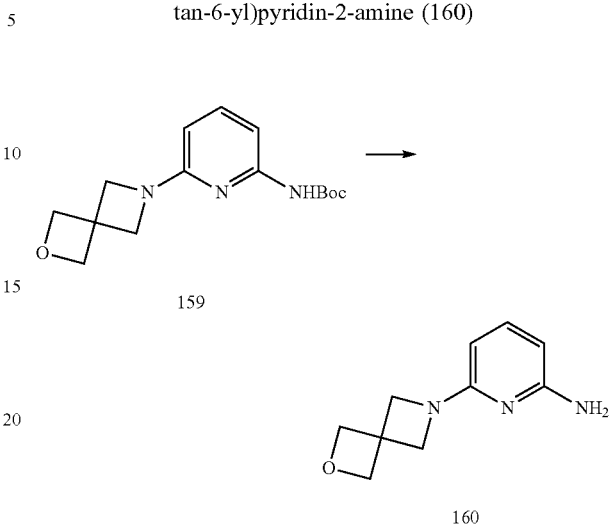

To a solution of tert-butyl (6-(2-oxa-6-azaspiro[3.3]heptan-6-yl)pyridin-2-yl)carbamate (159; 4.4 g, 0.015 mol) in $CH_2Cl_2$ (50 ml) was added $CF_3COOH$ (20 ml). The mixture was stirred at room temperature for about 4 hours. The solvent was removed and $CH_3CN$ (50 ml) was added.

The pH was adjusted to 7. After evaporating the volatiles, 6-(2-oxa-6-azaspiro[3.3]heptan-6-yl)pyridin-2-amine was as obtained by purification on a silica gel column. (160; 2.05 g, 70%). MS (ESI) calcd for $C_{10}H_{13}N_3O$ 191.1. found 192.2 [M+H].

Example 40

Biological Activity

A mass spectrometry based assay was used to identify modulators of SIRT1 activity. The mass spectrometry based assay utilizes a peptide having 20 amino acid residues as follows: Ac-EE-K(biotin)-GQSTSSHSK(Ac)NleSTEG-K (5TMR)-EE-NH2 (SEQ ID NO: 1) wherein K(Ac) is an acetylated lysine residue and Nle is a norleucine. The peptide is labeled with the fluorophore 5TMR (excitation 540 nm/emission 580 nm) at the C-terminus. The sequence of the peptide substrate is based on p53 with several modifications. In addition, the methionine residue naturally present in the sequence was replaced with the norleucine because the methionine may be susceptible to oxidation during synthesis and purification.

The mass spectrometry assay is conducted as follows: 0.5 M peptide substrate and 120 μM βNAD$^+$ is incubated with 10 nM SIRT1 for 25 minutes at 25° C. in a reaction buffer (50 mM Tris-acetate pH 8, 137 mM NaCl, 2.7 mM KCl, 1 mM $MgCl_2$, 5 mM DTT, 0.05% BSA). Test compounds may be added to the reaction as described above. The SirT1 gene is cloned into a T7-promoter containing vector and transformed into BL21(DE3). After the 25 minute incubation with SIRT1, 10 μL of 10% formic acid is added to stop the reaction. Reactions are sealed and frozen for later mass spec analysis. Determination of the mass of the substrate peptide allows for precise determination of the degree of acetylation (i.e. starting material) as compared to deacetylated peptide (product).

A control for inhibition of sirtuin activity is conducted by adding 1 µL of 500 mM nicotinamide as a negative control at the start of the reaction (e.g., permits determination of maximum sirtuin inhibition). A control for activation of sirtuin activity is conducted using 10 nM of sirtuin protein, with 1 µL of DMSO in place of compound, to determine the amount of deacetylation of the substrate at a given timepoint within the linear range of the assay. This timepoint is the same as that used for test compounds and, within the linear range, the endpoint represents a change in velocity.

For the above assay, SIRT1 protein was expressed and purified as follows. The SirT1 gene was cloned into a T7-promoter containing vector and transformed into BL21 (DE3). The protein was expressed by induction with 1 mM IPTG as an N-terminal His-tag fusion protein at 18° C. overnight and harvested at 30,000×g. Cells were lysed with lysozyme in lysis buffer (50 mM Tris-HCl, 2 mM Tris[2-carboxyethyl]phosphine (TCEP), 10 µM $ZnCl_2$, 200 mM NaCl) and further treated with sonication for 10 min for complete lysis. The protein was purified over a Ni-NTA column (Amersham) and fractions containing pure protein were pooled, concentrated and run over a sizing column (Sephadex S200 26/60 global). The peak containing soluble protein was collected and run on an Ion-exchange column (MonoQ). Gradient elution (200 mM-500 mM NaCl) yielded pure protein. This protein was concentrated and dialyzed against dialysis buffer (20 mM Tris-HCl, 2 mM TCEP) overnight. The protein was aliquoted and frozen at −80° C. until further use.

The $EC_{1.5}$ values for the activating compounds of Formula (I) are represented by A ($EC_{1.5}$<1.0 µM), B ($EC_{1.5}$ 1-25 µM), C ($EC_{1.5}$>25 µM). The percent maximum fold activation is represented by A (Fold activation>200%) or B (Fold Activation≤200%). The $IC_{50}$ values for the activating compounds of Formula (I) are represented by A ($IC_{50}$<20 µM) or B ($IC_{50}$≥20 M) "NT" means not tested; "ND" means not determinable. (*Note that numbers in parenthesis refer to numbering of compounds in U.S. Provisional Application No. 61/256,269 to which this application claims priority.)

TABLE 1

Compounds of Formula (I).

| Compound No. | [M + H]+ | STRUCTURE | $EC_{1.5}$ µM | % FOLD ACT. | TNF $IC_{50}$ µM |
|---|---|---|---|---|---|
| 500 (405) | 407 | 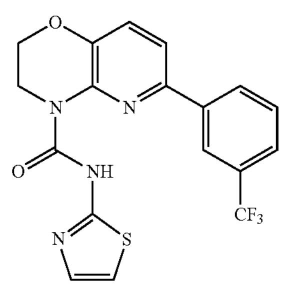 [SMILES: O=C(Nc1nccs1)N1CCOc2ccc(-c3cccc(C(F)(F)F)c3)nc21] | A | A | NT |
| 501 (402) | 401 | 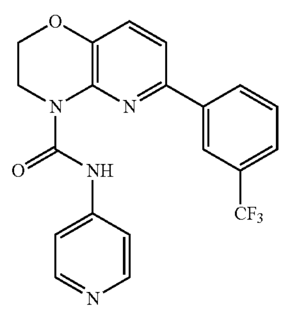 [SMILES: O=C(Nc1ccncc1)N1CCOc2ccc(-c3cccc(C(F)(F)F)c3)nc21] | A | A | A |
| 502 (403) | 401 | 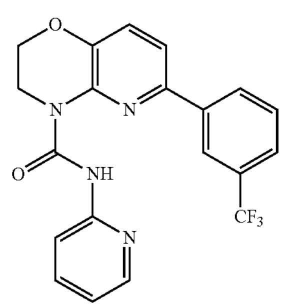 [SMILES: O=C(Nc1ccccn1)N1CCOc2ccc(-c3cccc(C(F)(F)F)c3)nc21] | A | A | B |

TABLE 1-continued

Compounds of Formula (I).

| Compound No. | [M + H]+ | STRUCTURE | EC1.5 µM | % FOLD ACT. | TNF IC50 µM |
|---|---|---|---|---|---|
| 503 (404) | 402 | 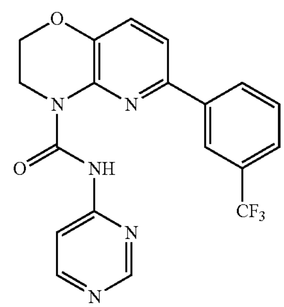 [SMILES: O=C(Nc1ccncn1)N1CCOc2ccc(-c3cccc(C(F)(F)F)c3)nc21] | A | A | B |
| 504 (407) | 430 | 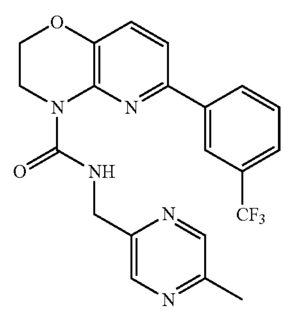 [SMILES: Cc1cnc(CNC(=O)N2CCOc3ccc(-c4cccc(C(F)(F)F)c4)nc32)cn1] | C | B | NT |
| 505 (414) | 491 | 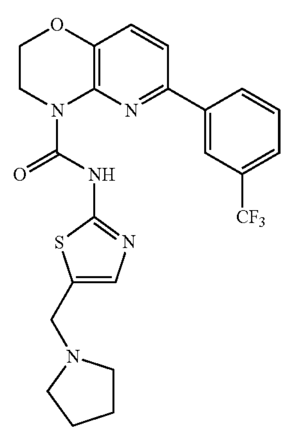 [SMILES: O=C(Nc1ncc(CN2CCCC2)s1)N1CCOc2ccc(-c3cccc(C(F)(F)F)c3)nc21] | C | B | NT |
| 506 (413) | 486 | 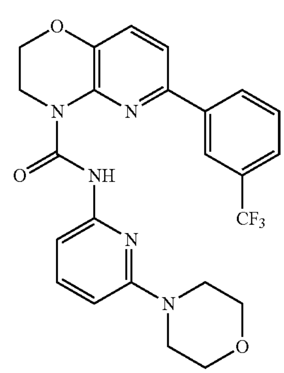 [SMILES: O=C(Nc1cccc(N2CCOCC2)n1)N1CCOc2ccc(-c3cccc(C(F)(F)F)c3)nc21] | A | A | B |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 507 (415) | 500 | 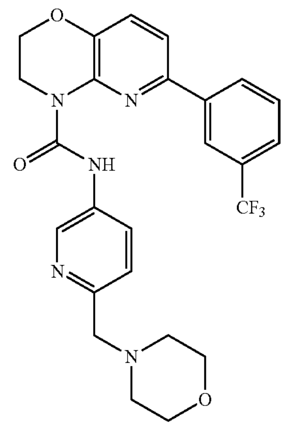 [SMILES: O=C(Nc1ccc(CN2CCOCC2)nc1)N1CCOc2ccc(-c3cccc(C(F)(F)F)c3)nc21] | A | A | NT |
| 508 (411) | 470 | 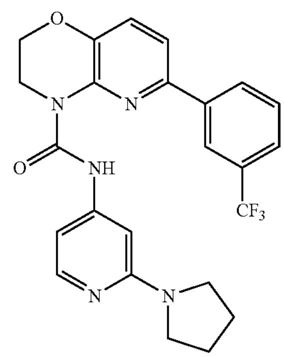 [SMILES: O=C(Nc1ccnc(N2CCCC2)c1)N1CCOc2ccc(-c3cccc(C(F)(F)F)c3)nc21] | A | A | B |
| 509 (406) | 419 | 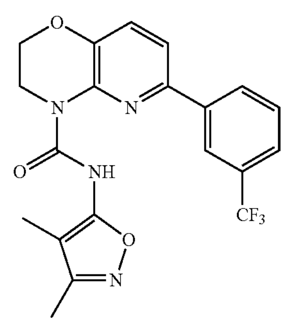 [SMILES: Cc1noc(NC(=O)N2CCOc3ccc(-c4cccc(C(F)(F)F)c4)nc32)c1C] | B | A | NT |
| 510 (416) | 500 | 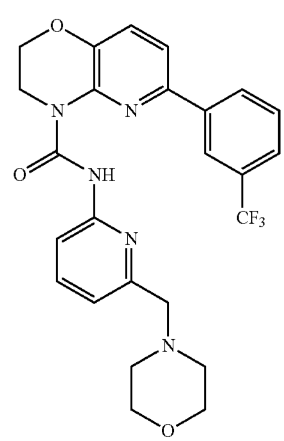 [SMILES: O=C(Nc1cccc(CN2CCOCC2)n1)N1CCOc2ccc(-c3cccc(C(F)(F)F)c3)nc21] | A | A | B |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 511 (408) | 429 | 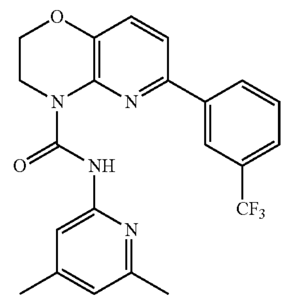 [SMILES: Cc1cc(C)nc(NC(=O)N2CCOc3ccc(-c4cccc(C(F)(F)F)c4)nc32)c1] | A | A | B |
| 512 (409) | 456 | 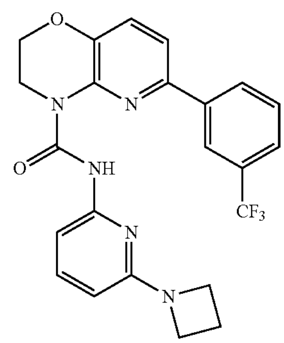 [SMILES: O=C(Nc1cccc(N2CCC2)n1)N1CCOc2ccc(-c3cccc(C(F)(F)F)c3)nc21] | B | A | NT |
| 513 (410) | 456 | 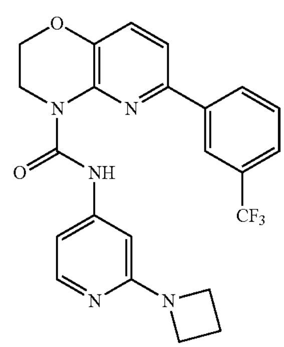 [SMILES: O=C(Nc1ccnc(N2CCC2)c1)N1CCOc2ccc(-c3cccc(C(F)(F)F)c3)nc21] | A | A | B |
| 514 (417) | 352 | 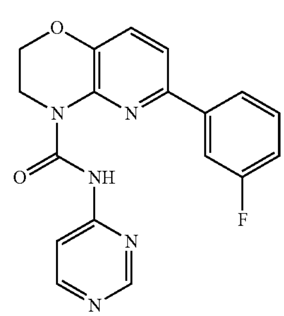 [SMILES: O=C(Nc1ccncn1)N1CCOc2ccc(-c3cccc(F)c3)nc21] | A | A | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 515 (419) | 364 | 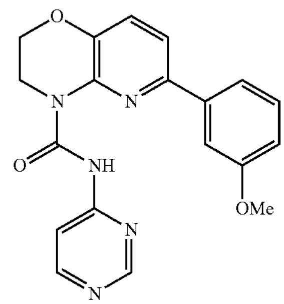 [SMILES: COc1cccc(-c2ccc3c(n2)N(C(=O)Nc2ccncn2)CCO3)c1] | B | A | NT |
| 516 (420) | 335 | 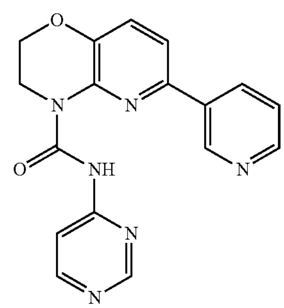 [SMILES: O=C(Nc1ccncn1)N1CCOc2ccc(-c3cccnc3)nc21] | C | B | NT |
| 517 (421) | 348 | 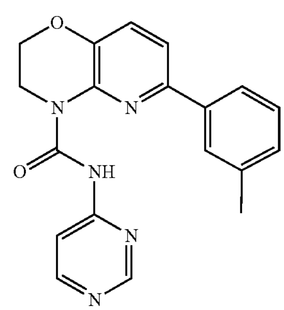 [SMILES: Cc1cccc(-c2ccc3c(n2)N(C(=O)Nc2ccncn2)CCO3)c1] | A | A | NT |
| 518 (412) | 476 | 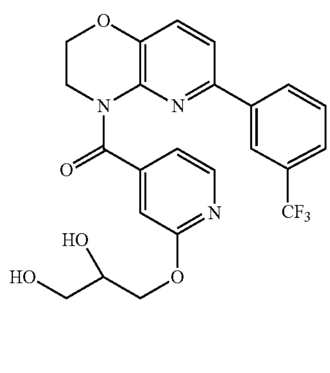 [SMILES: O=C(c1ccnc(OCC(O)CO)c1)N1CCOc2ccc(-c3cccc(C(F)(F)F)c3)nc21] | B | B | NT |

TABLE 1-continued

Compounds of Formula (I).

| Compound No. | [M + H]+ | STRUCTURE | EC1.5 µM | % FOLD ACT. | TNF IC50 µM |
|---|---|---|---|---|---|
| 519 (418) | 406 | 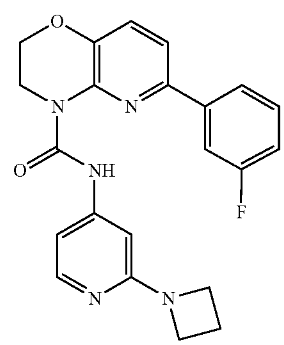 [SMILES: O=C(Nc1ccnc(N2CCC2)c1)N1CCOc2ccc(-c3cccc(F)c3)nc21] | A | A | A |
| 520 (422) | 434 | 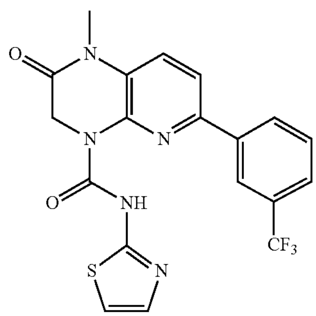 [SMILES: CN1C(=O)CN(C(=O)Nc2nccs2)c2nc(-c3cccc(C(F)(F)F)c3)ccc21] | B | B | NT |
| 521 (423) | 448 | 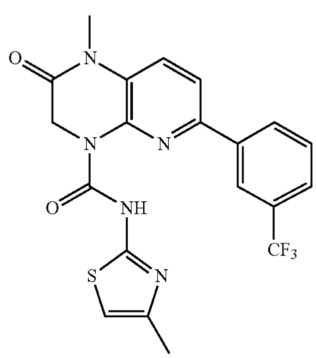 [SMILES: Cc1csc(NC(=O)N2CC(=O)N(C)c3ccc(-c4cccc(C(F)(F)F)c4)nc32)n1] | B | B | NT |
| 522 (424) | 435 | 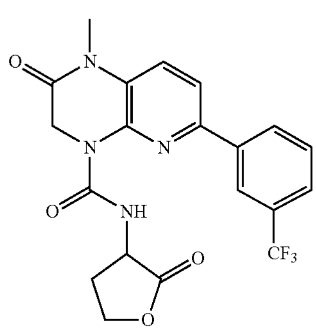 [SMILES: CN1C(=O)CN(C(=O)NC2CCOC2=O)c2nc(-c3cccc(C(F)(F)F)c3)ccc21] | C | B | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 523 (425) | 418 | 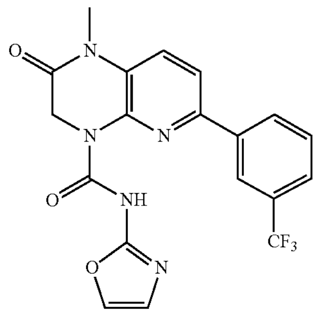 [SMILES: CN1C(=O)CN(C(=O)Nc2ncco2)c2nc(-c3cccc(C(F)(F)F)c3)ccc21] | C | B | NT |
| 524 (426) | 418 | 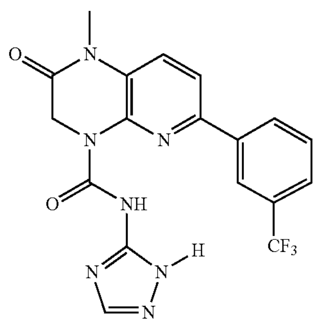 [SMILES: CN1C(=O)CN(C(=O)Nc2ncn[nH]2)c2nc(-c3cccc(C(F)(F)F)c3)ccc21] | C | B | NT |
| 525 (427) | 428 | 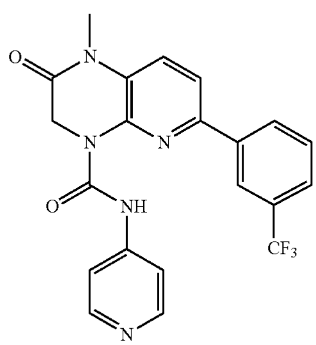 [SMILES: CN1C(=O)CN(C(=O)Nc2ccncc2)c2nc(-c3cccc(C(F)(F)F)c3)ccc21] | B | A | NT |
| 526 (428) | 429 | 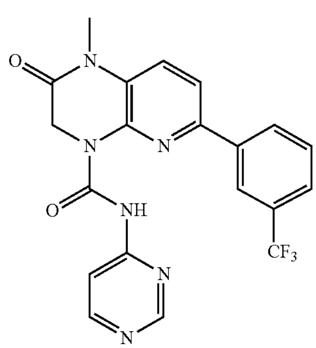 [SMILES: CN1C(=O)CN(C(=O)Nc2ccncn2)c2nc(-c3cccc(C(F)(F)F)c3)ccc21] | B | A | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 527 (429) | 429 | 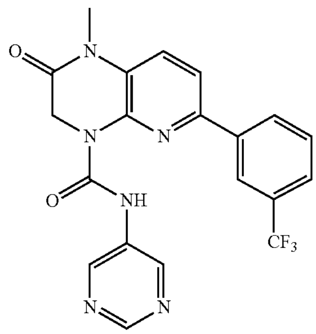 [SMILES: CN1C(=O)CN(C(=O)Nc2cncnc2)c2nc(-c3cccc(C(F)(F)F)c3)ccc21] | B | B | NT |
| 528 (430) | 429 | 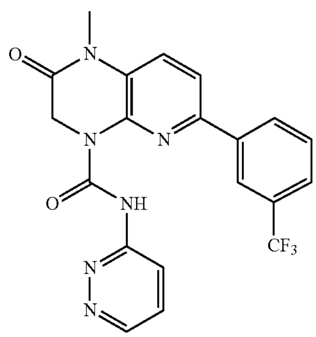 [SMILES: CN1C(=O)CN(C(=O)Nc2cccnn2)c2nc(-c3cccc(C(F)(F)F)c3)ccc21] | C | B | NT |
| 529 (431) | 420 | 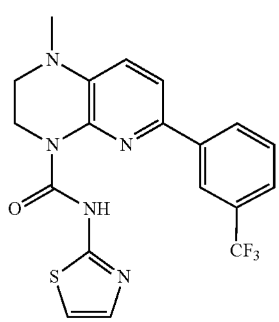 [SMILES: CN1CCN(C(=O)Nc2nccs2)c2nc(-c3cccc(C(F)(F)F)c3)ccc21] | A | A | NT |
| 530 (432) | 434 | 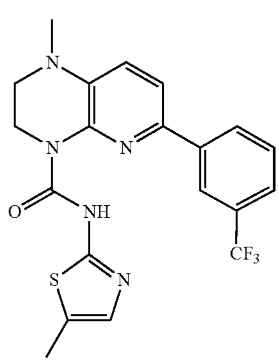 [SMILES: Cc1cnc(NC(=O)N2CCN(C)c3ccc(-c4cccc(C(F)(F)F)c4)nc32)s1] | B | B | NT |

TABLE 1-continued
Compounds of Formula (I).
| Compound No. | [M + H]+ | STRUCTURE | EC1.5 µM | % FOLD ACT. | TNF IC50 µM |
|---|---|---|---|---|---|
| 531 (433) | 414 | 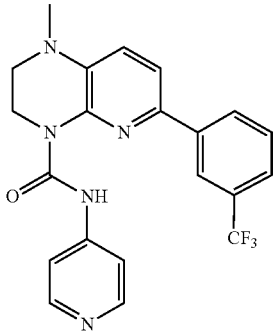 [SMILES: CN1CCN(C(=O)Nc2ccncc2)c2nc(-c3cccc(C(F)(F)F)c3)ccc21] | A | A | A |
| 532 (434) | 442 | 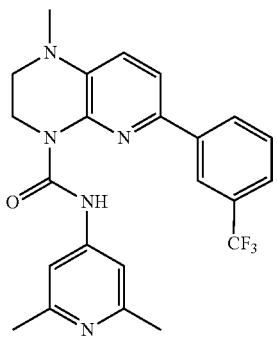 [SMILES: Cc1cc(NC(=O)N2CCN(C)c3ccc(-c4cccc(C(F)(F)F)c4)nc32)cc(C)n1] | B | B | B |
| 533 (435) | 434 | 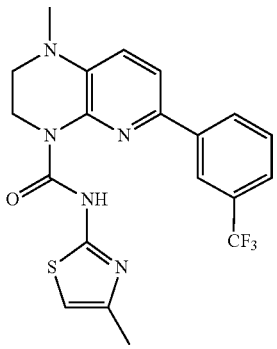 [SMILES: Cc1csc(NC(=O)N2CCN(C)c3ccc(-c4cccc(C(F)(F)F)c4)nc32)n1] | A | A | B |
| 534 (436) | 442 | 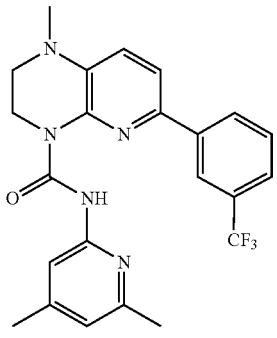 [SMILES: Cc1cc(C)nc(NC(=O)N2CCN(C)c3ccc(-c4cccc(C(F)(F)F)c4)nc32)c1] | A | B | B |

TABLE 1-continued

Compounds of Formula (I).

| Compound No. | [M + H]+ | STRUCTURE | EC1.5 µM | % FOLD ACT. | TNF IC50 µM |
|---|---|---|---|---|---|
| 535 (437) | 415 | 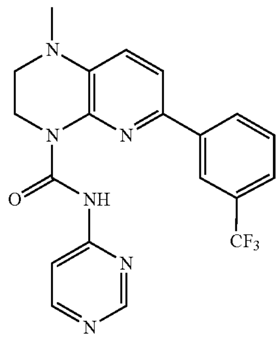 [SMILES: CN1CCN(C(=O)Nc2ccncn2)c2nc(-c3cccc(C(F)(F)F)c3)ccc21] | A | A | B |
| 536 (438) | 415 | 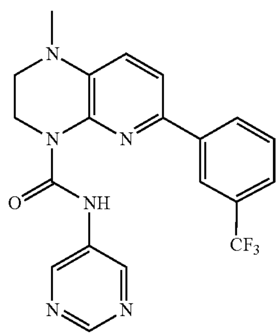 [SMILES: CN1CCN(C(=O)Nc2cncnc2)c2nc(-c3cccc(C(F)(F)F)c3)ccc21] | A | A | NT |
| 537 (439) | 415 | 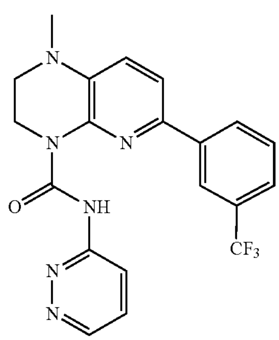 [SMILES: CN1CCN(C(=O)Nc2cccnn2)c2nc(-c3cccc(C(F)(F)F)c3)ccc21] | A | A | B |
| 538 (440) | 469 | 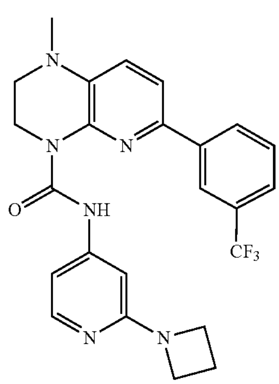 [SMILES: CN1CCN(C(=O)Nc2ccnc(N3CCC3)c2)c2nc(-c3cccc(C(F)(F)F)c3)ccc21] | A | A | A |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 539 (441) | 514 | 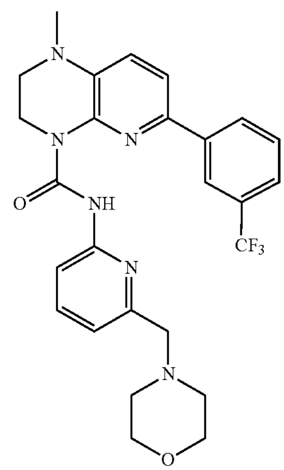 [SMILES: CN1CCN(C(=O)Nc2cccc(CN3CCOCC3)n2)c2nc(-c3cccc(C(F)(F)F)c3)ccc21] | A | A | A |
| 540 (442) | 421 | 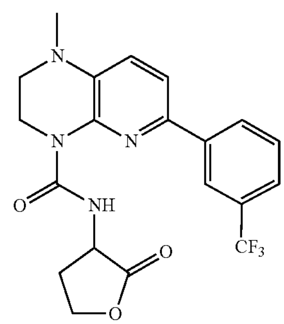 [SMILES: CN1CCN(C(=O)NC2CCOC2=O)c2nc(-c3cccc(C(F)(F)F)c3)ccc21] | C | B | NT |
| 541 (460) | 368 | 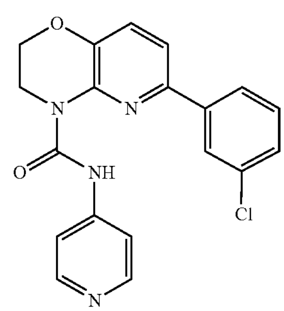 [SMILES: O=C(Nc1ccncc1)N1CCOc2ccc(-c3cccc(Cl)c3)nc21] | A | A | NT |
| 542 (461) | 351 | 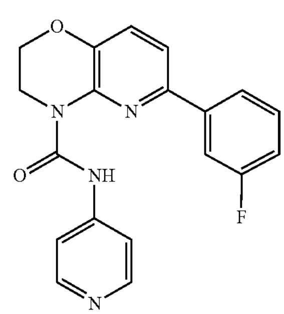 [SMILES: O=C(Nc1ccncc1)N1CCOc2ccc(-c3cccc(F)c3)nc21] | B | A | NT |

TABLE 1-continued

Compounds of Formula (I).

| Compound No. | [M + H]+ | STRUCTURE | EC1.5 µM | % FOLD ACT. | TNF IC50 µM |
|---|---|---|---|---|---|
| 543 (462) | 351 | 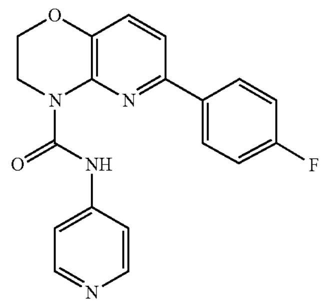 [SMILES: O=C(Nc1ccncc1)N1CCOc2ccc(-c3ccc(F)cc3)nc21] | ND | ND | NT |
| 544 (463) | 351 | 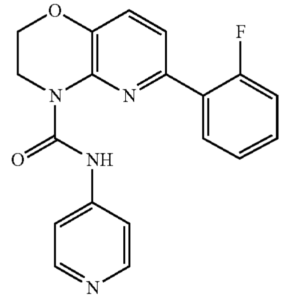 [SMILES: O=C(Nc1ccncc1)N1CCOc2ccc(-c3ccccc3F)nc21] | B | A | NT |
| 545 (464) | 401 | 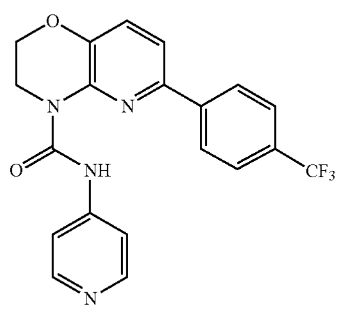 [SMILES: O=C(Nc1ccncc1)N1CCOc2ccc(-c3ccc(C(F)(F)F)cc3)nc21] | ND | ND | NT |
| 546 (465) | 401 | 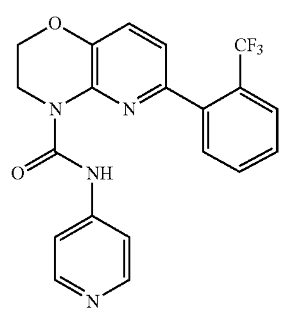 [SMILES: O=C(Nc1ccncc1)N1CCOc2ccc(-c3ccccc3C(F)(F)F)nc21] | B | A | NT |
| 547 (467) | 419 | 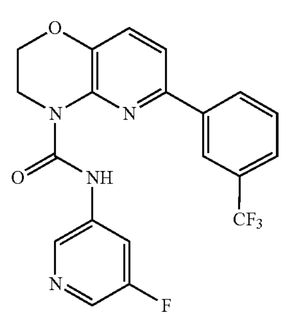 [SMILES: O=C(Nc1cncc(F)c1)N1CCOc2ccc(-c3cccc(C(F)(F)F)c3)nc21] | A | A | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 548 (473) | 415 | 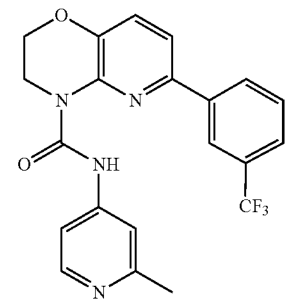 [SMILES: Cc1cc(NC(=O)N2CCOc3ccc(-c4cccc(C(F)(F)F)c4)nc32)ccn1] | A | A | B |
| 549 (475) | 419 | 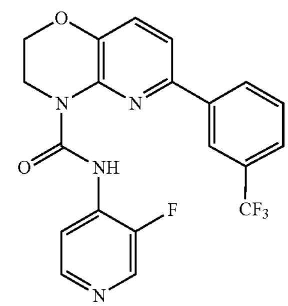 [SMILES: O=C(Nc1ccncc1F)N1CCOc2ccc(-c3cccc(C(F)(F)F)c3)nc21] | A | A | B |
| 550 (489) | 365 | 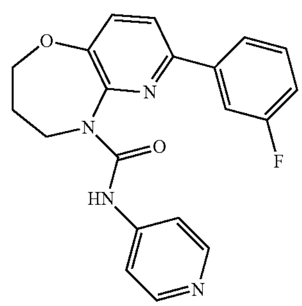 [SMILES: O=C(Nc1ccncc1)N1CCCOc2ccc(-c3cccc(F)c3)nc21] | B | A | NT |
| 551 (466) | 415 | 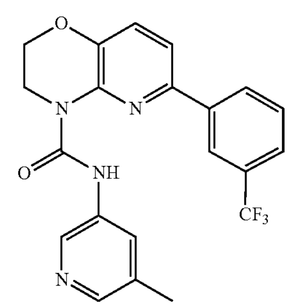 [SMILES: Cc1cncc(NC(=O)N2CCOc3ccc(-c4cccc(C(F)(F)F)c4)nc32)c1] | A | A | B |
| 552 (468) | 429 | 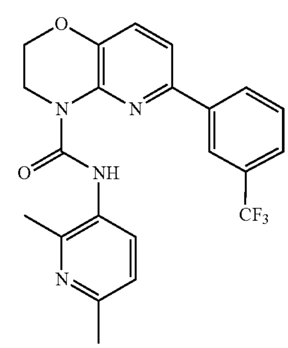 [SMILES: Cc1ccc(NC(=O)N2CCOc3ccc(-c4cccc(C(F)(F)F)c4)nc32)c(C)n1] | B | A | NT |

TABLE 1-continued
Compounds of Formula (I).
| Compound No. | [M + H]+ | STRUCTURE | EC1.5 μM | % FOLD ACT. | TNF IC50 μM |
|---|---|---|---|---|---|
| 553 (469) | 429 | 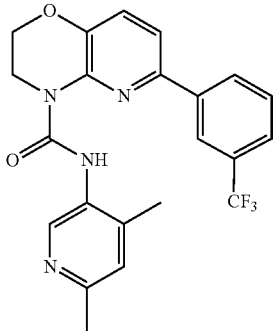 [SMILES: Cc1cc(C)c(NC(=O)N2CCOc3ccc(-c4cccc(C(F)(F)F)c4)nc32)cn1] | B | B | NT |
| 554 (470) | 415 | 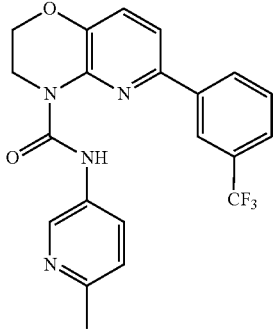 [SMILES: Cc1ccc(NC(=O)N2CCOc3ccc(-c4cccc(C(F)(F)F)c4)nc32)cn1] | A | A | NT |
| 555 (472) | 415 | 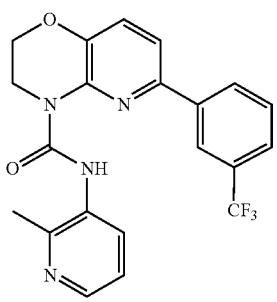 [SMILES: Cc1ncccc1NC(=O)N1CCOc2ccc(-c3cccc(C(F)(F)F)c3)nc21] | B | B | NT |
| 556 (474) | 429 | 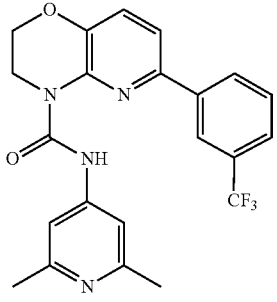 [SMILES: Cc1cc(NC(=O)N2CCOc3ccc(-c4cccc(C(F)(F)F)c4)nc32)cc(C)n1] | A | A | A |

TABLE 1-continued

Compounds of Formula (I).

| Compound No. | [M + H]+ | STRUCTURE | EC1.5 µM | % FOLD ACT. | TNF IC50 µM |
|---|---|---|---|---|---|
| 557 (485) | 418 | 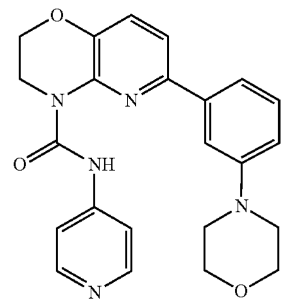 [SMILES: O=C(Nc1ccncc1)N1CCOc2ccc(-c3cccc(N4CCOCC4)c3)nc21] | A | A | B |
| 558 (488) | 415 | 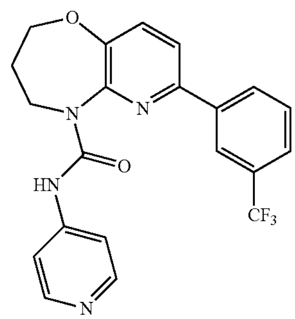 [SMILES: O=C(Nc1ccncc1)N1CCCOc2ccc(-c3cccc(C(F)(F)F)c3)nc21] | B | A | NT |
| 559 (484) | 402 | 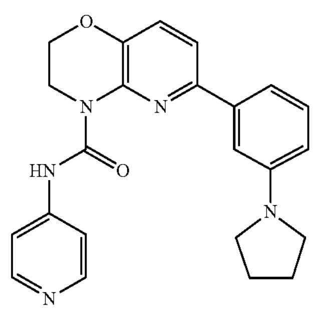 [SMILES: O=C(Nc1ccncc1)N1CCOc2ccc(-c3cccc(N4CCCC4)c3)nc21] | A | A | A |
| 560 (486) | 429 | 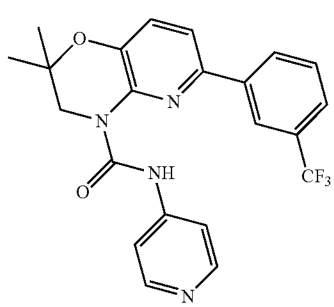 [SMILES: CC1(C)CN(C(=O)Nc2ccncc2)c2nc(-c3cccc(C(F)(F)F)c3)ccc2O1] | A | A | B |
| 561 (487) | 379 | 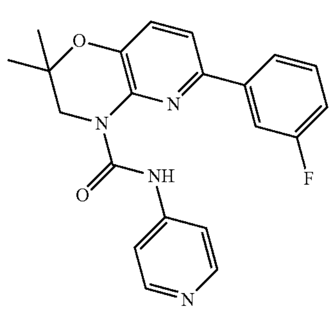 [SMILES: CC1(C)CN(C(=O)Nc2ccncc2)c2nc(-c3cccc(F)c3)ccc2O1] | B | A | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 562 (492) | 402 | 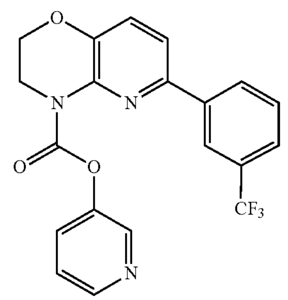 [SMILES: O=C(Oc1cccnc1)N1CCOc2ccc(-c3cccc(C(F)(F)F)c3)nc21] | C | B | NT |
| 563 (458) | 513 | 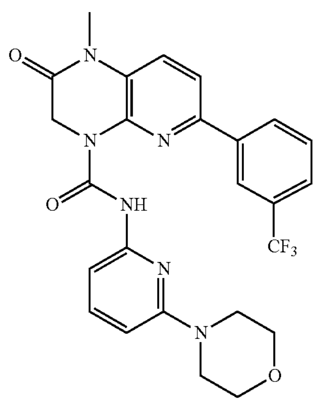 [SMILES: CN1C(=O)CN(C(=O)Nc2cccc(N3CCOCC3)n2)c2nc(-c3cccc(C(F)(F)F)c3)ccc21] | A | A | C |
| 564 (476) | 415 | 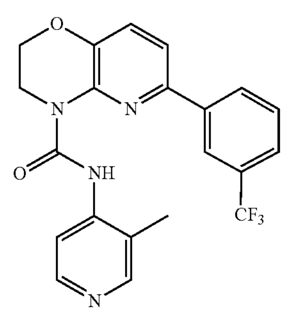 | B | B | NT |
| 565 (477) | 469 | 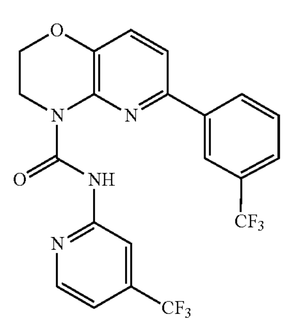 [SMILES: O=C(Nc1cc(C(F)(F)F)ccn1)N1CCOc2ccc(-c3cccc(C(F)(F)F)c3)nc21] | B | B | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 566 (478) | 419 | 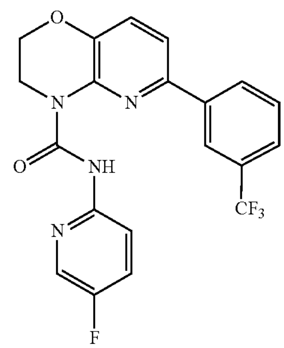 [SMILES: O=C(Nc1ccc(F)cn1)N1CCOc2ccc(-c3cccc(C(F)(F)F)c3)nc21] | A | A | B |
| 567 (479) | 437 | 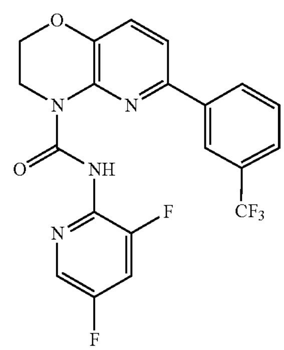 [SMILES: O=C(Nc1ncc(F)cc1F)N1CCOc2ccc(-c3cccc(C(F)(F)F)c3)nc21] | B | A | NT |
| 568 (480) | 419 | 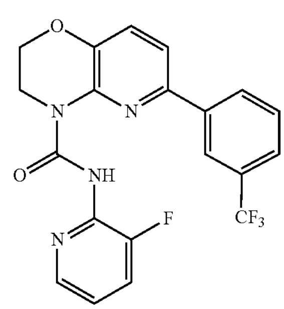 [SMILES: O=C(Nc1ncccc1F)N1CCOc2ccc(-c3cccc(C(F)(F)F)c3)nc21] | B | A | NT |
| 569 (481) | 415 | 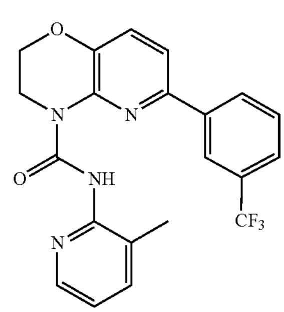 [SMILES: Cc1cccnc1NC(=O)N1CCOc2ccc(-c3cccc(C(F)(F)F)c3)nc21] | C | B | NT |

TABLE 1-continued
Compounds of Formula (I).
| Compound No. | [M + H]+ | STRUCTURE | EC1.5 μM | % FOLD ACT. | TNF IC50 μM |
|---|---|---|---|---|---|
| 570 (482) | 491 | 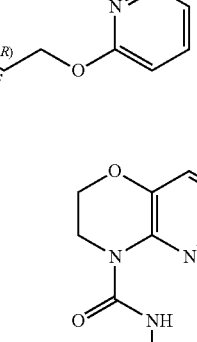 | A | A | A |
| 571 (483) | 491 | 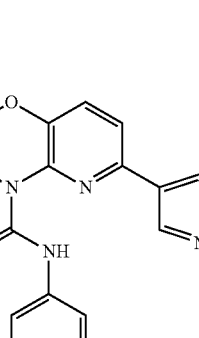 | A | A | A |
| 572 | 379 | 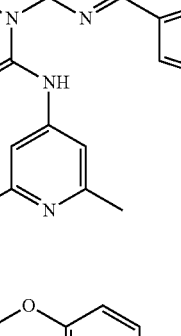 | B | A | NT |
| 573 | 380 | 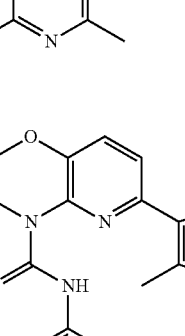 | B | A | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 574 | 403 | 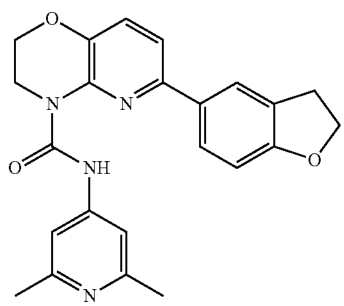 [SMILES: Cc1cc(NC(=O)N2CCOc3ccc(-c4ccc5c(c4)CCO5)nc32)cc(C)n1] | A | A | B |
| 575 | 365 | 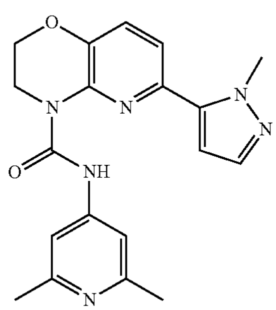 [SMILES: Cc1cc(NC(=O)N2CCOc3ccc(-c4ccnn4C)nc32)cc(C)n1] | B | A | NT |
| 576 | 429 | 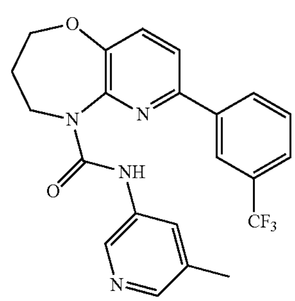 [SMILES: Cc1cncc(NC(=O)N2CCCOc3ccc(-c4cccc(C(F)(F)F)c4)nc32)c1] | B | A | NT |
| 577 | 429 | 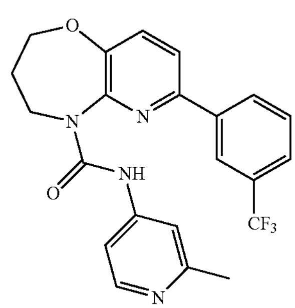 [SMILES: Cc1cc(NC(=O)N2CCCOc3ccc(-c4cccc(C(F)(F)F)c4)nc32)ccn1] | B | A | NT |
| 578 | 435 | 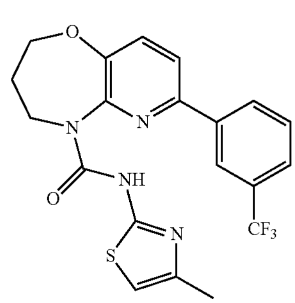 [SMILES: Cc1csc(NC(=O)N2CCCOc3ccc(-c4cccc(C(F)(F)F)c4)nc32)n1] | A | A | B |

TABLE 1-continued

Compounds of Formula (I).

| Compound No. | [M + H]+ | STRUCTURE | EC1.5 µM | % FOLD ACT. | TNF IC50 µM |
|---|---|---|---|---|---|
| 579 | 470 | 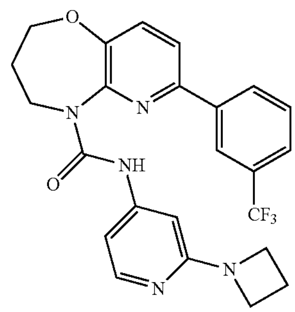 [SMILES: O=C(Nc1ccnc(N2CCC2)c1)N1CCCOc2ccc(-c3cccc(C(F)(F)F)c3)nc21] | A | A | NT |
| 580 | 366 | 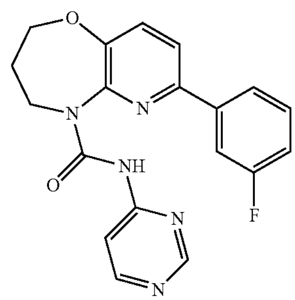 [SMILES: O=C(Nc1ccncn1)N1CCCOc2ccc(-c3cccc(F)c3)nc21] | B | A | NT |
| 581 | 379 | 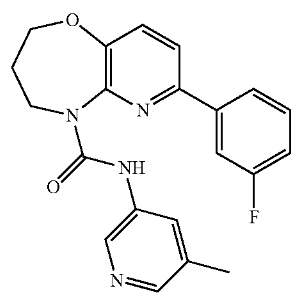 [SMILES: Cc1cncc(NC(=O)N2CCCOc3ccc(-c4cccc(F)c4)nc32)c1] | B | A | NT |
| 582 | 379 | 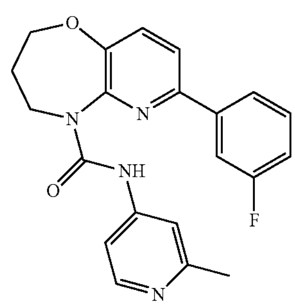 [SMILES: Cc1cc(NC(=O)N2CCCOc3ccc(-c4cccc(F)c4)nc32)ccn1] | B | A | NT |
| 583 | 385 | 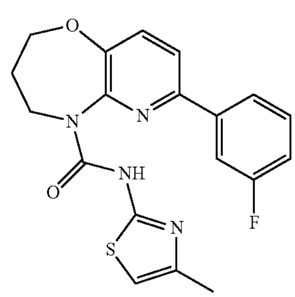 [SMILES: Cc1csc(NC(=O)N2CCCOc3ccc(-c4cccc(F)c4)nc32)n1] | B | A | NT |

TABLE 1-continued

Compounds of Formula (I).

| Compound No. | [M + H]+ | STRUCTURE | EC1.5 µM | % FOLD ACT. | TNF IC50 µM |
|---|---|---|---|---|---|
| 584 | 420 | 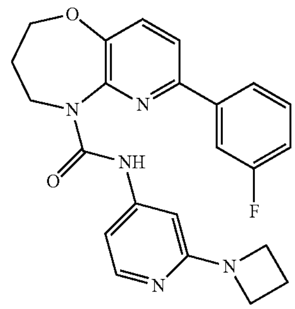 [SMILES: O=C(Nc1ccnc(N2CCC2)c1)N1CCCOc2ccc(-c3cccc(F)c3)nc21] | B | A | NT |
| 585 | 413 | 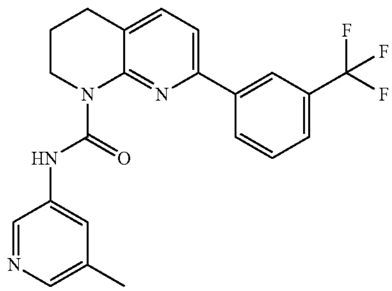 [SMILES: Cc1cncc(NC(=O)N2CCCc3ccc(-c4cccc(C(F)(F)F)c4)nc32)c1] | A | A | A |
| 586 | 417 | 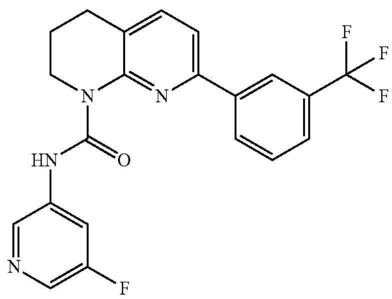 [SMILES: O=C(Nc1cncc(F)c1)N1CCCc2ccc(-c3cccc(C(F)(F)F)c3)nc21] | A | A | A |
| 587 | 427 | 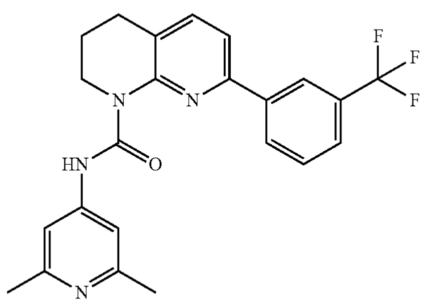 [SMILES: Cc1cc(NC(=O)N2CCCc3ccc(-c4cccc(C(F)(F)F)c4)nc32)cc(C)n1] | A | A | A |
| 588 | 419 | 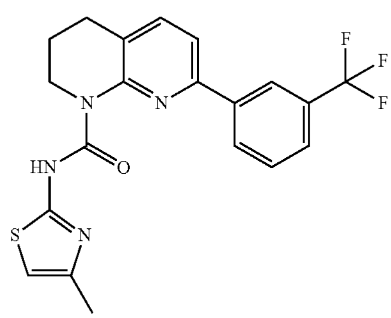 [SMILES: Cc1csc(NC(=O)N2CCCc3ccc(-c4cccc(C(F)(F)F)c4)nc32)n1] | A | A | B |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 589 | 454 | 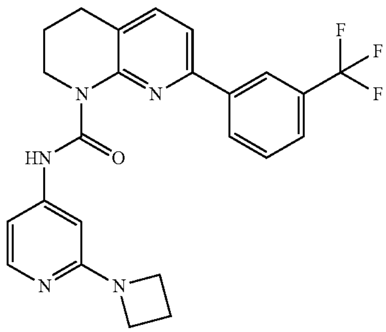 [SMILES: O=C(Nc1ccnc(N2CCC2)c1)N1CCCc2ccc(-c3cccc(C(F)(F)F)c3)nc21] | A | A | A |
| 590 | 363 | 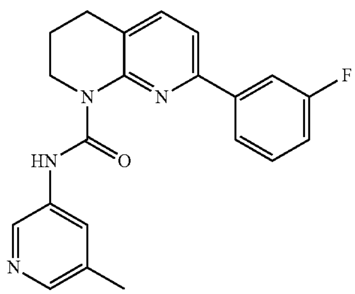 [SMILES: Cc1cncc(NC(=O)N2CCCc3ccc(-c4cccc(F)c4)nc32)c1] | A | A | A |
| 591 | 393 | 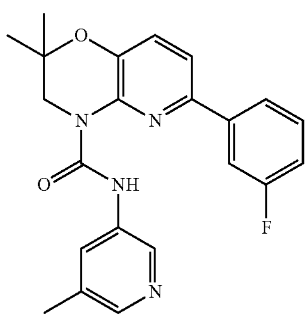 [SMILES: Cc1cncc(NC(=O)N2CC(C)(C)Oc3ccc(-c4cccc(F)c4)nc32)c1] | A | A | A |
| 592 | 407 | 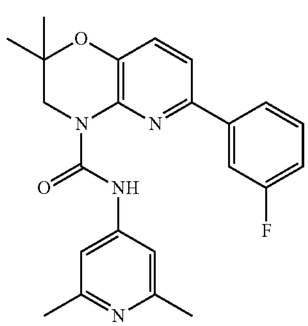 [SMILES: Cc1cc(NC(=O)N2CC(C)(C)Oc3ccc(-c4cccc(F)c4)nc32)cc(C)n1] | A | A | B |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 593 | 419 | 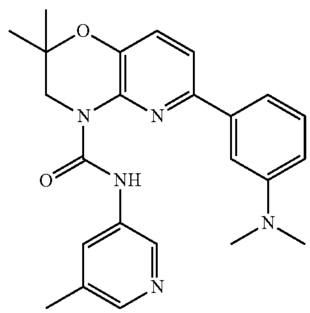 | A | A | B |
| 594 | 367 | 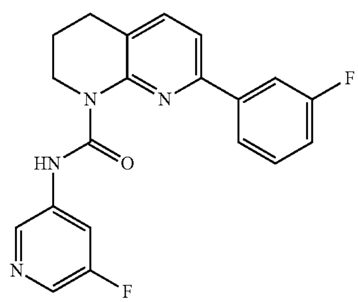 [SMILES: O=C(Nc1cncc(F)c1)N1CCCc2ccc(-c3cccc(F)c3)nc21] | A | a | B |
| 595 | 377 | 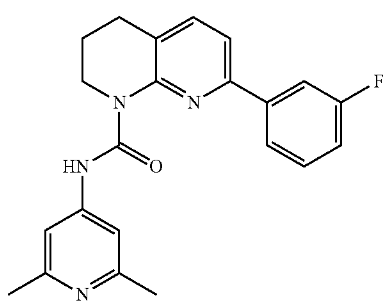 [SMILES: Cc1cc(NC(=O)N2CCCc3ccc(-c4cccc(F)c4)nc32)cc(C)n1] | A | A | A |
| 596 | 404 | 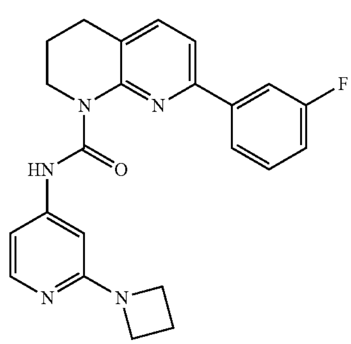 [SMILES: O=C(Nc1ccnc(N2CCC2)c1)N1CCCc2ccc(-c3cccc(F)c3)nc21] | A | A | A |

TABLE 1-continued
Compounds of Formula (I).
| Compound No. | [M + H]+ | STRUCTURE | EC1.5 μM | % FOLD ACT. | TNF IC50 μM |
|---|---|---|---|---|---|
| 597 | 433 | 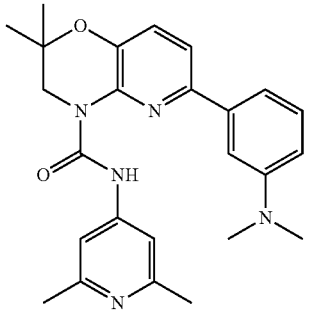 | A | A | A |
| 598 | 396 | 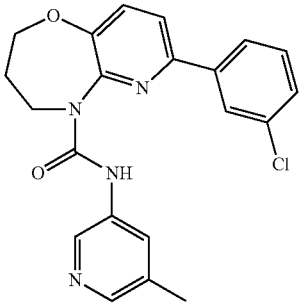 [SMILES: Cc1cncc(NC(=O)N2CCCOc3ccc(-c4cccc(Cl)c4)nc32)c1] | A | A | A |
| 599 | 380 | 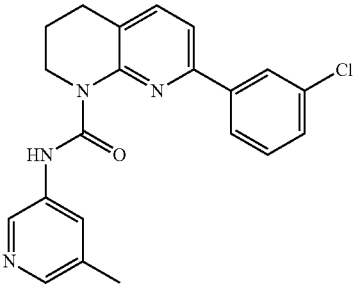 [SMILES: Cc1cncc(NC(=O)N2CCCc3ccc(-c4cccc(Cl)c4)nc32)c1] | A | A | B |
| 600 | 410 | 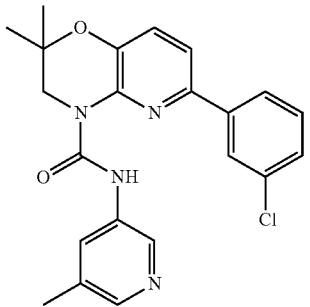 [SMILES: Cc1cncc(NC(=O)N2CC(C)(C)Oc3ccc(-c4cccc(Cl)c4)nc32)c1] | A | A | A |

TABLE 1-continued
Compounds of Formula (I).
| Compound No. | [M + H]+ | STRUCTURE | EC1.5 μM | % FOLD ACT. | TNF IC50 μM |
|---|---|---|---|---|---|
| 601 | 414 | 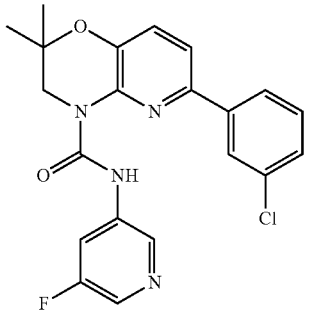 [SMILES: CC1(C)CN(C(=O)Nc2cncc(F)c2)c2nc(-c3cccc(Cl)c3)ccc2O1] | A | A | NT |
| 602 | 424 | 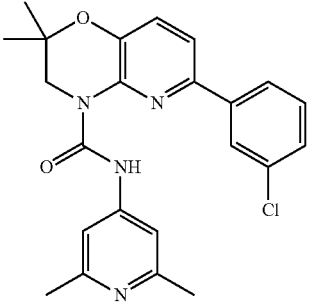 [SMILES: Cc1cc(NC(=O)N2CC(C)(C)Oc3ccc(-c4cccc(Cl)c4)nc32)cc(C)n1] | A | A | B |
| 603 | 445 | 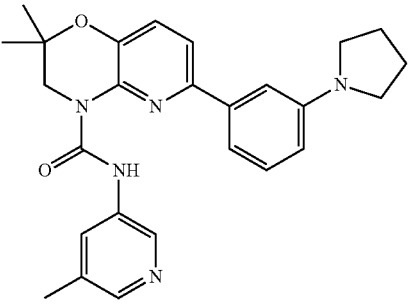 [SMILES: Cc1cncc(NC(=O)N2CC(C)(C)Oc3ccc(-c4cccc(N5CCCC5)c4)nc32)c1] | A | A | B |
| 604 | 449 | 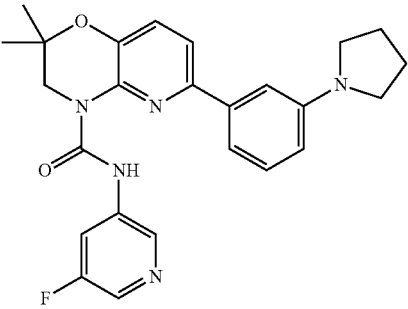 [SMILES: CC1(C)CN(C(=O)Nc2cncc(F)c2)c2nc(-c3cccc(N4CCCC4)c3)ccc2O1] | A | A | B |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 605 | 459 | 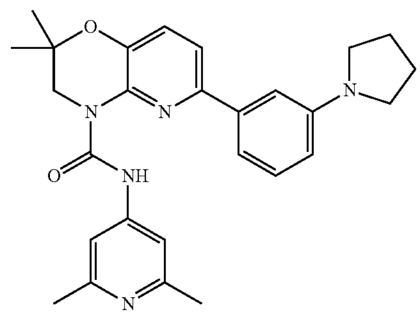 [SMILES: Cc1cc(NC(=O)N2CC(C)(C)Oc3ccc(-c4cccc(N5CCCC5)c4)nc32)cc(C)n1] | A | A | B |
| 606 | 451 | 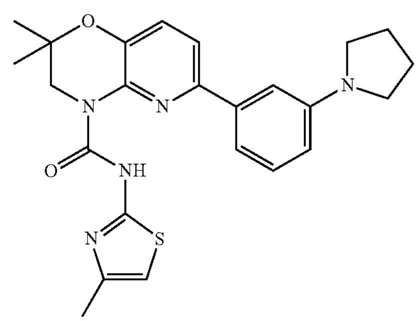 [SMILES: Cc1csc(NC(=O)N2CC(C)(C)Oc3ccc(-c4cccc(N5CCCC5)c4)nc32)n1] | A | B | B |
| 607 | 402 | 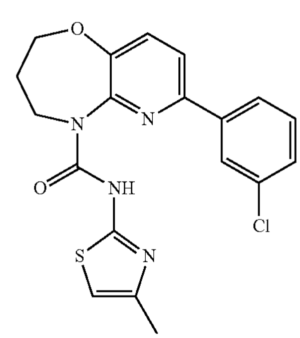 [SMILES: Cc1csc(NC(=O)N2CCCOc3ccc(-c4cccc(Cl)c4)nc32)n1] | A | A | B |
| 608 | 437 | 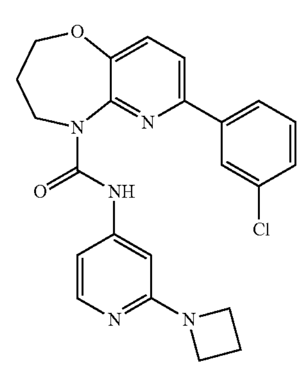 [SMILES: O=C(Nc1ccnc(N2CCC2)c1)N1CCCOc2ccc(-c3cccc(Cl)c3)nc21] | A | A | A |

TABLE 1-continued
Compounds of Formula (I).
| Compound No. | [M + H]+ | STRUCTURE | EC1.5 µM | % FOLD ACT. | TNF IC50 µM |
|---|---|---|---|---|---|
| 609 | 451 | 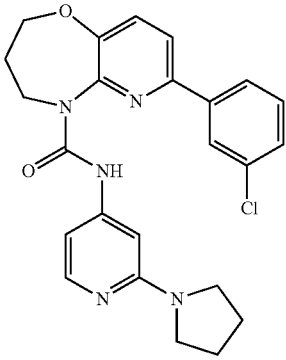 [SMILES: O=C(Nc1ccnc(N2CCCC2)c1)N1CCCOc2ccc(-c3cccc(Cl)c3)nc21] | A | A | A |
| 610 | 431 | 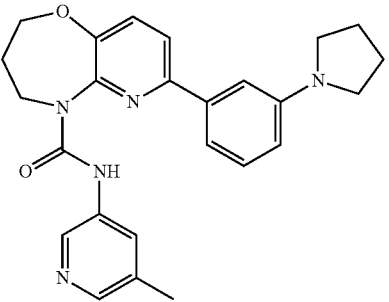 [SMILES: Cc1cncc(NC(=O)N2CCCOc3ccc(-c4cccc(N5CCCC5)c4)nc32)c1] | B | A | NT |
| 611 | 472 | 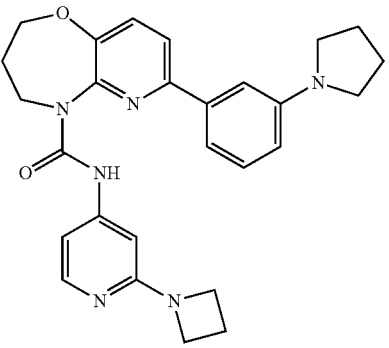 [SMILES: O=C(Nc1ccnc(N2CCC2)c1)N1CCCOc2ccc(-c3cccc(N4CCCC4)c3)nc21] | A | A | A |
| 612 | 486 | 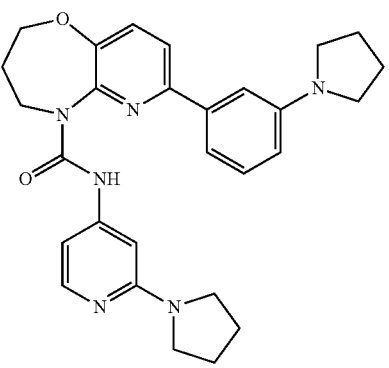 [SMILES: O=C(Nc1ccnc(N2CCCC2)c1)N1CCCOc2ccc(-c3cccc(N4CCCC4)c3)nc21] | A | A | A |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 613 | 396 | 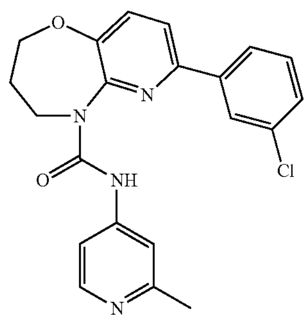 [SMILES: Cc1cc(NC(=O)N2CCCOc3ccc(-c4cccc(Cl)c4)nc32)ccn1] | A | A | A |
| 614 | 431 | 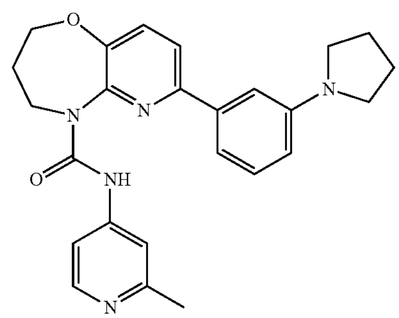 [SMILES: Cc1cc(NC(=O)N2CCCOc3ccc(-c4cccc(N5CCCC5)c4)nc32)ccn1] | A | A | B |
| 615 | 445 | 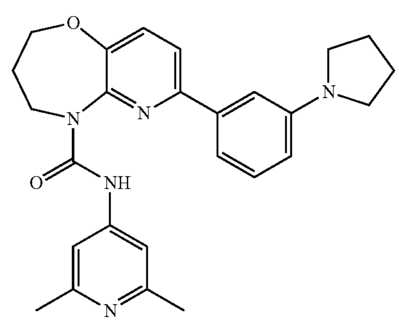 [SMILES: Cc1cc(NC(=O)N2CCCOc3ccc(-c4cccc(N5CCCC5)c4)nc32)cc(C)n1] | A | A | A |
| 616 | 386 | 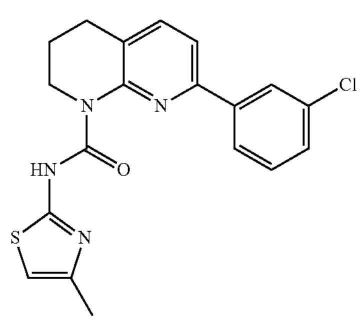 [SMILES: Cc1csc(NC(=O)N2CCCc3ccc(-c4cccc(Cl)c4)nc32)n1] | A | A | B |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 617 | 421 | 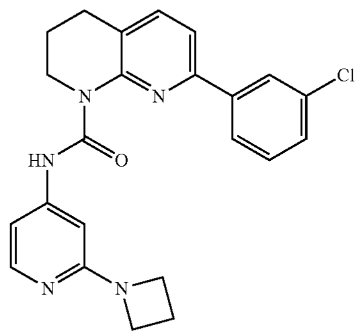 [SMILES: O=C(Nc1ccnc(N2CCC2)c1)N1CCCc2ccc(-c3cccc(Cl)c3)nc21] | A | A | A |
| 618 | 431 | 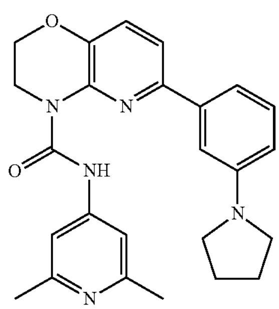 [SMILES: Cc1cc(NC(=O)N2CCOc3ccc(-c4cccc(N5CCCC5)c4)nc32)cc(C)n1] | A | A | B |
| 619 | 404 | 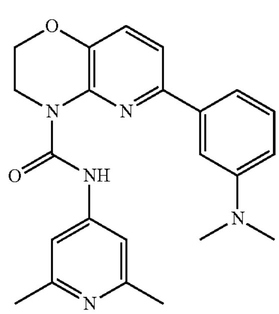 [SMILES: Cc1cc(NC(=O)N2CCOc3ccc(-c4cccc(N(C)C)c4)nc32)cc(C)n1] | A | A | A |
| 620 | 369 | 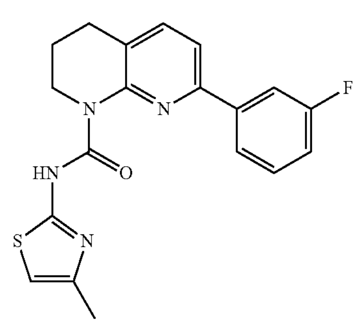 [SMILES: Cc1csc(NC(=O)N2CCCc3ccc(-c4cccc(F)c4)nc32)n1] | A | A | A |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 621 | 397 | 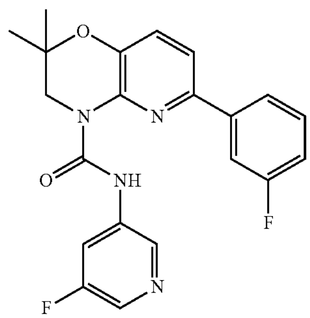 [SMILES: CC1(C)CN(C(=O)Nc2cncc(F)c2)c2nc(-c3cccc(F)c3)ccc2O1] | B | A | NT |
| 622 | 399 | 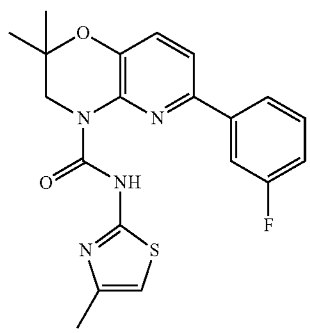 [SMILES: Cc1csc(NC(=O)N2CC(C)(C)Oc3ccc(-c4cccc(F)c4)nc32)n1] | A | A | B |
| 623 | 422 | 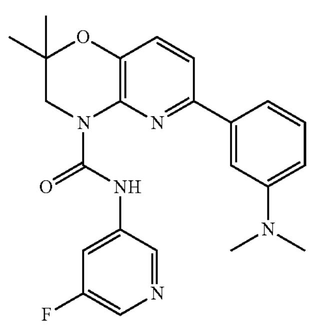 | A | A | B |
| 624 | 425 | 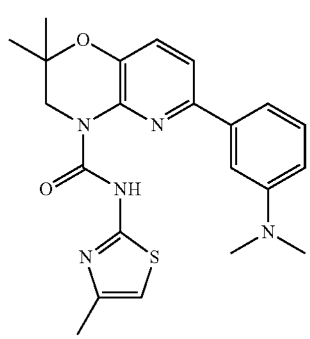 | A | A | A |

TABLE 1-continued
Compounds of Formula (I).
| Compound No. | [M + H]+ | STRUCTURE | EC1.5 μM | % FOLD ACT. | TNF IC50 μM |
|---|---|---|---|---|---|
| 625 | 383 | 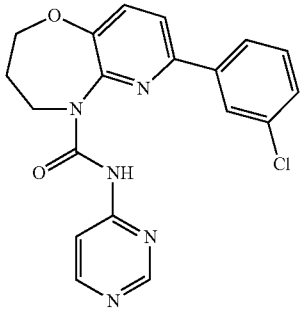 [SMILES: O=C(Nc1ccncn1)N1CCCOc2ccc(-c3cccc(Cl)c3)nc21] | A | A | NT |
| 626 | 410 | 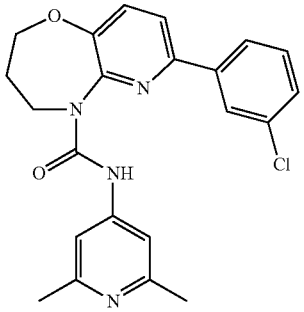 [SMILES: Cc1cc(NC(=O)N2CCCOc3ccc(-c4cccc(Cl)c4)nc32)cc(C)n1] | A | A | A |
| 627 | 417 | 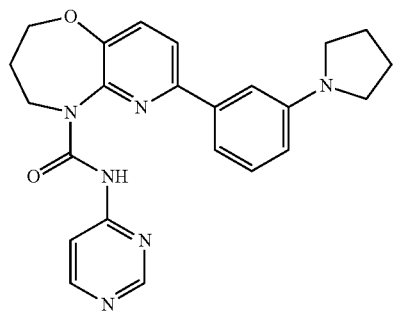 [SMILES: O=C(Nc1ccncn1)N1CCCOc2ccc(-c3cccc(N4CCCC4)c3)nc21] | B | A | NT |
| 628 | 437 | 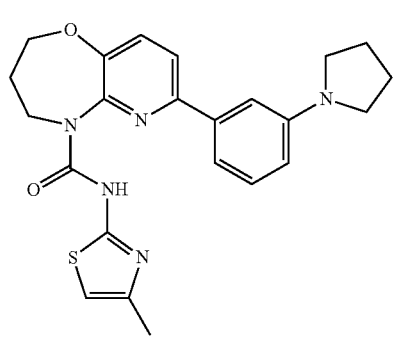 [SMILES: Cc1csc(NC(=O)N2CCCOc3ccc(-c4cccc(N5CCCC5)c4)nc32)n1] | B | B | NT |

TABLE 1-continued

Compounds of Formula (I).

| Compound No. | [M + H]+ | STRUCTURE | EC1.5 µM | % FOLD ACT. | TNF IC50 µM |
|---|---|---|---|---|---|
| 629 | 459 | 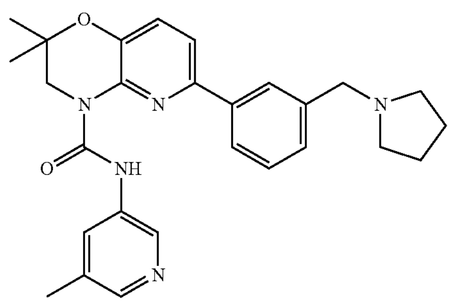 [SMILES: Cc1cncc(NC(=O)N2CC(C)(C)Oc3ccc(-c4cccc(CN5CCCC5)c4)nc32)c1] | B | A | NT |
| 630 | 445 | 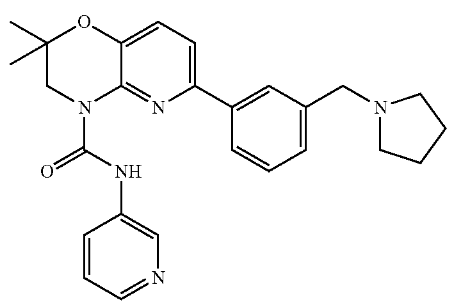 [SMILES: CC1(C)CN(C(=O)Nc2cccnc2)c2nc(-c3cccc(CN4CCCC4)c3)ccc2O1] | B | A | NT |
| 631 | 386 | 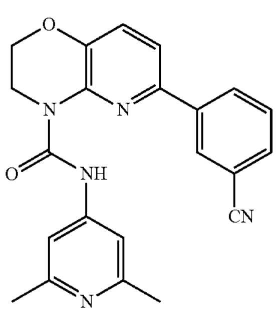 [SMILES: Cc1cc(NC(=O)N2CCOc3ccc(-c4cccc(C#N)c4)nc32)cc(C)n1] | A | A | B |
| 632 | 379 | 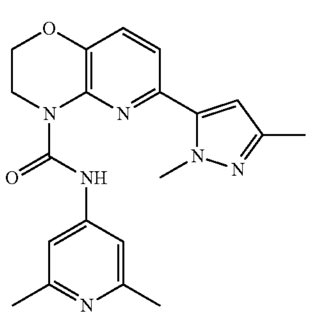 [SMILES: Cc1cc(NC(=O)N2CCOc3ccc(-c4cc(C)nn4C)nc32)cc(C)n1] | B | A | NT |
| 633 | 441 | 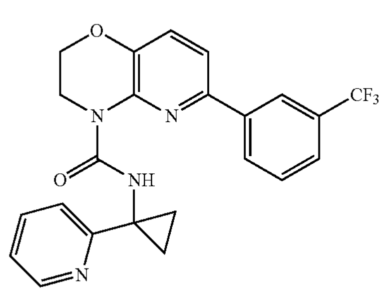 [SMILES: O=C(NC1(c2ccccn2)CC1)N1CCOc2ccc(-c3cccc(C(F)(F)F)c3)nc21] | C | B | NT |

TABLE 1-continued

Compounds of Formula (I).

| Compound No. | [M + H]+ | STRUCTURE | EC1.5 µM | % FOLD ACT. | TNF IC50 µM |
|---|---|---|---|---|---|
| 634 | 464 | 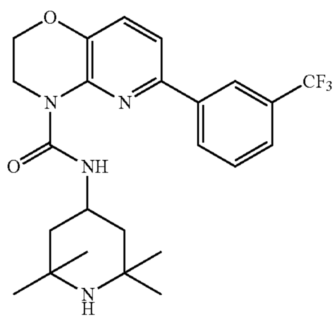 | C | B | NT |
| 635 | 376 | 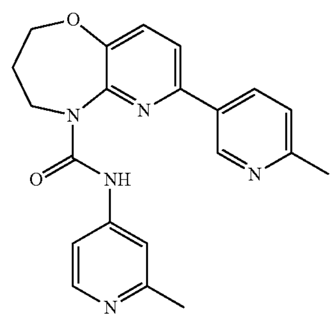 [SMILES: Cc1ccc(-c2ccc3c(n2)N(C(=O)Nc2ccnc(C)c2)CCCO3)cn1] | C | B | NT |
| 636 | 376 | 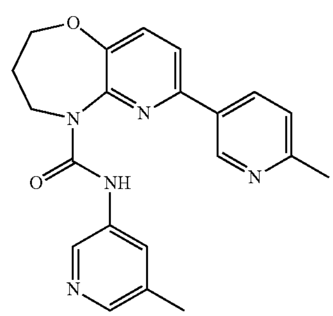 [SMILES: Cc1cncc(NC(=O)N2CCCOc3ccc(-c4ccc(C)nc4)nc32)c1] | C | B | NT |
| 637 | 390 | 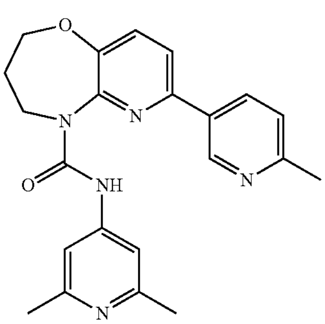 [SMILES: Cc1ccc(-c2ccc3c(n2)N(C(=O)Nc2cc(C)nc(C)c2)CCCO3)cn1] | B | A | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 638 | 490 | 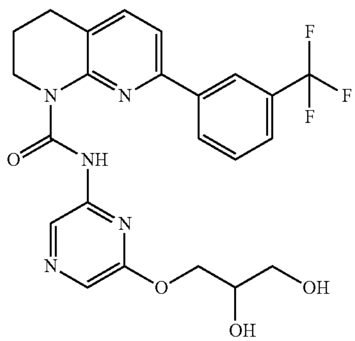 [SMILES: O=C(Nc1cncc(OCC(O)CO)n1)N1CCCc2ccc(-c3cccc(C(F)(F)F)c3)nc21] | A | A | A |
| 639 | 490 | 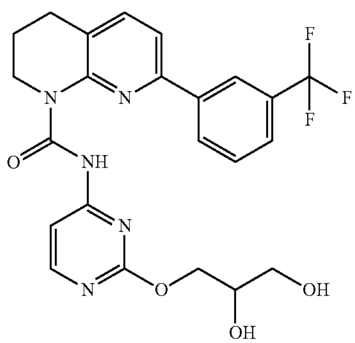 [SMILES: O=C(Nc1ccnc(OCC(O)CO)n1)N1CCCc2ccc(-c3cccc(C(F)(F)F)c3)nc21] | A | A | A |
| 640 | 504 | 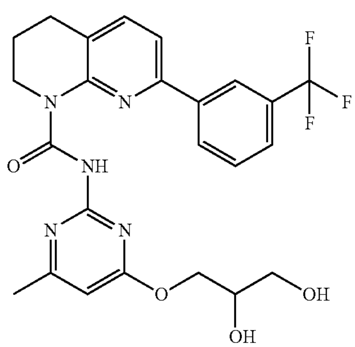 [SMILES: Cc1cc(OCC(O)CO)nc(NC(=O)N2CCCc3ccc(-c4cccc(C(F)(F)F)c4)nc32)n1] | B | A | NT |
| 641 | 489 | 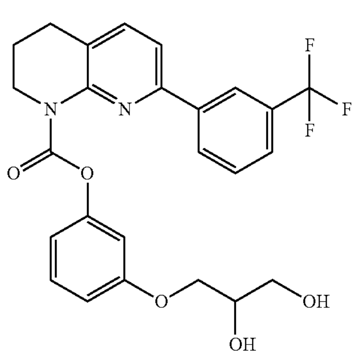 [SMILES: O=C(Oc1cccc(OCC(O)CO)c1)N1CCCc2ccc(-c3cccc(C(F)(F)F)c3)nc21] | B | B | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 642 | 473 | 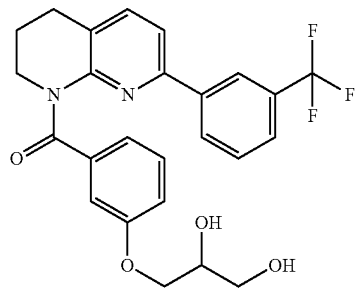 [SMILES: O=C(c1cccc(OCC(O)CO)c1)N1CCCc2ccc(-c3cccc(C(F)(F)F)c3)nc21] | C | B | NT |
| 643 | 416 | 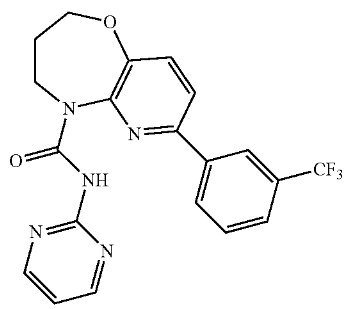 [SMILES: O=C(Nc1ncccn1)N1CCCOc2ccc(-c3cccc(C(F)(F)F)c3)nc21] | B | A | NT |
| 644 | 416 | 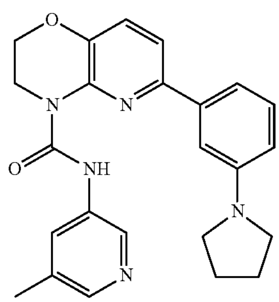 [SMILES: Cc1cncc(NC(=O)N2CCOc3ccc(-c4cccc(N5CCCC5)c4)nc32)c1] | A | A | A |
| 645 | 399 | 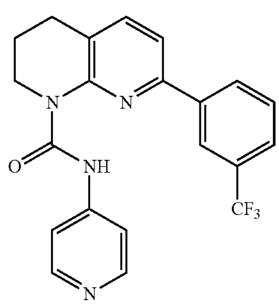 [SMILES: O=C(Nc1ccncc1)N1CCCc2ccc(-c3cccc(C(F)(F)F)c3)nc21] | A | A | A |
| 646 | 399 | 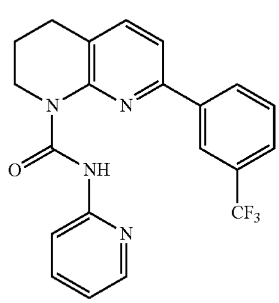 [SMILES: O=C(Nc1ccccn1)N1CCCc2ccc(-c3cccc(C(F)(F)F)c3)nc21] | A | A | A |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 647 | 427 | 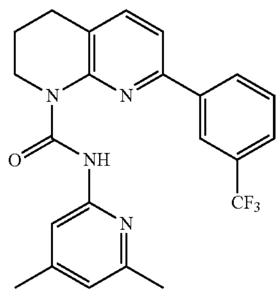 [SMILES: Cc1cc(C)nc(NC(=O)N2CCCc3ccc(-c4cccc(C(F)(F)F)c4)nc32)c1] | A | A | B |
| 648 | 349 | 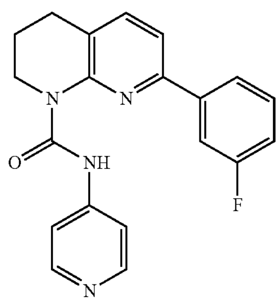 [SMILES: O=C(Nc1ccncc1)N1CCCc2ccc(-c3cccc(F)c3)nc21] | A | A | NT |
| 649 | 349 | 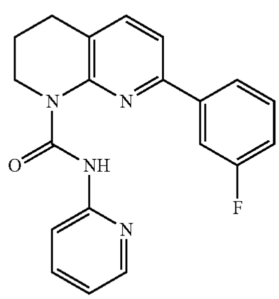 [SMILES: O=C(Nc1ccccn1)N1CCCc2ccc(-c3cccc(F)c3)nc21] | A | A | NT |
| 650 | 349 | 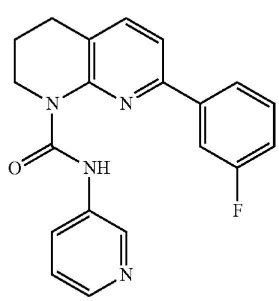 [SMILES: O=C(Nc1cccnc1)N1CCCc2ccc(-c3cccc(F)c3)nc21] | B | A | NT |
| 651 | 366 | 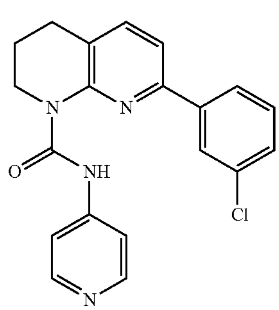 [SMILES: O=C(Nc1ccncc1)N1CCCc2ccc(-c3cccc(Cl)c3)nc21] | A | A | NT |

TABLE 1-continued
Compounds of Formula (I).
| Compound No. | [M + H]+ | STRUCTURE | EC1.5 μM | % FOLD ACT. | TNF IC50 μM |
|---|---|---|---|---|---|
| 652 | 366 | 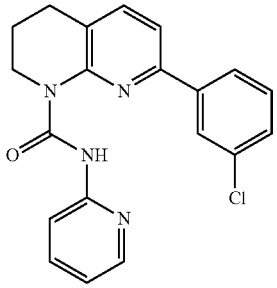 [SMILES: O=C(Nc1ccccn1)N1CCCc2ccc(-c3cccc(Cl)c3)nc21] | A | A | NT |
| 653 | 366 | 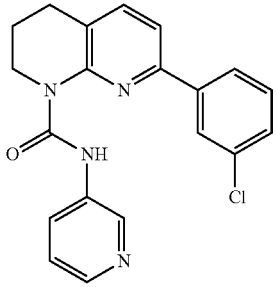 [SMILES: O=C(Nc1cccnc1)N1CCCc2ccc(-c3cccc(Cl)c3)nc21] | A | A | B |
| 654 | 394 | 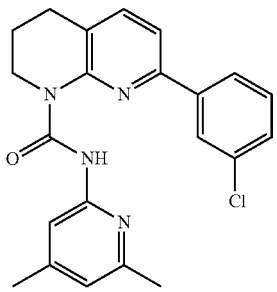 [SMILES: Cc1cc(C)nc(NC(=O)N2CCCc3ccc(-c4cccc(Cl)c4)nc32)c1] | A | A | B |
| 655 | 376 | 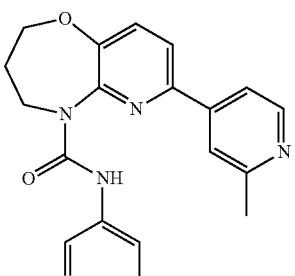 | B | B | NT |
| 656 | 376 | 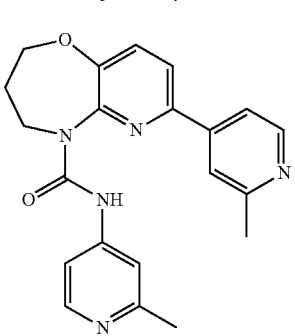 | B | A | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 657 | 390 | 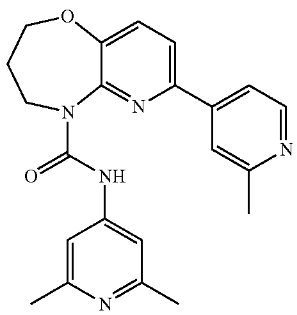 [SMILES: Cc1cc(-c2ccc3c(n2)N(C(=O)Nc2cc(C)nc(C)c2)CCCO3)ccn1] | B | A | NT |
| 658 | 477 | 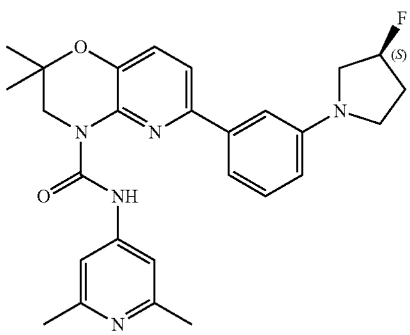 | A | A | B |
| 659 | 475 | 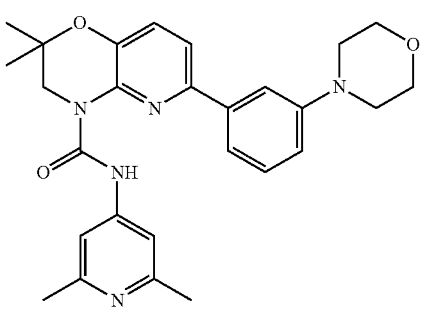 [SMILES: Cc1cc(NC(=O)N2CC(C)(C)Oc3ccc(-c4cccc(N5CCOCC5)c4)nc32)cc(C)n1] | A | A | A |
| 660 | 463 | 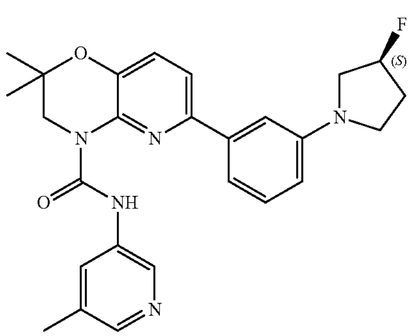 | A | A | B |

TABLE 1-continued

Compounds of Formula (I).

| Compound No. | [M + H]+ | STRUCTURE | EC1.5 µM | % FOLD ACT. | TNF IC50 µM |
|---|---|---|---|---|---|
| 661 | 466 | 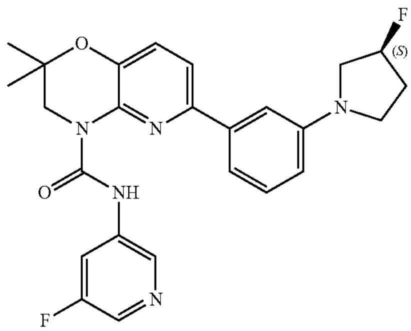 | A | A | B |
| 662 | 415 | 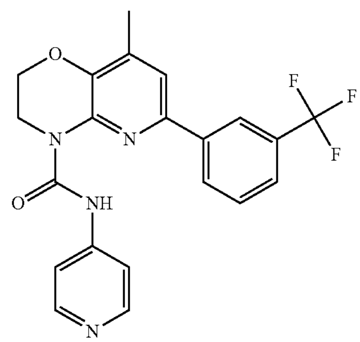 [SMILES: Cc1cc(-c2cccc(C(F)(F)F)c2)nc2c1OCCN2C(=O)Nc1ccncc1] | A | A | A |
| 663 | 433 | 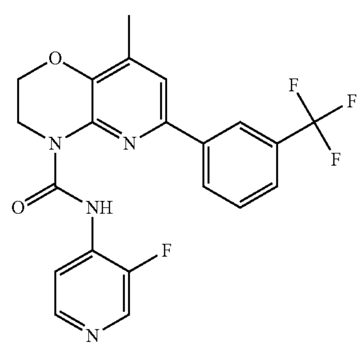 [SMILES: Cc1cc(-c2cccc(C(F)(F)F)c2)nc2c1OCCN2C(=O)Nc1ccncc1F] | A | A | B |
| 664 | 377 | 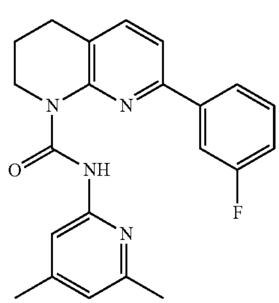 [SMILES: Cc1cc(C)nc(NC(=O)N2CCCc3ccc(-c4cccc(F)c4)nc32)c1] | A | A | B |

TABLE 1-continued

Compounds of Formula (I).

| Compound No. | [M + H]+ | STRUCTURE | EC1.5 µM | % FOLD ACT. | TNF IC50 µM |
|---|---|---|---|---|---|
| 665 | 350 | 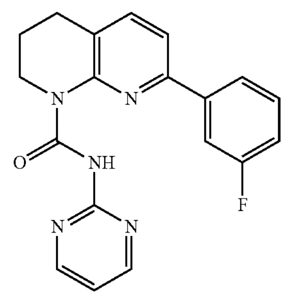 [SMILES: O=C(Nc1ncccn1)N1CCCc2ccc(-c3cccc(F)c3)nc21] | B | A | NT |
| 666 | 400 | 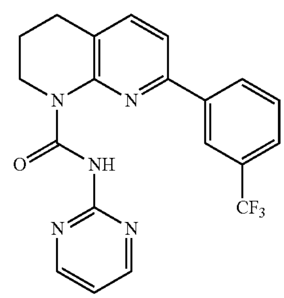 [SMILES: O=C(Nc1ncccn1)N1CCCc2ccc(-c3cccc(C(F)(F)F)c3)nc21] | A | A | NT |
| 667 | 367 | 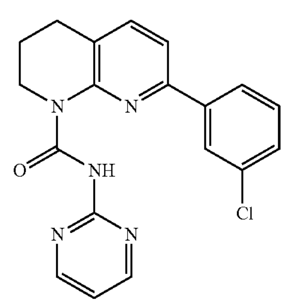 [SMILES: O=C(Nc1ncccn1)N1CCCc2ccc(-c3cccc(Cl)c3)nc21] | B | A | NT |
| 668 | 435 | 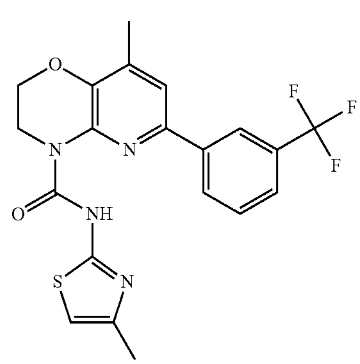 [SMILES: Cc1csc(NC(=O)N2CCOc3c(C)cc(-c4cccc(C(F)(F)F)c4)nc32)n1] | A | A | B |

TABLE 1-continued

Compounds of Formula (I).

| Compound No. | [M + H]+ | STRUCTURE | EC1.5 µM | % FOLD ACT. | TNF IC50 µM |
|---|---|---|---|---|---|
| 669 | 416 | 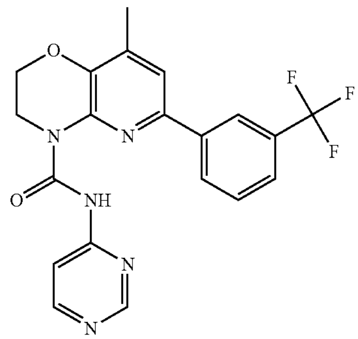 [SMILES: Cc1cc(-c2cccc(C(F)(F)F)c2)nc2c1OCCN2C(=O)Nc1ccncn1] | A | A | B |
| 670 | 429 | 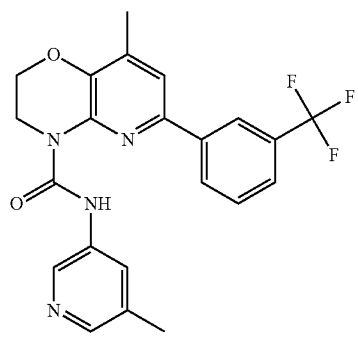 [SMILES: Cc1cncc(NC(=O)N2CCOc3c(C)cc(-c4cccc(C(F)(F)F)c4)nc32)c1] | A | A | B |
| 671 | 443 | 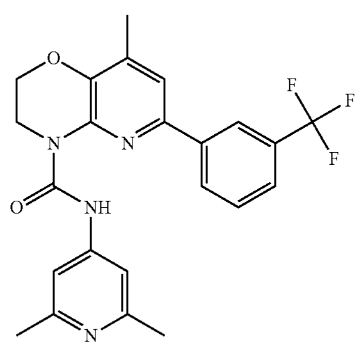 [SMILES: Cc1cc(NC(=O)N2CCOc3c(C)cc(-c4cccc(C(F)(F)F)c4)nc32)cc(C)n1] | A | A | A |
| 672 | 443 | 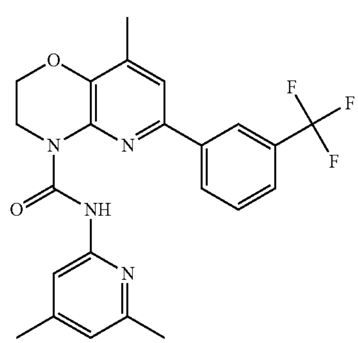 [SMILES: Cc1cc(C)nc(NC(=O)N2CCOc3c(C)cc(-c4cccc(C(F)(F)F)c4)nc32)c1] | A | B | B |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 673 | 333 | 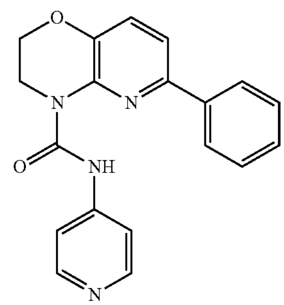 [SMILES: O=C(Nc1ccncc1)N1CCOc2ccc(-c3ccccc3)nc21] | A | A | NT |
| 674 | 363 | 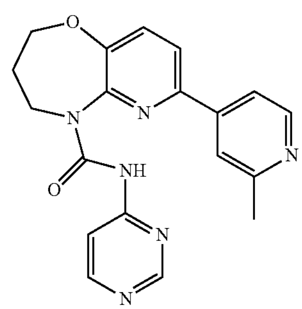 [SMILES: Cc1cc(-c2ccc3c(n2)N(C(=O)Nc2ccncn2)CCCO3)ccn1] | B | A | NT |
| 675 | 467 | 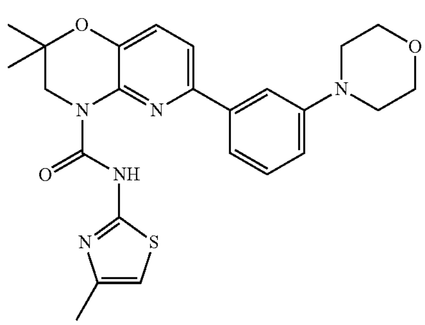 [SMILES: Cc1csc(NC(=O)N2CC(C)(C)Oc3ccc(-c4cccc(N5CCOCC5)c4)nc32)n1] | A | A | A |
| 676 | 382 | 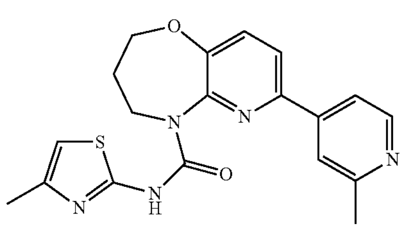 [SMILES: Cc1cc(-c2ccc3c(n2)N(C(=O)Nc2nc(C)cs2)CCCO3)ccn1] | B | A | NT |
| 677 | 419 | 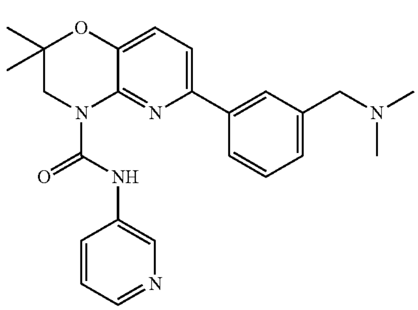 | B | A | NT |

TABLE 1-continued

Compounds of Formula (I).

| Compound No. | [M + H]+ | STRUCTURE | EC1.5 µM | % FOLD ACT. | TNF IC50 µM |
|---|---|---|---|---|---|
| 678 | 489 | 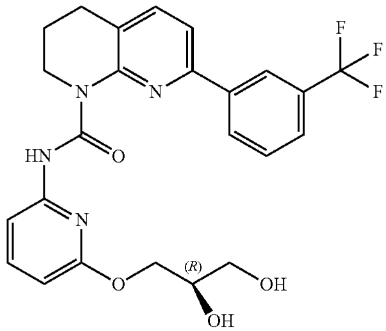 | A | A | B |
| 679 | 439 | 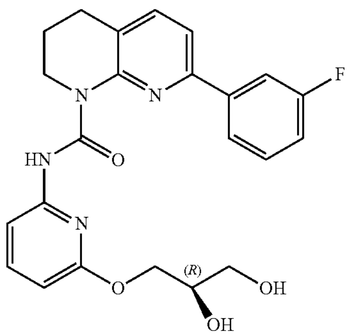 | A | A | NT |
| 680 | 382 | 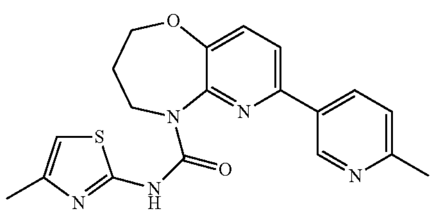 | B | A | NT |
| 681 | 363 | 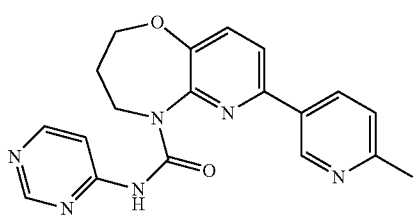 [SMILES: Cc1ccc(-c2ccc3c(n2)N(C(=O)Nc2ccncn2)CCCO3)cn1] | C | B | NT |
| 682 | 505 | 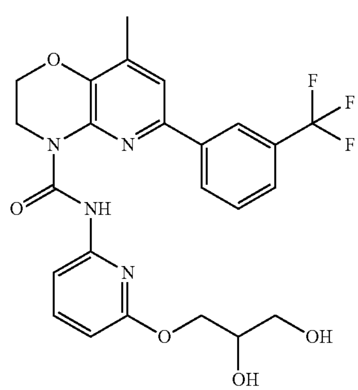 [SMILES: Cc1cc(-c2cccc(C(F)(F)F)c2)nc2c1OCCN2C(=O)Nc1cccc(OCC(O)CO)n1] | A | A | A |

TABLE 1-continued

Compounds of Formula (I).

| Compound No. | [M + H]+ | STRUCTURE | EC1.5 µM | % FOLD ACT. | TNF IC50 µM |
|---|---|---|---|---|---|
| 683 | 470 | 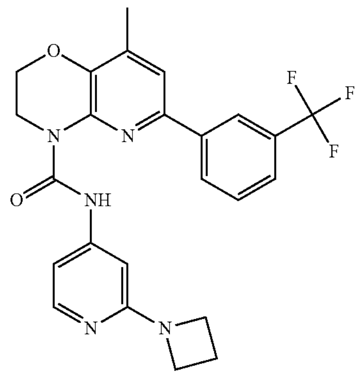 [SMILES: Cc1cc(-c2cccc(C(F)(F)F)c2)nc2c1OCCN2C(=O)Nc1ccnc(N2CCC2)c1] | A | A | B |
| 684 | 402 | 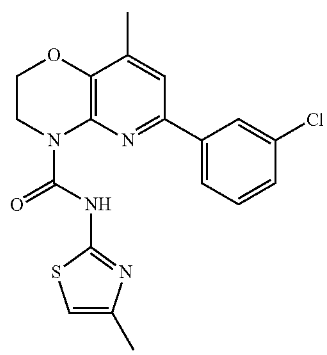 [SMILES: Cc1csc(NC(=O)N2CCOc3c(C)cc(-c4cccc(Cl)c4)nc32)n1] | A | A | B |
| 685 | 383 | 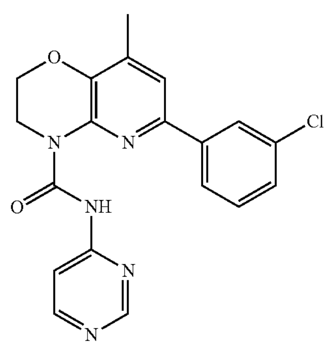 [SMILES: Cc1cc(-c2cccc(Cl)c2)nc2c1OCCN2C(=O)Nc1ccncn1] | A | A | NT |
| 686 | 382 | 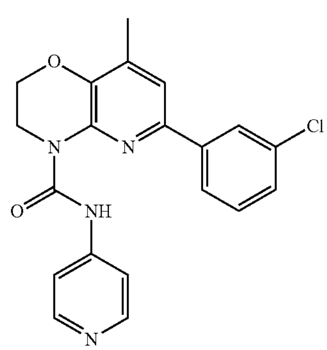 [SMILES: Cc1cc(-c2cccc(Cl)c2)nc2c1OCCN2C(=O)Nc1ccncc1] | A | A | NT |

TABLE 1-continued

Compounds of Formula (I).

| Compound No. | [M + H]+ | STRUCTURE | EC1.5 µM | % FOLD ACT. | TNF IC50 µM |
|---|---|---|---|---|---|
| 687 | 400 | 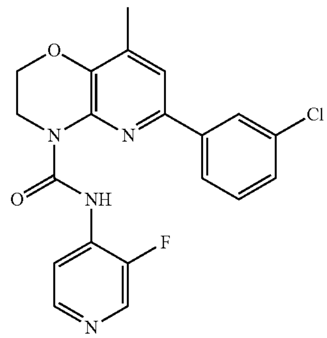 [SMILES: Cc1cc(-c2cccc(Cl)c2)nc2c1OCCN2C(=O)Nc1ccncc1F] | A | A | NT |
| 688 | 396 | 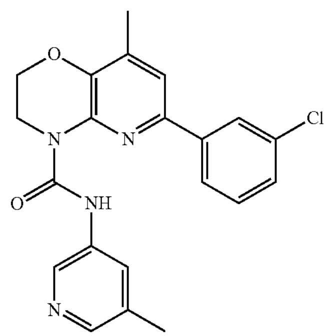 [SMILES: Cc1cncc(NC(=O)N2CCOc3c(C)cc(-c4cccc(Cl)c4)nc32)c1] | A | A | B |
| 689 | 410 | 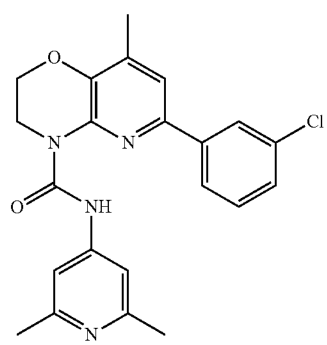 [SMILES: Cc1cc(NC(=O)N2CCOc3c(C)cc(-c4cccc(Cl)c4)nc32)cc(C)n1] | A | A | B |
| 690 | 410 | 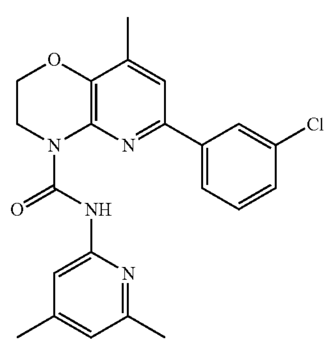 [SMILES: Cc1cc(C)nc(NC(=O)N2CCOc3c(C)cc(-c4cccc(Cl)c4)nc32)c1] | A | A | B |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 691 | 472 | 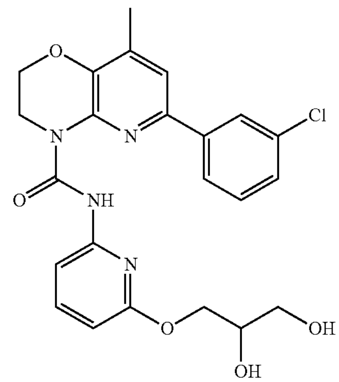 [SMILES: Cc1cc(-c2cccc(Cl)c2)nc2c1OCCN2C(=O)Nc1cccc(OCC(O)CO)n1] | A | A | A |
| 692 | 437 | 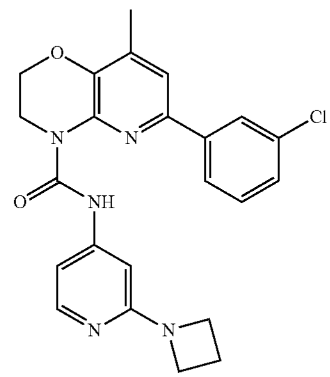 [SMILES: Cc1cc(-c2cccc(Cl)c2)nc2c1OCCN2C(=O)Nc1ccnc(N2CCC2)c1] | A | A | B |
| 693 | 504 | 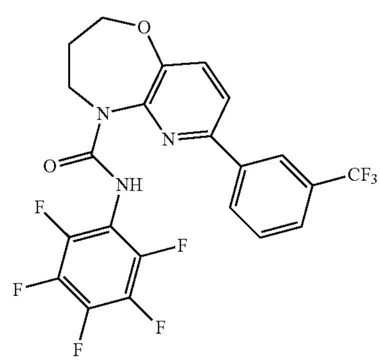 [SMILES: O=C(Nc1c(F)c(F)c(F)c(F)c1F)N1CCCOc2ccc(-c3cccc(C(F)(F)F)c3)nc21] | C | B | NT |
| 694 | 438 | 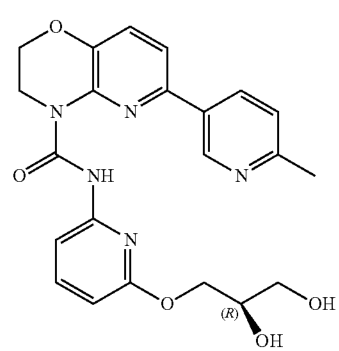 | B | A | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 695 | 465 | 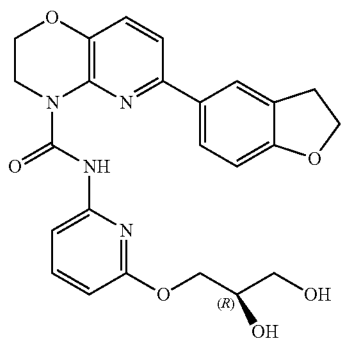 | A | A | A |
| 696 | 492 | 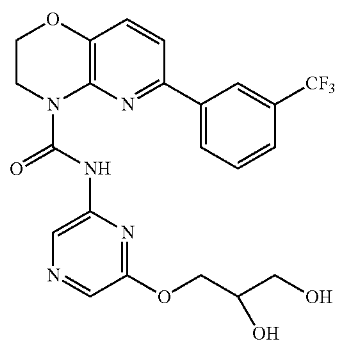 [SMILES: O=C(Nc1cncc(OCC(O)CO)n1)N1CCOc2ccc(-c3cccc(C(F)(F)F)c3)nc21] | A | A | A |
| 697 | 492 | 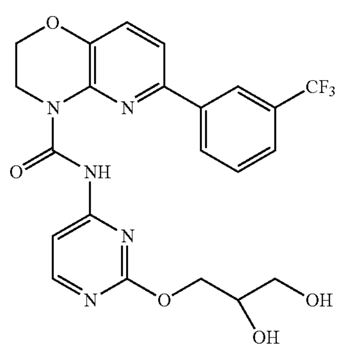 [SMILES: O=C(Nc1ccnc(OCC(O)CO)n1)N1CCOc2ccc(-c3cccc(C(F)(F)F)c3)nc21] | A | A | B |
| 698 | 506 | 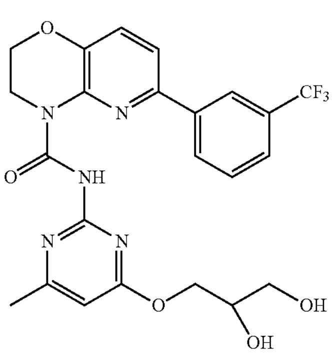 [SMILES: Cc1cc(OCC(O)CO)nc(NC(=O)N2CCOc3ccc(-c4cccc(C(F)(F)F)c4)nc32)n1] | B | B | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 699 | 465 | 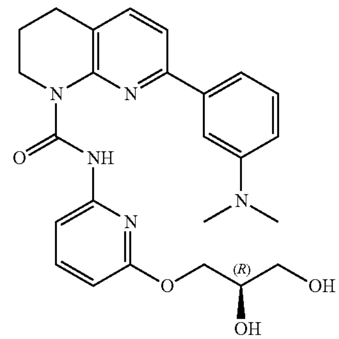 | A | A | A |
| 700 | 446 | 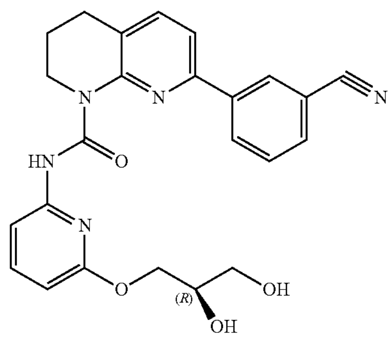 | A | A | A |
| 701 | 463 | 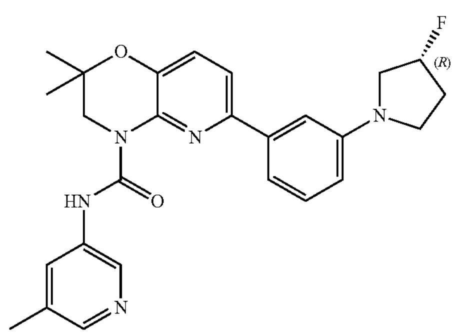 | A | A | A |
| 702 | 463 | 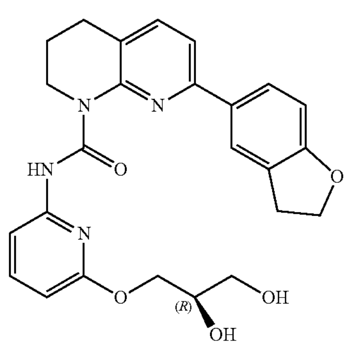 | A | A | NT |

TABLE 1-continued

Compounds of Formula (I).

| Compound No. | [M + H]+ | STRUCTURE | EC1.5 µM | % FOLD ACT. | TNF IC50 µM |
|---|---|---|---|---|---|
| 703 | 416 | 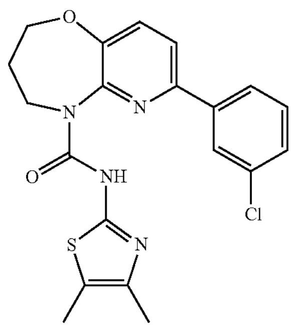 [SMILES: Cc1nc(NC(=O)N2CCCOc3ccc(-c4cccc(Cl)c4)nc32)sc1C] | A | A | NT |
| 704 | 402 | 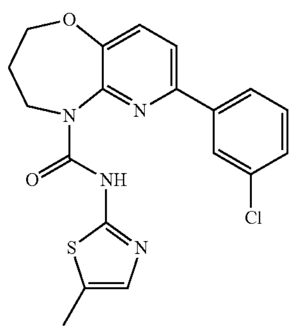 [SMILES: Cc1cnc(NC(=O)N2CCCOc3ccc(-c4cccc(Cl)c4)nc32)s1] | B | B | NT |
| 705 | 385 | 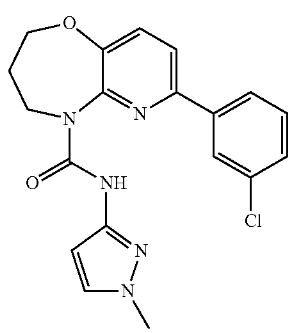 [SMILES: Cn1ccc(NC(=O)N2CCCOc3ccc(-c4cccc(Cl)c4)nc32)n1] | B | A | NT |
| 706 | 385 | 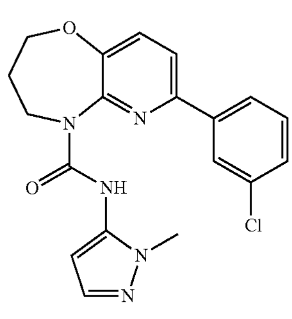 [SMILES: Cn1nccc1NC(=O)N1CCCOc2ccc(-c3cccc(Cl)c3)nc21] | C | B | NT |

TABLE 1-continued

Compounds of Formula (I).

| Compound No. | [M + H]+ | STRUCTURE | EC1.5 µM | % FOLD ACT. | TNF IC50 µM |
|---|---|---|---|---|---|
| 707 | 469 | 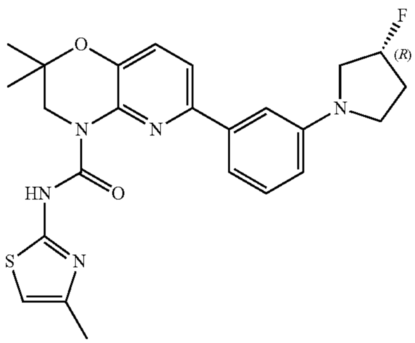 | A | A | B |
| 708 | 385 | 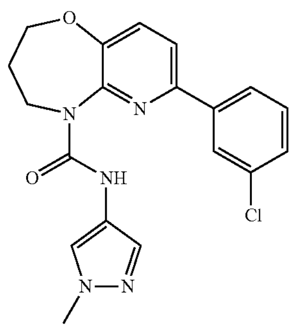 [SMILES: Cn1cc(NC(=O)N2CCCOc3ccc(-c4cccc(Cl)c4)nc32)cn1] | B | A | NT |
| 709 | 422 | 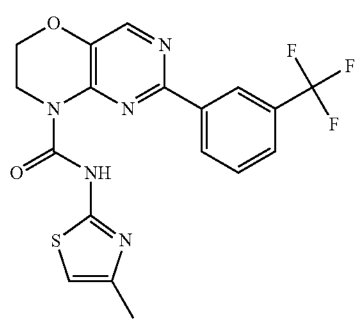 [SMILES: Cc1csc(NC(=O)N2CCOc3cnc(-c4cccc(C(F)(F)F)c4)nc32)n1] | C | B | NT |
| 710 | 416 | 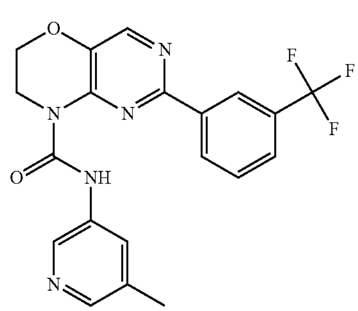 [SMILES: Cc1cncc(NC(=O)N2CCOc3cnc(-c4cccc(C(F)(F)F)c4)nc32)c1] | A | A | B |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 711 | 430 | 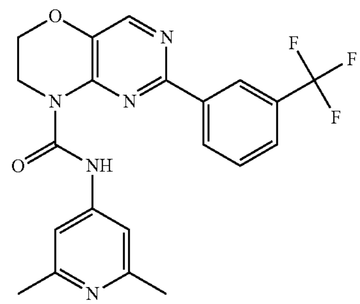 [SMILES: Cc1cc(NC(=O)N2CCOc3cnc(-c4cccc(C(F)(F)F)c4)nc32)cc(C)n1] | A | A | B |
| 712 | 430 | 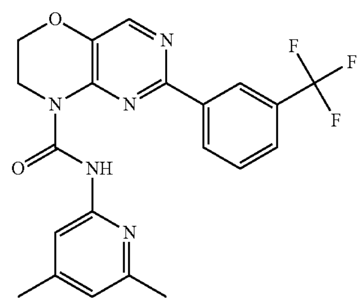 [SMILES: Cc1cc(C)nc(NC(=O)N2CCOc3cnc(-c4cccc(C(F)(F)F)c4)nc32)c1] | C | B | NT |
| 713 | 457 | 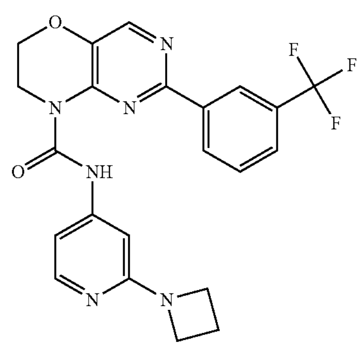 [SMILES: O=C(Nc1ccnc(N2CCC2)c1)N1CCOc2cnc(-c3cccc(C(F)(F)F)c3)nc21] | A | A | B |
| 714 | 403 | 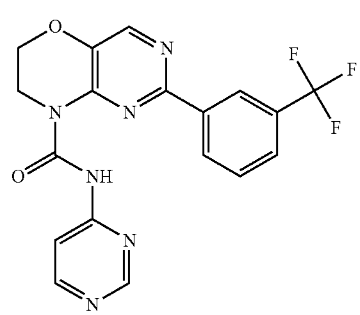 [SMILES: O=C(Nc1ccncn1)N1CCOc2cnc(-c3cccc(C(F)(F)F)c3)nc21] | B | B | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 715 | 402 | 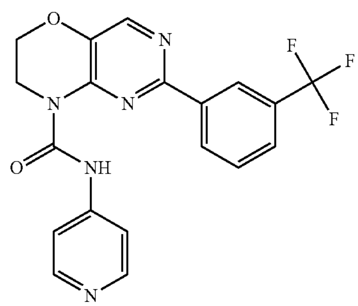 [SMILES: O=C(Nc1ccncc1)N1CCOc2cnc(-c3cccc(C(F)(F)F)c3)nc21] | B | B | NT |
| 716 | 420 | 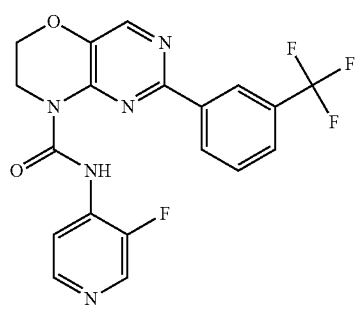 [SMILES: O=C(Nc1ccncc1F)N1CCOc2cnc(-c3cccc(C(F)(F)F)c3)nc21] | B | A | NT |
| 717 | 492 | 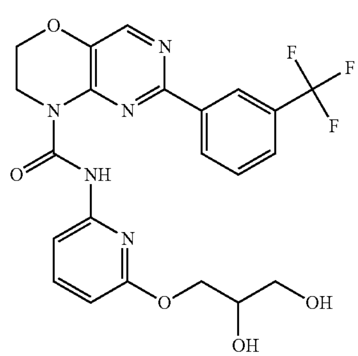 [SMILES: O=C(Nc1cccc(OCC(O)CO)n1)N1CCOc2cnc(-c3cccc(C(F)(F)F)c3)nc21] | A | B | B |
| 718 | 449 | 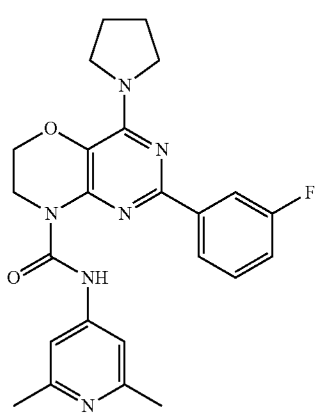 [SMILES: Cc1cc(NC(=O)N2CCOc3c(N4CCCC4)nc(-c4cccc(F)c4)nc32)cc(C)n1] | B | B | NT |

TABLE 1-continued
Compounds of Formula (I).
| Compound No. | [M + H]+ | STRUCTURE | EC1.5 µM | % FOLD ACT. | TNF IC50 µM |
|---|---|---|---|---|---|
| 719 | 413 | 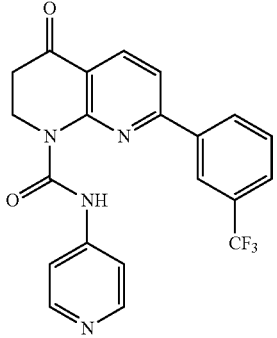 [SMILES: O=C1CCN(C(=O)Nc2ccncc2)c2nc(-c3cccc(C(F)(F)F)c3)ccc21] | B | A | NT |
| 720 | 369 | 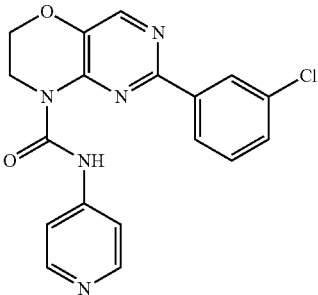 [SMILES: O=C(Nc1ccncc1)N1CCOc2cnc(-c3cccc(Cl)c3)nc21] | B | B | NT |
| 721 | 419 | 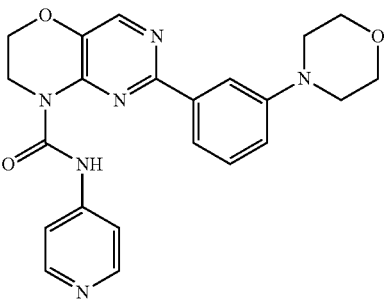 [SMILES: O=C(Nc1ccncc1)N1CCOc2cnc(-c3cccc(N4CCOCC4)c3)nc21] | B | A | NT |
| 722 | 403 | 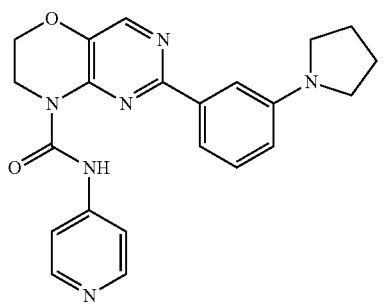 [SMILES: O=C(Nc1ccncc1)N1CCOc2cnc(-c3cccc(N4CCCC4)c3)nc21] | B | A | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 723 | 402 | 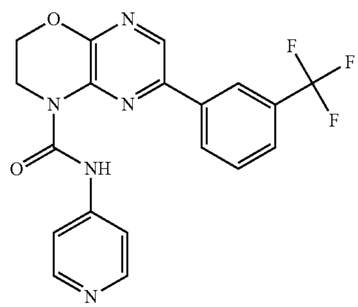 [SMILES: O=C(Nc1ccncc1)N1CCOc2ncc(-c3cccc(C(F)(F)F)c3)nc21] | B | B | NT |
| 724 | 420 | 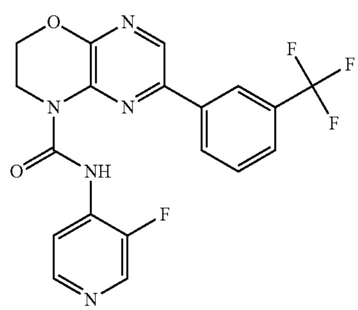 [SMILES: O=C(Nc1ccncc1F)N1CCOc2ncc(-c3cccc(C(F)(F)F)c3)nc21] | B | A | NT |
| 725 | 416 | 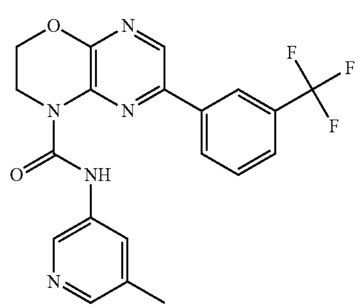 [SMILES: Cc1cncc(NC(=O)N2CCOc3ncc(-c4cccc(C(F)(F)F)c4)nc32)c1] | B | A | NT |
| 726 | 430 | 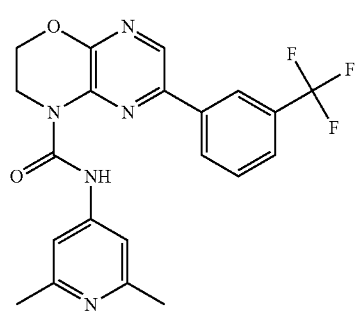 [SMILES: Cc1cc(NC(=O)N2CCOc3ncc(-c4cccc(C(F)(F)F)c4)nc32)cc(C)n1] | A | A | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 727 | 423 | 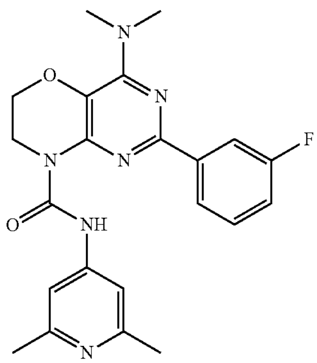 [SMILES: Cc1cc(NC(=O)N2CCOc3c(N(C)C)nc(-c4cccc(F)c4)nc32)cc(C)n1] | A | B | NT |
| 728 | 380 | 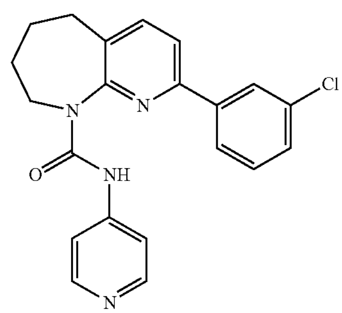 [SMILES: O=C(Nc1ccncc1)N1CCCCc2ccc(-c3cccc(Cl)c3)nc21] | B | A | NT |
| 729 | 413 | 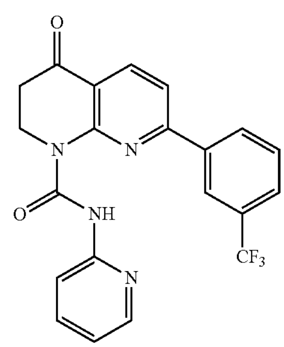 [SMILES: O=C1CCN(C(=O)Nc2ccccn2)c2nc(-c3cccc(C(F)(F)F)c3)ccc21] | B | A | NT |
| 730 | 431 | 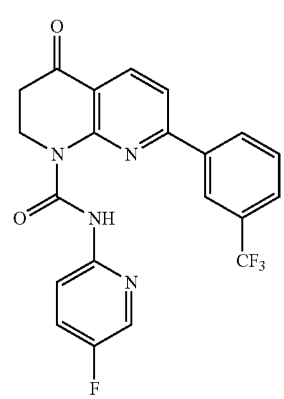 [SMILES: O=C1CCN(C(=O)Nc2ccc(F)cn2)c2nc(-c3cccc(C(F)(F)F)c3)ccc21] | B | B | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 731 | 492 | 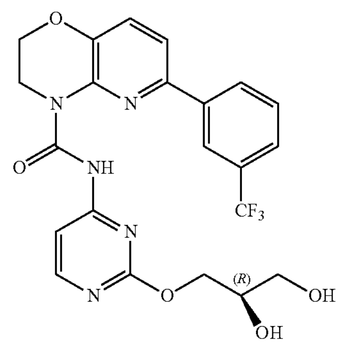 | C | B | NT |
| 732 | 492 | 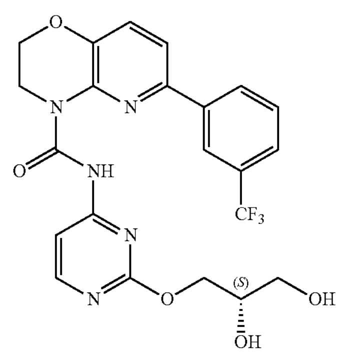 | C | B | NT |
| 733 | 394 | 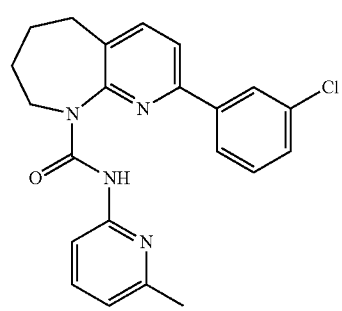 [SMILES: Cc1cccc(NC(=O)N2CCCCc3ccc(-c4cccc(Cl)c4)nc32)n1] | C | B | NT |
| 734 | 398 | 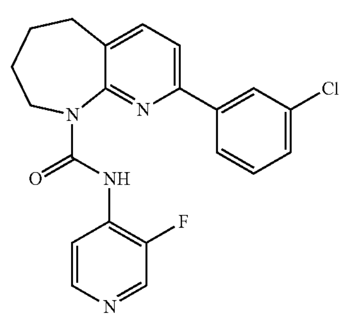 [SMILES: O=C(Nc1ccncc1F)N1CCCCc2ccc(-c3cccc(Cl)c3)nc21] | B | A | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 735 | 398 | 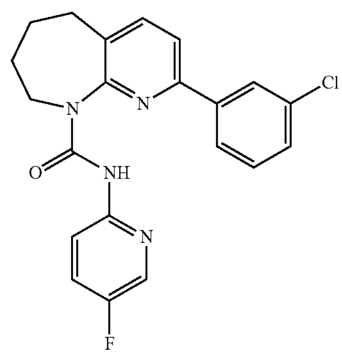 [SMILES: O=C(Nc1ccc(F)cn1)N1CCCCc2ccc(-c3cccc(Cl)c3)nc21] | C | B | NT |
| 736 | 395 | 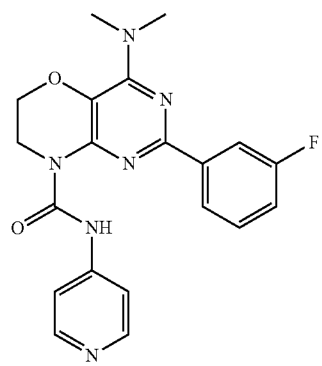 [SMILES: CN(C)c1nc(-c2cccc(F)c2)nc2c1OCCN2C(=O)Nc1ccncc1] | C | B | NT |
| 737 | 421 | 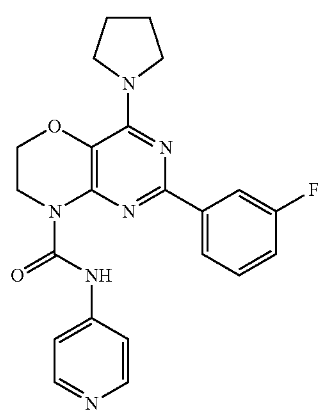 [SMILES: O=C(Nc1ccncc1)N1CCOc2c(N3CCCC3)nc(-c3cccc(F)c3)nc21] | C | B | NT |
| 738 | 437 | 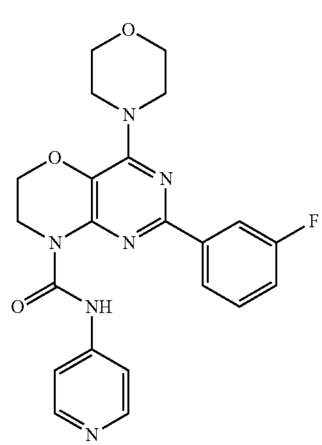 [SMILES: O=C(Nc1ccncc1)N1CCOc2c(N3CCOCC3)nc(-c3cccc(F)c3)nc21] | C | B | NT |

TABLE 1-continued

Compounds of Formula (I).

| Compound No. | [M + H]+ | STRUCTURE | EC1.5 µM | % FOLD ACT. | TNF IC50 µM |
|---|---|---|---|---|---|
| 739 | 465 | 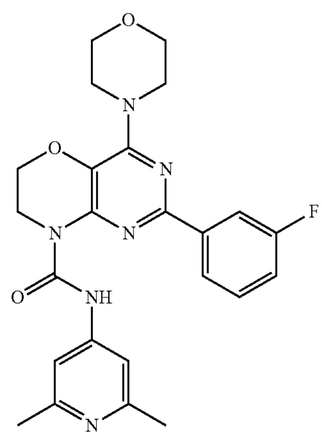 [SMILES: Cc1cc(NC(=O)N2CCOc3c(N4CCOCC4)nc(-c4cccc(F)c4)nc32)cc(C)n1] | B | B | NT |
| 740 | 422 | 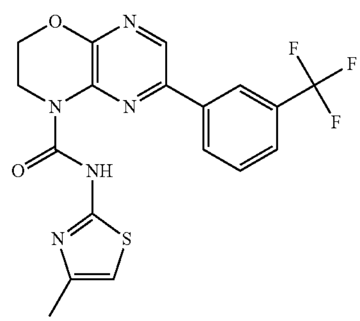 [SMILES: Cc1csc(NC(=O)N2CCOc3ncc(-c4cccc(C(F)(F)F)c4)nc32)n1] | C | B | NT |
| 741 | 430 | 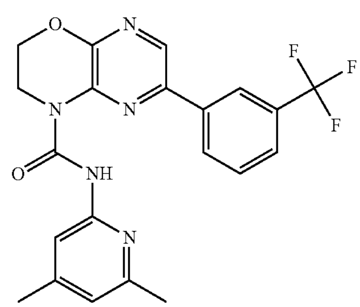 [SMILES: Cc1cc(C)nc(NC(=O)N2CCOc3ncc(-c4cccc(C(F)(F)F)c4)nc32)c1] | B | A | NT |
| 742 | 492 | 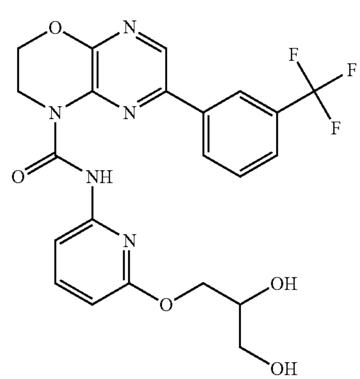 [SMILES: O=C(Nc1cccc(OCC(O)CO)n1)N1CCOc2ncc(-c3cccc(C(F)(F)F)c3)nc21] | A | A | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 743 | 435 | 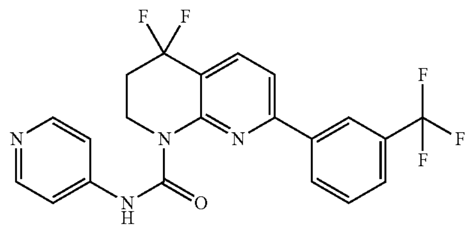 [SMILES: O=C(Nc1ccncc1)N1CCC(F)(F)c2ccc(-c3cccc(C(F)(F)F)c3)nc21] | B | A | NT |
| 744 | 449 | 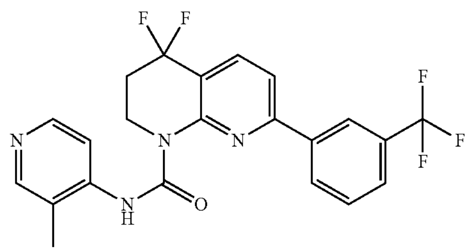 [SMILES: Cc1cnccc1NC(=O)N1CCC(F)(F)c2ccc(-c3cccc(C(F)(F)F)c3)nc21] | C | B | NT |
| 745 | 525 | 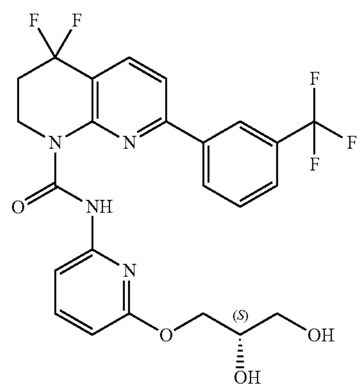 | A | A | A |
| 746 | 453 | 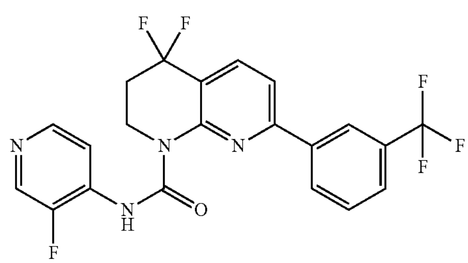 [SMILES: O=C(Nc1ccncc1F)N1CCC(F)(F)c2ccc(-c3cccc(C(F)(F)F)c3)nc21] | B | B | NT |
| 747 | 394 | 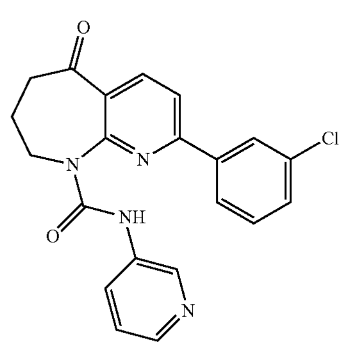 [SMILES: O=C1CCCN(C(=O)Nc2cccnc2)c2nc(-c3cccc(Cl)c3)ccc21] | B | A | NT |

TABLE 1-continued

Compounds of Formula (I).

| Compound No. | [M + H]+ | STRUCTURE | EC1.5 µM | % FOLD ACT. | TNF IC50 µM |
|---|---|---|---|---|---|
| 748 | 457 | 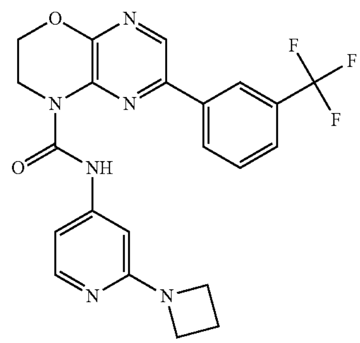 [SMILES: O=C(Nc1ccnc(N2CCC2)c1)N1CCOc2ncc(-c3cccc(C(F)(F)F)c3)nc21] | A | A | NT |
| 749 | 422 | 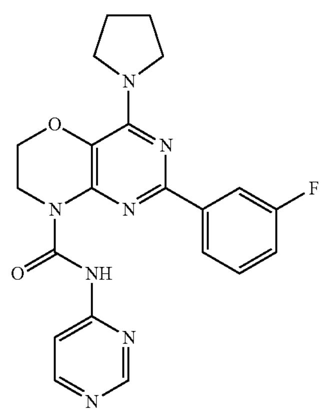 [SMILES: O=C(Nc1ccncn1)N1CCOc2c(N3CCCC3)nc(-c3cccc(F)c3)nc21] | NT | NT | NT |
| 750 | 408 | 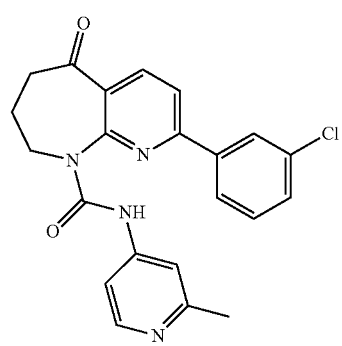 [SMILES: Cc1cc(NC(=O)N2CCCC(=O)c3ccc(-c4cccc(Cl)c4)nc32)ccn1] | A | A | B |
| 751 | 436 | 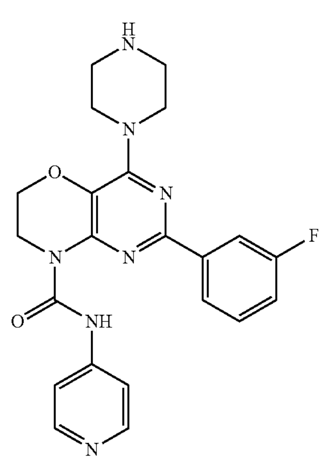 [SMILES: O=C(Nc1ccncc1)N1CCOc2c(N3CCNCC3)nc(-c3cccc(F)c3)nc21] | B | B | NT |

TABLE 1-continued
Compounds of Formula (I).
| Compound No. | [M + H]+ | STRUCTURE | EC1.5 µM | % FOLD ACT. | TNF IC50 µM |
|---|---|---|---|---|---|
| 752 | 465 | 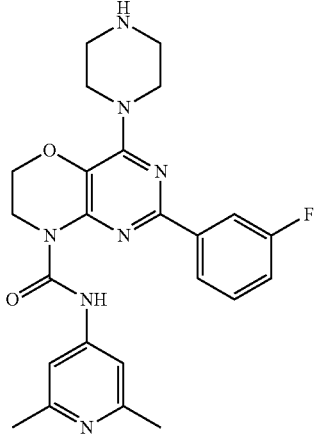 [SMILES: Cc1cc(NC(=O)N2CCOc3c(N4CCNCC4)nc(-c4cccc(F)c4)nc32)cc(C)n1] | B | A | NT |
| 753 | 436 | 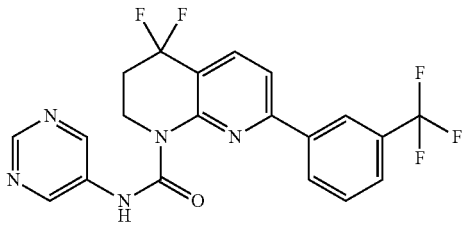 [SMILES: O=C(Nc1cncnc1)N1CCC(F)(F)c2ccc(-c3cccc(C(F)(F)F)c3)nc21] | B | A | NT |
| 754 | 380 | 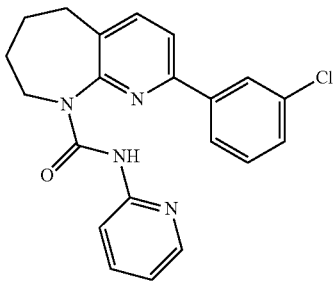 [SMILES: O=C(Nc1ccccn1)N1CCCCc2ccc(-c3cccc(Cl)c3)nc21] | B | B | NT |
| 755 | 381 | 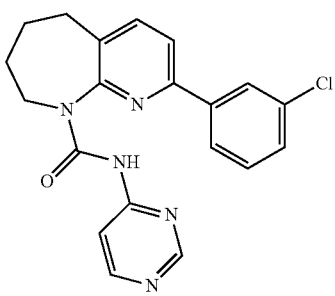 [SMILES: O=C(Nc1ccncn1)N1CCCCc2ccc(-c3cccc(Cl)c3)nc21] | B | A | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 756 | 394 | 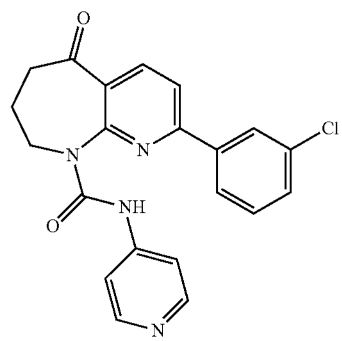 [SMILES: O=C1CCCN(C(=O)Nc2ccncc2)c2nc(-c3cccc(Cl)c3)ccc21] | B | A | NT |
| 757 | 396 | 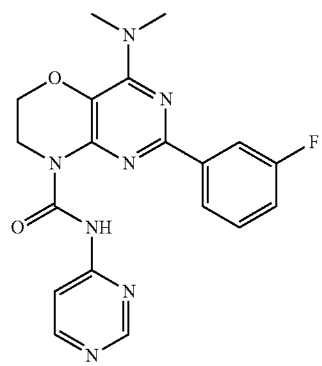 [SMILES: CN(C)c1nc(-c2cccc(F)c2)nc2c1OCCN2C(=O)Nc1ccncn1] | C | B | NT |
| 758 | 438 | 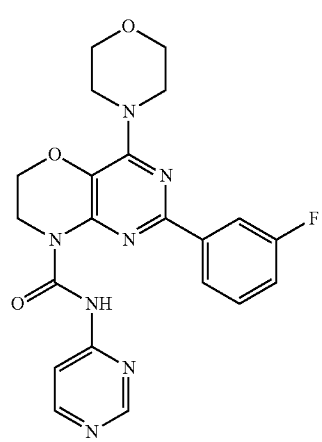 [SMILES: O=C(Nc1ccncn1)N1CCOc2c(N3CCOCC3)nc(-c3cccc(F)c3)nc21] | C | B | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 759 | 437 | 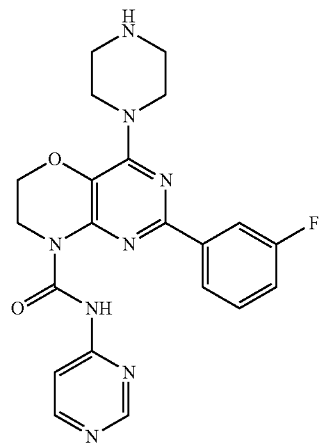 [SMILES: O=C(Nc1ccncn1)N1CCOc2c(N3CCNCC3)nc(-c3cccc(F)c3)nc21] | B | A | NT |
| 760 | 379 | 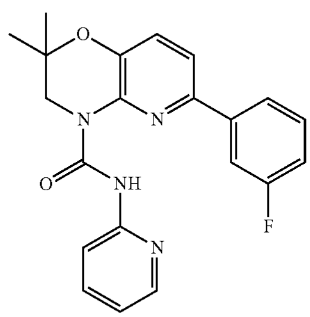 [SMILES: CC1(C)CN(C(=O)Nc2ccccn2)c2nc(-c3cccc(F)c3)ccc2O1] | B | A | NT |
| 761 | 382 | 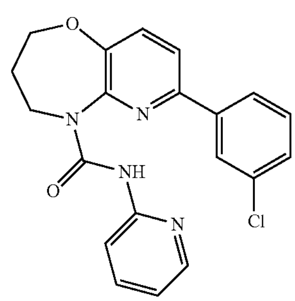 [SMILES: O=C(Nc1ccccn1)N1CCCOc2ccc(-c3cccc(Cl)c3)nc21] | B | A | NT |
| 762 | 400 | 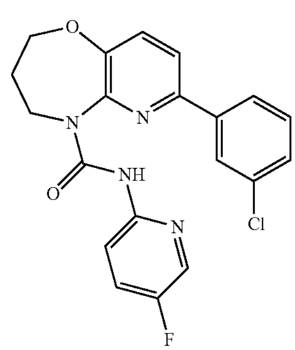 [SMILES: O=C(Nc1ccc(F)cn1)N1CCCOc2ccc(-c3cccc(Cl)c3)nc21] | B | B | NT |

TABLE 1-continued
Compounds of Formula (I).
| Compound No. | [M + H]+ | STRUCTURE | EC1.5 μM | % FOLD ACT. | TNF IC50 μM |
|---|---|---|---|---|---|
| 763 | 396 | 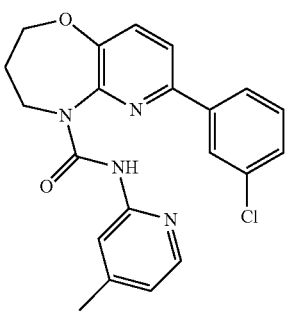 [SMILES: Cc1ccnc(NC(=O)N2CCCOc3ccc(-c4cccc(Cl)c4)nc32)c1] | B | A | NT |
| 764 | 423 | 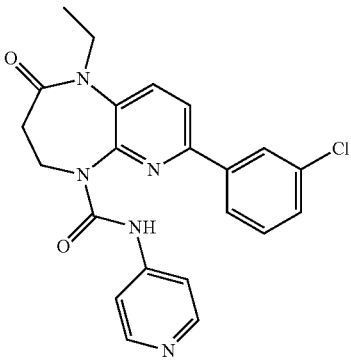 [SMILES: CCN1C(=O)CCN(C(=O)Nc2ccncc2)c2nc(-c3cccc(Cl)c3)ccc21] | NT | NT | NT |
| 765 | 423 | 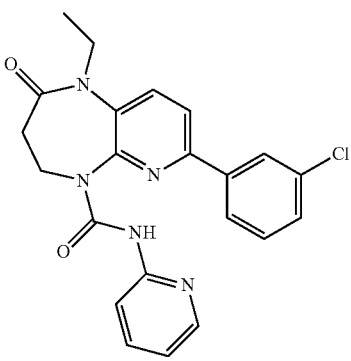 [SMILES: CCN1C(=O)CCN(C(=O)Nc2ccccn2)c2nc(-c3cccc(Cl)c3)ccc21] | C | B | NT |
| 766 | 437 | 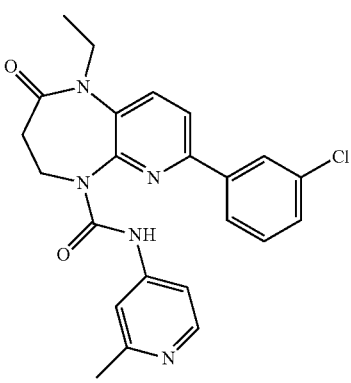 [SMILES: CCN1C(=O)CCN(C(=O)Nc2ccnc(C)c2)c2nc(-c3cccc(Cl)c3)ccc21] | NT | NT | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 767 | 412 | 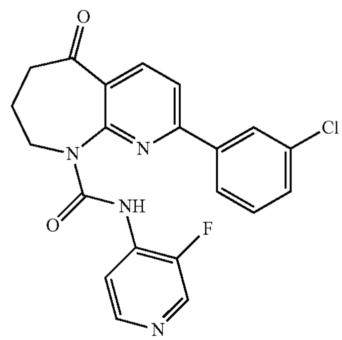 [SMILES: O=C1CCCN(C(=O)Nc2ccncc2F)c2nc(-c3cccc(Cl)c3)ccc21] | B | B | NT |
| 768 | 394 | 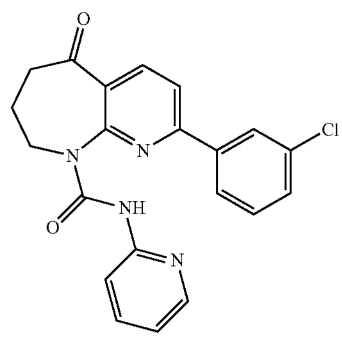 [SMILES: O=C1CCCN(C(=O)Nc2ccccn2)c2nc(-c3cccc(Cl)c3)ccc21] | A | A | NT |
| 769 | 400 | 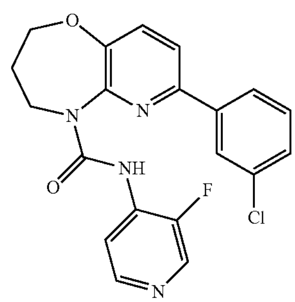 [SMILES: O=C(Nc1ccncc1F)N1CCCOc2ccc(-c3cccc(Cl)c3)nc21] | B | A | NT |
| 770 | 416 | 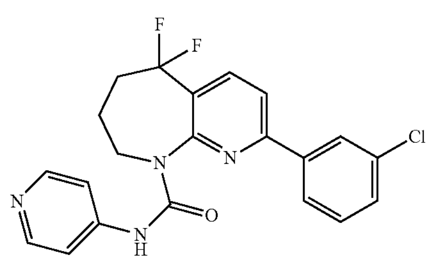 [SMILES: O=C(Nc1ccncc1)N1CCCC(F)(F)c2ccc(-c3cccc(Cl)c3)nc21] | C | B | NT |
| 771 | 416 | 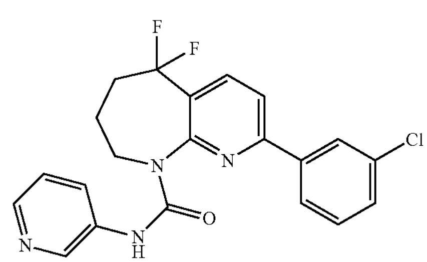 [SMILES: O=C(Nc1cccnc1)N1CCCC(F)(F)c2ccc(-c3cccc(Cl)c3)nc21] | C | B | NT |

TABLE 1-continued
Compounds of Formula (I).
| Compound No. | [M + H]+ | STRUCTURE | EC1.5 µM | % FOLD ACT. | TNF IC50 µM |
|---|---|---|---|---|---|
| 772 | 444 | 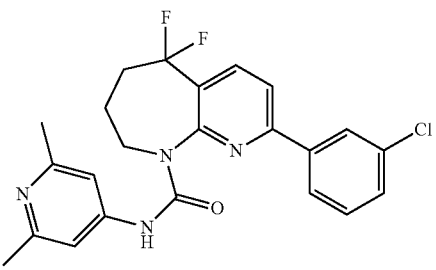 [SMILES: Cc1cc(NC(=O)N2CCCC(F)(F)c3ccc(-c4cccc(Cl)c4)nc32)cc(C)n1] | B | A | NT |
| 773 | 430 | 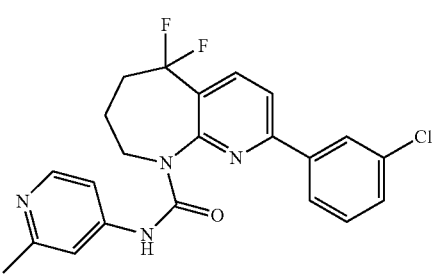 [SMILES: Cc1cc(NC(=O)N2CCCC(F)(F)c3ccc(-c4cccc(Cl)c4)nc32)ccn1] | B | A | NT |
| 774 | 441 | 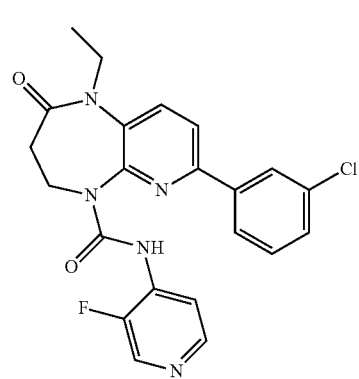 [SMILES: CCN1C(=O)CCN(C(=O)Nc2ccncc2F)c2nc(-c3cccc(Cl)c3)ccc21] | C | B | NT |
| 775 | 424 | 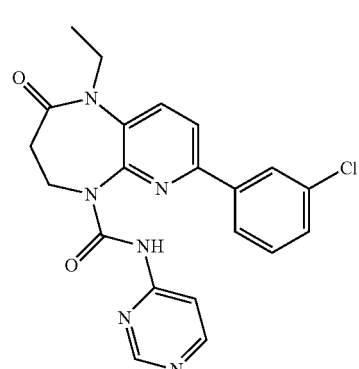 | C | B | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 776 | 437 | 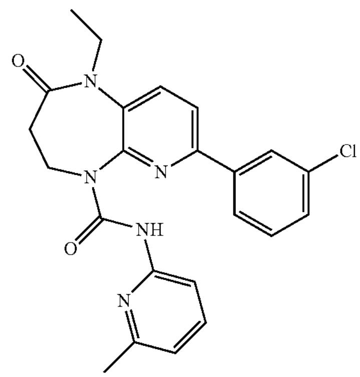 [SMILES: CCN1C(=O)CCN(C(=O)Nc2cccc(C)n2)c2nc(-c3cccc(Cl)c3)ccc21] | C | B | NT |
| 777 | 409 | 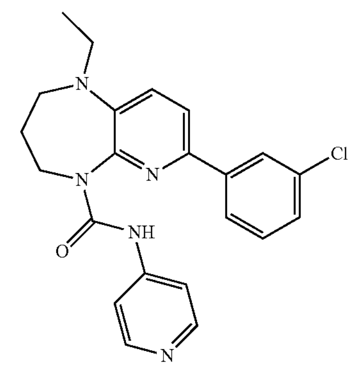 [SMILES: CCN1CCCN(C(=O)Nc2ccncc2)c2nc(-c3cccc(Cl)c3)ccc21] | B | A | NT |
| 778 | 416 | 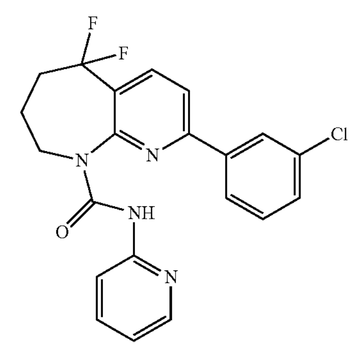 [SMILES: O=C(Nc1ccccn1)N1CCCC(F)(F)c2ccc(-c3cccc(Cl)c3)nc21] | C | B | NT |
| 779 | 436 | 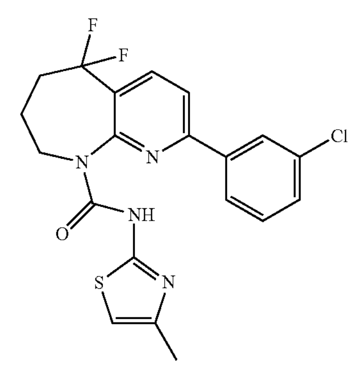 [SMILES: Cc1csc(NC(=O)N2CCCC(F)(F)c3ccc(-c4cccc(Cl)c4)nc32)n1] | C | B | NT |

TABLE 1-continued
Compounds of Formula (I).
| Compound No. | [M + H]+ | STRUCTURE | EC1.5 μM | % FOLD ACT. | TNF IC50 μM |
|---|---|---|---|---|---|
| 780 | 430 | 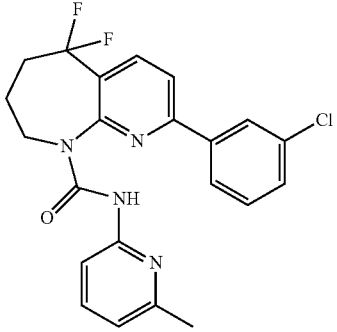 [SMILES: Cc1cccc(NC(=O)N2CCCC(F)(F)c3ccc(-c4cccc(Cl)c4)nc32)n1] | C | B | NT |
| 781 | 506 | 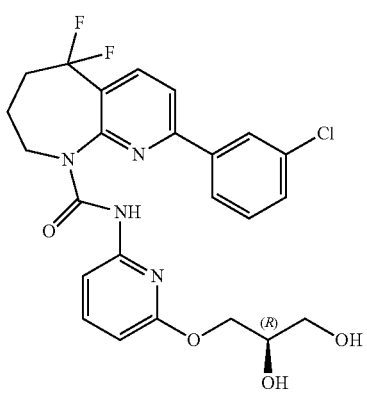 | B | A | NT |
| 782 | 434 | 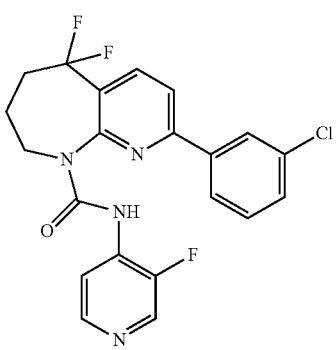 [SMILES: O=C(Nc1ccncc1F)N1CCCC(F)(F)c2ccc(-c3cccc(Cl)c3)nc21] | C | B | NT |
| 783 | 422 | 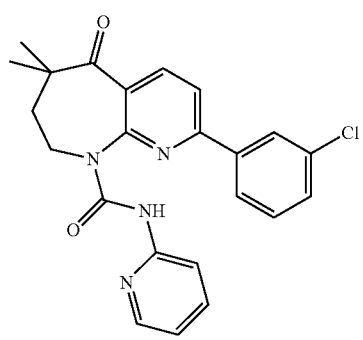 [SMILES: CC1(C)CCN(C(=O)Nc2ccccn2)c2nc(-c3cccc(Cl)c3)ccc2C1=O] | C | B | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 784 | 427 | 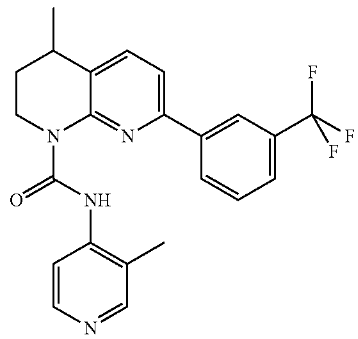 [SMILES: Cc1cnccc1NC(=O)N1CCC(C)c2ccc(-c3cccc(C(F)(F)F)c3)nc21] | B | A | NT |
| 785 | 413 | 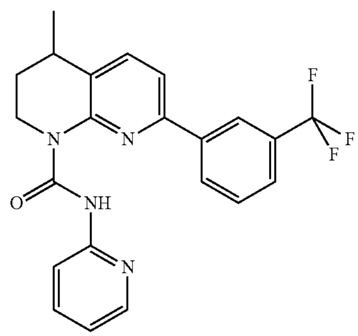 [SMILES: CC1CCN(C(=O)Nc2ccccn2)c2nc(-c3cccc(C(F)(F)F)c3)ccc21] | A | A | NT |
| 786 | 413 | 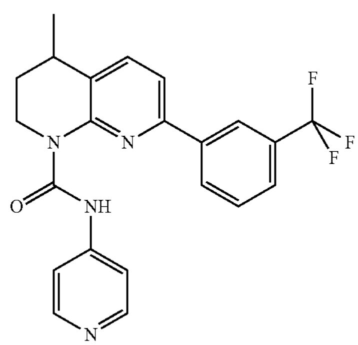 [SMILES: CC1CCN(C(=O)Nc2ccncc2)c2nc(-c3cccc(C(F)(F)F)c3)ccc21] | A | A | A |
| 787 | 433 | 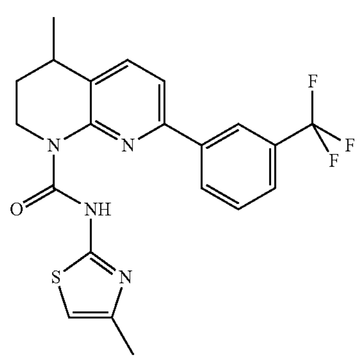 [SMILES: Cc1csc(NC(=O)N2CCC(C)c3ccc(-c4cccc(C(F)(F)F)c4)nc32)n1] | A | A | B |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 788 | 513 | 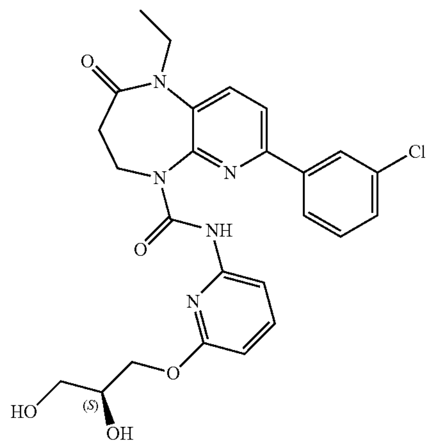 | C | B | NT |
| 789 | 409 | 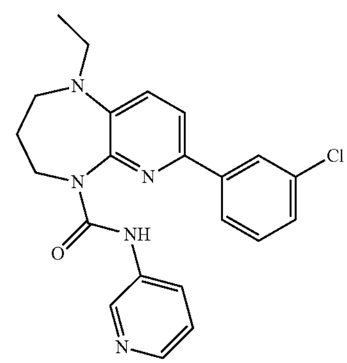 [SMILES: CCN1CCCN(C(=O)Nc2cccnc2)c2nc(-c3cccc(Cl)c3)ccc21] | B | A | NT |
| 790 | 409 | 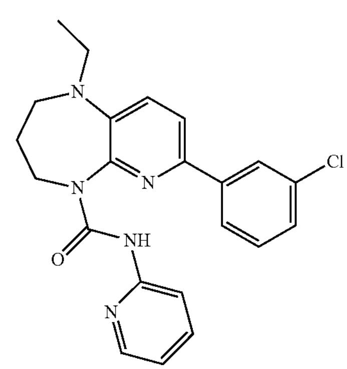 [SMILES: CCN1CCCN(C(=O)Nc2ccccn2)c2nc(-c3cccc(Cl)c3)ccc21] | C | B | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 791 | 441 | 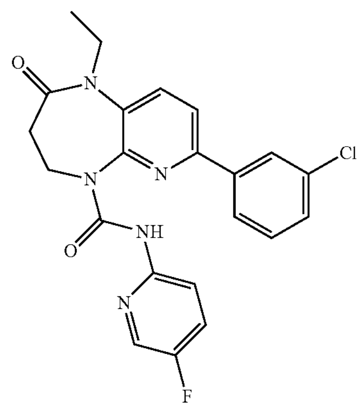 [SMILES: CCN1C(=O)CCN(C(=O)Nc2ccc(F)cn2)c2nc(-c3cccc(Cl)c3)ccc21] | C | B | NT |
| 792 | 454 | 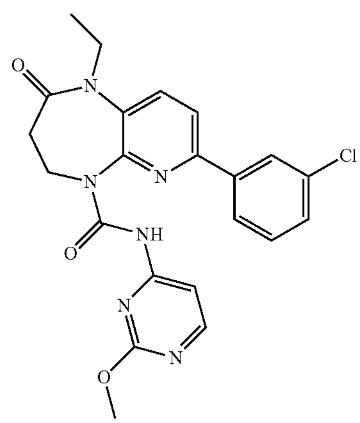 [SMILES: CCN1C(=O)CCN(C(=O)Nc2ccnc(OC)n2)c2nc(-c3cccc(Cl)c3)ccc21] | C | B | NT |
| 793 | 437 | 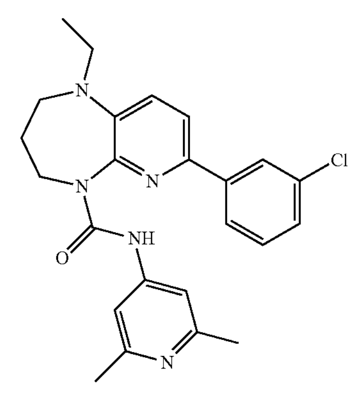 [SMILES: CCN1CCCN(C(=O)Nc2cc(C)nc(C)c2)c2nc(-c3cccc(Cl)c3)ccc21] | A | A | A |

TABLE 1-continued
Compounds of Formula (I).
| Compound No. | [M + H]+ | STRUCTURE | EC1.5 μM | % FOLD ACT. | TNF IC50 μM |
|---|---|---|---|---|---|
| 794 | 429 | 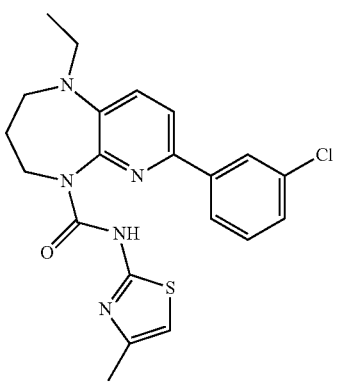 [SMILES: CCN1CCCN(C(=O)Nc2nc(C)cs2)c2nc(-c3cccc(Cl)c3)ccc21] | A | A | A |
| 795 | 423 | 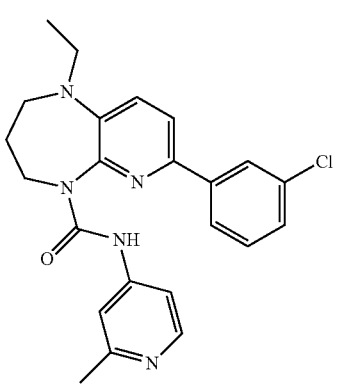 [SMILES: CCN1CCCN(C(=O)Nc2ccnc(C)c2)c2nc(-c3cccc(Cl)c3)ccc21] | A | A | A |
| 796 | 499 | 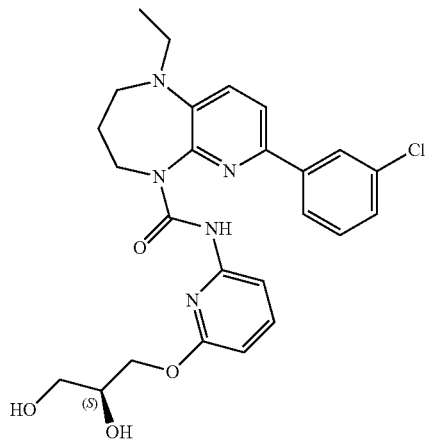 | B | A | NT |

TABLE 1-continued
Compounds of Formula (I).
| Compound No. | [M + H]+ | STRUCTURE | EC1.5 µM | % FOLD ACT. | TNF IC50 µM |
|---|---|---|---|---|---|
| 797 | 423 | 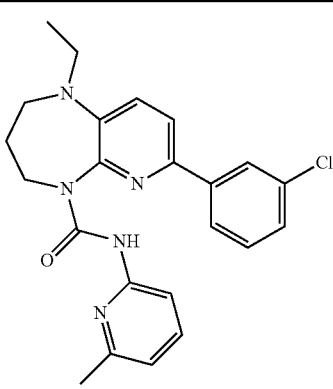 | C | B | NT |
| 798 | 434 | 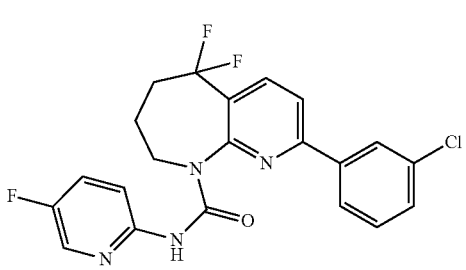 [SMILES: O=C(Nc1ccc(F)cn1)N1CCCC(F)(F)c2ccc(-c3cccc(Cl)c3)nc21] | C | B | NT |
| 799 | 417 | 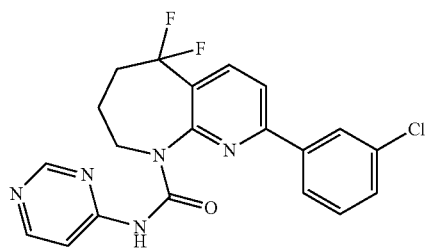 [SMILES: O=C(Nc1ccncn1)N1CCCC(F)(F)c2ccc(-c3cccc(Cl)c3)nc21] | B | B | NT |
| 800 | 431 | 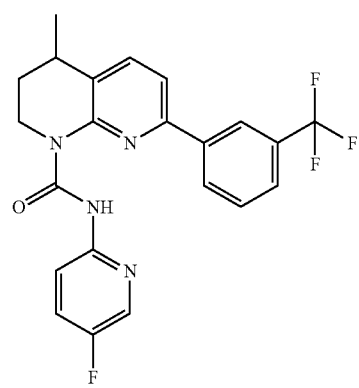 [SMILES: CC1CCN(C(=O)Nc2ccc(F)cn2)c2nc(-c3cccc(C(F)(F)F)c3)ccc21] | A | B | A |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 801 | 503 | 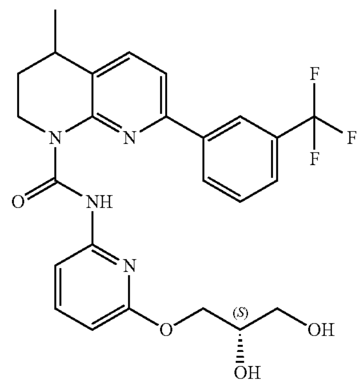 | A | A | A |
| 802 | 414 | 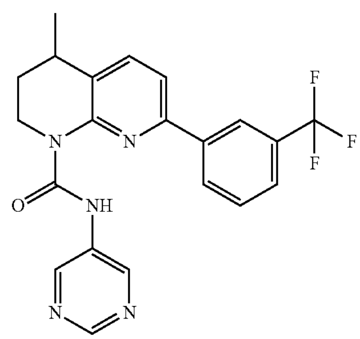 [SMILES: CC1CCN(C(=O)Nc2cncnc2)c2nc(-c3cccc(C(F)(F)F)c3)ccc21] | A | A | NT |
| 803 | 431 | 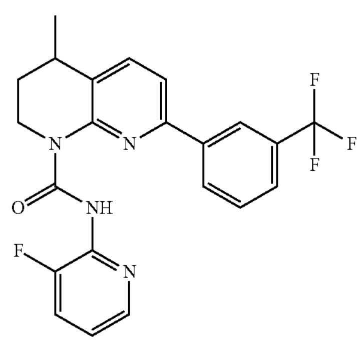 [SMILES: CC1CCN(C(=O)Nc2ncccc2F)c2nc(-c3cccc(C(F)(F)F)c3)ccc21] | B | A | NT |
| 804 | 431 | 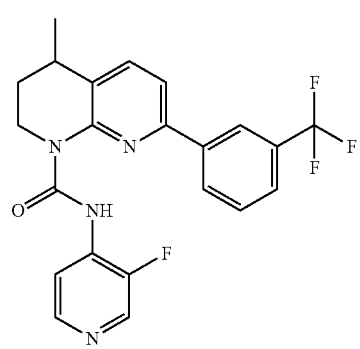 [SMILES: CC1CCN(C(=O)Nc2ccncc2F)c2nc(-c3cccc(C(F)(F)F)c3)ccc21] | A | A | A |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 805 | 414 | 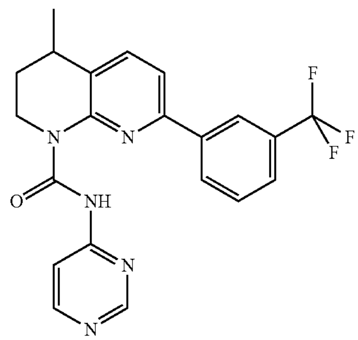 [SMILES: CC1CCN(C(=O)Nc2ccncn2)c2nc(-c3cccc(C(F)(F)F)c3)ccc21] | A | A | A |
| 806 | 437 | 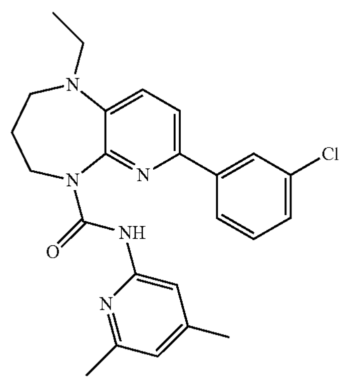 [SMILES: CCN1CCCN(C(=O)Nc2cc(C)cc(C)n2)c2nc(-c3cccc(Cl)c3)ccc21] | C | B | NT |
| 807 | 427 | 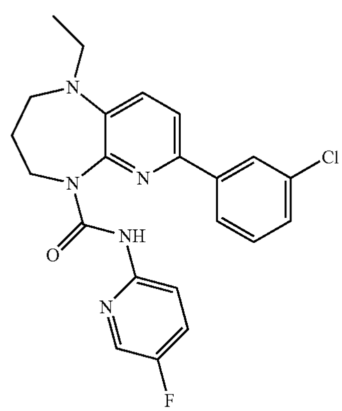 [SMILES: CCN1CCCN(C(=O)Nc2ccc(F)cn2)c2nc(-c3cccc(Cl)c3)ccc21] | C | B | NT |
| 808 | 427 | 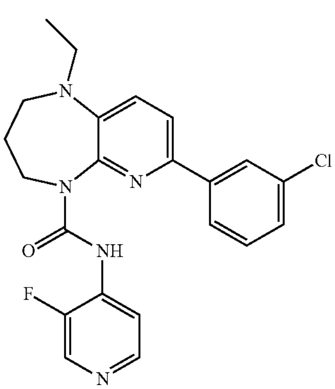 [SMILES: CCN1CCCN(C(=O)Nc2ccncc2F)c2nc(-c3cccc(Cl)c3)ccc21] | B | A | NT |

TABLE 1-continued
Compounds of Formula (I).
| Compound No. | [M + H]+ | STRUCTURE | EC1.5 μM | % FOLD ACT. | TNF IC50 μM |
|---|---|---|---|---|---|
| 809 | 410 | 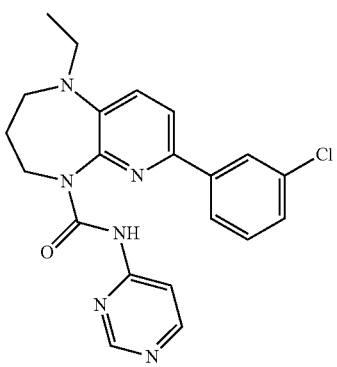 [SMILES: CCN1CCCN(C(=O)Nc2ccncn2)c2nc(-c3cccc(Cl)c3)ccc21] | B | A | NT |
| 810 | 413 | 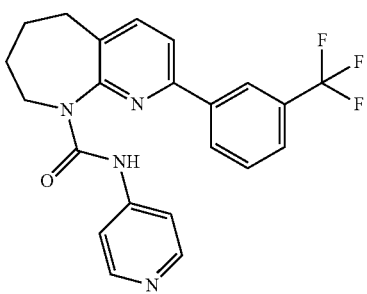 [SMILES: O=C(Nc1ccncc1)N1CCCCc2ccc(-c3cccc(C(F)(F)F)c3)nc21] | B | A | NT |
| 811 | 444 | 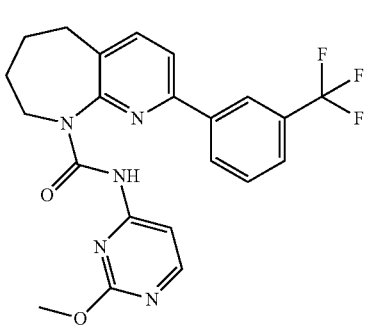 [SMILES: COc1nccc(NC(=O)N2CCCCc3ccc(-c4cccc(C(F)(F)F)c4)nc32)n1] | B | B | NT |
| 812 | 413 | 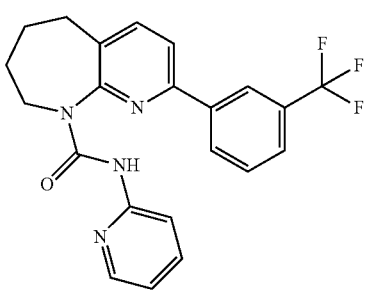 [SMILES: O=C(Nc1ccccn1)N1CCCCc2ccc(-c3cccc(C(F)(F)F)c3)nc21] | B | B | NT |

TABLE 1-continued
Compounds of Formula (I).
| Compound No. | [M + H]+ | STRUCTURE | EC1.5 μM | % FOLD ACT. | TNF IC50 μM |
|---|---|---|---|---|---|
| 813 | 526 | 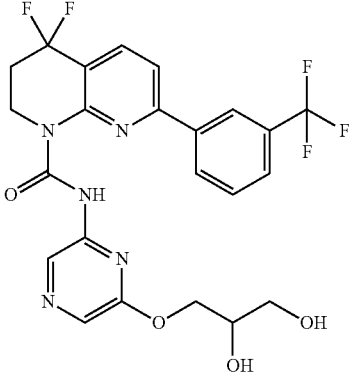 [SMILES: O=C(Nc1cncc(OCC(O)CO)n1)N1CCC(F)(F)c2ccc(-c3cccc(C(F)(F)F)c3)nc21] | A | A | A |
| 814 | 435 | 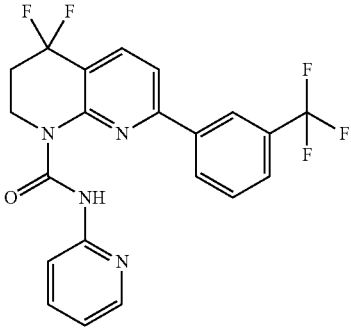 [SMILES: O=C(Nc1ccccn1)N1CCC(F)(F)c2ccc(-c3cccc(C(F)(F)F)c3)nc21] | C | B | NT |
| 815 | 414 | 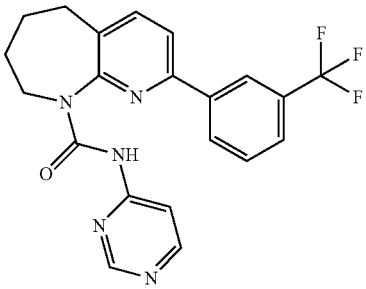 [SMILES: O=C(Nc1ccncn1)N1CCCCc2ccc(-c3cccc(C(F)(F)F)c3)nc21] | B | A | NT |
| 816 | 431 | 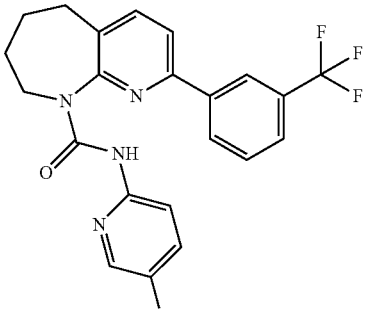 | C | B | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 817 | 431 | 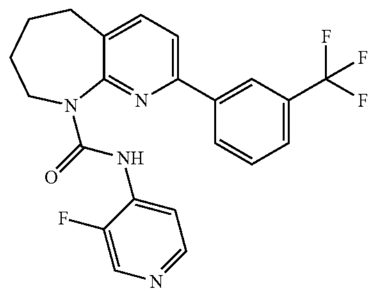 [SMILES: O=C(Nc1ccncc1F)N1CCCCc2ccc(-c3cccc(C(F)(F)F)c3)nc21] | B | A | NT |
| 818 | 427 | 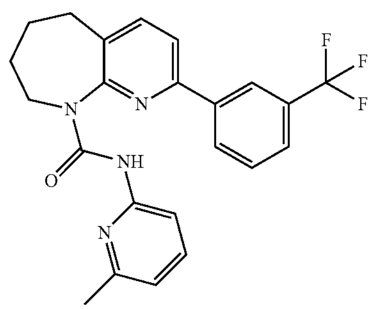 [SMILES: Cc1cccc(NC(=O)N2CCCCc3ccc(-c4cccc(C(F)(F)F)c4)nc32)n1] | C | B | NT |
| 819 | 427 | 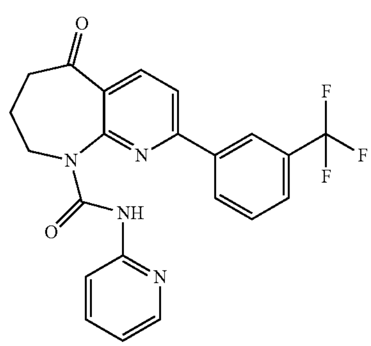 [SMILES: O=C1CCCN(C(=O)Nc2ccccn2)c2nc(-c3cccc(C(F)(F)F)c3)ccc21] | A | A | NT |
| 820 | 441 | 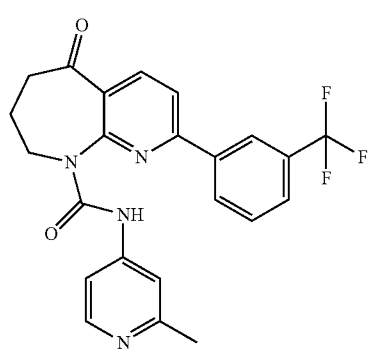 [SMILES: Cc1cc(NC(=O)N2CCCC(=O)c3ccc(-c4cccc(C(F)(F)F)c4)nc32)ccn1] | A | A | NT |

TABLE 1-continued
Compounds of Formula (I).
| Compound No. | [M + H]+ | STRUCTURE | EC1.5 µM | % FOLD ACT. | TNF IC50 µM |
|---|---|---|---|---|---|
| 821 | 445 | 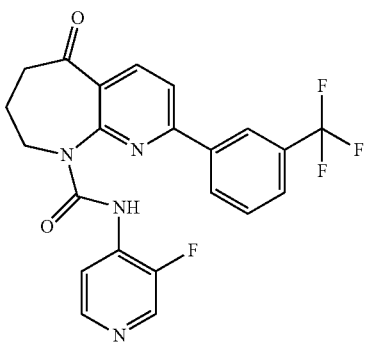 [SMILES: O=C1CCCN(C(=O)Nc2ccncc2F)c2nc(-c3cccc(C(F)(F)F)c3)ccc21] | B | A | NT |
| 822 | 453 | 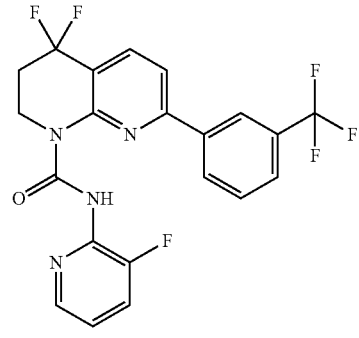 [SMILES: O=C(Nc1ncccc1F)N1CCC(F)(F)c2ccc(-c3cccc(C(F)(F)F)c3)nc21] | B | B | NT |
| 823 | 498 | 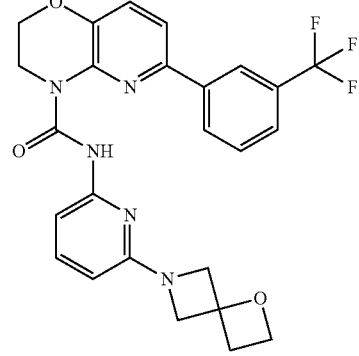 | A | A | B |
| 824 | 540 | 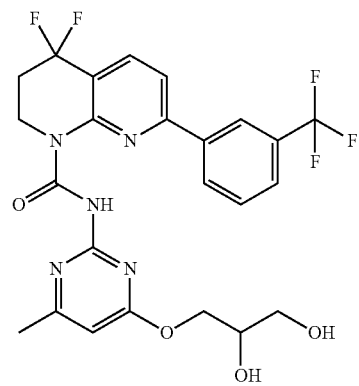 [SMILES: Cc1cc(OCC(O)CO)nc(NC(=O)N2CCC(F)(F)c3ccc(-c4cccc(C(F)(F)F)c4)nc32)n1] | B | B | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 825 | 526 | 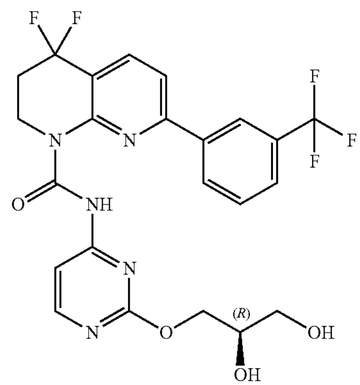 | A | A | A |
| 826 | 427 | 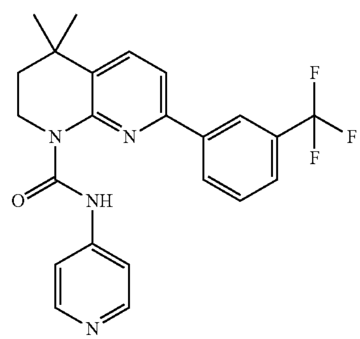 [SMILES: CC1(C)CCN(C(=O)Nc2ccncc2)c2nc(-c3cccc(C(F)(F)F)c3)ccc21] | A | A | NT |
| 827 | 427 | 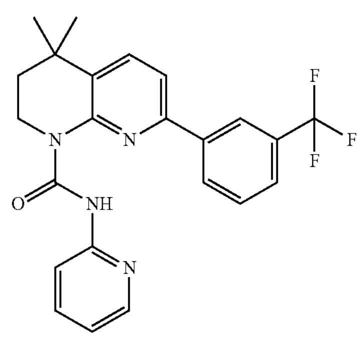 [SMILES: CC1(C)CCN(C(=O)Nc2ccccn2)c2nc(-c3cccc(C(F)(F)F)c3)ccc21] | A | A | NT |
| 828 | 427 | 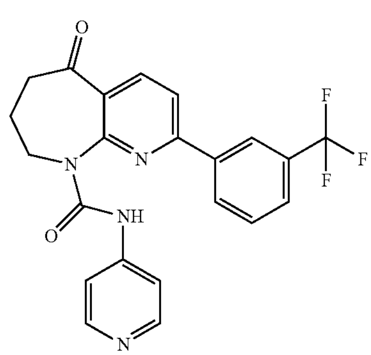 [SMILES: O=C1CCCN(C(=O)Nc2ccncc2)c2nc(-c3cccc(C(F)(F)F)c3)ccc21] | B | A | NT |

TABLE 1-continued
Compounds of Formula (I).
| Compound No. | [M + H]+ | STRUCTURE | EC1.5 µM | % FOLD ACT. | TNF IC50 µM |
|---|---|---|---|---|---|
| 829 | 427 | 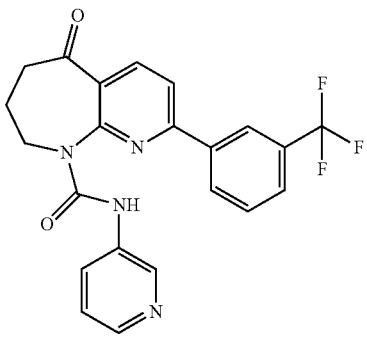 [SMILES: O=C1CCCN(C(=O)Nc2cccnc2)c2nc(-c3cccc(C(F)(F)F)c3)ccc21] | B | A | NT |
| 830 | 458 | 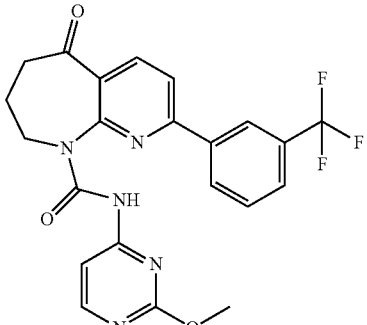 | A | A | B |
| 831 | 423 | 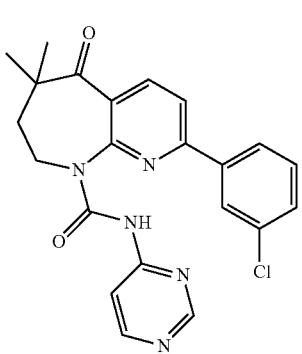 [SMILES: CC1(C)CCN(C(=O)Nc2ccncn2)c2nc(-c3cccc(Cl)c3)ccc2C1=O] | NT | NT | NT |
| 832 | 422 | 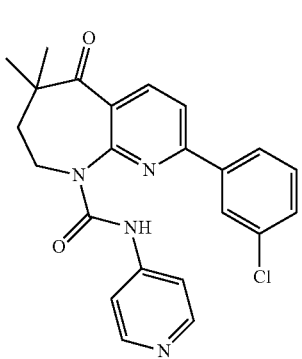 [SMILES: CC1(C)CCN(C(=O)Nc2ccncc2)c2nc(-c3cccc(Cl)c3)ccc2C1=O] | B | B | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 833 | 422 | 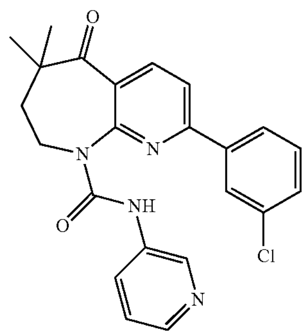 [SMILES: CC1(C)CCN(C(=O)Nc2cccnc2)c2nc(-c3cccc(Cl)c3)ccc2C1=O] | C | B | NT |
| 834 | 441 | 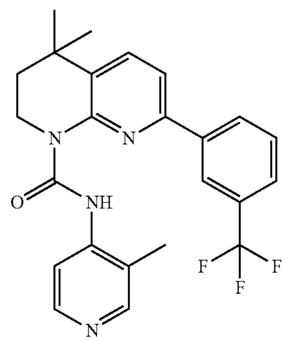 [SMILES: Cc1cnccc1NC(=O)N1CCC(C)(C)c2ccc(-c3cccc(C(F)(F)F)c3)nc21] | B | B | NT |
| 835 | 428 | 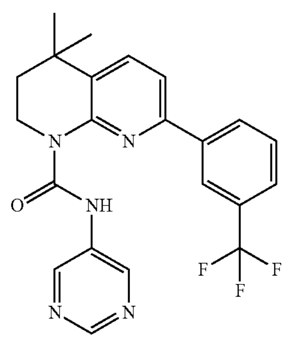 [SMILES: CC1(C)CCN(C(=O)Nc2cncnc2)c2nc(-c3cccc(C(F)(F)F)c3)ccc21] | B | A | NT |
| 836 | 440 | 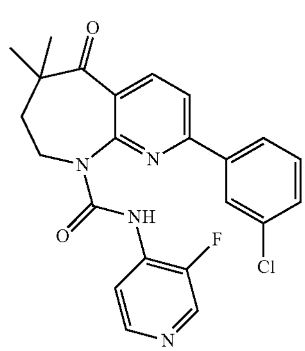 [SMILES: CC1(C)CCN(C(=O)Nc2ccncc2F)c2nc(-c3cccc(Cl)c3)ccc2C1=O] | B | B | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 837 | 442 | 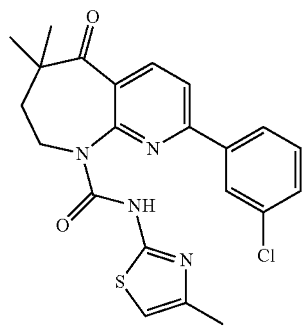 [SMILES: Cc1csc(NC(=O)N2CCC(C)(C)C(=O)c3ccc(-c4cccc(Cl)c4)nc32)n1] | B | B | NT |
| 838 | 428 | 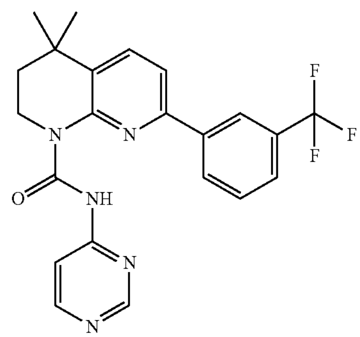 [SMILES: CC1(C)CCN(C(=O)Nc2ccncn2)c2nc(-c3cccc(C(F)(F)F)c3)ccc21] | A | A | B |
| 839 | 447 | 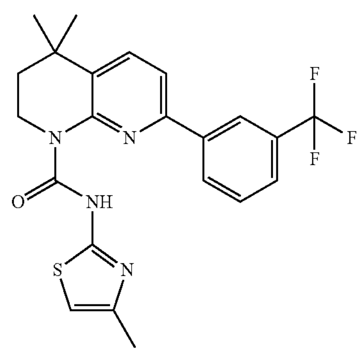 [SMILES: Cc1csc(NC(=O)N2CCC(C)(C)c3ccc(-c4cccc(C(F)(F)F)c4)nc32)n1] | A | A | A |
| 840 | 518 | 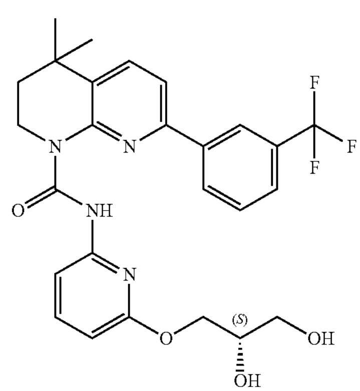 | A | A | A |

TABLE 1-continued

Compounds of Formula (I).

| Compound No. | [M + H]+ | STRUCTURE | EC1.5 µM | % FOLD ACT. | TNF IC50 µM |
|---|---|---|---|---|---|
| 841 | 524 | 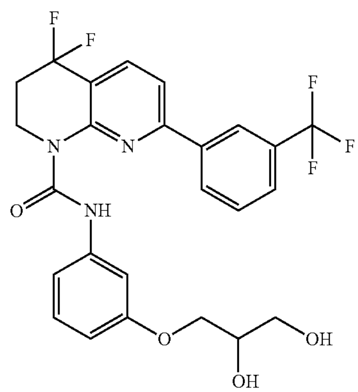 [SMILES: O=C(Nc1cccc(OCC(O)CO)c1)N1CCC(F)(F)c2ccc(-c3cccc(C(F)(F)F)c3)nc21] | A | A | NT |
| 842 | 445 | 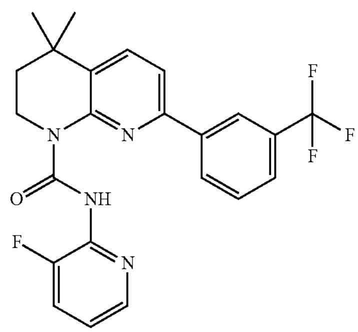 [SMILES: CC1(C)CCN(C(=O)Nc2ncccc2F)c2nc(-c3cccc(C(F)(F)F)c3)ccc21] | B | B | NT |
| 843 | 445 | 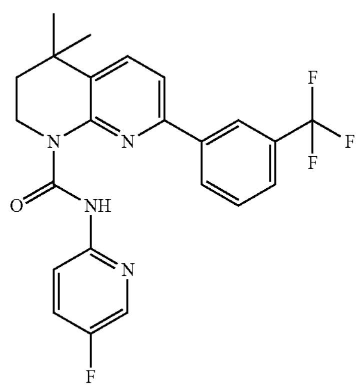 [SMILES: CC1(C)CCN(C(=O)Nc2ccc(F)cn2)c2nc(-c3cccc(C(F)(F)F)c3)ccc21] | B | B | NT |
| 844 | 533 | 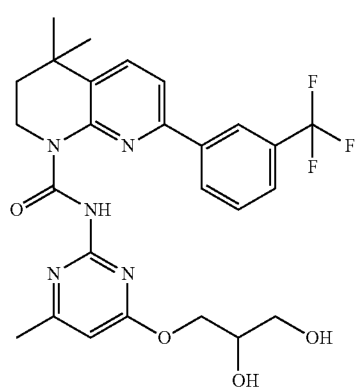 [SMILES: Cc1cc(OCC(O)CO)nc(NC(=O)N2CCC(C)(C)c3ccc(-c4cccc(C(F)(F)F)c4)nc32)n1] | B | A | NT |

TABLE 1-continued
Compounds of Formula (I).
| Compound No. | [M + H]+ | STRUCTURE | EC1.5 µM | % FOLD ACT. | TNF IC50 µM |
|---|---|---|---|---|---|
| 845 | 519 | 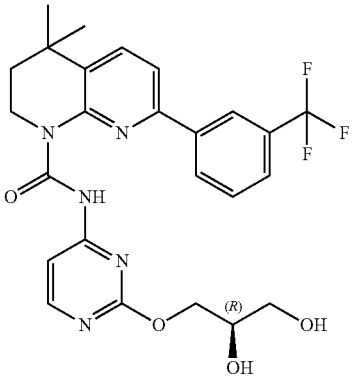 | A | A | A |
| 846 | 518 | 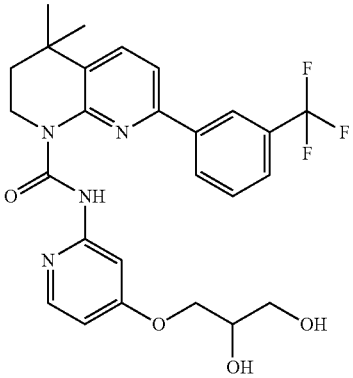 [SMILES: CC1(C)CCN(C(=O)Nc2cc(OCC(O)CO)ccn2)c2nc(-c3cccc(C(F)(F)F)c3)ccc21] | A | A | NT |
| 847 | 445 | 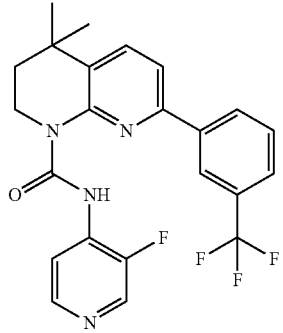 [SMILES: CC1(C)CCN(C(=O)Nc2ccncc2F)c2nc(-c3cccc(C(F)(F)F)c3)ccc21] | C | B | NT |
| 848 | 519 | 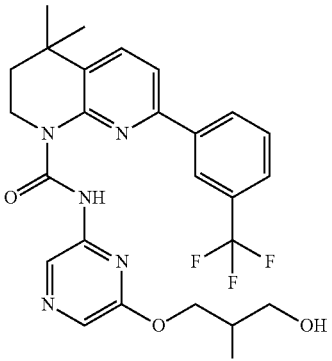 | A | A | A |

TABLE 1-continued

Compounds of Formula (I).

| Compound No. | [M + H]+ | STRUCTURE | EC1.5 µM | % FOLD ACT. | TNF IC50 µM |
|---|---|---|---|---|---|
| 849 | 385 | 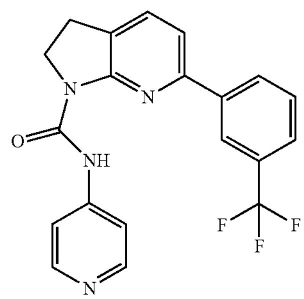 [SMILES: O=C(Nc1ccncc1)N1CCc2ccc(-c3cccc(C(F)(F)F)c3)nc21] | A | A | A |
| 850 | 386 | 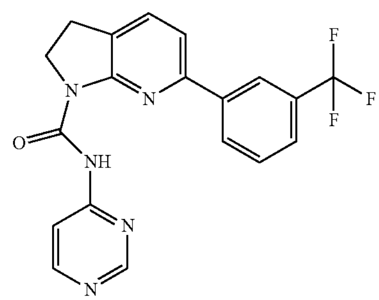 [SMILES: O=C(Nc1ccncn1)N1CCc2ccc(-c3cccc(C(F)(F)F)c3)nc21] | A | A | B |
| 851 | 405 | 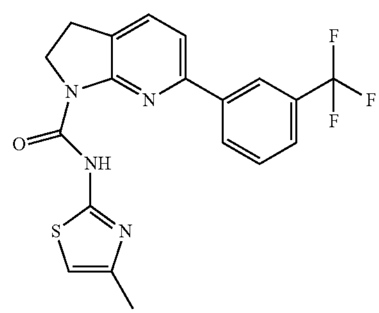 [SMILES: Cc1csc(NC(=O)N2CCc3ccc(-c4cccc(C(F)(F)F)c4)nc32)n1] | A | A | B |
| 852 | 383 | 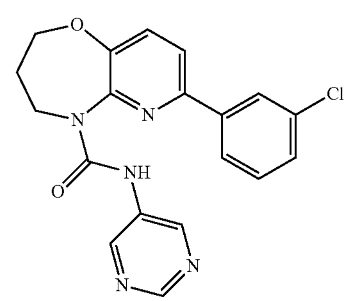 [SMILES: O=C(Nc1cncnc1)N1CCCOc2ccc(-c3cccc(Cl)c3)nc21] | B | A | NT |
| 853 | 400 | 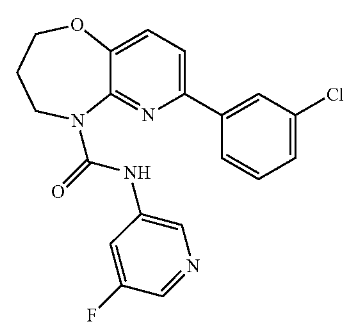 [SMILES: O=C(Nc1cncc(F)c1)N1CCCOc2ccc(-c3cccc(Cl)c3)nc21] | B | A | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 854 | 413 | 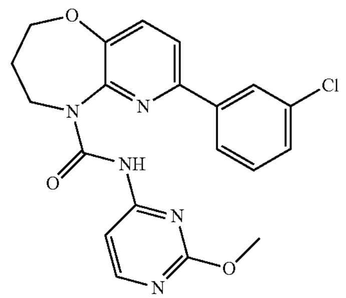 [SMILES: COc1nccc(NC(=O)N2CCCOc3ccc(-c4cccc(Cl)c4)nc32)n1] | B | A | NT |
| 855 | 396 | 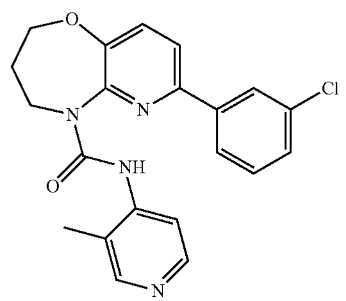 [SMILES: Cc1cnccc1NC(=O)N1CCCOc2ccc(-c3cccc(Cl)c3)nc21] | B | B | NT |
| 856 | 382 | 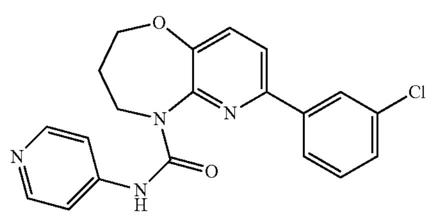 [SMILES: O=C(Nc1ccncc1)N1CCCOc2ccc(-c3cccc(Cl)c3)nc21] | B | A | NT |
| 857 | 410 | 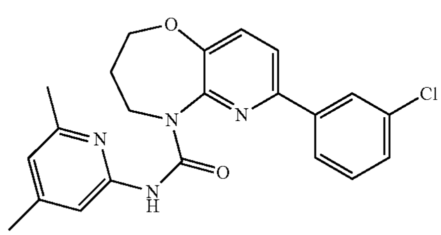 [SMILES: Cc1cc(C)nc(NC(=O)N2CCCOc3ccc(-c4cccc(Cl)c4)nc32)c1] | C | B | NT |
| 858 | 473 | 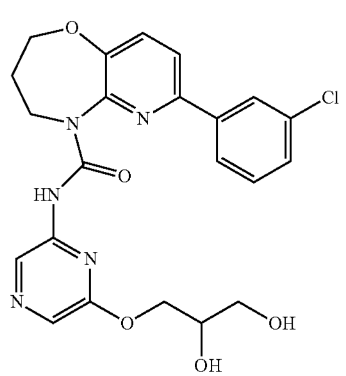 [SMILES: O=C(Nc1cncc(OCC(O)CO)n1)N1CCCOc2ccc(-c3cccc(Cl)c3)nc21] | A | A | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 859 | 487 | 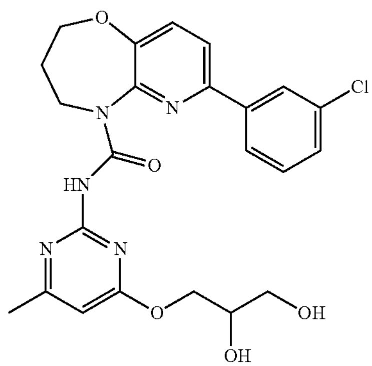 [SMILES: Cc1cc(OCC(O)CO)nc(NC(=O)N2CCCOc3ccc(-c4cccc(Cl)c4)nc32)n1] | B | A | NT |
| 860 | 525 | 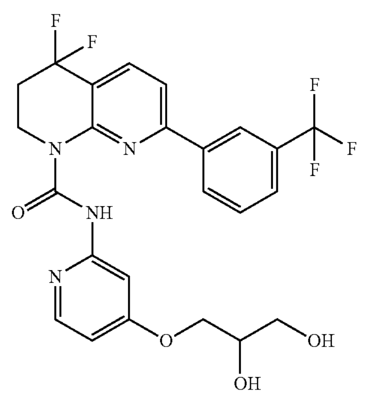 [SMILES: O=C(Nc1cc(OCC(O)CO)ccn1)N1CCC(F)(F)c2ccc(-c3cccc(C(F)(F)F)c3)nc21] | A | A | A |
| 861 | 385 | 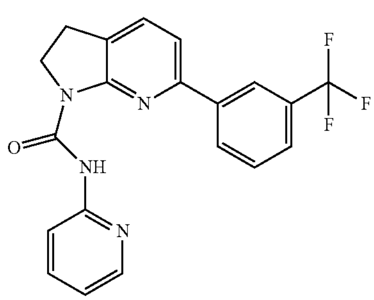 [SMILES: O=C(Nc1ccccn1)N1CCc2ccc(-c3cccc(C(F)(F)F)c3)nc21] | A | A | B |
| 862 | 403 | 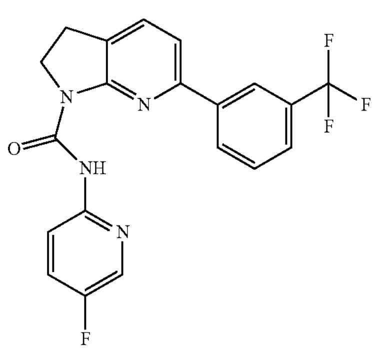 [SMILES: O=C(Nc1ccc(F)cn1)N1CCc2ccc(-c3cccc(C(F)(F)F)c3)nc21] | NT | NT | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 863 | 414 | 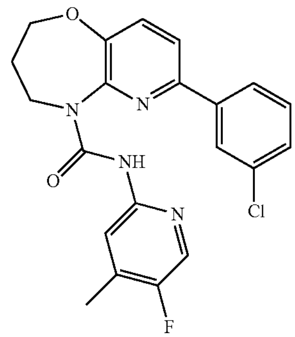 [SMILES: Cc1cc(NC(=O)N2CCCOc3ccc(-c4cccc(Cl)c4)nc32)ncc1F] | B | B | NT |
| 864 | 472 | 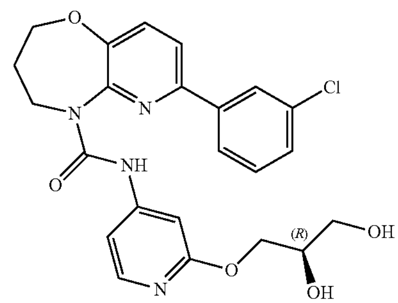 | B | A | A |
| 865 | 383 | 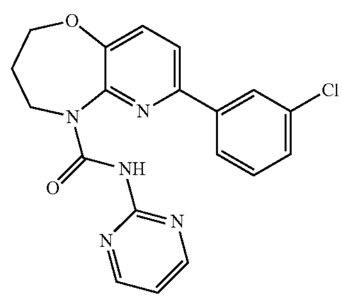 [SMILES: O=C(Nc1ncccn1)N1CCCOc2ccc(-c3cccc(Cl)c3)nc21] | B | A | NT |
| 866 | 383 | 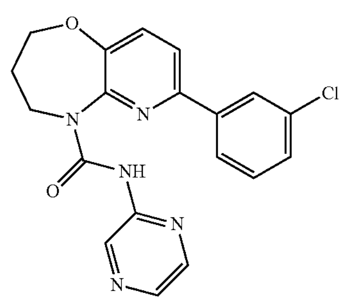 [SMILES: O=C(Nc1cnccn1)N1CCCOc2ccc(-c3cccc(Cl)c3)nc21] | B | A | NT |
| 867 | 383 | 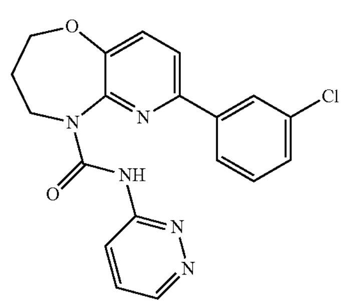 [SMILES: O=C(Nc1cccnn1)N1CCCOc2ccc(-c3cccc(Cl)c3)nc21] | B | A | NT |

TABLE 1-continued

Compounds of Formula (I).

| Compound No. | [M + H]+ | STRUCTURE | EC1.5 µM | % FOLD ACT. | TNF IC50 µM |
|---|---|---|---|---|---|
| 868 | 476 | 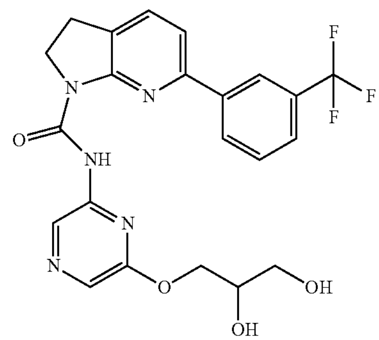 [SMILES: O=C(Nc1cncc(OCC(O)CO)n1)N1CCc2ccc(-c3cccc(C(F)(F)F)c3)nc21] | A | A | A |
| 869 | 482 | 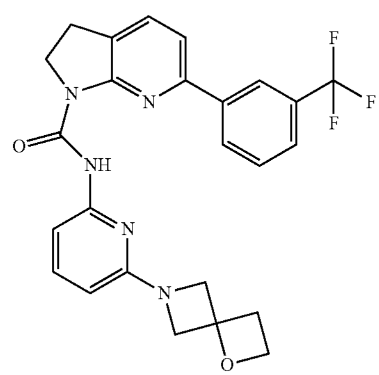 [SMILES: O=C(Nc1cccc(N2CC3(CCO3)C2)n1)N1CCc2ccc(-c3cccc(C(F)(F)F)c3)nc21] | A | A | A |
| 870 | 403 | 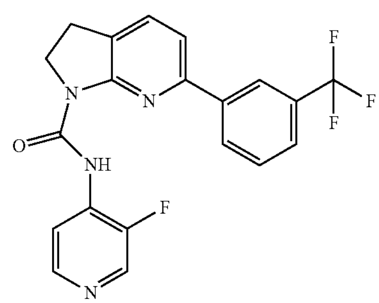 [SMILES: O=C(Nc1ccncc1F)N1CCc2ccc(-c3cccc(C(F)(F)F)c3)nc21] | A | A | A |
| 871 | 396 | 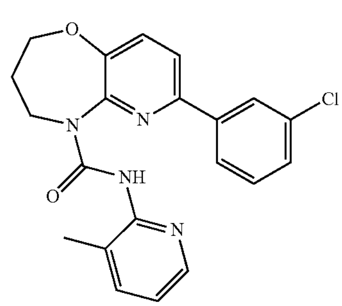 [SMILES: Cc1cccnc1NC(=O)N1CCCOc2ccc(-c3cccc(Cl)c3)nc21] | C | B | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 872 | 413 | 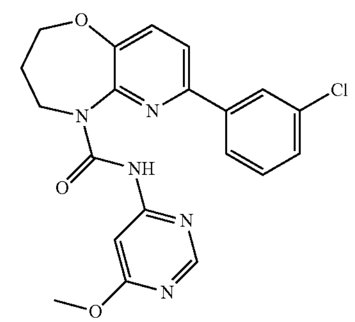 [SMILES: COc1cc(NC(=O)N2CCCOc3ccc(-c4cccc(Cl)c4)nc32)ncn1] | A | A | NT |
| 873 | 443 | 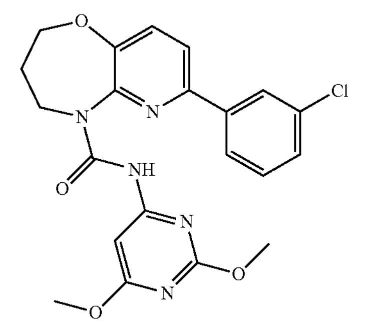 [SMILES: COc1cc(NC(=O)N2CCCOc3ccc(-c4cccc(Cl)c4)nc32)nc(OC)n1] | A | A | B |
| 874 | 476 | 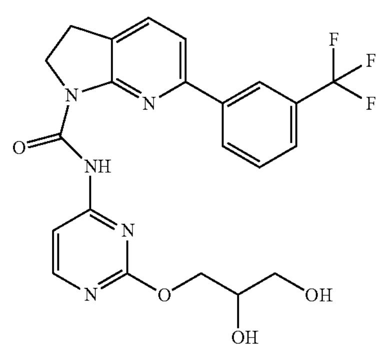 [SMILES: O=C(Nc1ccnc(OCC(O)CO)n1)N1CCc2ccc(-c3cccc(C(F)(F)F)c3)nc21] | A | A | B |
| 875 | 475 | 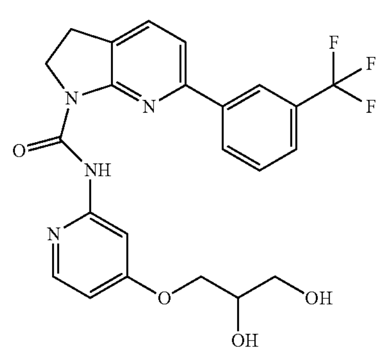 [SMILES: O=C(Nc1cc(OCC(O)CO)ccn1)N1CCc2ccc(-c3cccc(C(F)(F)F)c3)nc21] | A | A | A |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 876 | 473 | 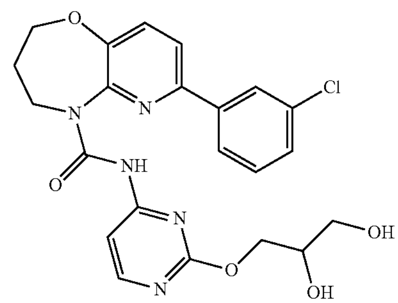 [SMILES: O=C(Nc1ccnc(OCC(O)CO)n1)N1CCCOc2ccc(-c3cccc(Cl)c3)nc21] | A | A | A |
| 877 | 482 | 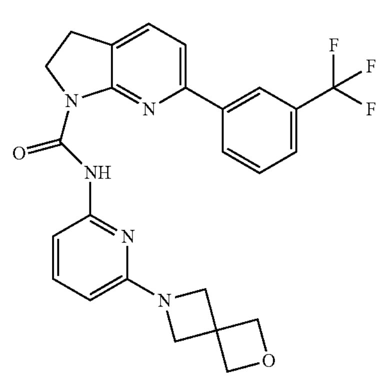 [SMILES: O=C(Nc1cccc(N2CC3(COC3)C2)n1)N1CCc2ccc(-c3cccc(C(F)(F)F)c3)nc21] | A | A | A |
| 878 | 473 | 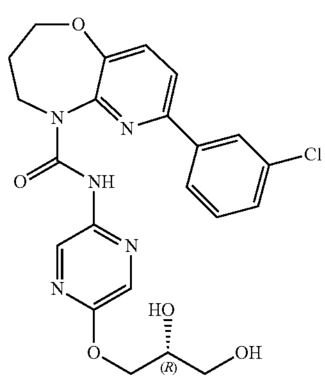 | A | A | A |
| 879 | 413 | 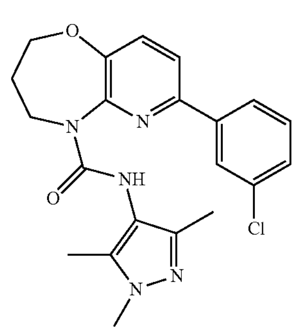 [SMILES: Cc1nn(C)c(C)c1NC(=O)N1CCCOc2ccc(-c3cccc(Cl)c3)nc21] | C | B | NT |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 880 | 421 | 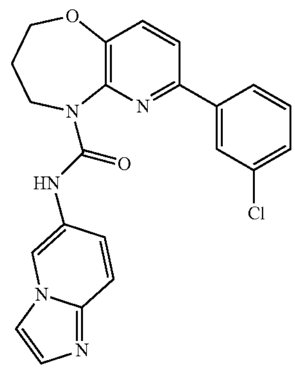 [SMILES: O=C(Nc1ccc2nccn2c1)N1CCCOc2ccc(-c3cccc(Cl)c3)nc21] | A | A | A |
| 881 | 433 | 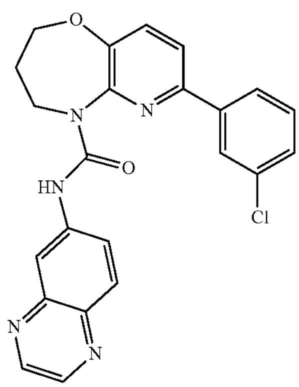 [SMILES: O=C(Nc1ccc2nccnc2c1)N1CCCOc2ccc(-c3cccc(Cl)c3)nc21] | A | A | B |
| 882 | 412 | 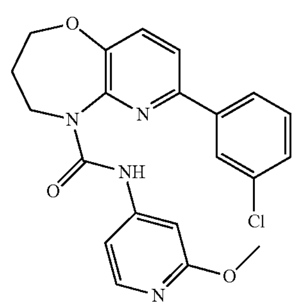 [SMILES: COc1cc(NC(=O)N2CCCOc3ccc(-c4cccc(Cl)c4)nc32)ccn1] | A | A | B |
| 883 | 435 | 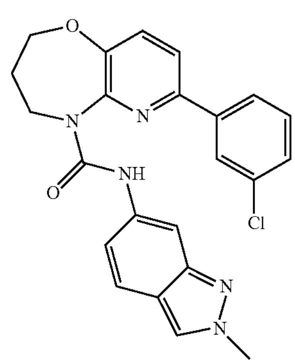 [SMILES: Cn1cc2ccc(NC(=O)N3CCCOc4ccc(-c5cccc(Cl)c5)nc43)cc2n1] | A | A | A |

TABLE 1-continued

Compounds of Formula (I).

| Compound No. | [M + H]+ | STRUCTURE | EC1.5 μM | % FOLD ACT. | TNF IC50 μM |
|---|---|---|---|---|---|
| 884 | 433 | 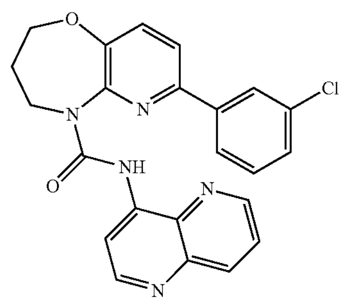 [SMILES: O=C(Nc1ccnc2cccnc12)N1CCCOc2ccc(-c3cccc(Cl)c3)nc21] | B | A | NT |
| 885 | 436 | 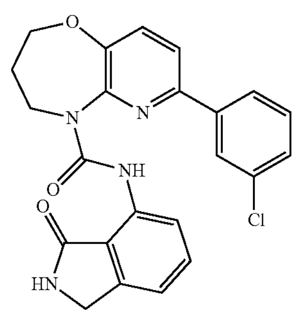 [SMILES: O=C1NCc2cccc(NC(=O)N3CCCOc4ccc(-c5cccc(Cl)c5)nc43)c21] | B | B | NT |
| 886 (400) | 332 | 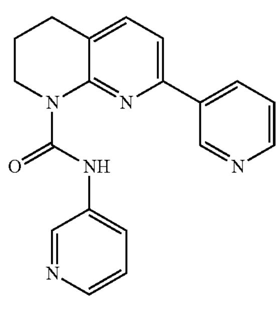 [SMILES: O=C(Nc1cccnc1)N1CCCc2ccc(-c3cccnc3)nc21] | B | A | B |
| 887 (401) | 401 | 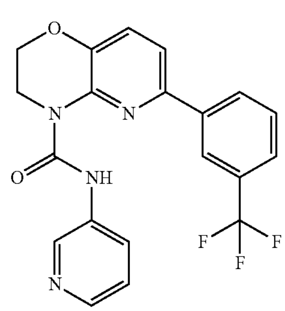 [SMILES: O=C(Nc1cccnc1)N1CCOc2ccc(-c3cccc(C(F)(F)F)c3)nc21] | A | A | B |

Compounds in Table 2 could be made using the methodology described above.

TABLE 2

| Compound No. | Calculated [M + H]+ | Structure |
|---|---|---|
| 443 | 448 | 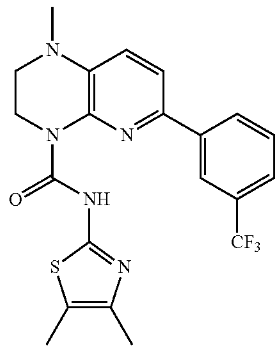 [SMILES: Cc1nc(NC(=O)N2CCN(C)c3ccc(-c4cccc(C(F)(F)F)c4)nc32)sc1C] |
| 444 | 505 | 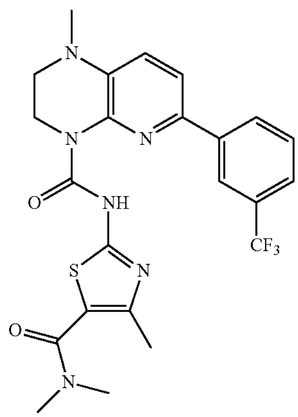 [SMILES: Cc1nc(NC(=O)N2CCN(C)c3ccc(-c4cccc(C(F)(F)F)c4)nc32)sc1C(=O)N(C)C] |
| 445 | 404 | 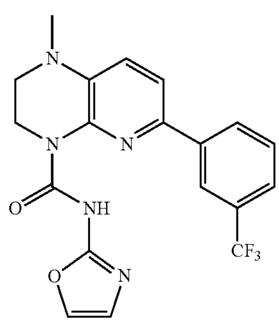 [SMILES: CN1CCN(C(=O)Nc2ncco2)c2nc(-c3cccc(C(F)(F)F)c3)ccc21] |
| 446 | 404 | 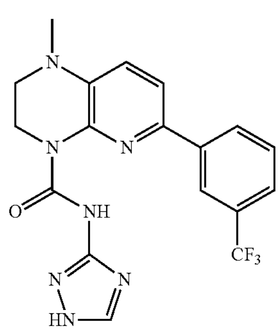 [SMILES: CN1CCN(C(=O)Nc2nc[nH]n2)c2nc(-c3cccc(C(F)(F)F)c3)ccc21] |

TABLE 2-continued

| Compound No. | Calculated [M + H]+ | Structure |
|---|---|---|
| 447 | 415 | 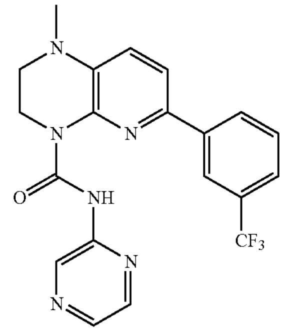 [SMILES: CN1CCN(C(=O)Nc2cnccn2)c2nc(-c3cccc(C(F)(F)F)c3)ccc21] |
| 448 | 415 | 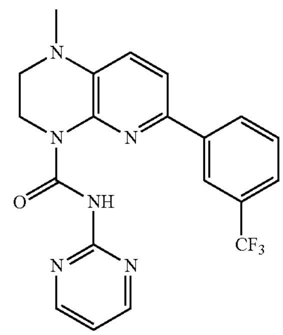 [SMILES: CN1CCN(C(=O)Nc2ncccn2)c2nc(-c3cccc(C(F)(F)F)c3)ccc21] |
| 449 | 499 | 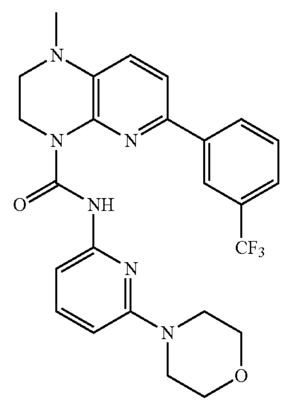 [SMILES: CN1CCN(C(=O)Nc2cccc(N3CCOCC3)n2)c2nc(-c3cccc(C(F)(F)F)c3)ccc21] |
| 450 | 462 | 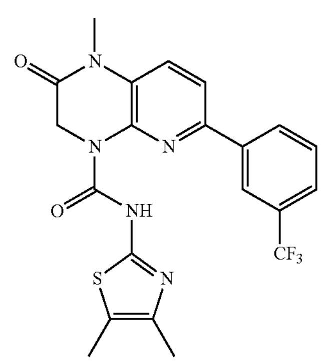 [SMILES: Cc1nc(NC(=O)N2CC(=O)N(C)c3ccc(-c4cccc(C(F)(F)F)c4)nc32)sc1C] |

TABLE 2-continued

| Compound No. | Calculated [M + H]⁺ | Structure |
|---|---|---|
| 451 | 448 | 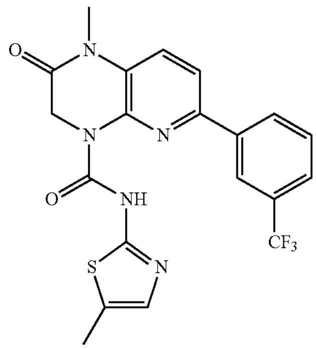 [SMILES: Cc1cnc(NC(=O)N2CC(=O)N(C)c3ccc(-c4cccc(C(F)(F)F)c4)nc32)s1] |
| 452 | 519 | 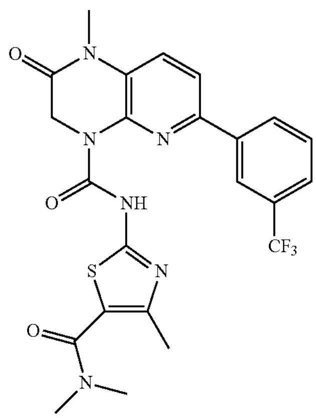 [SMILES: Cc1nc(NC(=O)N2CC(=O)N(C)c3ccc(-c4cccc(C(F)(F)F)c4)nc32)sc1C(=O)N(C)C] |
| 453 | 456 | 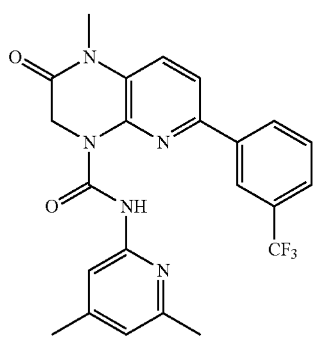 [SMILES: Cc1cc(C)nc(NC(=O)N2CC(=O)N(C)c3ccc(-c4cccc(C(F)(F)F)c4)nc32)c1] |
| 454 | 429 | 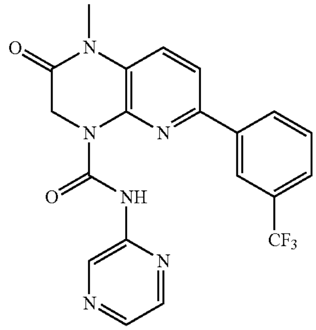 [SMILES: CN1C(=O)CN(C(=O)Nc2cnccn2)c2nc(-c3cccc(C(F)(F)F)c3)ccc21] |
| 455 | 429 | 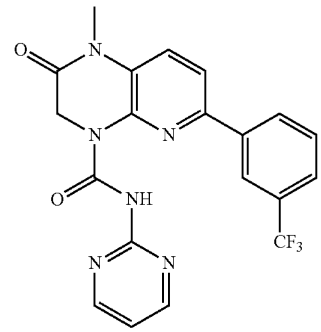 [SMILES: CN1C(=O)CN(C(=O)Nc2ncccn2)c2nc(-c3cccc(C(F)(F)F)c3)ccc21] |
| 456 | 483 | 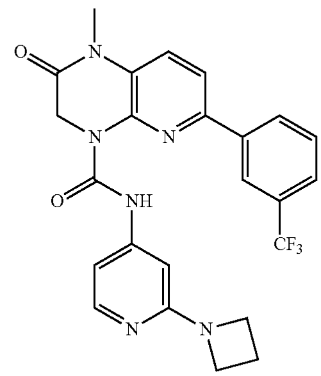 [SMILES: CN1C(=O)CN(C(=O)Nc2ccnc(N3CCC3)c2)c2nc(-c3cccc(C(F)(F)F)c3)ccc21] |
| 457 | 527 | 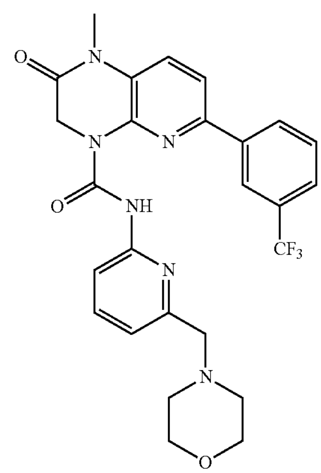 [SMILES: CN1C(=O)CN(C(=O)Nc2cccc(CN3CCOCC3)n2)c2nc(-c3cccc(C(F)(F)F)c3)ccc21] |
| 459 | 483 | 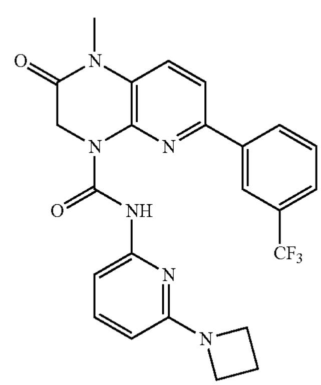 [SMILES: CN1C(=O)CN(C(=O)Nc2cccc(N3CCC3)n2)c2nc(-c3cccc(C(F)(F)F)c3)ccc21] |

TABLE 2-continued

| Compound No. | Calculated [M + H]+ | Structure |
|---|---|---|
| 471 | 469 | (structure) |
| 490 | 415 | (structure) |
| 491 | 365 | (structure) |
| 493 | 487 | (structure) |
| 494 | 437 | (structure) |
| 495 | 438 | (structure) |

In one embodiment, the compound of the invention is selected from any one of Compound Numbers 500, 501, 502, 503, 506, 507, 508, 510, 511, 513, 514, 517, 519, 529, 531, 533, 535, 536, 537, 538, 539, 541, 547, 548, 549, 551, 554, 556, 557, 559, 560, 563, 566, 570, 571, 574, 578, 579, 585, 586, 587, 588, 589, 590, 591, 592, 593, 594, 595, 596, 597, 598, 599, 600, 601, 602, 603, 604, 605, 607, 608, 609, 611, 612, 613, 614, 615, 616, 617, 618, 619, 620, 622, 623, 624, 625, 626, 631, 638, 639, 644, 645, 646, 647, 648, 649, 651, 652, 653, 654, 658, 659, 660, 661, 662, 663, 664, 666, 668, 669, 670, 671, 673, 675, 678, 679, 682, 683, 684, 685, 686, 687, 688, 689, 690, 691, 692, 695, 696, 697, 699, 700, 701, 702, 703, 707, 710, 711, 713, 726, 742, 745, 748, 750, 768, 785, 786, 787, 793, 794, 795, 801, 802, 804, 805, 813, 819, 820, 823, 825, 826, 827, 830, 838, 839, 840, 841, 845, 846, 848, 849, 850, 851, 858, 860, 861, 868, 869, 870, 872, 873, 874, 875, 876, 877, 878, 880, 881, 882, 883 and 887

EQUIVALENTS

The present invention provides among other things sirtuin-activating compounds and methods of use thereof. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) (www.tigr.org) and/or the National Center for Biotechnology Information (NCBI) (www.ncbi.nlm.nih.gov).

The invention claimed is:
1. A compound of Formula (I):

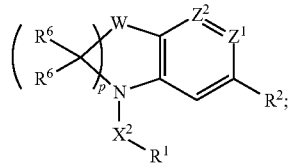

(I)

wherein:
each $Z^1$ and $Z^2$ independently is selected from N and CR;
wherein:
at least one of $Z^1$ and $Z^2$ is CR; and
each R independently is selected from hydrogen, halo, —OH, —C≡N, fluoro-substituted $C_1$-$C_2$ alkyl, —O—($C_1$-$C_2$) fluoro-substituted alkyl, —S—($C_1$-$C_2$) fluoro-substituted alkyl, $C_1$-$C_4$ alkyl, —O—($C_1$-$C_4$) alkyl, —S—($C_1$-$C_4$) alkyl; $C_3$-$C_7$ cycloalkyl, —($C_1$-$C_2$) alkyl-N($R^3$)($R^3$), —O—CH$_2$CH(OH)CH$_2$OH, —O—($C_1$-$C_3$) alkyl-N($R^3$)($R^3$), and —N($R^3$)($R^3$);
W is —N($C_1$-$C_4$ alkyl)-;
each $R^6$ is independently selected from hydrogen, $C_1$-$C_4$ alkyl and fluoro-substituted $C_1$-$C_4$ alkyl; or
two $R^6$ bound to the same carbon atom are taken together to form =O;
$R^1$ is selected from an aliphatic carbocycle and a heterocycle;
wherein:
$R^1$ is optionally substituted with one or more substituents independently selected from halo, —C≡N, $C_1$-$C_4$ alkyl, =O, $C_3$-$C_7$ cycloalkyl, fluoro-substituted $C_1$-$C_2$ alkyl, —O—$R^3$, —S—$R^3$, —($C_1$-$C_4$ alkyl)-N($R^3$)($R^3$), —N($R^3$)($R^3$), —O—($C_1$-$C_4$ alkyl)-N($R^3$)($R^3$), —($C_1$-$C_4$ alkyl)-O—($C_1$-$C_4$ alkyl)-N($R^3$)($R^3$), —C(O)—N($R^3$)($R^3$), and —($C_1$-$C_4$ alkyl)-C(O)—N($R^3$)($R^3$);
$R^2$ is selected from a carbocycle and a heterocycle;
wherein:
$R^2$ is optionally substituted with one or more substituents independently selected from halo, —C≡N, $C_1$-$C_4$ alkyl, $C_3$-$C_7$ cycloalkyl, $C_1$-$C_2$ fluoro-substituted alkyl, —O—$R^3$, —S—$R^3$, —SO$_2$—$R^3$, =O, —($C_1$-$C_4$ alkyl)-N($R^3$)($R^3$), —N($R^3$)($R^3$), —O—($C_1$-$C_4$ alkyl)-N($R^3$)($R^3$), —($C_1$-$C_4$ alkyl)-O—($C_1$-$C_4$ alkyl)-N($R^3$)($R^3$), —C(O)—N($R^3$)($R^3$), —($C_1$-$C_4$ alkyl)-C(O)—N($R^3$)($R^3$), —O-phenyl, phenyl, and a second heterocycle, and when $R^2$ is phenyl;
$R^2$ is also optionally substituted with —O-(saturated heterocycle), 3,4-methylenedioxy, fluoro-substituted 3,4-methylenedioxy, 3,4-ethylenedioxy, or fluoro-substituted 3,4-ethylenedioxy, wherein any phenyl, saturated heterocycle, or second heterocycle substituent of $R^2$ is optionally substituted with halo, —C≡N, $C_1$-$C_4$ alkyl, fluoro-substituted $C_1$-$C_2$ alkyl, —O—($C_1$-$C_2$) fluoro-substituted alkyl, —O—($C_1$-$C_4$) alkyl, —S—($C_1$-$C_4$) alkyl, —S—($C_1$-$C_2$) fluoro-substituted alkyl, —NH—($C_1$-$C_4$) alkyl, and —N—($C_1$-$C_4$)$_2$ alkyl;
each $R^3$ is independently selected from hydrogen and —$C_1$-$C_4$ alkyl; or
two $R^3$ are taken together with the nitrogen atom to which they are bound to form a 4- to 8-membered saturated heterocycle optionally comprising one additional heteroatom selected from N, S, S(=O), S(=O)$_2$, and O;
wherein:
when $R^3$ is alkyl, the alkyl is optionally substituted with one or more substituents selected from —OH, fluoro, —NH$_2$, —NH($C_1$-$C_4$ alkyl), —N($C_1$-$C_4$ alkyl)$_2$, —NH(CH$_2$CH$_2$OCH$_3$), and —N(CH$_2$CH$_2$OCH$_3$)$_2$ and
when two $R^3$ are taken together with the nitrogen atom to which they are bound to form a 4- to 8-membered saturated heterocycle, the saturated heterocycle is optionally substituted at any carbon atom with —OH, —$C_1$-$C_4$ alkyl, fluoro, —NH$_2$, —NH($C_1$-$C_4$ alkyl), —N($C_1$-$C_4$ alkyl)$_2$, —NH(CH$_2$CH$_2$OCH$_3$), or —N(CH$_2$CH$_2$OCH$_3$)$_2$; and optionally substituted at any substitutable nitrogen atom with hydrogen, —$C_1$-$C_4$ alkyl, fluoro-substituted $C_1$-$C_4$ alkyl, or —(CH$_2$)$_2$—O—CH$_3$;
p is 2; and
$X^2$ is selected from —C(=O)-†, —C(=O)—O†, —S(=O)$_2$-†, and —C(=O)—NH-†,
wherein:
† represents where $X^2$ is bound to $R^1$; and
a corresponding tautomer or a pharmaceutically acceptable salt thereof.

2. A compound of Formula (VI):

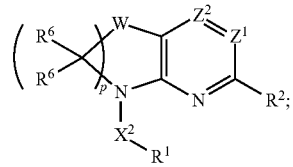

(VI)

wherein:
each of $Z^1$ and $Z^2$ is independently selected from N and CR;
wherein:
at least one of $Z^1$ and $Z^2$ is CR; and
each R is independently selected from hydrogen, halo, —OH, —C≡N, fluoro-substituted $C_1$-$C_2$ alkyl, —O—($C_1$-$C_2$) fluoro-substituted alkyl, —S—($C_1$-$C_2$) fluoro-substituted alkyl, $C_1$-$C_4$ alkyl, —O—($C_1$-$C_4$) alkyl, —S—($C_1$-$C_4$) alkyl; $C_3$-$C_7$ cycloalkyl, —($C_1$-$C_2$) alkyl-N($R^3$)($R^3$), —O—CH$_2$CH(OH)CH$_2$OH, —O—($C_1$-$C_3$) alkyl-N($R^3$)($R^3$), and —N($R^3$)($R^3$);
W is —N($C_1$-$C_4$ alkyl)-;
wherein:
each $R^6$ is independently selected from hydrogen, halogen, $C_1$-$C_4$ alkyl and fluoro-substituted $C_1$-$C_4$ alkyl, or two $R^6$ bound to the same carbon atom are taken together to form =O,
$R^1$ is substituted with a spiro bicycle;
wherein:
$R^1$ is optionally further substituted with one or more substituents independently selected from halo, —C≡N, $C_1$-$C_4$ alkyl, =O, $C_3$-$C_7$ cycloalkyl, fluoro-substituted $C_1$-$C_2$ alkyl, —O—$R^3$, —S—$R^3$, —($C_1$-$C_4$ alkyl)-N($R^3$)($R^3$), —N($R^3$)($R^3$), —O—($C_1$-$C_4$ alkyl)-N($R^3$)($R^3$), —($C_1$-$C_4$ alkyl)-O—($C_1$-$C_4$ alkyl)-N($R^3$)($R^3$), —C(O)—N($R^3$)($R^3$), and —($C_1$-$C_4$ alkyl)-C(O)—N($R^3$)($R^3$); and when $R^1$ is phenyl, $R^1$ is also optionally further substituted with —O-(saturated heterocycle), —O-(fluoro-substituted saturated heterocycle), $C_1$-$C_4$ alkyl-substituted saturated heterocycle, 3,4-methylenedioxy, fluoro-substituted 3,4-methylenedioxy, 3,4-ethylenedioxy, or fluoro-substituted 3,4-ethylenedioxy;

$R^2$ is selected from a carbocycle and a heterocycle; wherein:

$R^2$ is optionally substituted with one or more substituents independently selected from halo, —C≡N, $C_1$-$C_4$ alkyl, $C_3$-$C_7$ cycloalkyl, $C_1$-$C_2$ fluoro-substituted alkyl, —O—$R^3$, —S—$R^3$, —$SO_2$—$R^3$, =O, —($C_1$-$C_4$ alkyl)-N($R^3$)($R^3$), —N($R^3$)($R^3$), —O—($C_1$-$C_4$ alkyl)-N($R^3$)($R^3$), —($C_1$-$C_4$ alkyl)-O—($C_1$-$C_4$ alkyl)-N($R^3$)($R^3$), —C(O)—N($R^3$)($R^3$), —($C_1$-$C_4$ alkyl)-C(O)—N($R^3$)($R^3$), —O-phenyl, phenyl, and a second heterocycle;

when $R^2$ is phenyl, $R^2$ is also optionally substituted with —O-(saturated heterocycle), 3,4-methylenedioxy, fluoro-substituted 3,4-methylenedioxy, 3,4-ethylenedioxy, or fluoro-substituted 3,4-ethylenedioxy;

wherein:

any phenyl, saturated heterocycle, or second heterocycle substituent of $R^2$ is optionally substituted with halo, —C≡N, $C_1$-$C_4$ alkyl, fluoro-substituted $C_1$-$C_2$ alkyl, —O—($C_1$-$C_2$) fluoro-substituted alkyl, —O—($C_1$-$C_4$) alkyl, —S—($C_1$-$C_4$) alkyl, —S—($C_1$-$C_2$) fluoro-substituted alkyl, —NH—($C_1$-$C_4$) alkyl, and —N—($C_1$-$C_4$)$_2$ alkyl;

each $R^3$ is independently selected from hydrogen and —$C_1$-$C_4$ alkyl; or two $R^3$ are taken together with the nitrogen atom to which they are bound to form a 4- to 8-membered saturated heterocycle optionally comprising one additional heteroatom selected from N, S, S(=O), S(=O)$_2$, and O;

wherein:

when $R^3$ is alkyl, the alkyl is optionally substituted with one or more substituents selected from —OH, fluoro, —$NH_2$, —NH($C_1$-$C_4$ alkyl), —N($C_1$-$C_4$ alkyl)$_2$, —NH($CH_2CH_2OCH_3$), and —N($CH_2CH_2OCH_3$)$_2$;

when two $R^3$ are taken together with the nitrogen atom to which they are bound to form a 4- to 8-membered saturated heterocycle, the saturated heterocycle is optionally substituted at any carbon atom with —OH, —$C_1$-$C_4$ alkyl, fluoro, —$NH_2$, —NH($C_1$-$C_4$ alkyl), —N($C_1$-$C_4$ alkyl)$_2$, —NH($CH_2CH_2OCH_3$), or —N($CH_2CH_2OCH_3$)$_2$; and optionally substituted at any substitutable nitrogen atom with hydrogen, —$C_1$-$C_4$ alkyl, fluoro-substituted $C_1$-$C_4$ alkyl, or —($CH_2$)$_2$—O—$CH_3$;

p is 2;

$X^2$ is selected from —C(=O)-†, —C(=O)—O†, —S(=O)$_2$-†, and —C(=O)—NH-†;

wherein:

† represents where $X^2$ is bound to $R^1$; or a corresponding tautomer or pharmaceutically acceptable salt thereof.

3. The compound of claim 1, wherein $R^1$ is a heterocycle.

4. The compound of claim 1, wherein the compound is represented by the following Structural Formula:

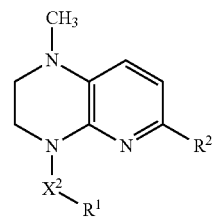

and wherein:

$X^2$ is as defined in claim 1.

5. The compound of claim 1, wherein $R^1$ is selected from:

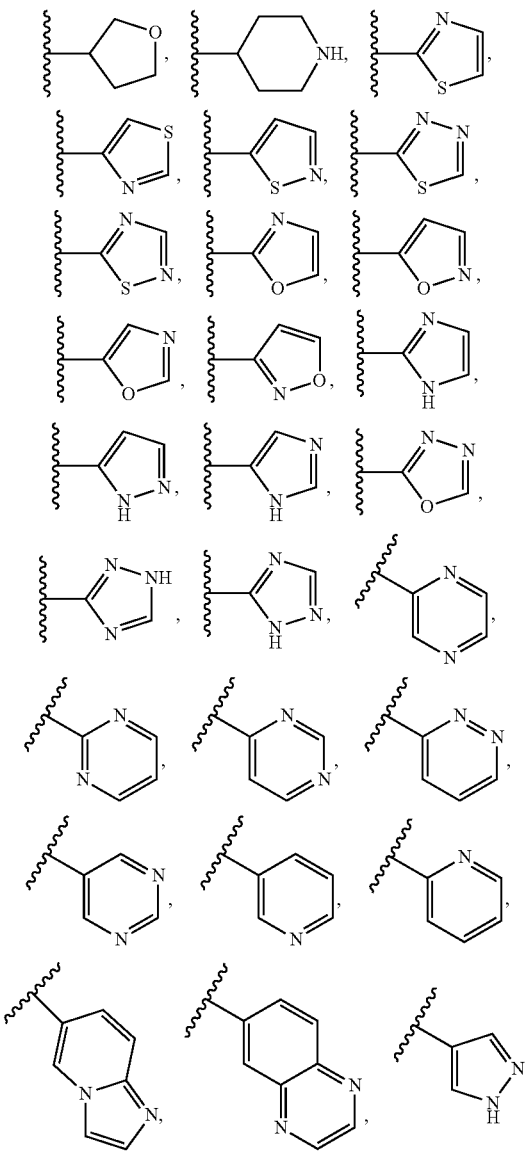

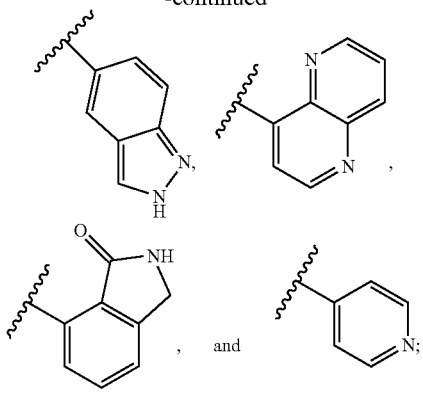
wherein:
R[1] is optionally substituted with one or more substituents independently selected from halo, $C_1$-$C_4$ alkyl, fluoro-substituted $C_1$-$C_2$ alkyl, —($C_1$-$C_4$ alkyl)-N(R[3])(R[3]), —N(R[3])(R[3]), —C(O)—N(R[3])(R[3]), =O, and —O—R[3].
6. The compound of claim 5, wherein R[1] is substituted with one or more groups independently selected from —F, —Cl, —CH$_3$, —OCH$_3$,
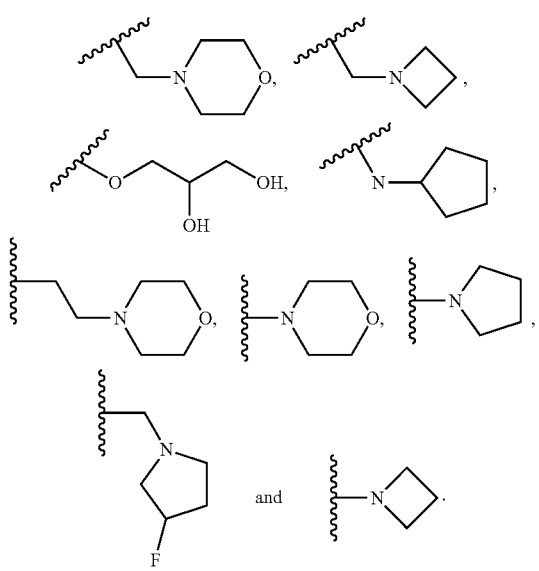
7. The compound of claim 1, wherein R[1] is selected from:
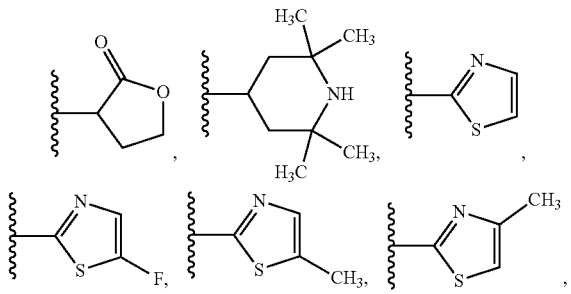
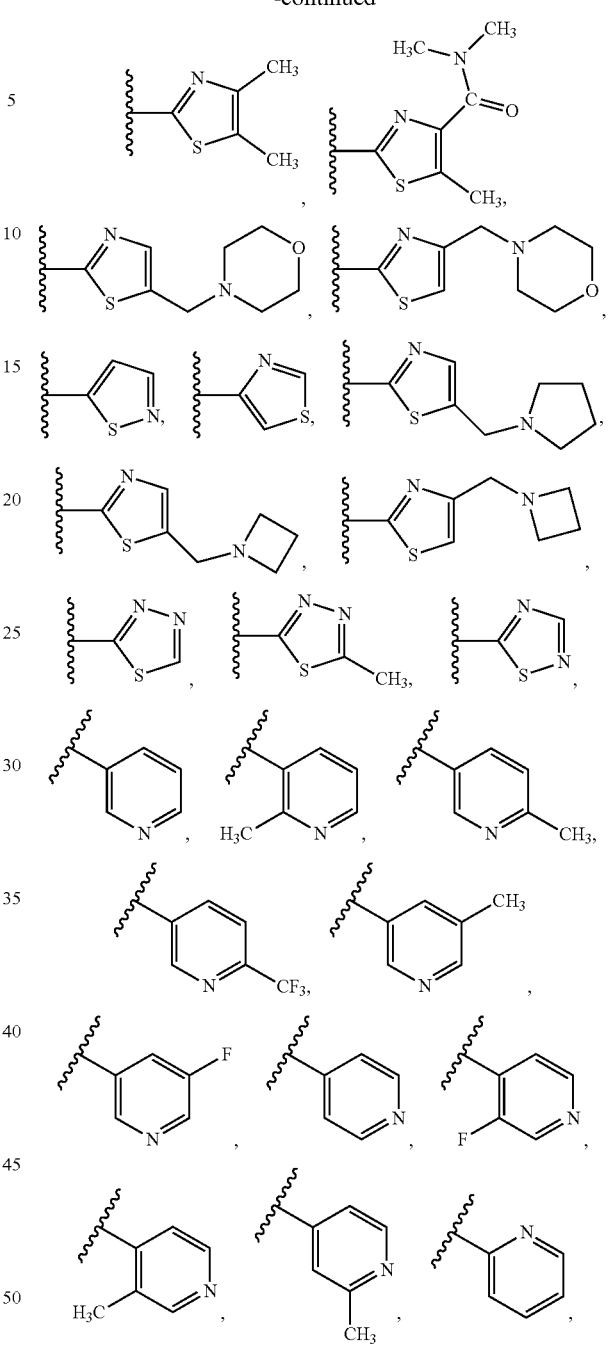

363
-continued
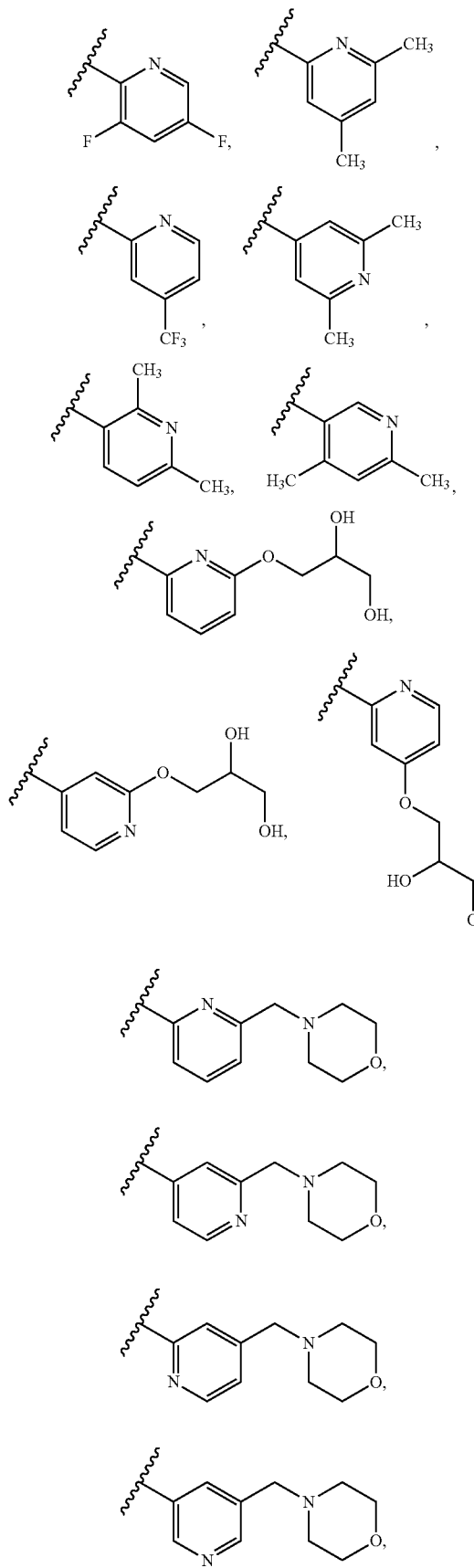
364
-continued
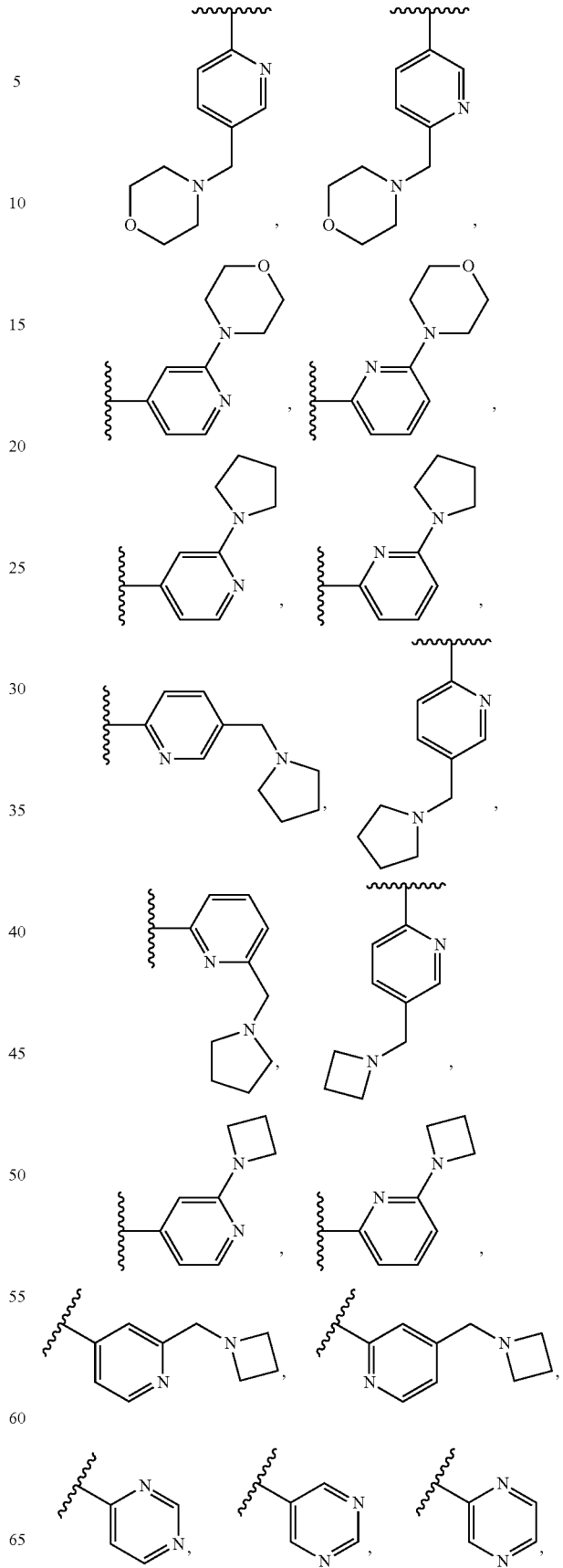

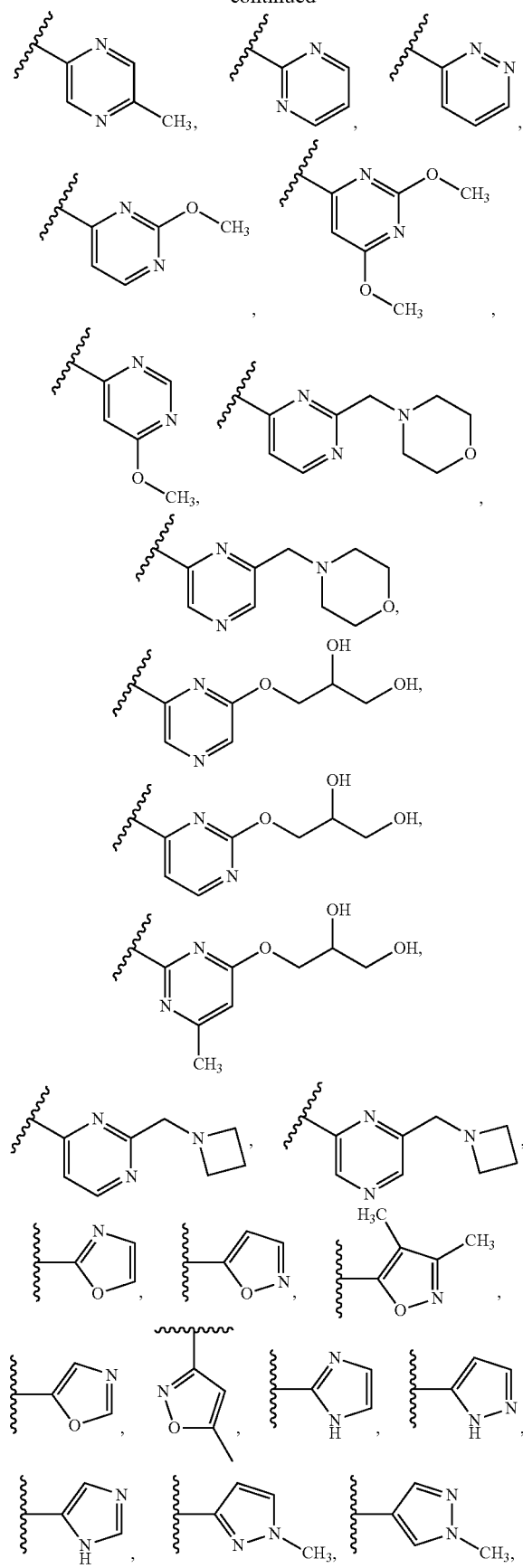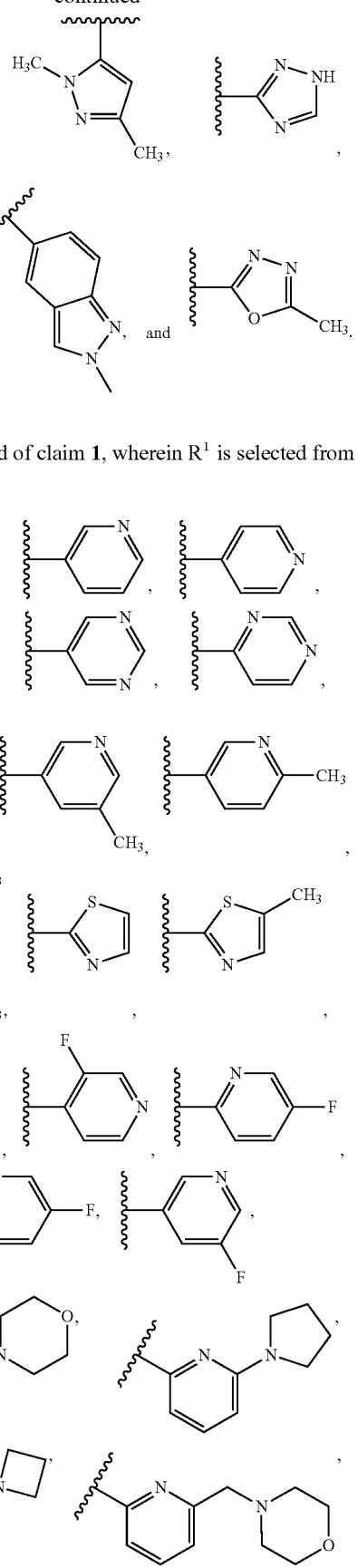
8. The compound of claim 1, wherein $R^1$ is selected from 367
-continued

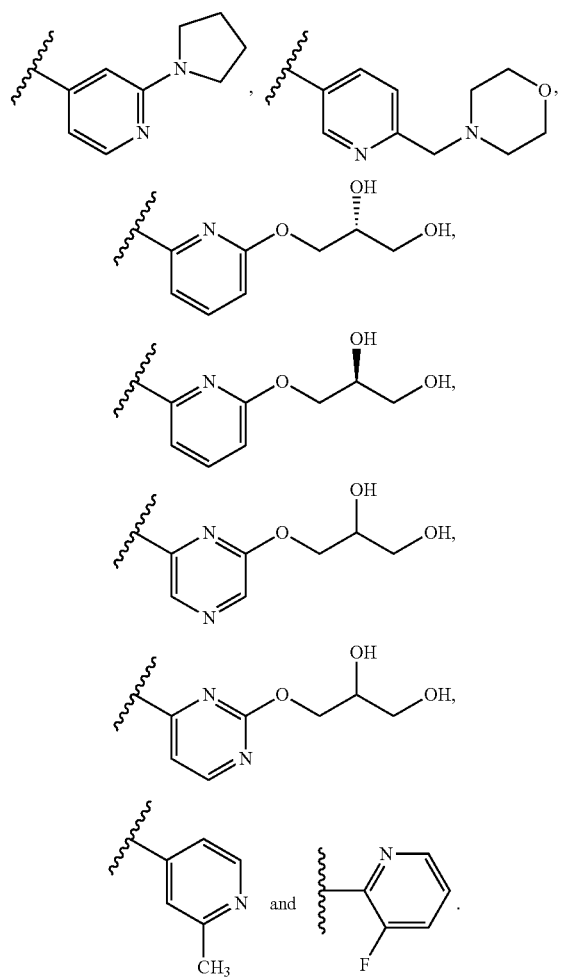

9. The compound of claim 1, wherein $R^2$ is selected from:

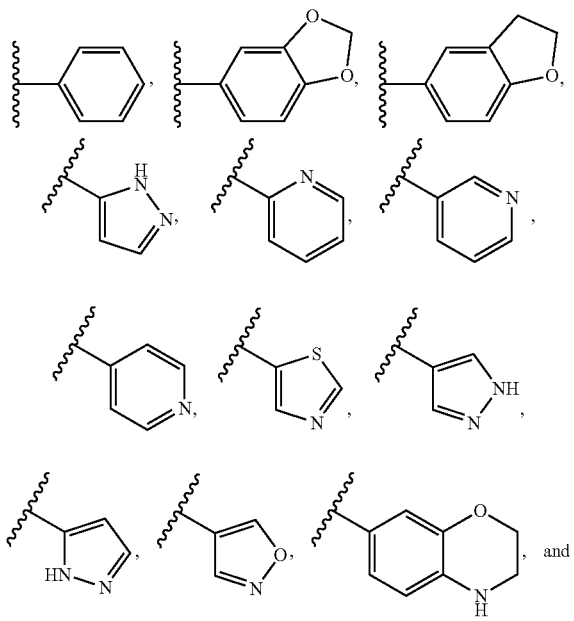

368
-continued

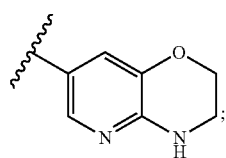

wherein:
R² is optionally substituted with one or more groups independently selected from halo, $C_1$-$C_4$ alkyl, —($C_1$-$C_4$ alkyl)-N($R^3$)($R^3$), $C_1$-$C_2$ fluoro-substituted alkyl, —O—$R^3$, —SO$_2$—$R^3$, —N($R^3$)($R^3$), and —O—($C_1$-$C_4$ alkyl)-N($R^3$)($R^3$).

10. The compound of claim 1, wherein $R^2$ is optionally substituted with one or more groups independently selected from =O, —F, —Cl, —CN, —CH$_3$, —OCH$_3$, —CF$_2$H, —N(CH$_3$)$_2$, —CH$_2$N(CH$_3$)$_2$,

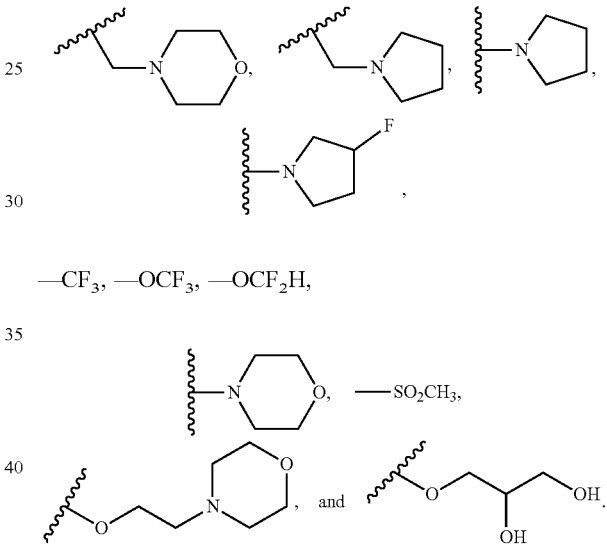

—CF$_3$, —OCF$_3$, —OCF$_2$H,

11. The compound of claim 1, wherein $R^2$ is selected from:

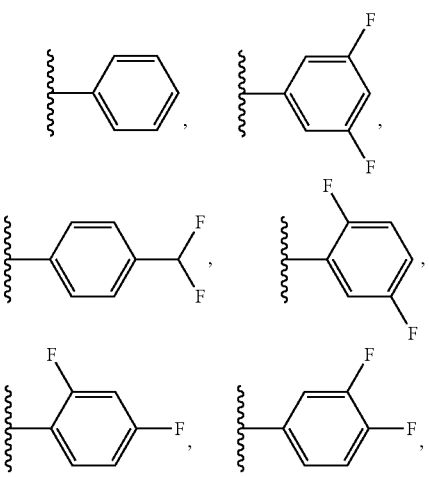

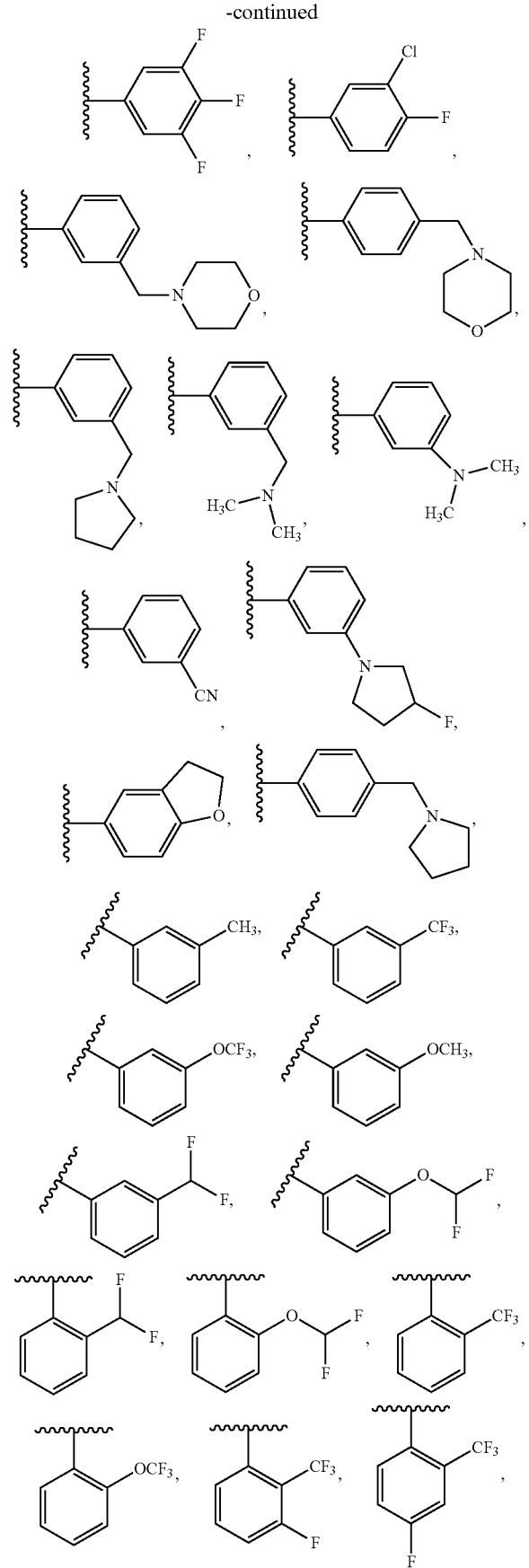
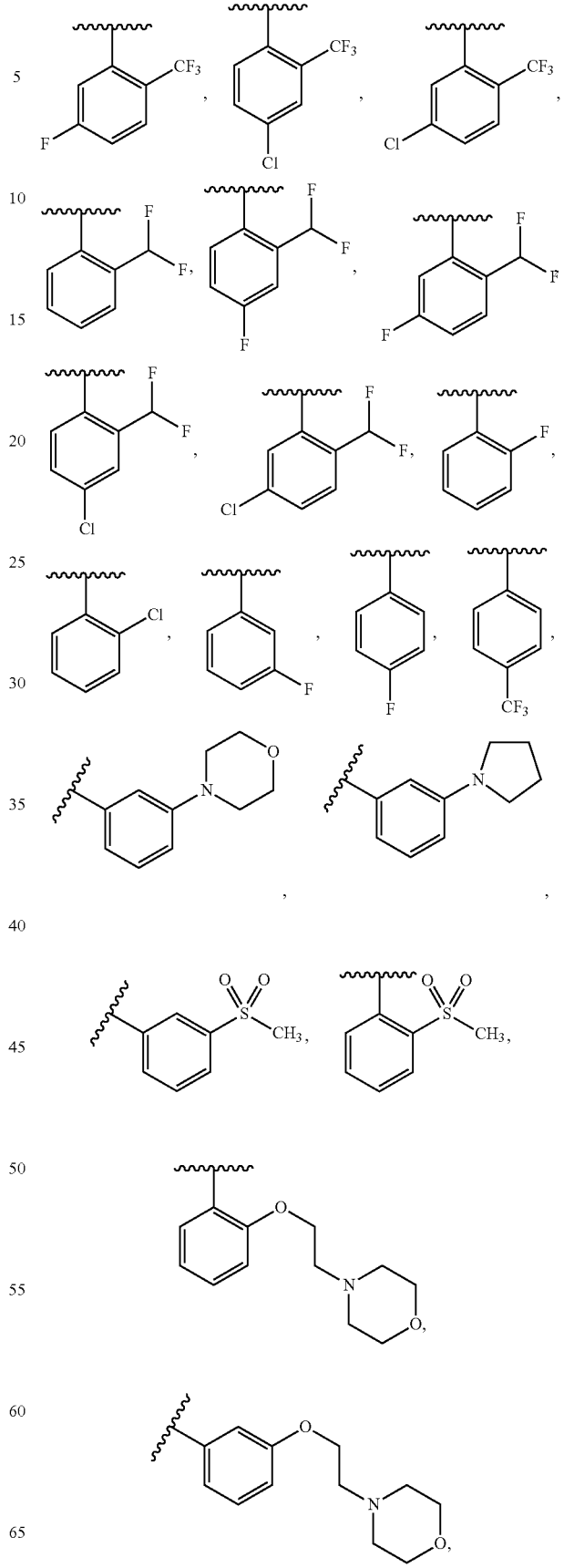

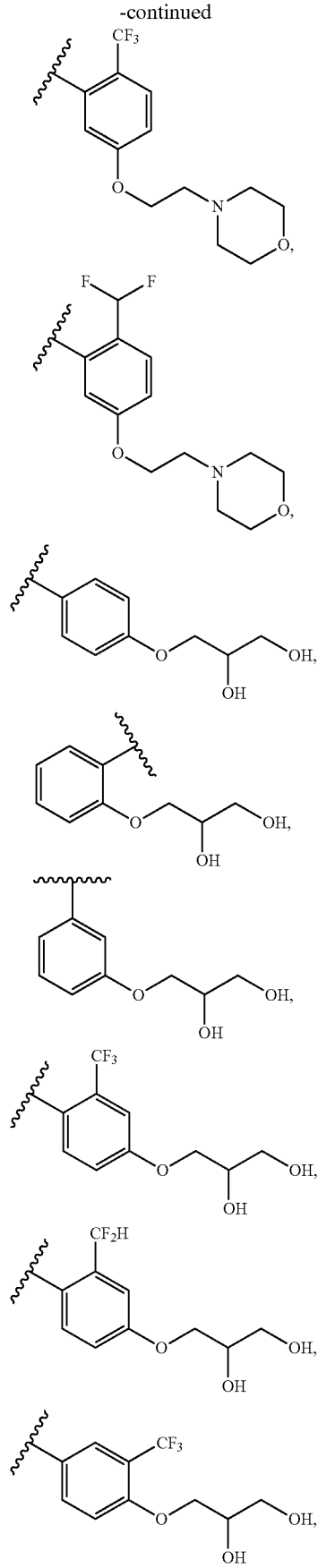
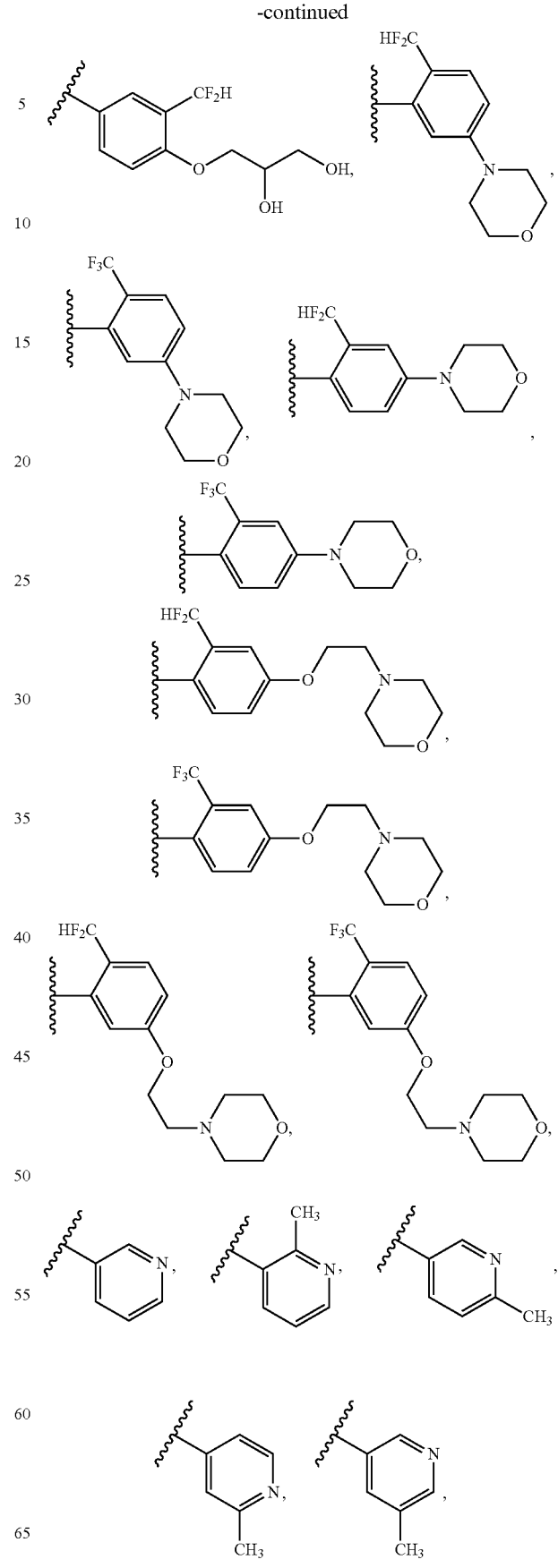

-continued

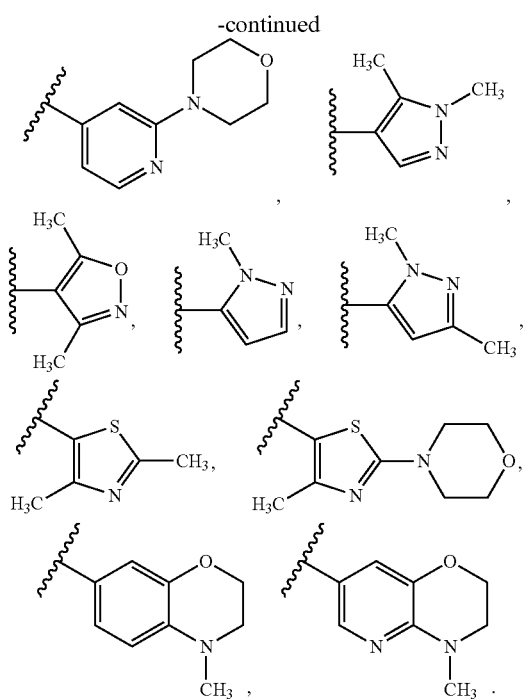

12. The compound of claim 11, wherein R² is selected from

13. The compound of claim 1, wherein X² is C(=O)—NH-†.

14. A pharmaceutical composition comprising a compound of Formula (I) according to claim 1 and a pharmaceutically acceptable carrier or diluent.

15. A method for treating a subject suffering from or susceptible to insulin resistance, a metabolic syndrome, diabetes, or complications thereof, or for increasing insulin sensitivity in a subject, comprising administering a pharmaceutical composition according to claim 14 to a subject in need thereof.

16. A compound which is:

TABLE 2

| Compound No. | Structure |
|---|---|
| 443 | 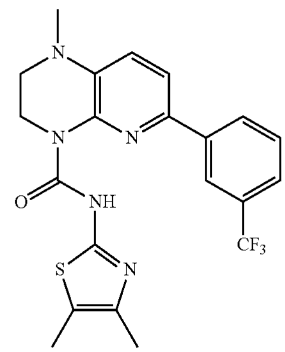 [SMILES: Cc1nc(NC(=O)N2CCN(C)c3ccc(-c4cccc(C(F)(F)F)c4)nc32)sc1C] |
| 444 | 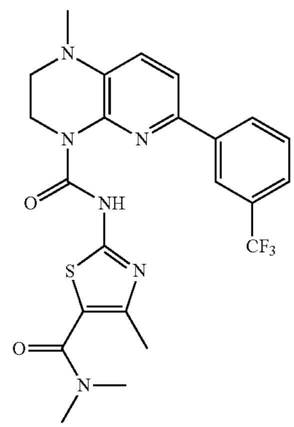 [SMILES: Cc1nc(NC(=O)N2CCN(C)c3ccc(-c4cccc(C(F)(F)F)c4)nc32)sc1C(=O)N(C)C] |
| 445 | 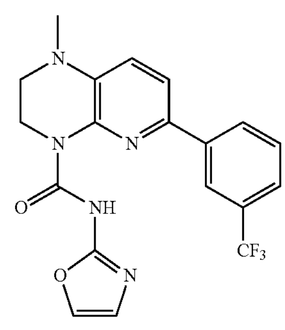 |
| 446 | 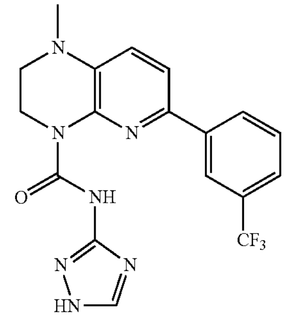 [SMILES: CN1CCN(C(=O)Nc2nc[nH]n2)c2nc(-c3cccc(C(F)(F)F)c3)ccc21] |

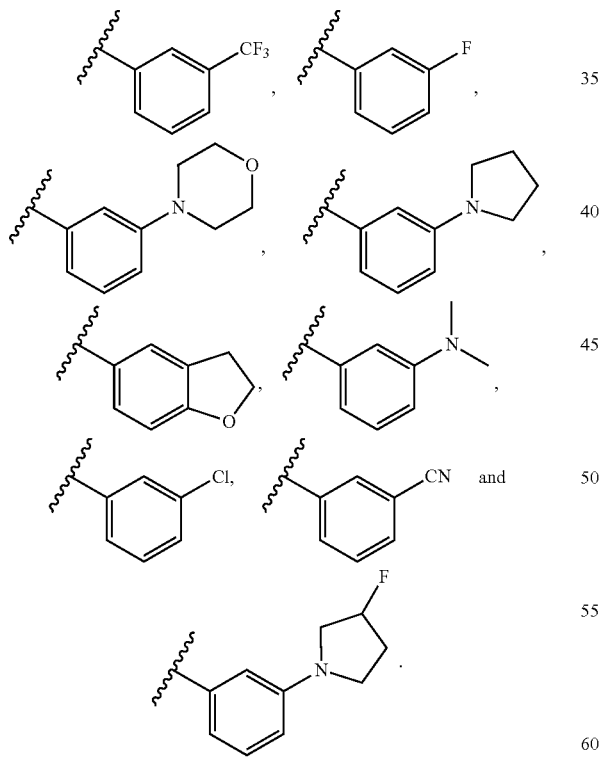

TABLE 2-continued

| Compound No. | Structure |
|---|---|
| 447 | 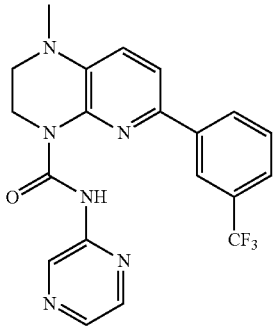 [SMILES: CN1CCN(C(=O)Nc2cnccn2)c2nc(-c3cccc(C(F)(F)F)c3)ccc21] |
| 448 | 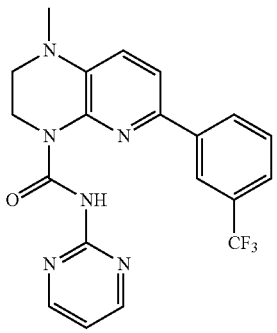 [SMILES: CN1CCN(C(=O)Nc2ncccn2)c2nc(-c3cccc(C(F)(F)F)c3)ccc21] |
| 449 | 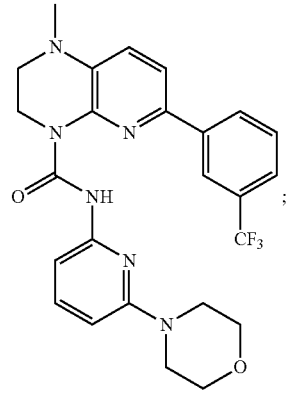 [SMILES: CN1CCN(C(=O)Nc2cccc(N3CCOCC3)n2)c2nc(-c3cccc(C(F)(F)F)c3)ccc21] | or
a pharmaceutically acceptable salt thereof.

17. A method for treating a subject suffering from or susceptible to insulin resistance, a metabolic syndrome, diabetes, or complications thereof, or for increasing insulin sensitivity in a subject, comprising administering a compound of Formula (I) according to claim 1 to a subject in need thereof.

18. A method for treating a subject suffering from or susceptible to insulin resistance, a metabolic syndrome, diabetes, or complications thereof, or for increasing insulin sensitivity in a subject, comprising administering a compound according to claim 16 to a subject in need thereof.

* * * * *